(12) United States Patent
Dai

(10) Patent No.: US 11,091,481 B2
(45) Date of Patent: Aug. 17, 2021

(54) HETEROCYCLIC COMPOUNDS, PREPARATION AND METHODS AND USES THEREOF

(71) Applicant: InventisBio Co., Ltd., Shanghai (CN)

(72) Inventor: Xing Dai, Short Hills, NJ (US)

(73) Assignee: INVENTISBIO CO., LTD., Shanghai (CN)

( * ) Notice: Subject to any disclaimer, the term of this patent is extended or adjusted under 35 U.S.C. 154(b) by 0 days.

(21) Appl. No.: 17/172,988

(22) Filed: Feb. 10, 2021

(65) Prior Publication Data

US 2021/0198255 A1 Jul. 1, 2021

Related U.S. Application Data

(63) Continuation of application No. PCT/CN2020/091274, filed on May 20, 2020.

(30) Foreign Application Priority Data

| May 21, 2019 | (WO) | ................ PCT/CN2019/087772 |
| Jul. 15, 2019 | (WO) | ................ PCT/CN2019/095947 |
| Dec. 5, 2019 | (WO) | ................ PCT/CN2019/123223 |

(51) Int. Cl.

| C07D 471/04 | (2006.01) |
| C07D 519/00 | (2006.01) |
| A61P 35/00 | (2006.01) |
| A61K 31/519 | (2006.01) |
| A61K 33/243 | (2019.01) |
| A61K 31/438 | (2006.01) |
| A61K 31/282 | (2006.01) |

(52) U.S. Cl.
CPC .......... *C07D 471/04* (2013.01); *A61K 31/282* (2013.01); *A61K 31/438* (2013.01); *A61K 31/519* (2013.01); *A61K 33/243* (2019.01); *A61P 35/00* (2018.01); *C07D 519/00* (2013.01)

(58) Field of Classification Search
None
See application file for complete search history.

(56) References Cited

U.S. PATENT DOCUMENTS

| 10,519,146 B2 | 12/2019 | Lanman et al. |
| 10,532,042 B2 | 1/2020 | Lanman et al. |
| 10,640,504 B2 | 5/2020 | Lanman et al. |
| 2018/0334454 A1 | 11/2018 | Lanman et al. |
| 2019/0343838 A1 | 11/2019 | Allen et al. |
| 2019/0374542 A1 | 12/2019 | Allen et al. |
| 2020/0181118 A1 | 6/2020 | Malhotra et al. |

(Continued)

FOREIGN PATENT DOCUMENTS

| CN | 108658972 A | 10/2018 |
| CN | 110256421 A | 9/2019 |
| CN | 111205286 A | 5/2020 |

(Continued)

OTHER PUBLICATIONS

McCormick, F., KRAS as a Therapeutic Target, Clin Cancer Res., 21:1797-1801 (2015).

(Continued)

*Primary Examiner* — Brian J Davis
(74) *Attorney, Agent, or Firm* — Nixon & Vanderhye P.C.

(57) ABSTRACT

Provided herein are novel compounds, for example, compounds having a Formula (I) or Formula (II), or a pharmaceutically acceptable salt thereof. Also provided herein are methods of preparing the compounds and methods of using the compounds, for example, in inhibiting KRAS G12C in a cell, and/or in treating various cancer such as pancreatic cancer, endometrial cancer, colorectal cancer, or lung cancer (e.g., non-small cell lung cancer).

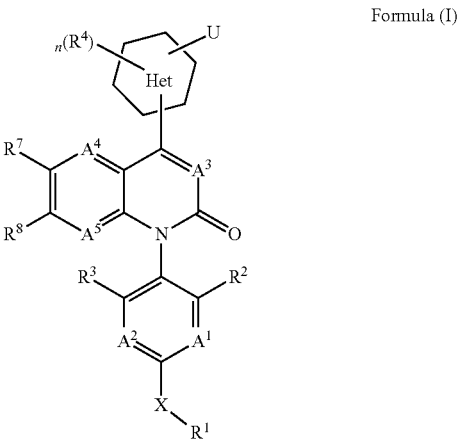

Formula (I)

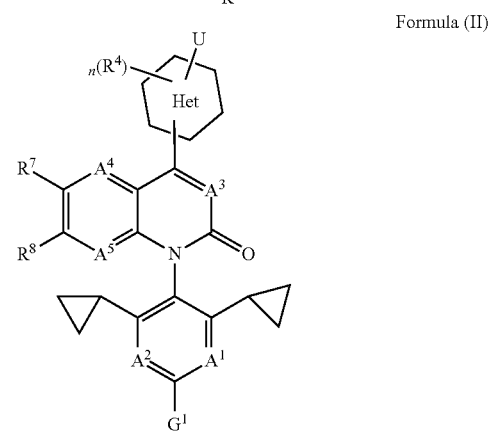

Formula (II)

10 Claims, 3 Drawing Sheets

(56) References Cited

U.S. PATENT DOCUMENTS

2020/0207766 A1    7/2020  Lanman et al.
2020/0222407 A1    7/2020  Lipford et al.

FOREIGN PATENT DOCUMENTS

| CN | 111377918    A  | 7/2020  |
|----|-----------------|---------|
| WO | 2018119183  A2  | 6/2018  |
| WO | 2018217651  A1  | 11/2018 |
| WO | 2019051291  A1  | 3/2019  |
| WO | 2019213516  A1  | 11/2019 |
| WO | 2020097537  A2  | 5/2020  |

OTHER PUBLICATIONS

Simanshu, D. K., et al., RAS Proteins and Their Regulators in Human Disease, Cell, 170:17-33 (2017).

Liu, L. and Wei, S., Research Progress of KRAS Mutation in Non-small Cell Lung Cancer, Chin J Lung Cancer, 21(5):419-424 (2018).

International Search Report and Written Opinion dated Feb. 24, 2020 in International Patent Application No. PCT/CN2019/087772, 13 pages.

International Search Report and Written Opinion dated Feb. 27, 2020 in International Patent Application No. PCT/CN2019/095947, 14 pages.

International Search Report and Written Opinion dated Mar. 12, 2020 in International Patent Application No. PCT/CN2019/123223, 12 pages.

U.S. Appl. No. 17/172,984, filed Feb. 10, 2021, Dai, X., et al.

Lanman, B.A., et al. Discovery of a covalent inhibitor of KRASGI2C (AMG 510) for the treatment of solid tumors, J Med Chem., 63:52-65 (2019).

International Search Report and Written Opinion dated Aug. 19, 2020 in International Patent Application No. PCT/CN2020/091274, 14 pages.

International Search Report and Written Opinion dated Mar. 17, 2021 in International Patent Application No. PCT/CN2020/137276, 16 pages.

International Search Report and Written Opinion dated Sep. 22, 2020 in International Patent Application No. PCT/CN2019/126230, 14 pages.

HETEROCYCLIC COMPOUNDS, PREPARATION AND METHODS AND USES THEREOF

CROSS REFERENCE TO RELATED APPLICATIONS

This application is a continuation of PCT Application No. PCT/CN2020/091274, filed May 20, 2020, which claims priority to International Application Nos. PCT/CN2019/123223, filed on Dec. 5, 2019, PCT/CN2019/087772, filed on May 21, 2019, and PCT/CN2019/095947, filed on Jul. 15, 2019, the content of each of which is incorporated herein by reference in its entirety.

BACKGROUND OF THE INVENTION

Field of the Invention

In various embodiments, the present invention generally relates to novel heterocyclic compounds, compositions of the same, methods of preparing and methods of using the same, e.g., for inhibiting RAS and/or for treating a number of diseases or disorders, such as pancreatic, colorectal, and lung cancers.

Background

RAS proteins regulate key cellular pathway transmitting signal received from cellular membrane receptor to downstream molecules such as Raf, MEK, ERK and PI3K, which are crucial for cell proliferation and survival. RAS cycles between the inactive GDP-bound form and active GTP-bound form. RAS proteins have three gene isoforms: KRAS, NRAS and HRAS and share extensive homology (>90%) in the N-terminal domain (amino acid 1-165). RAS is frequently mutated cancers with KRAS accounted for ~80% of all RAS mutations. KRAS mutation occurs in approximately 60% of pancreatic cancer, 40% of colorectal cancer, 30% of lung cancer and 20% of endometrial carcinoma (F. McCormick, 2017, Clin Cancer Res 21: 1797-1801). The RAS hot-spot mutations occur at codons 12, 13 and 61, with 75% of KRAS mutations occurs at codon 12 (Glycine) (D. K. Simanshu, D. V. Nissley and F. McCormick, 2017, Cell, 170: 17-33).

There is a medical need for therapeutic treatments of cancer patients with RAS mutation such as KRAS G12C mutation.

BRIEF SUMMARY OF THE INVENTION

In various embodiments, the present disclosure provides novel compounds, pharmaceutical compositions, methods of preparing and using the same. Typically, the compounds herein are RAS inhibitors, such as KRAS G12C inhibitors. The compounds and compositions herein are useful for treating various diseases or disorders, such as cancer associated with KRAS G12C mutation.

In various embodiments, the present disclosure provides a compound of Formula I or Formula II, or a pharmaceutically acceptable salt thereof:

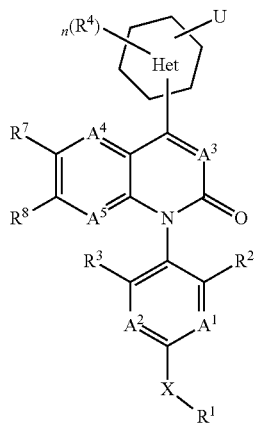

Formula I

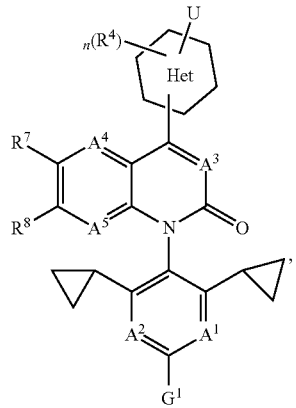

Formula II wherein the variables are defined herein. In some embodiments, the compound of Formula I can have a subformula of Formula I-1, I-2, I-3A, I-3A-1, I-3A-C, I-3A-N, I-3B, I-3C, I-4A, I-4B, I-4C, I-3B-1, I-3C-1, I-4A-1, I-4B-1, I-4C-1, I-5, I-6, I-7, or I-8, as defined herein. In some embodiments, the present disclosure provides a compound selected from compound Nos. 1-186, or a pharmaceutically acceptable salt thereof. In some embodiments, when applicable, the compound can exist as a mixture of atropisomers in any ratio. In some embodiments, when applicable, the compound can exist as an isolated individual atropisomer substantially free (e.g., with less than 20%, less than 10%, less than 5%, less than 1%, by weight, by HPLC area, or both, or with a non-detectable amount) of the other atropisomer(s).

Certain embodiments are directed to a pharmaceutical composition comprising one or more of the compounds of the present disclosure (e.g., a compound of Formula I (e.g., Formula I-1, I-2, I-3A, I-3A-1, I-3A-C, I-3A-N, I-3B, I-3C, I-4A, I-4B, I-4C, I-3B-1, I-3C-1, I-4A-1, I-4B-1, I-4C-1, I-5, I-6, I-7, or I-8), Formula II, Formula III, Formula IV, any of compound Nos. 1-186, or a pharmaceutically acceptable salt thereof) and optionally a pharmaceutically acceptable excipient. The pharmaceutical composition described herein can be formulated for different routes of administration, such as oral administration, parenteral administration, or inhalation etc.

Certain embodiments are directed to a method of treating a disease or disorder associated with RAS, e.g., KRAS G12C. In some embodiments, the method comprises administering to a subject in need thereof a therapeutically effective amount of a compound of the present disclosure (e.g., a compound of Formula I (e.g., Formula I-1, I-2, I-3A, I-3A-1, I-3A-C, I-3A-N, I-3B, I-3C, I-4A, I-4B, I-4C, I-3B-1, I-3C-1, I-4A-1, I-4B-1, I-4C-1, I-5, I-6, I-7, or I-8), Formula II, Formula III, Formula IV, any of compound Nos. 1-186, or a pharmaceutically acceptable salt thereof) or a therapeutically effective amount of a pharmaceutical composition described herein. In some embodiments, a method of treating cancer is provided. In some embodiments, the method comprises administering to a subject in need thereof a therapeutically effective amount of a compound of the present disclosure or a therapeutically effective amount of a pharmaceutical composition described herein. In various embodiments, the cancer can be pancreatic cancer, endometrial cancer, colorectal cancer or lung cancer (e.g., non-small cell lung cancer). In some embodiments, the cancer is a hematological cancer (e.g., described herein). In some embodiments, the cancer is MYH associated polyposis. In some embodiments, the cancer can be gall bladder cancer, thyroid cancer, or bile duct cancer. The administering is not limited to any particular route of administration. For example, in some embodiments, the administering can be orally, nasally, transdermally, pulmonary, inhalationally, buccally, sublingually, intraperintoneally, subcutaneously, intramuscularly, intravenously, rectally, intrapleurally, intrathecally and parenterally. The compounds of the present disclosure can be used as a monotherapy or in a combination therapy. In some embodiments, the combination therapy includes treating the subject with a chemotherapeutic agent, therapeutic antibody, radiation, cell therapy, or immunotherapy.

It is to be understood that both the foregoing summary and the following detailed description are exemplary and explanatory only, and are not restrictive of the invention herein.

BRIEF DESCRIPTION OF THE DRAWINGS/FIGURES

DETAILED DESCRIPTION OF THE INVENTION

Figure 1:
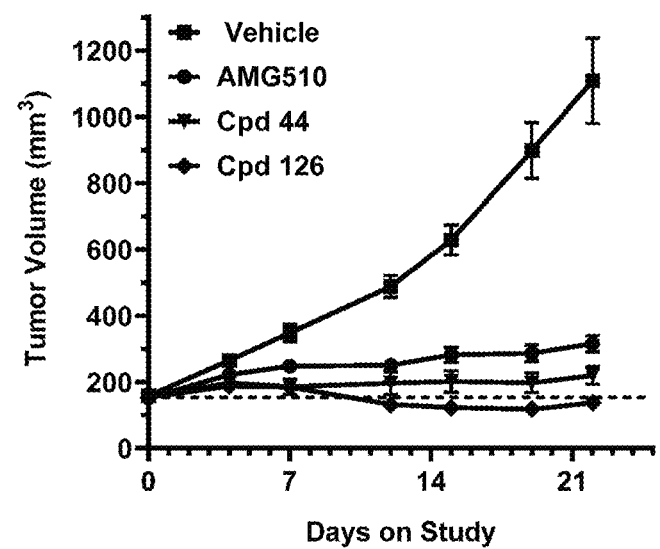
FIG. 1 is a graph showing the tumor volume growth profile vs. days on study in a colorectal adenocarcinoma SW837 xenograft model, following treatments with vehicle, AMG510 (60 mg/kg), Compound No. 44 (60 mg/kg), or Compound No. 126 (30 mg/kg).

In various embodiments, provided herein are novel compounds, pharmaceutical compositions, methods of preparation and methods of use.

Compounds

Some embodiments of the present disclosure are directed to novel compounds. The compounds herein typically can be an inhibitor of a KRAS protein, particularly, a KRAS G12C mutant protein.

In some embodiments, the present disclosure provides a compound of Formula I, or a pharmaceutically acceptable salt thereof:

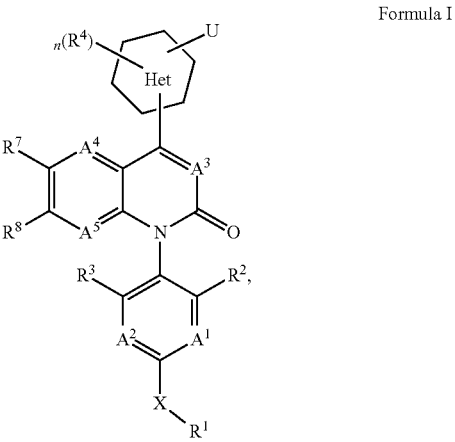

Formula I wherein:

X is O, $NR^{10}$, S, $SO_2$, or an optionally substituted heterocyclic ring (e.g., 4 to 7 membered heterocyclic ring);

$R^1$ is hydrogen, optionally substituted alkyl (e.g., $C_{1-4}$ alkyl), or -L-$R^{20}$, wherein L is absent or an optionally substituted alkylene (e.g., $C_{1-4}$ alkylene), optionally substituted heteroalkylene (e.g., $C_{1-4}$ heteroalkylene), optionally substituted carbocyclic ring (e.g., $C_{3-6}$ carbocyclic ring), or optionally substituted heterocyclic ring (e.g., 4 to 7 membered heterocyclic ring), wherein $R^{20}$ is hydrogen, optionally substituted alkyl, alkenyl, or alkynyl, e.g., optionally substituted $C_{1-4}$ alkyl, $C_{2-4}$ alkenyl, or $C_{2-4}$ alkynyl, $-NR^{21}R^{22}$, $-OR^{23}$, an optionally substituted heterocyclyl (e.g., 4 to 7 membered heterocyclyl), or X-$R^1$ represents -COOH, -COOR$^{23}$, -CONR$^{21}$R$^{22}$, -CN, optionally substituted alkyl, alkenyl, alkynyl, or carbocyclic ring (e.g., cycloalkyl), for example, $C_{1-6}$ alkyl, $C_{2-6}$ alkenyl, $C_{2-6}$ alkynyl, or $C_{3-6}$ cycloalkyl, wherein the $C_{1-6}$ alkyl, $C_{2-6}$ alkenyl, $C_{2-6}$ alkynyl, or $C_{3-6}$ cycloalkyl is optionally substituted, e.g., with 1-3 groups each independently selected from F, OH, protected OH, and $C_{1-4}$ alkoxy;

wherein each of $R^{10}$, $R^{21}$ and $R^{22}$ at each occurrence is independently hydrogen, an optionally substituted alkyl, alkenyl, or alkynyl, e.g., optionally substituted $C_{1-4}$ alkyl, $C_{2-4}$ alkenyl, or $C_{2-4}$ alkynyl, optionally substituted heteroalkyl (e.g., $C_{1-4}$ heteroalkyl), optionally substituted carbocyclic ring (e.g., $C_{3-6}$ carbocyclic ring), optionally substituted heterocyclic ring (e.g., 4 to 7 membered heterocyclic ring), or a nitrogen protecting group; $R^{23}$ at each occurrence is independently hydrogen, an optionally substituted alkyl, alkenyl, or alkynyl, e.g., optionally substituted $C_{1-4}$ alkyl, $C_{2-4}$ alkenyl, or $C_{2-4}$ alkynyl, optionally substituted heteroalkyl (e.g., $C_{1-4}$ heteroalkyl), optionally substituted carbocyclic ring (e.g., $C_{3-6}$ carbocyclic ring), optionally substituted heterocyclic ring (e.g., 4 to 7 membered heterocyclic ring), or an oxygen protecting group;

each of $A^1$, $A^2$, $A^3$, $A^4$, and $A^5$ is independently $CR^{30}$ or N, wherein $R^{30}$ at each occurrence is independently hydrogen, halogen (e.g., F, Cl), optionally substituted $C_{1-4}$ alkyl, or optionally substituted alkoxy (e.g., $C_{1-4}$ alkoxy);

or $R^1$, X, and $A^1$ can join together to form an optionally substituted ring structure, for example, an optionally substituted heterocyclic or heteroaryl ring;

$R^2$ and $R^3$ are each independently hydrogen, halogen, —OH, —CN, optionally substituted alkyl, alkenyl, or alkynyl, e.g., optionally substituted $C_{1-4}$ alkyl, $C_{2-4}$ alkenyl, or $C_{2-4}$ alkynyl, optionally substituted carbocyclic ring (e.g., $C_{3-6}$ carbocyclic ring), optionally substituted heterocyclic ring (e.g., 4 to 7 membered heterocyclic ring), or optionally substituted alkoxy (e.g., $C_{1-4}$ alkoxy);

(hereinafter simplified as "Het") is a heterocyclic ring (e.g., a 4-10 membered heterocyclic ring), which is optionally substituted, for example, with independently selected $R^4$ group(s), $(R^4)_n$, wherein n is 0, 1, 2, or 3, and $R^4$ at each occurrence is independently optionally substituted alkyl, alkenyl, or alkynyl or a 3 or 4 membered ring, e.g., $R^4$ at each occurrence can be $C_{1-4}$ alkyl, $C_{2-4}$ alkenyl, $C_{2-4}$ alkynyl, 3 or 4 membered ring (e.g., cyclopropyl), fluorine substituted $C_{1-4}$ alkyl, hydroxyl substituted $C_{1-4}$ alkyl, or cyano substituted $C_{1-4}$ alkyl; or two $R^4$ groups can join together to form a ring structure, e.g., a 3-6 membered ring structure;

U represents an electrophilic moiety capable of forming a covalent bond with a cysteine residue of a KRAS protein, e.g., a KRAS G12C mutant protein;

$R^7$ is hydrogen, halogen, —CN, a 3-4 membered ring, (e.g., cyclopropyl), optionally substituted alkyl, alkenyl, alkynyl, or alkoxy, for example, optionally substituted $C_{1-4}$ alkyl, optionally substituted $C_{2-4}$ alkenyl, optionally substituted $C_{2-4}$ alkynyl, or optionally substituted $C_{1-4}$ alkoxyl; and $R^8$ is an optionally substituted aryl or optionally substituted heteroaryl.

In some embodiments, X in Formula I can be or include a heteroatom. For example, in some embodiments, X can be O. In some embodiments, X can be $NR^{10}$. In some embodiments, X can also be S or $SO_2$. In some embodiments, X can also be a heterocyclic ring, such as an optionally substituted 4-7 membered heterocyclic ring. In some embodiments, the 4-7 membered heterocyclic ring has 1 or 2 heteroatoms, such as 1 or 2 nitrogen atoms. Various heterocyclic rings are suitable. Non-limiting suitable examples include:

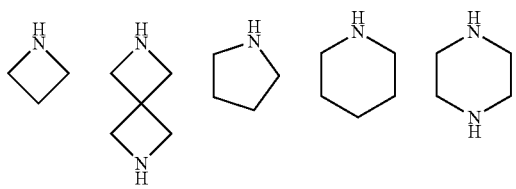

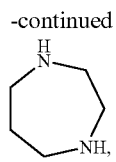

wherein each of which can be optionally substituted, for example, with 1-3 substituents each independently selected from halogen, —OH, oxo, $C_{1-4}$ alkyl, and $C_{1-4}$ alkoxy, wherein the $C_{1-4}$ alkyl or $C_{1-4}$ alkoxy is optionally substituted with 1-3 fluorine, wherein the heterocyclic rings can be attached to the remainder of Formula I via any two available positions. For example, when X in Formula I is an optionally substituted piperazine, the piperazine ring can be attached to the remainder of Formula I via the two nitrogen atoms, two carbon atoms, a single carbon atom, or one nitrogen atom and one carbon atom, e.g.,

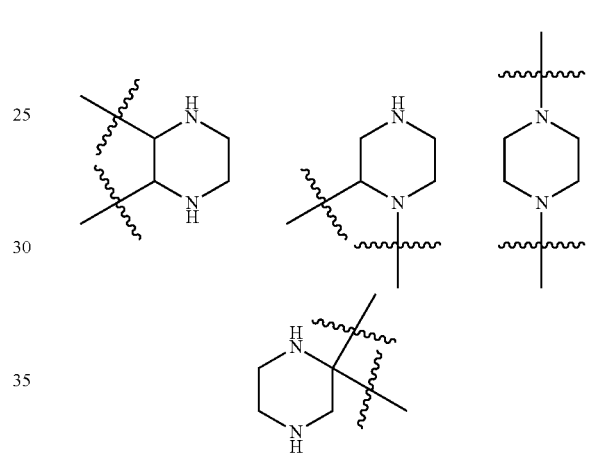

(optional substituent(s) not shown). Other heterocyclic rings should be understood similarly.

Different $R^1$ groups can be attached to X in Formula I. In some embodiments, $R^1$ can be hydrogen. In some embodiments, $R^1$ can be optionally substituted $C_{1-4}$ alkyl, for example, methyl, ethyl, isopropyl, $CHF_2$, $CF_3$, etc.

In some embodiments, $R^1$ can be -L-$R^{20}$. In some embodiments, L can be absent. In some embodiments, L can be a linker, for example, an optionally substituted $C_{1-4}$ alkylene, optionally substituted $C_{1-4}$ heteroalkylene, optionally substituted $C_{3-6}$ carbocyclic ring, or optionally substituted 4 to 7 membered heterocyclic ring. In some embodiments, L can be a $C_{1-4}$ alkylene, such as —$CH_2$—, —$CH_2$—$CH_2$—, —$CH(CH_3)$—$CH_2$—, etc. In some embodiments, L can be an optionally substituted $C_{1-4}$ alkylene, such as with 1 or 2 substituents each independently F, OH, or methyl. As used herein, optionally substituted $C_{1-4}$ alkylene also includes a $C_{1-4}$ alkylene wherein two substituents, including two gem substituents, form a cyclic structure, such as

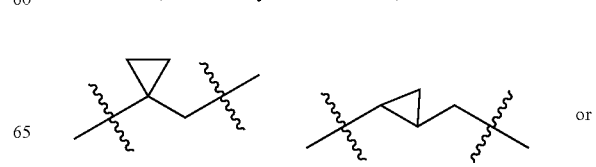

or

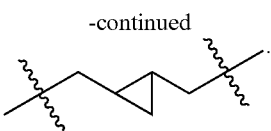

In some embodiments, L can also be a $C_{1-4}$ heteroalkylene, for example, —CH$_2$—CH$_2$—O—CH$_2$—CH$_2$—, —CH$_2$—CH$_2$—O—CH$_2$—CH$_2$—O—, —CH$_2$—CH$_2$—N(H)—CH$_2$—CH$_2$—, —CH$_2$—CH$_2$—, etc. Typically, when L is a $C_{1-4}$ heteroalkylene, the heteroalkylene has one or two heteroatoms, such as one oxygen, one nitrogen, or two oxygen atoms, etc. Generally, —X-L-R$^{20}$ does not contain two consecutive heteroatoms. In some embodiments, L can be an optionally substituted $C_{1-4}$ heteroalkylene, such as with 1 or 2 substituents each independently F, —OH, or methyl. Similarly, as used herein, optionally substituted $C_{1-4}$ heteroalkylene also includes a $C_{1-4}$ heteroalkylene, wherein two substituents, including two gem substituents, form a cyclic structure, such as

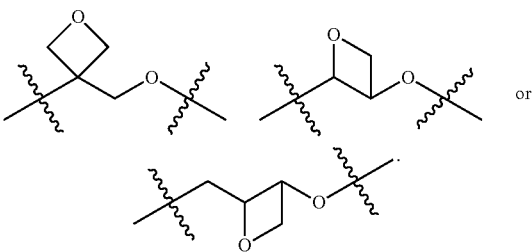

In some embodiments, L can also be an optionally substituted $C_{3-6}$ carbocyclic ring. For example, in some embodiments, L can be cyclopropylene, cyclobutylene, cyclopentylene, etc. Heterocyclic rings are also suitable in some embodiments. For example, L can be a 4-7 membered heterocyclic ring having one or two heteroatoms independently selected from O, N, and S, wherein any two available positions of the heterocyclic ring can be used to link X with R$^{20}$. Non-limiting suitable heterocyclic rings include those described herein, such as azetidinyl, tetrahydrofuranyl, pyrrolidinyl, piperazinyl, morpholinyl, etc. The heterocyclic ring can be optionally substituted, for example, with 1-3 substituents each independently selected from halogen, —OH, oxo, $C_{1-4}$ alkyl, and $C_{1-4}$ alkoxy, wherein the $C_{1-4}$ alkyl or $C_{1-4}$ alkoxy is optionally substituted with 1-3 fluorine.

R$^{20}$ typically can be hydrogen, optionally substituted $C_{1-4}$ alkyl, optionally substituted $C_{2-4}$ alkenyl, optionally substituted $C_{2-4}$ alkynyl, —NR$^{21}$R$^{22}$, —OR$^{23}$, or an optionally substituted 4 to 7 membered heterocyclyl. For example, in some embodiments, R$^{20}$ can be hydrogen. In some embodiments, R$^{20}$ can be a $C_{1-4}$ alkyl, such as methyl, ethyl, isopropyl, etc. In some embodiments, R$^{20}$ can be a $C_{1-4}$ alkyl substituted with 1-3 substituents each independently selected from F, —OH, —NH$_2$, —NH(C$_{1-4}$ alkyl) such as —NHMe, and —N(C$_{1-4}$ alkyl)(C$_{1-4}$ alkyl) such as —NMe$_2$ or —N(Me)(Et). For example, in some embodiments, R$^{20}$ can be —CH$_2$—OH, —CH$_2$—NMe$_2$, etc. In some embodiments, R$^{20}$ can be —OR$^{23}$. For example, in some embodiments, R$^{20}$ can be —OH or —O—C$_{1-4}$ alkyl etc. In some embodiments, R$^{20}$ can be a protected OH, such as —O—C(O)—C$_{1-4}$ alkyl, or a silyl protected hydroxyl, such as —O-TMS. Compounds with such protected OH as R$^{20}$ can in some embodiments be used during a synthesis to provide compounds with R$^{20}$ being OH. In some embodiments, R$^{20}$ can be —NR$^{21}$R$^{22}$. For example, in some embodiments, R$^{20}$ can be —NH$_2$, —NH(C$_{1-4}$ alkyl) such as —NHMe, or —N(C$_{1-4}$ alkyl)(C$_{1-4}$ alkyl) such as —NMe$_2$ or —N(Me)(Et). In some embodiments, one or both R$^{21}$ and R$^{22}$ can be a nitrogen protecting group. When both R$^{21}$ and R$^{22}$ are nitrogen protecting groups, it also includes situations where R$^{21}$ and R$^{22}$ are joined to form a ring structure, such as

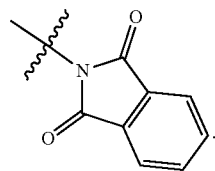 [SMILES: *N1C(=O)c2ccccc2C1=O]

Compounds with such protected NH(R) or NH$_2$ as R$^{20}$ can in some embodiments be used during a synthesis to provide compounds with R$^{20}$ being NH(R) or NH$_2$. In some embodiments, R$^{20}$ can also be a 4-7 membered heterocyclyl, typically having one or two heteroatoms independently selected from O, N, and S. Non-limiting suitable heterocyclyl include those described herein, such as azetidinyl, tetrahydrofuranyl, pyrrolidinyl, piperazinyl, morpholinyl, etc. The heterocyclyl can be optionally substituted, for example, with 1-3 substituents each independently selected from halogen, —OH, oxo, $C_{1-4}$ alkyl, and $C_{1-4}$ alkoxy, wherein the $C_{1-4}$ alkyl or $C_{1-4}$ alkoxy is optionally substituted with 1-3 fluorine.

In some embodiments, X, R$^1$, and A$^1$ in Formula I can join together to form an optionally substituted ring structure, typically an optionally substituted heterocyclic or heteroaryl ring. For example, X, R$^1$, and A$^1$ can together form a 4, 5, or 6 membered heterocyclic ring structure or a 5 or 6-membered heteroaryl ring structure. Those skilled in the art understand that when X, R$^1$, and A$^1$ together form a ring structure, a fused bicyclic ring is formed in Formula I, with ═══A$^1$ being shared. Non-limiting suitable ring structures include the following, for illustration purposes, the fused ring structure is showing instead of just the ring structure formed from X, R$^1$, and A$^1$ in Formula I, and optional substituents are also not shown:

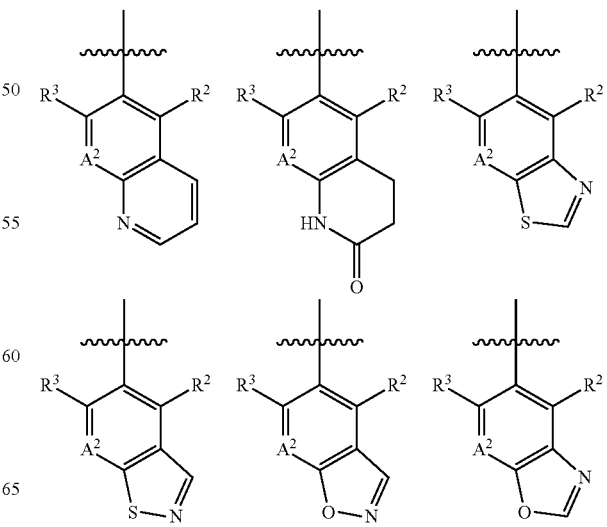

-continued

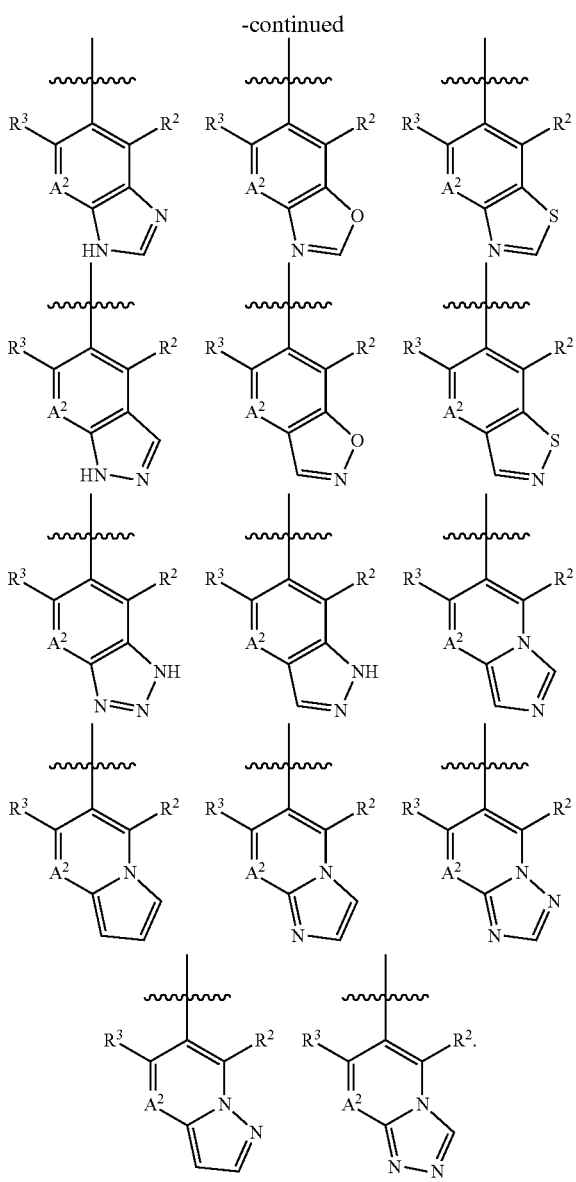

In some embodiments, $A^2$ is CH. In some embodiments, $A^2$ is N.

In some embodiments, —X—$R^1$ in Formula I can represent a carbon linked moiety, where X is not a heteroatom. For example, in some embodiments, —X—$R^1$ in Formula I can be —COOH, —COOR$^{23}$, —CONR$^{21}$R$^{22}$, —CN, $C_{1-6}$ alkyl, $C_{2-6}$ alkenyl, $C_{2-6}$ alkynyl, or $C_{3-6}$ cycloalkyl, wherein the $C_{1-6}$ alkyl, $C_{2-6}$ alkenyl, $C_{2-6}$ alkynyl, or $C_{3-6}$ cycloalkyl is optionally substituted, e.g., with 1-3 groups each independently selected from F, —OH, protected OH, and $C_{1-4}$ alkoxy. In some embodiments, —X—$R^1$ in Formula I can be a hydroxyl substituted $C_{1-6}$ alkyl, for example, —C(CH$_3$)$_2$—OH.

In some embodiments, $A^1$ and $A^2$ in Formula I can both be N. In some embodiments, one of $A^1$ and $A^2$ in Formula I can be N, and the other of $A^1$ and $A^2$ can be CH.

$R^2$ and $R^3$ in Formula I can be the same or different. Typically, $R^2$ and $R^3$ can independently be hydrogen, $C_{1-4}$ alkyl optionally substituted with 1-3 fluorine, $C_{3-6}$ cycloalkyl, or halogen. For example, in some embodiments, $R^2$ and $R^3$ can be independently selected from hydrogen, methyl, ethyl, isopropyl, tert-butyl, cyclopropyl, F, and Cl. In some specific embodiments, both $R^2$ and $R^3$ are isopropyl. In some embodiments, both $R^2$ and $R^3$ are cyclopropyl. In some embodiments, $R^2$ and $R^3$ are the same. In some embodiments, $R^2$ and $R^3$ are different. In some embodiments, one of $R^2$ and $R^3$ is hydrogen or methyl.

Various heterocyclic rings are suitable as Het in Formula I. It should be clarified, although drawn in the formulae herein as

Het is not to be interpreted as only encompassing a 6-member monocyclic heterocyclic ring. Typically, Het can be a 4-9 membered heterocyclic ring, which can be monocyclic or polycyclic (e.g., bicyclic, fused or spiro bicyclic). Het generally includes one or two ring heteroatoms, such as one or two ring nitrogen atoms. Non-limiting examples of suitable heterocyclic rings include the following:

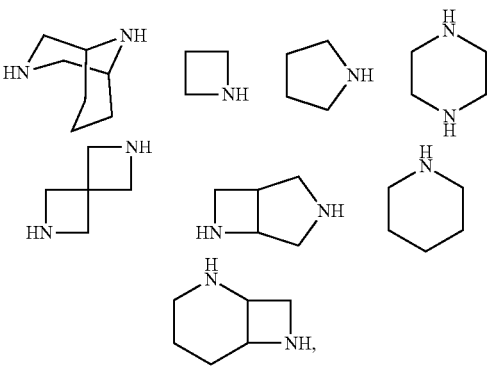

wherein the point of attachments can be any of the available positions. Generally, as applicable, the two ring nitrogen atoms are attached to the 6,6-bicyclic structure in Formula I and the electrophilic moiety U. For example, in some embodiments, Het is piperazine, which can be attached to the remainder of Formula I through the two nitrogen atoms:

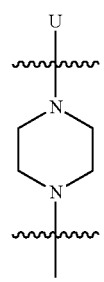

(optionally substituent(s) not shown).

The compounds herein include an electrophilic moiety, U, which can react with a cysteine residue of a KRAS protein to form a covalent bond. In some embodiments, U can be an electrophilic moiety containing a Michael acceptor. For example, in some embodiments, U can be an α,β-unsaturated carbonyl moiety, such as

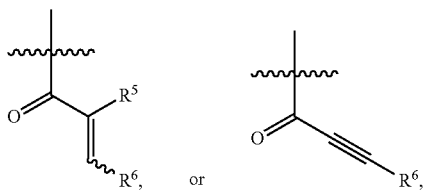

wherein $R^5$ and $R^6$ are defined herein. In some embodiments, U is connected with an nitrogen atom of the Het, for example, having a structural moiety of:

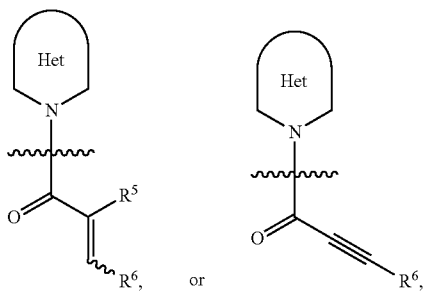

wherein $R^5$ and $R^6$ are defined herein. In some embodiments, U can be an electrophilic moiety, such as

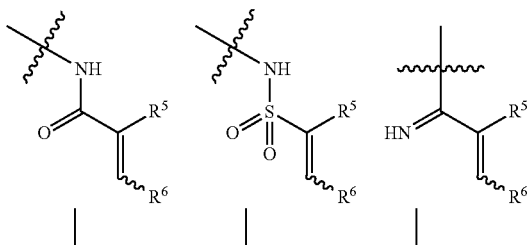

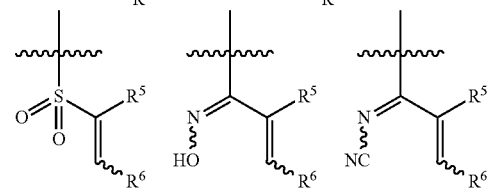

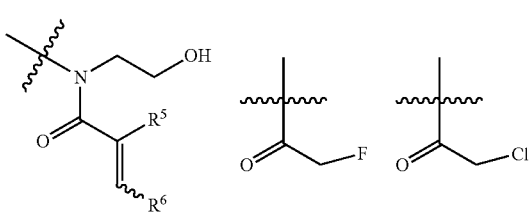

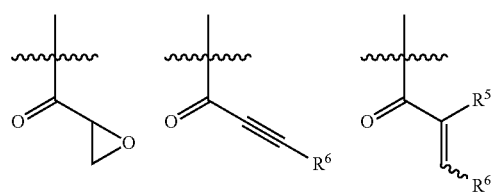

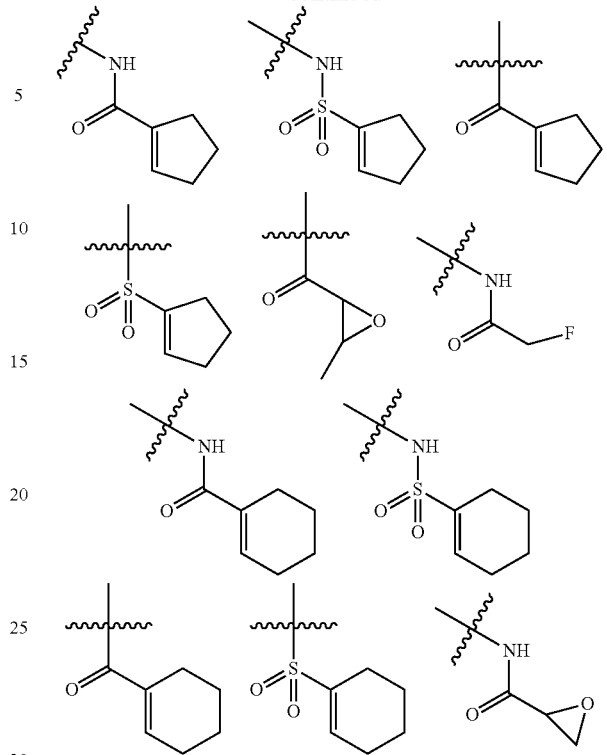

wherein $R^5$ and $R^6$ are defined herein. In some specific embodiments, U can be

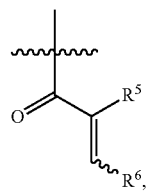

wherein $R^5$ and $R^6$ are defined herein. In some embodiments, U can be

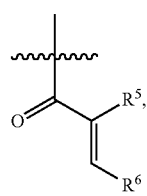

wherein $R^5$ and $R^6$ are defined herein.

Various $R^5$ and $R^6$ are suitable. For example, in some embodiments, $R^5$ and $R^6$ can each be independently hydrogen, halogen, —CN, —COOR$^{23A}$, —CONR$^{21A}$R$^{22A}$, optionally substituted $C_{1-6}$ alkyl, optionally substituted $C_{2-6}$ alkenyl, optionally substituted $C_{2-6}$ alkynyl, optionally substituted $C_{3-6}$ carbocyclic ring, optionally substituted phenyl, optionally substituted 5 or 6 membered heteroaryl, or optionally substituted 4 to 7 membered heterocyclic ring, or $R^5$ and $R^6$ can join together to form an optionally substituted $C_{3-6}$ carbocyclic ring, or optionally substituted 4 to 7 membered heterocyclic ring, wherein each of $R^{21A}$ and $R^{22A}$ at each occurrence is independently hydrogen, an optionally substituted $C_{1-4}$ alkyl, optionally substituted $C_{2-4}$ alkenyl, optionally substituted $C_{2-4}$ alkynyl, optionally substituted $C_{1-4}$ heteroalkyl, optionally substituted $C_{3-6}$ carbocyclic ring, optionally substituted 4 to 7 membered heterocyclic ring, or a nitrogen protecting group; and $R^{23A}$ at each occurrence is independently hydrogen, an optionally substituted $C_{1-4}$ alkyl, optionally substituted $C_{2-4}$ alkenyl, optionally substituted $C_{2-4}$ alkynyl, optionally substituted $C_{1-4}$ heteroalkyl, optionally substituted $C_{3-6}$ carbocyclic ring, optionally substituted 4 to 7 membered heterocyclic ring, or an oxygen protecting group.

In some specific embodiments, $R^5$ can be hydrogen. In some embodiments, $R^5$ can be a halogen, such as F or Cl. In some embodiments, $R^5$ can be —CN. In some embodiments, $R^6$ can be hydrogen. In some embodiments, $R^6$ can be a $C_{1-4}$ alkyl optionally substituted with 1-3 substituents each independently selected from F, —OH, —NH$_2$, —NH($C_{1-4}$ alkyl) such as —NHMe, —N($C_{1-4}$ alkyl)($C_{1-4}$ alkyl) such as —NMe$_2$ or —N(Me)(Et), an optionally substituted 4-7 membered heterocyclyl with 1 or 2 ring heteroatom independently selected from O, N, and S. For example, in some embodiments, $R^6$ can be —CH$_2$—OMe, —(CH$_2$)$_n$—OH, —(CH$_2$)$_n$—NMe$_2$,

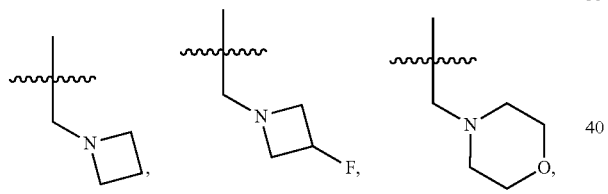

etc, wherein n is an integer of 1-4. In some embodiments, $R^6$ can be a halogen, such as F or Cl. In some embodiments, $R^6$ can be —CN. In some embodiments, $R^6$ can be —COOR$^{23A}$, for example, —COO($C_{1-4}$ alkyl). In some embodiments, $R^6$ can be —CONR$^{21A}$R$^{22A}$, for example, —CON($C_{1-4}$ alkyl)($C_{1-4}$ alkyl), —CONH($C_{1-4}$ alkyl), or —CONH$_2$. In some embodiments, $R^6$ can be an optionally substituted phenyl or 5 or 6 membered heteroaryl, e.g.,

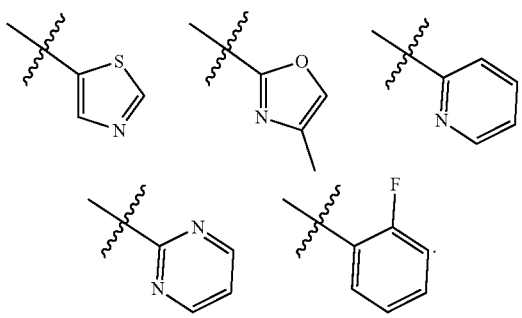

In some specific embodiments, both $R^5$ and $R^6$ are hydrogen. In some specific embodiments, $R^5$ is F or OMe, and $R^6$ is hydrogen. In some specific embodiments, $R^5$ is hydrogen, and $R^6$ is —CH$_2$—OMe or

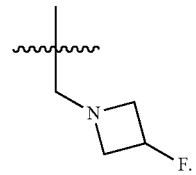 [SMILES: *CN1CC(F)C1]

As shown in Formula I, the Het is substituted with an electrophilic moiety U, and can be optionally further substituted with independently selected $R^4$ groups, $(R^4)_n$, wherein n typically is 0, 1, 2, or 3. In some embodiments, n is 0. In some embodiments, n is 1. In some embodiments, n is 2.

Typically, when present, $R^4$ at each occurrence can be independently $C_{1-4}$ alkyl, $C_{2-4}$ alkenyl, $C_{2-4}$ alkynyl, 3 or 4 membered ring (e.g., cyclopropyl), fluorine substituted $C_{1-4}$ alkyl, hydroxyl substituted $C_{1-4}$ alkyl, or cyano substituted $C_{1-4}$ alkyl; or two $R^4$ groups can join together to form a 3-6 membered ring structure. For example, in some embodiments, $R^4$ at each occurrence can be methyl, ethyl, —CF$_3$, —CF$_2$H, —CH$_2$OH, or —CH$_2$CN. In some embodiments, n can be 1, and $R^4$ can be methyl, ethyl, —CF$_3$, —CF$_2$H, —CH$_2$OH, or —CH$_2$CN. In some embodiments, n can be 2, and one $R^4$ can be methyl, and the other $R^4$ can be methyl, ethyl, —CF$_3$, —CF$_2$H, —CH$_2$OH, or —CH$_2$CN.

In some embodiments, Het in Formula I, together with $(R^4)_n$ and U, is represented by:

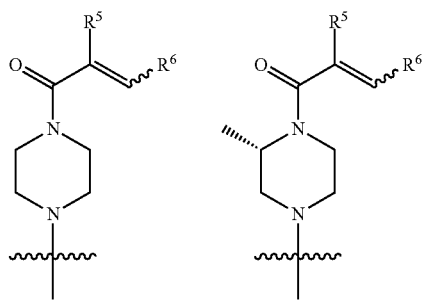

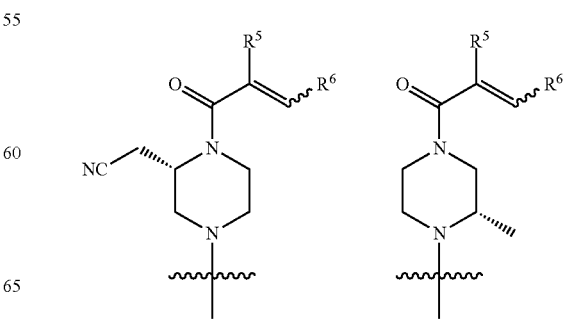

-continued

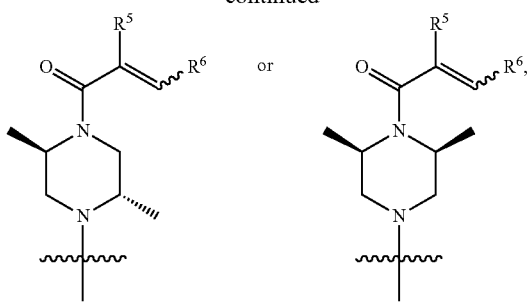

wherein $R^5$ and $R^6$ are defined herein, for example, both $R^5$ and $R^6$ can be hydrogen.

$A^3$ in Formula I typically is N. Although in some embodiments, $A^3$ can also be $CR^{30}$. For example, in some embodiments, $A^3$ can be CH.

$A^4$ in Formula I typically is CH. Although in some embodiments, $A^4$ can also be N.

$A^5$ in Formula I typically is N. Although in some embodiments, $A^5$ can also be $CR^{30}$. For example, in some embodiments, $A^5$ can be CH.

In some embodiments, $R^7$ in Formula I can be hydrogen, halogen, —CN, a 3-4 membered ring, (e.g., cyclopropyl), optionally substituted $C_{1-4}$ alkyl, optionally substituted $C_{2-4}$ alkenyl, optionally substituted $C_{2-4}$ alkynyl, or optionally substituted $C_{1-4}$ alkoxyl. For example, in some embodiments, $R^7$ can be hydrogen, F, Cl, methyl, —CN, or —$CF_3$. In some embodiments, $R^7$ can be F. In some embodiments, $R^7$ can be Cl.

$R^8$ in Formula I is typically an optionally substituted phenyl or naphthyl or an optionally substituted 5-10 membered heteroaryl. In some embodiments, $R^8$ can be a phenyl optionally substituted with 1-3 groups each independently selected from F, Cl, —OH, —$NH_2$, protected hydroxyl group, protected amino group, $C_{1-4}$ alkyl, $C_{2-4}$ alkenyl, $C_{2-4}$ alkynyl, 3 or 4 membered ring (e.g., cyclopropyl), $C_{1-4}$ alkoxy, fluorine substituted $C_{1-4}$ alkyl, and fluorine substituted $C_{1-4}$ alkoxy. In some embodiments, $R^8$ can be a phenyl substituted with F, and optionally further substituted with —OH, —$NH_2$, protected hydroxyl group, or protected amino group. In some embodiments, the substituent(s) of the phenyl group can be ortho to the 6,6-bicyclic structure in Formula I.

In some embodiments, $R^8$ can be a bicyclic heteroaryl (e.g., indazolyl) optionally substituted with 1-3 groups each independently selected from F, Cl, —OH, $NH_2$, protected hydroxyl group, protected amino group, $C_{1-4}$ alkyl, $C_{2-4}$ alkenyl, $C_{2-4}$ alkynyl, 3 or 4 membered ring (e.g., cyclopropyl), $C_{1-4}$ alkoxy, fluorine substituted $C_{1-4}$ alkyl, and fluorine substituted $C_{1-4}$ alkoxy.

In some specific embodiments, $R^8$ can be

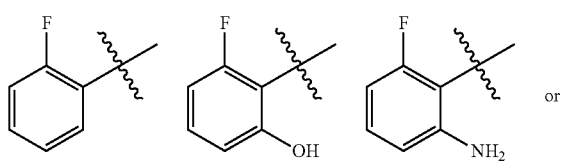

or

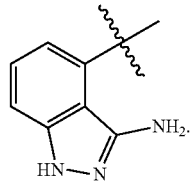

In some embodiments, the present disclosure provides exemplary compounds of Formula I having a Formula I-1 or I-2, or a pharmaceutically acceptable salt thereof:

Formula I-1

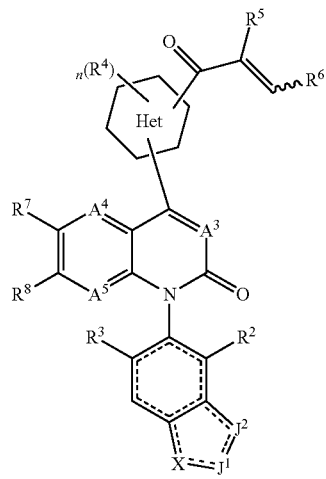

Formula I-2

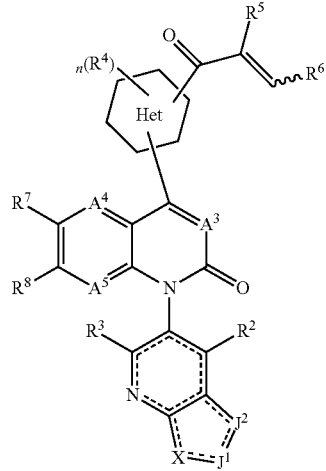

wherein:

X is O, S, N, or $NR^{10}$, each of $J^1$ and $J^2$ is independently selected from O, S, N, $CR^{40}$, and $NR^{41}$, wherein each of $R^{40}$ and $R^{41}$ at each occurrence is independently hydrogen, —OH, —CN, halogen, an optionally substituted $C_{1-4}$ alkyl, optionally substituted $C_{2-4}$ alkenyl, optionally substituted $C_{2-4}$ alkynyl, an optionally substituted $C_{1-4}$ alkoxy, optionally substituted $C_{1-4}$ heteroalkyl, optionally substituted $C_{3-6}$ carbocyclic ring, or optionally substituted 4 to 7 membered heterocyclic ring, wherein the dotted line indicates that the respective connection is a single or double bond, provided that the bicyclic ring as a whole is aromatic, wherein $R^2$, $R^3$, $R^4$, $R^5$, $R^6$, $R^7$, $R^8$, Het, n, $A^3$, $A^4$, and $A^5$ can be any of those defined herein for the respective variable.

In some embodiments, each of $R^{40}$ and $R^{41}$ at each occurrence is independently hydrogen or a $C_{1-4}$ alkyl such as methyl.

In some specific embodiments, the present disclosure also provides exemplary compounds of Formula I having a Formula I-3A, I-3B, I-3C, I-4A, I-4B, or I-4C, or a pharmaceutically acceptable salt thereof:

Formula I-3A

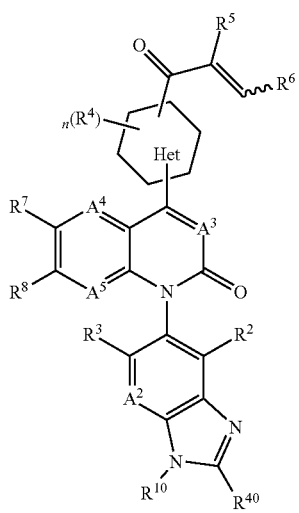

Formula I-3B

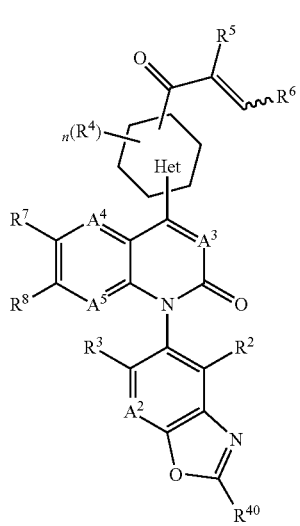

Formula I-3C

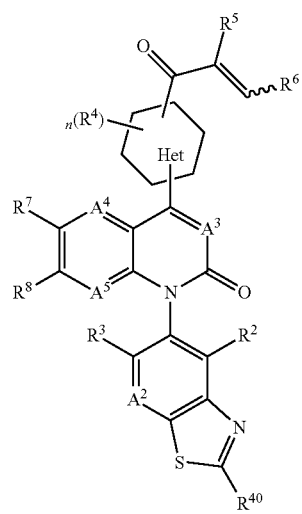

Formula I-4A

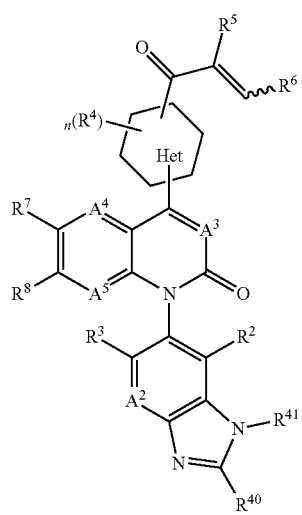

Formula I-4B

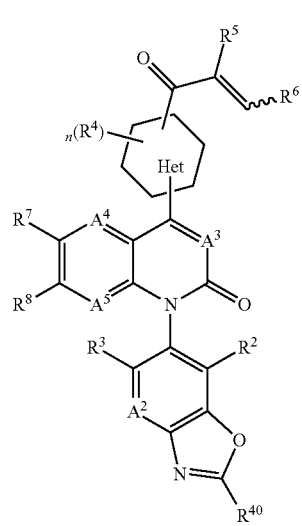

Formula I-4C

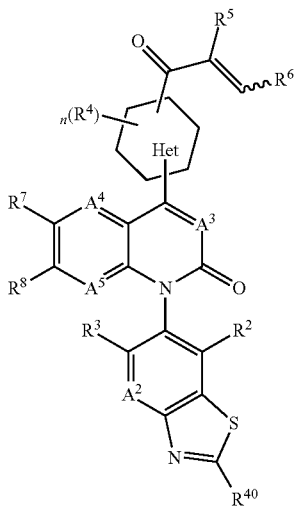

wherein:

A² is CH or N, wherein R², R³, R⁴, R⁵, R⁶, R⁷, R⁸, R¹⁰, R⁴⁰, R⁴¹, Het, n, A³, A⁴, and A⁵ can be any of those defined herein for the respective variable. In some embodiments, each of R¹⁰, R⁴⁰ and R⁴¹ at each occurrence is independently hydrogen or a $C_{1-4}$ alkyl (e.g., methyl). In some embodiments, A² is CH. In some embodiments, A² is N. In some embodiments, A³ is N, A⁴ is CH, and A⁵ is N.

In some specific embodiments, the present disclosure also provides exemplary compounds of Formula I having a Formula I-5 or I-6, or a pharmaceutically acceptable salt thereof:

Formula I-5

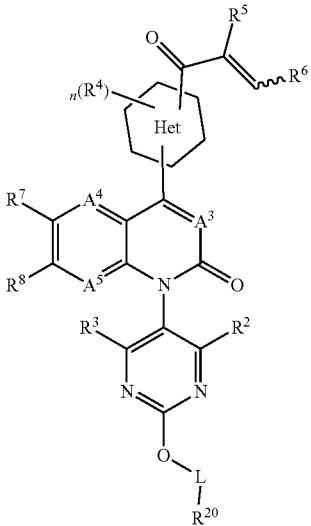

Formula I-6

wherein R², R³, R⁴, R⁵, R⁶, R⁷, R⁸, L, R²⁰, Het, n, A³, A⁴, and A⁵ can be any of those defined herein for the respective variable. In some embodiments, L is absent, an optionally substituted $C_{1-4}$ alkylene, or optionally substituted 4 to 7 membered heterocyclic ring containing 1 or 2 ring heteroatoms (e.g., 1 or 2 ring nitrogen atoms). In some embodiments, R²⁰ is hydrogen, optionally substituted $C_{1-4}$ alkyl, —NR²¹R²², —OR²³, an optionally substituted 4 to 7 membered heterocyclyl containing 1 or 2 ring heteroatoms (e.g., 1 or 2 ring nitrogen atoms), wherein R²¹, R²² and R²³ can be any of those defined herein for the respective variable. In some embodiments, each of R²¹, R²² and R²³ at each occurrence is independently hydrogen or an optionally substituted $C_{1-4}$ alkyl. In some embodiments, the —O-L-R²⁰ residue in Formula I-5 or I-6 can be:

In some specific embodiments, the present disclosure also provides exemplary compounds of Formula I having a Formula I-7 or I-8, or a pharmaceutically acceptable salt thereof:

Formula I-7

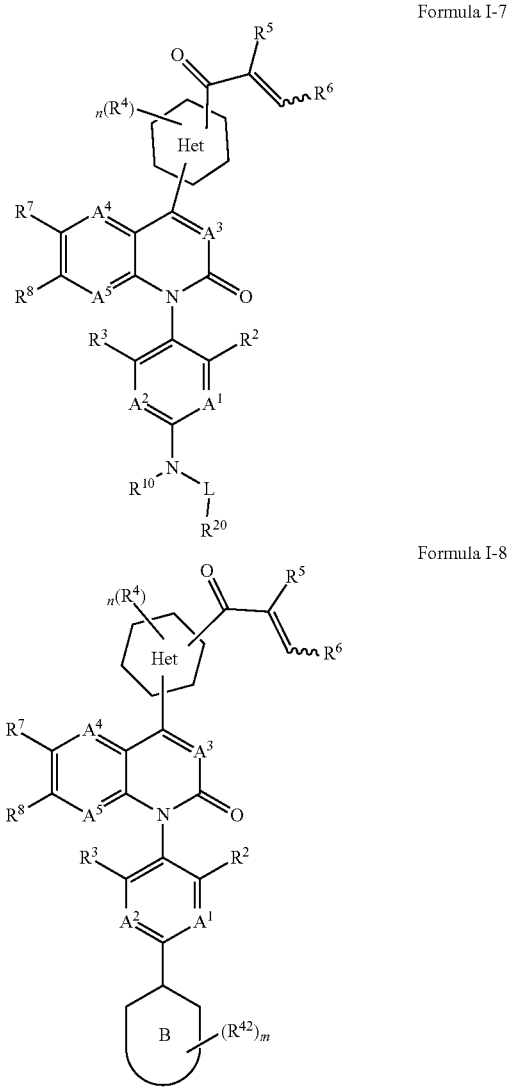

Formula I-8 wherein:
ring B is a 4-7 membered heterocyclic ring containing 1 or 2 ring heteroatoms, such as 1 or 2 ring nitrogen atoms, optionally substituted with $R^{42}$ group(s), $(R^{42})_m$, wherein $R^{42}$ at each occurrence is independently hydrogen, optionally substituted $C_{1-4}$ alkyl, optionally substituted $C_{2-4}$ alkenyl, optionally substituted $C_{2-4}$ alkynyl, $-NR^{21}R^{22}$, or $-OR^{23}$, and m is 0, 1, or 2; and $R^2$, $R^3$, $R^4$, $R^5$, $R^6$, $R^7$, $R^8$, L, $R^{10}$, $R^{20}$, $R^{21}$, $R^{22}$, $R^{23}$, Het, n, $A^1$, $A^2$, $A^3$, $A^4$, and $A^5$ can be any of those defined herein for the respective variable. In some embodiments, L is absent, an optionally substituted $C_{1-4}$ alkylene, or optionally substituted 4 to 7 membered heterocyclic ring containing 1 or 2 ring heteroatoms (e.g., 1 or 2 ring nitrogen atoms). In some embodiments, $R^{20}$ is hydrogen, optionally substituted $C_{1-4}$ alkyl, $-NR^{21}R^{22}$, $-OR^{23}$, an optionally substituted 4 to 7 membered heterocyclyl containing 1 or 2 ring heteroatoms (e.g., 1 or 2 ring nitrogen atoms), wherein $R^{21}$, $R^{22}$ and $R^{23}$ can be any of those defined herein for the respective variable. In some embodiments, each of $R^{10}$, $R^{21}$ and $R^{22}$, as applicable, at each occurrence is independently hydrogen, an optionally substituted $C_{1-4}$ alkyl, or a nitrogen protecting group. In some embodiments, $R^{23}$, as applicable, at each occurrence is hydrogen or an optionally substituted $C_{1-4}$ alkyl. In some embodiments, the

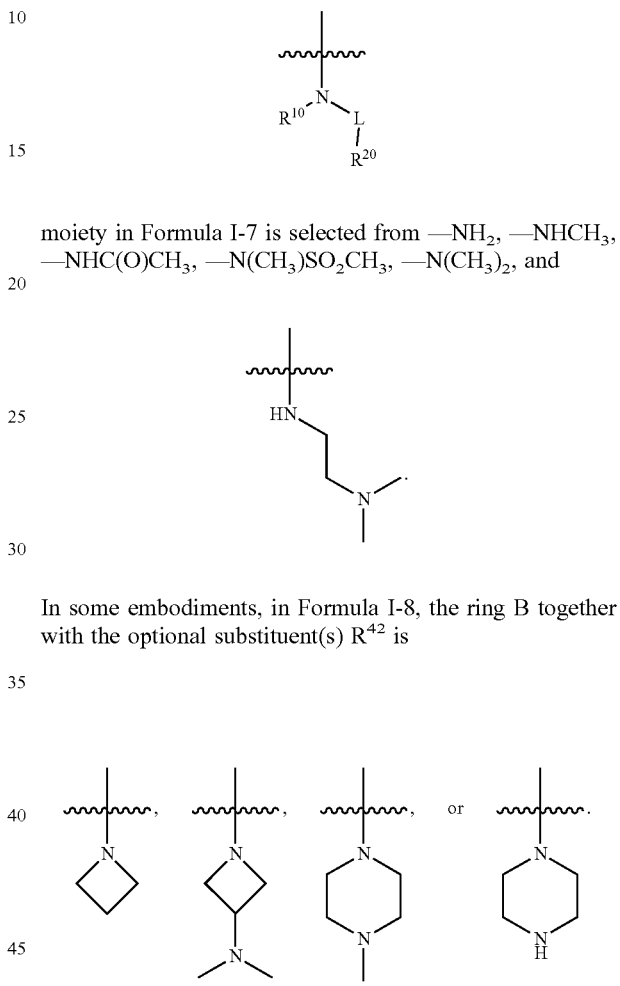

moiety in Formula I-7 is selected from $-NH_2$, $-NHCH_3$, $-NHC(O)CH_3$, $-N(CH_3)SO_2CH_3$, $-N(CH_3)_2$, and In some embodiments, in Formula I-8, the ring B together with the optional substituent(s) $R^{42}$ is As described above, the variables in the subformulae of Formula I, e.g., Formula I-1, I-2, I-3A, I-3B, I-3C, I-4A, I-4B, I-4C, I-5, I-6, I-7, or I-8, can have any of the applicable respective definition defined for Formula I. For example, in some embodiments, $R^2$ and $R^3$ in Formula I and any of its subformulae can be independently selected from hydrogen, $C_{1-4}$ alkyl optionally substituted with 1-3 fluorine, $C_{3-6}$ cycloalkyl, and halogen. In some embodiments, $R^2$ and $R^3$ in Formula I and any of its subformulae can be independently selected from hydrogen, methyl, ethyl, isopropyl, tert-butyl, cyclopropyl, F, and Cl. In some embodiments, $R^2$ and $R^3$ in Formula I and any of its subformulae can be both isopropyl or both cyclopropyl. In some embodiments, $R^2$ and $R^3$ in Formula I and any of its subformulae can be different, wherein one of $R^2$ and $R^3$ is hydrogen or methyl. In some embodiments, in Formula I and any of its subformulae, Het, together with $(R^4)_n$ and U, can be represented by

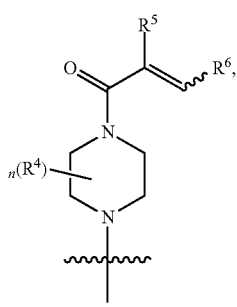

wherein n is 0, 1, or 2, wherein when n is 1 or 2, $R^4$ at each occurrence is independently methyl, ethyl, —$CF_3$, —$CF_2H$, —$CH_2OH$, or —$CH_2CN$. In some embodiments, in Formula I and any of its subformulae, Het, together with $(R^4)_n$ and U, can be represented by

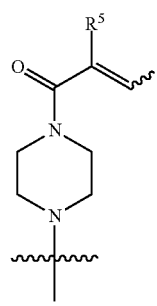 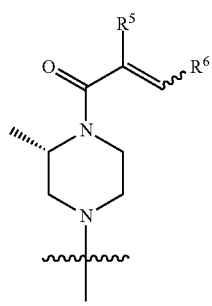

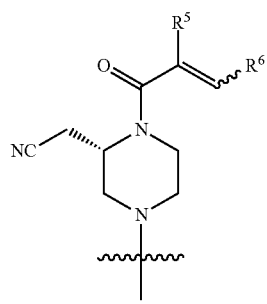 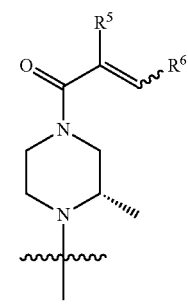

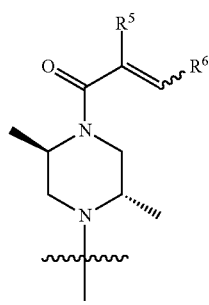 or 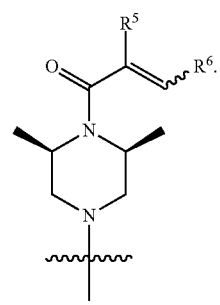

In some embodiments, in Formula I and any of its subformulae, Het, together with $(R^4)_n$ and U, can be represented by

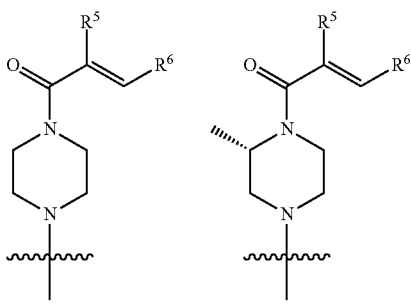

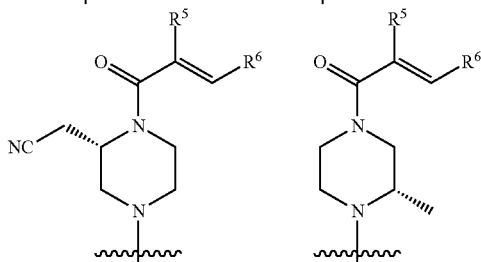

In some embodiments, both $R^5$ and $R^6$ can be hydrogen. In some specific embodiments, $R^5$ is F or OMe, and $R^6$ is hydrogen. In some specific embodiments, $R^5$ is hydrogen, and $R^6$ is —$CH_2$—OMe or

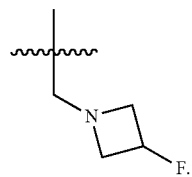 [SMILES: *CN1CC(F)C1]

In some embodiments, $A^1$ and $A^2$ in Formula I and any of its subformulae as applicable can be N. In some embodiments, $A^1$ and $A^2$ in Formula I and any of its subformulae as applicable can be different, for example, one of $A^1$ and $A^2$ is N and the other of $A^1$ and $A^2$ is CH. In some embodiments, $A^3$ in Formula I and any of its subformulae can be N. In some embodiments, $A^4$ in Formula I and any of its subformulae can be CH. In some embodiments, $A^5$ in Formula I and any of its subformulae can be N. In some embodiments, $R^7$ in Formula I and any of its subformulae can be hydrogen, F, Cl, methyl, or —$CF_3$. In some embodiments, $R^7$ can be F. In some embodiments, $R^7$ can be Cl. In some embodiments, $R^8$ in Formula I and any of its subformulae can be a phenyl optionally substituted with 1-3 groups each independently selected from F, Cl, —OH, NH₂, protected hydroxyl group, protected amino group, $C_{1-4}$ alkyl, $C_{2-4}$ alkenyl, $C_{2-4}$ alkynyl, 3 or 4 membered ring (e.g., cyclopropyl), $C_{1-4}$ alkoxy, fluorine substituted $C_{1-4}$ alkyl, and fluorine substituted $C_{1-4}$ alkoxy. In some embodiments, $R^8$ in Formula I and any of its subformulae can be a bicyclic heteroaryl (e.g., indazolyl) optionally substituted with 1-3 groups each independently selected from F, Cl, —OH, —NH₂, protected hydroxyl group, protected amino group, $C_{1-4}$ alkyl, $C_{2-4}$ alkenyl, $C_{2-4}$ alkynyl, 3 or 4 membered ring (e.g., cyclopropyl), $C_{1-4}$ alkoxy, fluorine substituted $C_{1-4}$ alkyl, and fluorine substituted $C_{1-4}$ alkoxy. In some embodiments, $R^8$ in Formula I and any of its subformulae can be selected from:

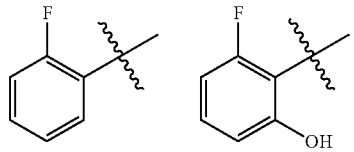

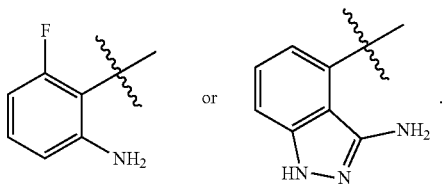

To further illustrate, using a subformula Formula I-3A as an example, some specific embodiments of the present disclosure include exemplary compounds of Formula I having a Formula I-3A-C or Formula I-3A-N, or a pharmaceutically acceptable salt thereof:

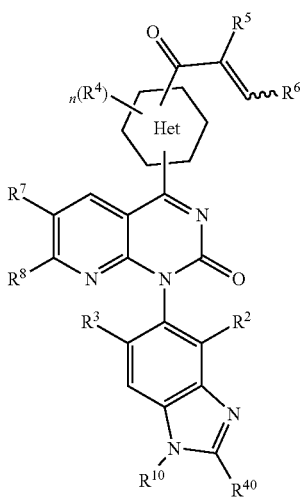

Formula I-3A-C

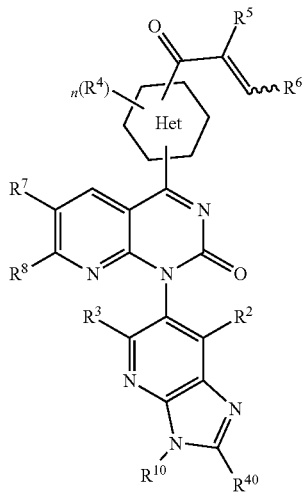

Formula I-3A-N wherein $R^2$, $R^3$, $R^4$, $R^5$, $R^6$, $R^7$, $R^8$, $R^{10}$, $R^{40}$, Het, and n can be any of those defined herein for the respective variable. For example, typically, $R^2$ and $R^3$ in Formula I-3A-C or Formula I-3A-N can be independently selected from hydrogen, $C_{1-4}$ alkyl optionally substituted with 1-3 fluorine, $C_{3-6}$ cycloalkyl, and halogen. In some embodiments, $R^2$ and $R^3$ in Formula I-3A-C or Formula I-3A-N can be independently selected from hydrogen, methyl, ethyl, isopropyl, tert-butyl, cyclopropyl, F, and Cl. In some embodiments, $R^2$ and $R^3$ in Formula I-3A-C or Formula I-3A-N can be both isopropyl or both cyclopropyl. In some embodiments, $R^2$ and $R^3$ in Formula I-3A-C or Formula I-3A-N can be different, for example, one of $R^2$ and $R^3$ is hydrogen, F or methyl, whereas the other of $R^2$ and $R^3$ is isopropyl or cyclopropyl. In some embodiments, in Formula I-3A-C or Formula I-3A-N, one of $R^2$ and $R^3$ can be F, whereas the other of $R^2$ and $R^3$ is isopropyl or cyclopropyl, e.g., $R^2$ is F and $R^3$ is isopropyl or cyclopropyl; or $R^3$ is F and $R^2$ is isopropyl or cyclopropyl. In some embodiments, in Formula I-3A-C or Formula I-3A-N, one of $R^2$ and $R^3$ can be methyl, whereas the other of $R^2$ and $R^3$ is isopropyl or cyclopropyl, e.g., $R^2$ is methyl and $R^3$ is isopropyl or cyclopropyl; or $R^3$ is methyl and $R^2$ is isopropyl or cyclopropyl. As understood by those skilled in the art, when $R^2$ and $R^3$ are different, the compounds of Formula I-3A-C or Formula I-3A-N can exist as a mixture of atropisomers, e.g., in any ratio. In some embodiments, when applicable, the compounds of Formula I-3A-C or Formula I-3A-N can exist as an isolated individual atropisomer substantially free (e.g., with less than 20%, less than 10%, less than 5%, less than 1%, by weight, by HPLC area, or both, or with a non-detectable amount) of the other atropisomer. Exemplary methods for isolating atropisomers are described herein, see for example, the Examples section.

Typically, $R^{10}$ and $R^{40}$ in Formula I-3A-C or Formula I-3A-N can be independently selected from hydrogen and $C_{1-4}$ alkyl. In some embodiments, $R^{40}$ in Formula I-3A-C or Formula I-3A-N can be hydrogen. In some embodiments, $R^{10}$ in Formula I-3A-C or Formula I-3A-N can be a $C_{1-4}$ alkyl, preferably, methyl.

Typically, in Formula I-3A-C or Formula I-3A-N, Het, together with $(R^4)_n$ and

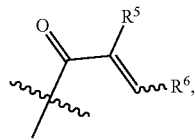

can be represented by

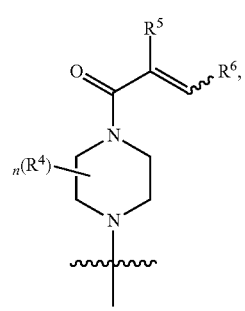

wherein n is 0, 1, or 2, wherein when n is 1 or 2, $R^4$ at each occurrence is independently methyl, ethyl, —CF$_3$, —CF$_2$H, —CH$_2$OH, or —CH$_2$CN. In some embodiments, in Formula I-3A-C or Formula I-3A-N, Het, together with $(R^4)_n$ and

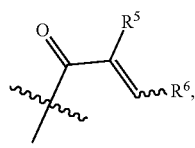

can be represented by

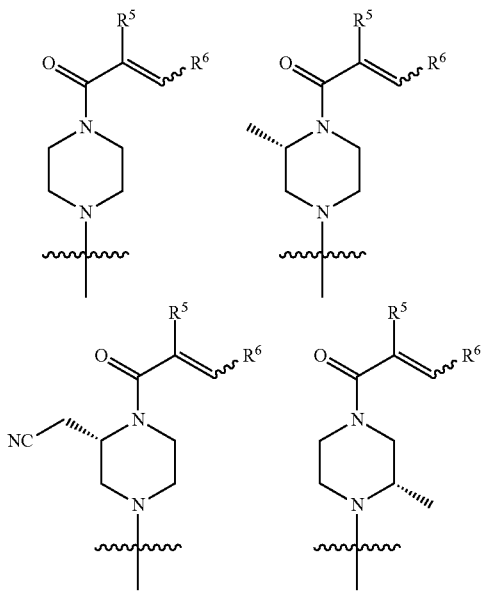

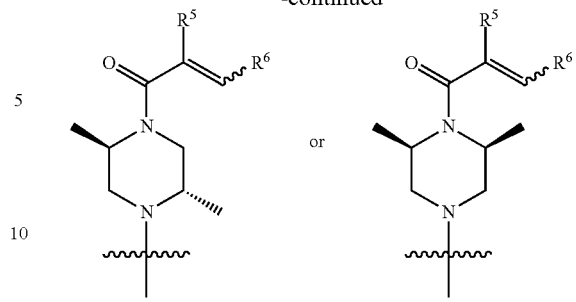

In some embodiments, in Formula I-3A-C or Formula I-3A-N, Het, together with $(R^4)_n$ and

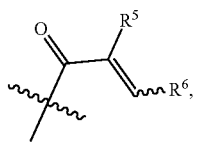

can be represented by

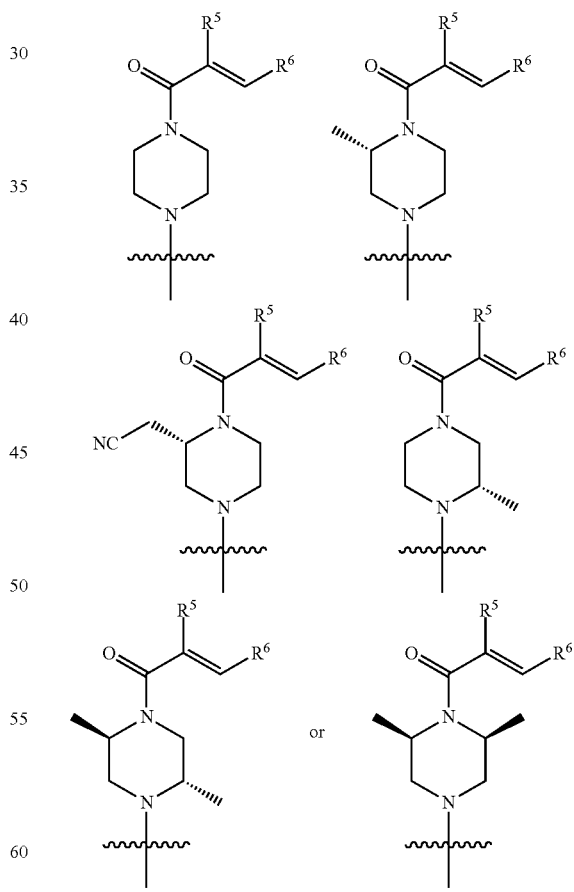

In some embodiments, both $R^5$ and $R^6$ can be hydrogen. In some specific embodiments, $R^5$ is F or OMe, and $R^6$ is hydrogen. In some specific embodiments, $R^5$ is hydrogen, and $R^6$ is —CH$_2$—OMe or

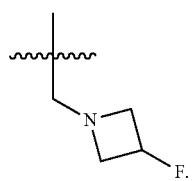 [SMILES: *CN1CC(F)C1]

In some preferred embodiments, in Formula I-3A-C or Formula I-3A-N, Het, together with $(R^4)_n$ and

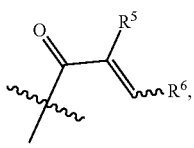

can be represented by

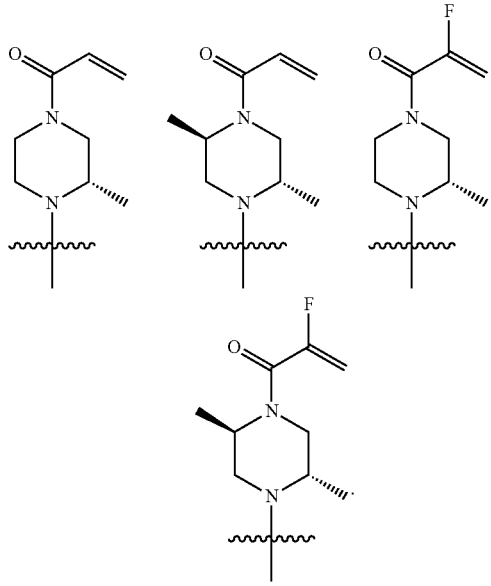

$R^7$ in Formula I-3A-C or Formula I-3A-N can typically be hydrogen, F, Cl, methyl, or —CF$_3$. In some embodiments, $R^7$ can be F. In some embodiments, $R^7$ can be Cl.

$R^8$ in Formula I-3A-C or Formula I-3A-N can typically be a phenyl optionally substituted with 1-3 groups each independently selected from F, Cl, —OH, NH$_2$, protected hydroxyl group, protected amino group, C$_{1-4}$ alkyl, C$_{2-4}$ alkenyl, C$_{2-4}$ alkynyl, 3 or 4 membered ring (e.g., cyclopropyl), C$_{1-4}$ alkoxy, fluorine substituted C$_{1-4}$ alkyl, and fluorine substituted C$_{1-4}$ alkoxy. In some embodiments, $R^8$ in Formula I-3A-C or Formula I-3A-N can be a bicyclic heteroaryl (e.g., indazolyl) optionally substituted with 1-3 groups each independently selected from F, Cl, —OH, —NH$_2$, protected hydroxyl group, protected amino group, C$_{1-4}$ alkyl, C$_{2-4}$ alkenyl, C$_{2-4}$ alkynyl, 3 or 4 membered ring (e.g., cyclopropyl), C$_{1-4}$ alkoxy, fluorine substituted C$_{1-4}$ alkyl, and fluorine substituted C$_{1-4}$ alkoxy. In some embodiments, $R^8$ in Formula I-3A-C or Formula I-3A-N can be selected from:

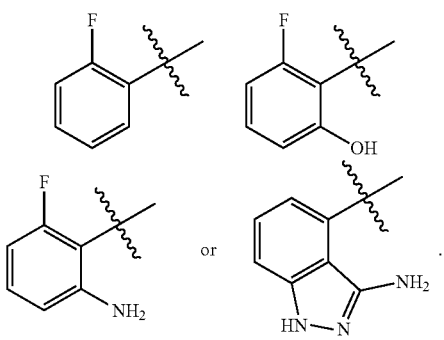

In some embodiments, $R^8$ in Formula I (such as any of the subformulae, Formula I-1, I-2, I-3A, I-3A-1, I-3A-C, I-3A-N, I-3B, I-3C, I-4A, I-4B, I-4C, I-3B-1, I-3C-1, I-4A-1, I-4B-1, I-4C-1, I-5, I-6, I-7, or I-8) is

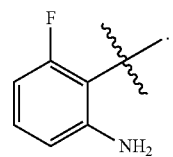

Some embodiments of the present disclosure are also directed to a compound of Formula II, or a pharmaceutically acceptable salt thereof:

Formula II

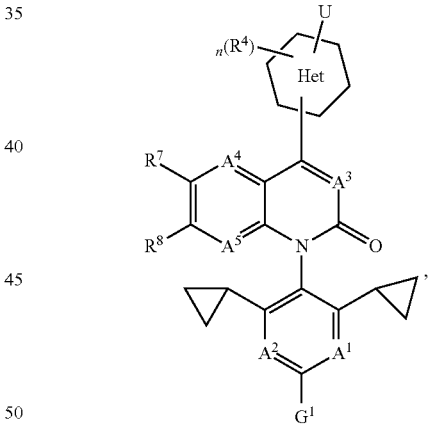

wherein:
$G^1$ is hydrogen, —COOH, —COOR$^{23}$, —CONR$^{21}$R$^{22}$, —CN, optionally substituted alkyl, alkenyl, alkynyl, or carbocyclic ring (e.g., cycloalkyl), e.g., C$_{1-6}$ alkyl, C$_{2-6}$ alkenyl, C$_{2-6}$ alkynyl, or C$_{3-6}$ cycloalkyl, wherein the C$_{1-6}$ alkyl, C$_{2-6}$ alkenyl, C$_{2-6}$ alkynyl, or C$_{3-6}$ cycloalkyl is optionally substituted with 1-3 groups each independently selected from F, OH, protected OH, and C$_{1-4}$ alkoxy; or $G^1$ is —X—R$^1$;
wherein X is O, NR$^{10}$, S, SO$_2$, or an optionally substituted 4 to 7 membered heterocyclic ring; R$^1$ is hydrogen, optionally substituted alkyl (e.g., C$_{1-4}$ alkyl), or -L-R$^{20}$,
wherein L is absent or an optionally substituted alkylene (e.g., C$_{1-4}$ alkylene), optionally substituted heteroalkylene (e.g., C$_{1-4}$ heteroalkylene), optionally substituted carbocyclic ring (e.g., $C_{3-6}$ carbocyclic ring), or optionally substituted heterocyclic ring (e.g., 4 to 7 membered heterocyclic ring), wherein $R^{20}$ is hydrogen, optionally substituted alkyl, alkenyl, or alkynyl, e.g., optionally substituted $C_{1-4}$ alkyl, optionally substituted $C_{2-4}$ alkenyl, optionally substituted $C_{2-4}$ alkynyl, —$NR^{21}R^{22}$, —$OR^{23}$, an optionally substituted 4 to 7 membered heterocyclyl, wherein each of $R^{10}$, $R^{21}$ and $R^{22}$ at each occurrence is independently hydrogen, an optionally substituted alkyl, alkenyl, or alkynyl, e.g., optionally substituted $C_{1-4}$ alkyl, optionally substituted $C_{2-4}$ alkenyl, optionally substituted $C_{2-4}$ alkynyl, optionally substituted $C_{1-4}$ heteroalkyl, optionally substituted $C_{3-6}$ carbocyclic ring, optionally substituted 4 to 7 membered heterocyclic ring, or a nitrogen protecting group; $R^{23}$ at each occurrence is independently hydrogen, an optionally substituted alkyl, alkenyl, or alkynyl, e.g., optionally substituted $C_{1-4}$ alkyl, optionally substituted $C_{2-4}$ alkenyl, optionally substituted $C_{2-4}$ alkynyl, optionally substituted $C_{1-4}$ heteroalkyl, optionally substituted $C_{3-6}$ carbocyclic ring, optionally substituted 4 to 7 membered heterocyclic ring, or an oxygen protecting group;

each of $A^1$, $A^2$, $A^3$, $A^4$, and $A^5$ is independently $CR^{30}$ or N, wherein $R^{30}$ at each occurrence is independently hydrogen, halogen (e.g., F, Cl), optionally substituted $C_{1-4}$ alkyl, optionally substituted alkoxy (e.g., $C_{1-4}$ alkoxy);

or when applicable, $R^1$, X, and $A^1$ together form an optionally substituted ring structure, for example, an optionally substituted heterocyclic or heteroaryl ring;

Het is a 4-10 membered heterocyclic ring, optionally substituted with $R^4$ group(s), $(R^4)_n$, wherein $R^4$ at each occurrence is independently optionally substituted alkyl, alkenyl, or alkynyl, or a 3 or 4 membered ring, e.g., $R^4$ at each occurrence can be $C_{1-4}$ alkyl, $C_{2-4}$ alkenyl, $C_{2-4}$ alkynyl, 3 or 4 membered ring (e.g., cyclopropyl), fluorine substituted $C_{1-4}$ alkyl, hydroxyl substituted $C_{1-4}$ alkyl, or cyano substituted $C_{1-4}$ alkyl; or two $R^4$ groups can join together to form a ring structure, e.g., a 3-6 membered ring structure;

U represents an electrophilic moiety capable of forming a covalent bond with a cysteine residue of a KRAS protein, e.g., a KRAS G12C mutant protein;

$R^7$ is hydrogen, halogen, —CN, a 3-4 membered ring, (e.g., cyclopropyl), optionally substituted $C_{1-4}$ alkyl, optionally substituted $C_{2-4}$ alkenyl, optionally substituted $C_{2-4}$ alkynyl, or optionally substituted $C_{1-4}$ alkoxyl; and $R^8$ is an optionally substituted aryl or optionally substituted heteroaryl.

Various groups can be suitable for $G^1$ in Formula II. In some embodiments, $G^1$ can be hydrogen. In some embodiments, $G^1$ can be —COOH, —$COOR^{23}$, —$CONR^{21}R^{22}$, —CN, $C_{1-6}$ alkyl, $C_{2-6}$ alkenyl, $C_{2-6}$ alkynyl, or $C_{3-6}$ cycloalkyl, wherein the $C_{1-6}$ alkyl, $C_{2-6}$ alkenyl, $C_{2-6}$ alkynyl, or $C_{3-6}$ cycloalkyl is optionally substituted, e.g., with 1-3 groups each independently selected from F, —OH, protected OH, and $C_{1-4}$ alkoxy. In some embodiments, $G^1$ in Formula II can be a hydroxyl substituted $C_{1-6}$ alkyl, for example, a hydroxyl substituted $C_{1-4}$ alkyl, such as —$C(CH_3)_2$—OH. In some embodiments, $G^1$ in Formula II can be a hydroxyl substituted $C_{3-6}$ cycloalkyl, for example, a hydroxyl substituted $C_{3-5}$ cycloalkyl. In some embodiments, $G^1$ in Formula II can also be —X—$R^1$, which can have any of the definitions defined in the context of Formula I and its subformulae. In some embodiments, $G^1$ in Formula II can be hydrogen, methyl, —COOH, $OCF_2H$, —$OCF_3$, cyclopropyl, —$C(CH_3)_2OH$, $CF_3$, or CN. In some preferred embodiments, $G^1$ in Formula II is hydrogen.

In some embodiments, the variables in Formula II, $R^4$, $R^7$, $R^8$, Het, n, U, $A^1$, $A^2$, $A^3$, $A^4$, and $A^5$ can be any of those defined herein in the context of Formula I and its subformulae. For example, in some embodiments, U in Formula II can represent

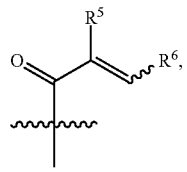

wherein $R^5$ and $R^6$ are defined herein. For example, in some embodiments, $R^5$ and $R^6$ are each independently hydrogen, halogen, —CN, —$COOR^{23A}$, —$CONR^{21A}R^{22A}$, optionally substituted $C_{1-6}$ alkyl, optionally substituted $C_{2-6}$ alkenyl, optionally substituted $C_{2-6}$ alkynyl, optionally substituted $C_{3-6}$ carbocyclic ring, optionally substituted phenyl, optionally substituted 5 or 6 membered heteroaryl, or optionally substituted 4 to 7 membered heterocyclic ring, or $R^5$ and $R^6$ can join together to form an optionally substituted $C_{3-6}$ carbocyclic ring, or optionally substituted 4 to 7 membered heterocyclic ring, wherein each of $R^{21A}$ and $R^{22A}$ at each occurrence is independently hydrogen, an optionally substituted $C_{1-4}$ alkyl, optionally substituted $C_{2-4}$ alkenyl, optionally substituted $C_{2-4}$ alkynyl, optionally substituted $C_{1-4}$ heteroalkyl, optionally substituted $C_{3-6}$ carbocyclic ring, optionally substituted 4 to 7 membered heterocyclic ring, or a nitrogen protecting group; and $R^{23A}$ at each occurrence is independently hydrogen, an optionally substituted $C_{1-4}$ alkyl, optionally substituted $C_{2-4}$ alkenyl, optionally substituted $C_{2-4}$ alkynyl, optionally substituted $C_{1-4}$ heteroalkyl, optionally substituted $C_{3-6}$ carbocyclic ring, optionally substituted 4 to 7 membered heterocyclic ring, or an oxygen protecting group. In some embodiments, in Formula II, Het, together with $(R^4)_n$ and U, can be represented by

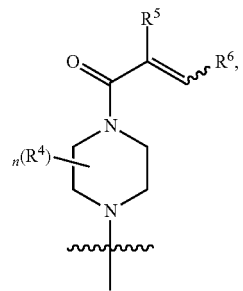

wherein n is 0, 1, or 2, wherein when n is 1 or 2, $R^4$ at each occurrence is independently methyl, ethyl, —$CF_3$, —$CF_2H$, —$CH_2OH$, or —$CH_2CN$. In some embodiments, in Formula II, Het, together with $(R^4)_n$ and U, can be represented by

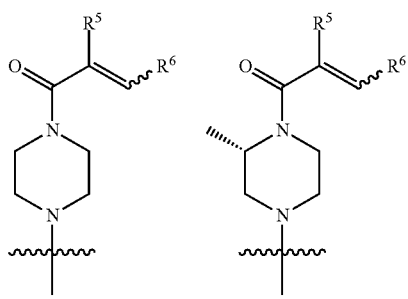

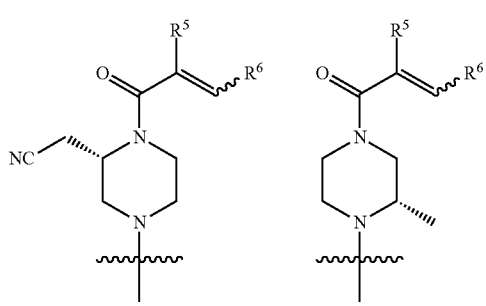

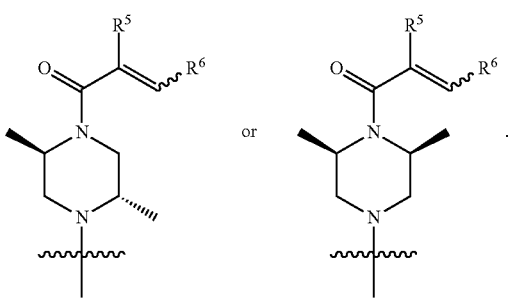

In some embodiments, in Formula II, Het, together with $(R^4)_n$ and U, can be represented by

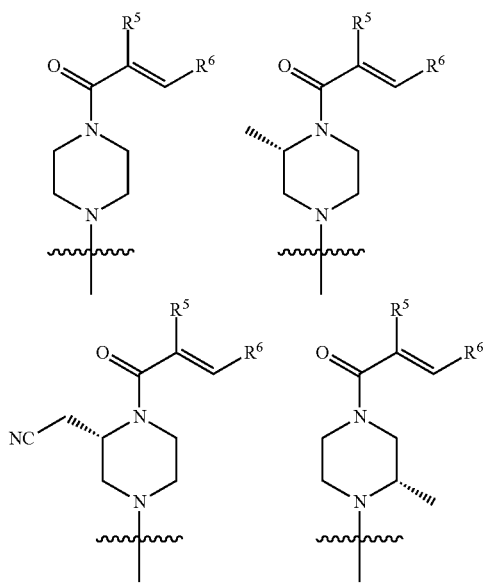

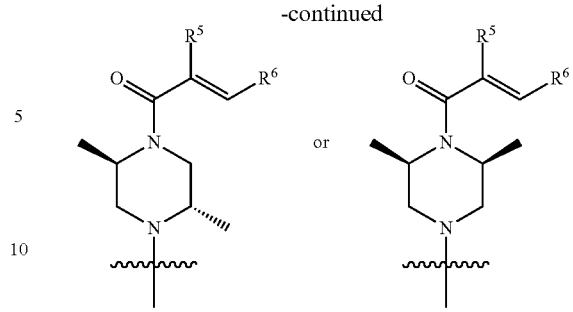

In some embodiments, both $R^5$ and $R^6$ can be hydrogen. In some specific embodiments, $R^5$ is F or OMe, and $R^6$ is hydrogen. In some specific embodiments, $R^5$ is hydrogen, and $R^6$ is —CH$_2$—OMe or

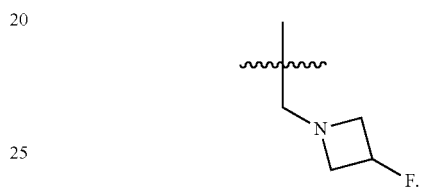

In some embodiments, $A^1$ and $A^2$ in Formula II can be N. In some embodiments, $A^1$ and $A^2$ in Formula II as applicable can be different, for example, one of $A^1$ and $A^2$ is N and the other of $A^1$ and $A^2$ is CH. In some embodiments, $A^3$ in Formula II can be N. In some embodiments, $A^4$ in Formula II can be CH. In some embodiments, $A^5$ in Formula II can be N. In some embodiments, $R^7$ in Formula II can be hydrogen, F, Cl, methyl, or CF$_3$. In some preferred embodiments, $R^7$ is F or Cl. In some embodiments, $R^7$ can be F. In some embodiments, $R^7$ can be Cl. In some embodiments, $R^8$ in Formula II can be a phenyl optionally substituted with 1-3 groups each independently selected from F, Cl, —OH, —NH$_2$, protected hydroxyl group, protected amino group, $C_{1-4}$ alkyl, $C_{2-4}$ alkenyl, $C_{2-4}$ alkynyl, 3 or 4 membered ring (e.g., cyclopropyl), $C_{1-4}$ alkoxy, fluorine substituted $C_{1-4}$ alkyl, and fluorine substituted $C_{1-4}$ alkoxy. In some embodiments, $R^8$ in Formula II can be a bicyclic heteroaryl (e.g., indazolyl) optionally substituted with 1-3 groups each independently selected from F, Cl, —OH, —NH$_2$, protected hydroxyl group, protected amino group, $C_{1-4}$ alkyl, $C_{1-4}$ alkoxy, fluorine substituted $C_{1-4}$ alkyl, and fluorine substituted $C_{1-4}$ alkoxy. In some embodiments, $R^8$ in Formula II can be selected from:

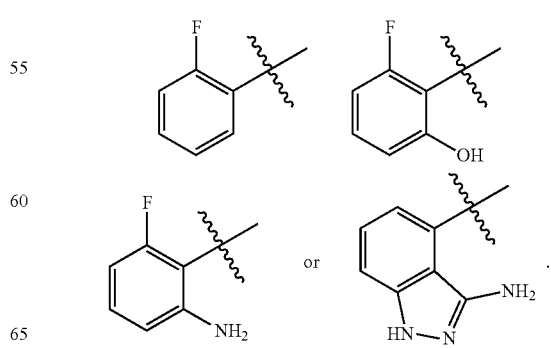

In some preferred embodiments, $R^8$ in Formula II is

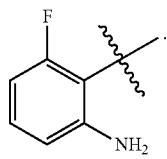

The introduction of dicyclopropyl groups in Formula II provides various advantages. As shown in the Examples section and FIGS. 1-3, certain compounds of Formula II, such as Compounds 44 and 126, have better anticancer efficacies in several animal models over the current clinical compound AMG-510. Introducing the 4,6-dicyclopropylpyrimidin-5-yl group can also lead to improved in vitro inhibition of RAS protein (such as KRAS G12C). As discussed herein, there are data showing that changing an isopropylpyrimidin-5-yl group into a corresponding cyclopropylpyrimidin-5-yl group would lead to a 2-6 fold potency drop. However, that trend is reversed when the $R^8$ group in Formula II is 2-amino-6-fluoro-phenyl group. For example, Compounds 44 and 126 were found to have a better potency in inhibiting KRAS G12C than their corresponding isopropyl analogs. Moreover, introducing the 4,6-dicyclopropylpyrimidin-5-yl group can also lead to improved in vivo profiles such as improved efficacy in treating cancer and/or safety profile. As discussed herein, when compared to control compounds, Compounds 44 and 126 have a better overall pharmacokinetic ("PK") profile, such as having a better human hepatocyte clearance profile and a better overall rat PK profile with a significantly improved oral bioavailability. These data are also expected to provide superior in vivo profile such as efficacy and/or safety profile.

In some embodiments, the present disclosure also provides a compound of Formula III, or a pharmaceutically acceptable salt thereof:

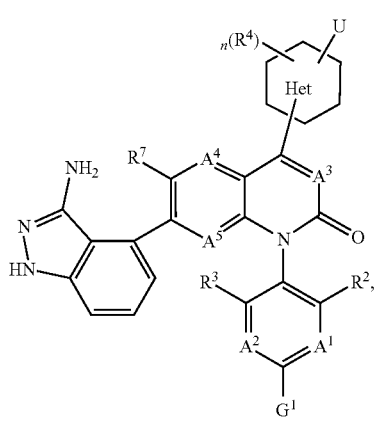

Formula III wherein $G^1$, $R^2$, $R^3$, $R^4$, $R^7$, Het, n, U, $A^1$, $A^2$, $A^3$, $A^4$, and $A^5$ can be any of those defined herein for the respective variable, for example, in the context of Formula I and its subformulae or Formula II.

For example, in some embodiments, $G^1$ in Formula III can be hydrogen, methyl, cyclopropyl, —C(CH$_3$)$_2$OH, CF$_3$, or CN. In some embodiments, U in Formula III can represent

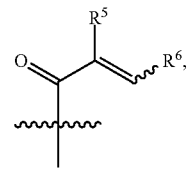

wherein $R^5$ and $R^6$ are defined herein. In some embodiments, in Formula III, Het, together with $(R^4)_n$ and U, can be represented by

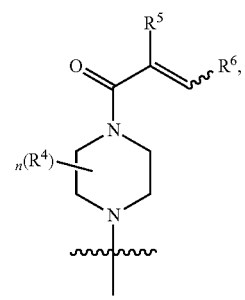

wherein n is 0, 1, or 2, wherein when n is 1 or 2, $R^4$ at each occurrence is independently methyl, ethyl, —CF$_3$, —CF$_2$H, —CH$_2$OH, or —CH$_2$CN. In some embodiments, in Formula III, Het, together with $(R^4)_n$ and U, can be represented by

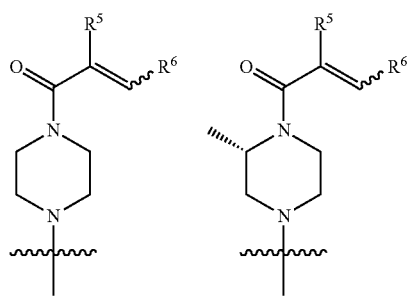

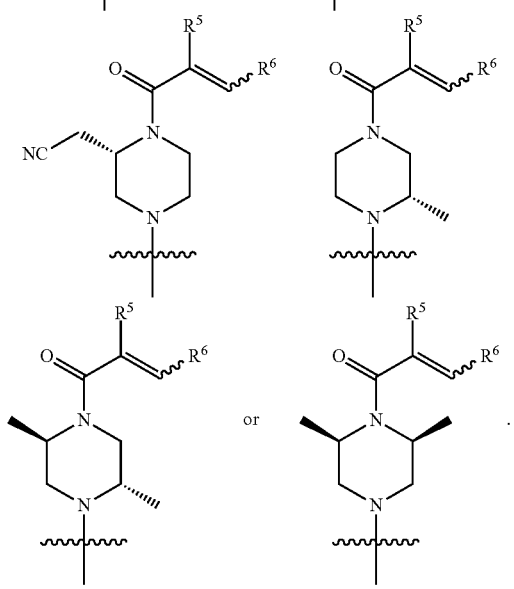

or

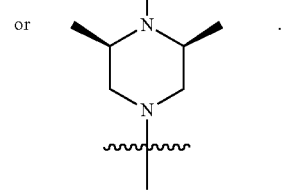

In some embodiments, in Formula III, Het, together with $(R^4)_n$ and U, can be represented by

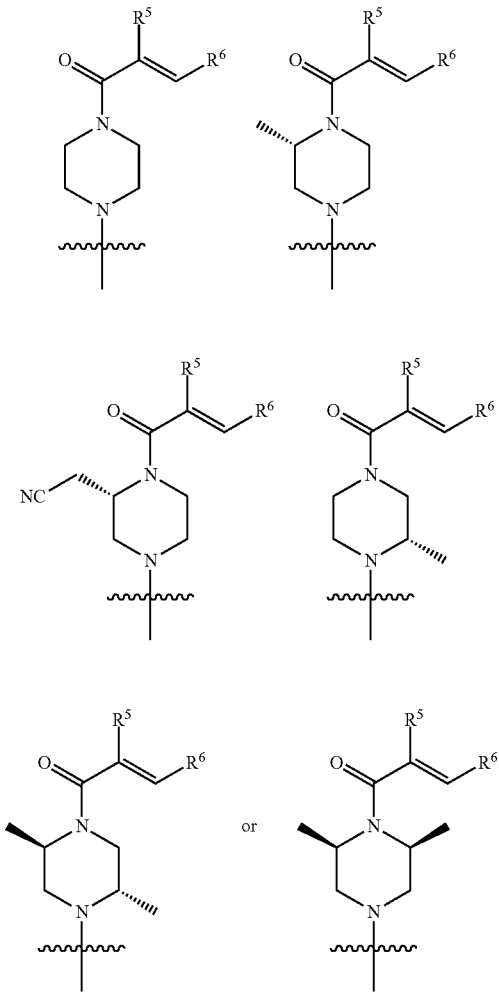

In some embodiments, both $R^5$ and $R^6$ can be hydrogen. In some specific embodiments, $R^5$ is F or OMe, and $R^6$ is hydrogen. In some specific embodiments, $R^5$ is hydrogen, and $R^6$ is —CH$_2$—OMe or

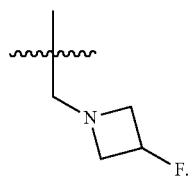 [SMILES: *CN1CC(F)C1]

In some embodiments, $R^2$ and $R^3$ can be independently selected from hydrogen, methyl, ethyl, isopropyl, tert-butyl, cyclopropyl, F, and Cl. In some specific embodiments, both $R^2$ and $R^3$ are isopropyl. In some embodiments, both $R^2$ and $R^3$ are cyclopropyl. In some embodiments, $R^2$ and $R^3$ are the same. In some embodiments, $R^2$ and $R^3$ are different. In some embodiments, one of $R^2$ and $R^3$ is hydrogen or methyl. In some embodiments, $A^1$ and $A^2$ in Formula III can be N. In some embodiments, $A^1$ and $A^2$ in Formula III can be different, for example, one of $A^1$ and $A^2$ is N and the other of $A^1$ and $A^2$ is CH. In some embodiments, $A^3$ in Formula III can be N. In some embodiments, $A^4$ in Formula III can be CH. In some embodiments, $A^5$ in Formula III can be N. In some embodiments, $R^7$ in Formula III can be hydrogen, F, Cl, methyl, or CF$_3$. In some embodiments, $R^7$ can be F. In some embodiments, $R^7$ can be Cl.

In some embodiments, the present disclosure also provides a compound of Formula IV, or a pharmaceutically acceptable salt thereof:

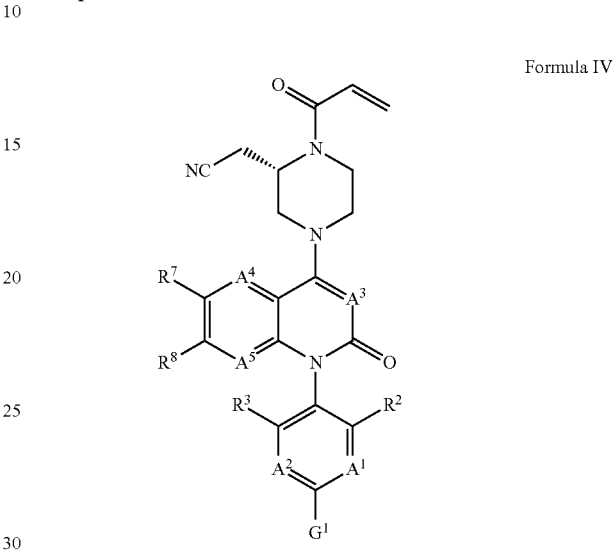

Formula IV wherein $G^1$, $R^2$, $R^3$, $R^7$, $R^8$, $A^1$, $A^2$, $A^3$, $A^4$, and $A^5$ can be any of those defined herein for the respective variable, for example, in the context of Formula I and its subformulae or Formula II.

For example, in some embodiments, $G^1$ in Formula IV can be hydrogen, methyl, cyclopropyl, —C(CH$_3$)$_2$OH, —CF$_3$, or —CN. In some embodiments, $R^2$ and $R^3$ can be independently selected from hydrogen, methyl, ethyl, isopropyl, tert-butyl, cyclopropyl, F, and Cl. In some specific embodiments, both $R^2$ and $R^3$ are isopropyl. In some embodiments, both $R^2$ and $R^3$ are cyclopropyl. In some embodiments, $R^2$ and $R^3$ are the same. In some embodiments, $R^2$ and $R^3$ are different. In some embodiments, one of $R^2$ and $R^3$ is hydrogen or methyl. In some embodiments, $A^1$ and $A^2$ in Formula IV can be N. In some embodiments, $A^1$ and $A^2$ in Formula IV can be different, for example, one of $A^1$ and $A^2$ is N and the other of $A^1$ and $A^2$ is CH. In some embodiments, $A^3$ in Formula IV can be N. In some embodiments, $A^4$ in Formula IV can be CH. In some embodiments, $A^5$ in Formula IV can be N. In some embodiments, $R^7$ in Formula IV can be hydrogen, F, Cl, methyl, or CF$_3$. In some embodiments, $R^7$ can be F. In some embodiments, $R^7$ can be Cl. In some embodiments, $R^8$ in Formula IV can be a phenyl optionally substituted with 1-3 groups each independently selected from F, Cl, —OH, NH$_2$, protected hydroxyl group, protected amino group, $C_{1-4}$ alkyl, $C_{2-4}$ alkenyl, $C_{2-4}$ alkynyl, 3 or 4 membered ring (e.g., cyclopropyl), $C_{1-4}$ alkoxy, fluorine substituted $C_{1-4}$ alkyl, and fluorine substituted $C_{1-4}$ alkoxy. In some embodiments, $R^8$ in Formula IV can be a bicyclic heteroaryl (e.g., indazolyl) optionally substituted with 1-3 groups each independently selected from F, Cl, —OH, NH$_2$, protected hydroxyl group, protected amino group, $C_{1-4}$ alkyl, $C_{2-4}$ alkenyl, $C_{2-4}$ alkynyl, 3 or 4 membered ring (e.g., cyclopropyl), $C_{1-4}$ alkoxy, fluorine substituted $C_{1-4}$ alkyl, and fluorine substituted $C_{1-4}$ alkoxy. In some embodiments, $R^8$ in Formula IV can be selected from:

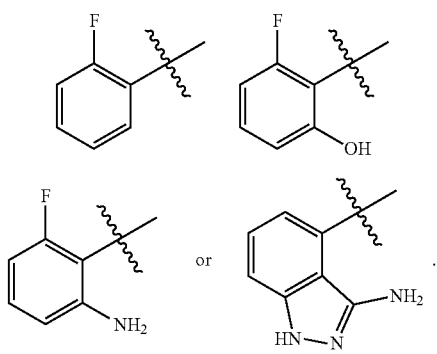
In some embodiments, $R^8$ in Formula IV is
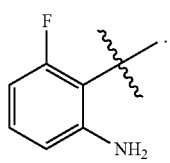
In some embodiments, the present disclosure also provides a compound selected from any of Compound Nos 1-186, or a pharmaceutically acceptable salt thereof:
1
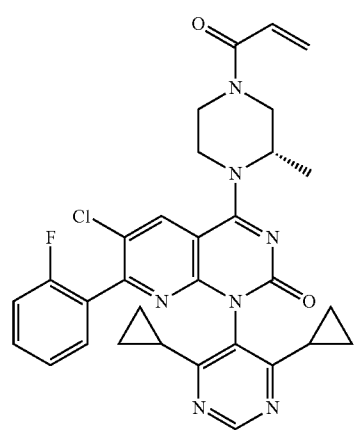
2
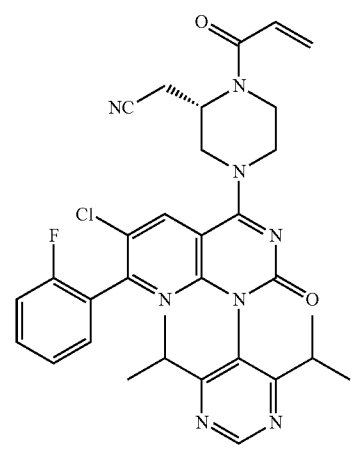
3
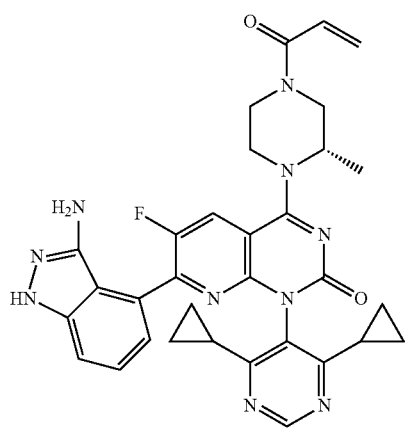
4
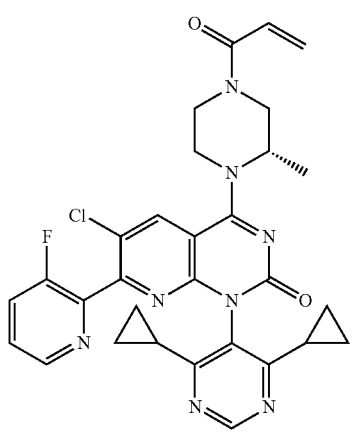
5
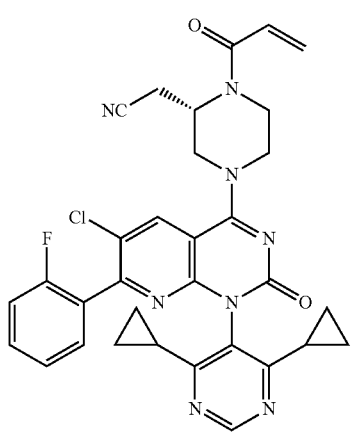

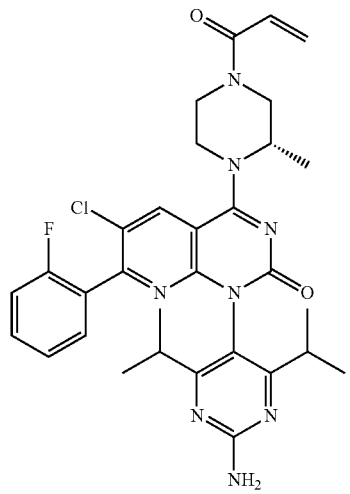
6
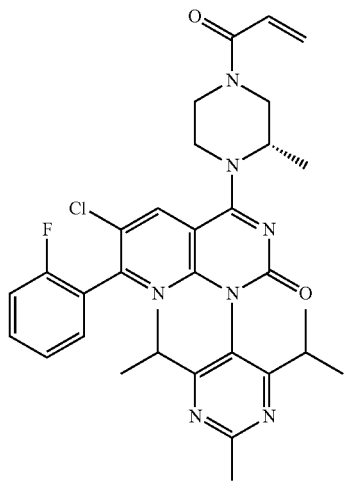
9
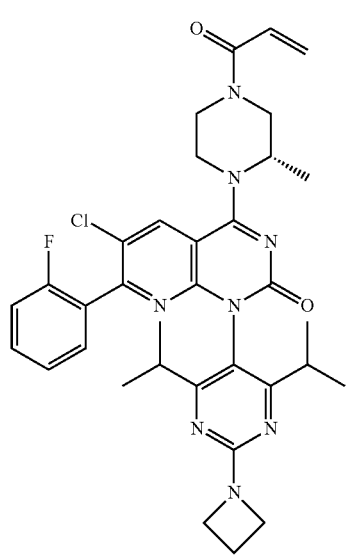
7
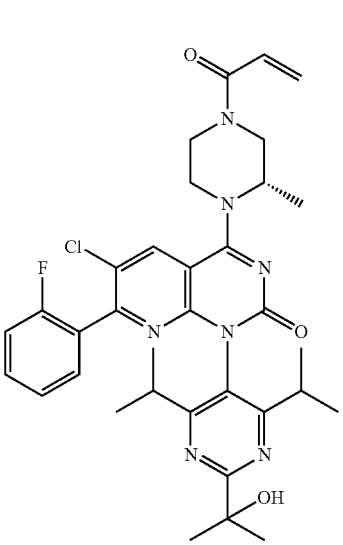
10
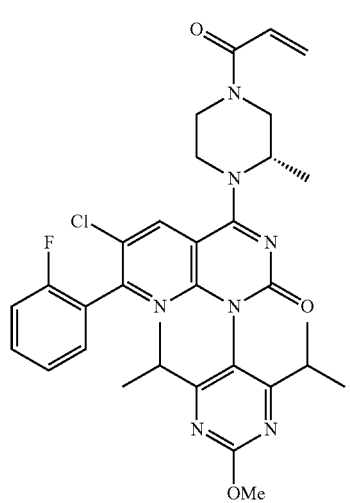
8

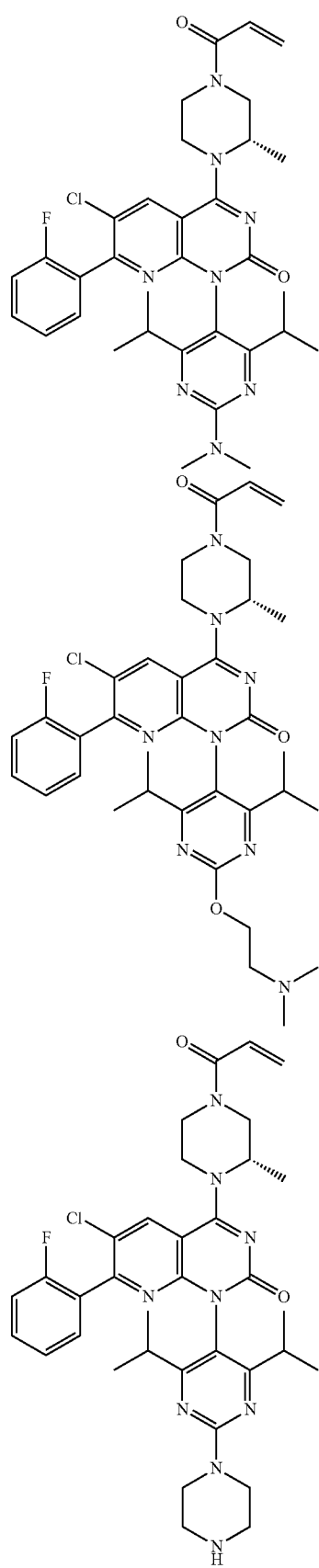
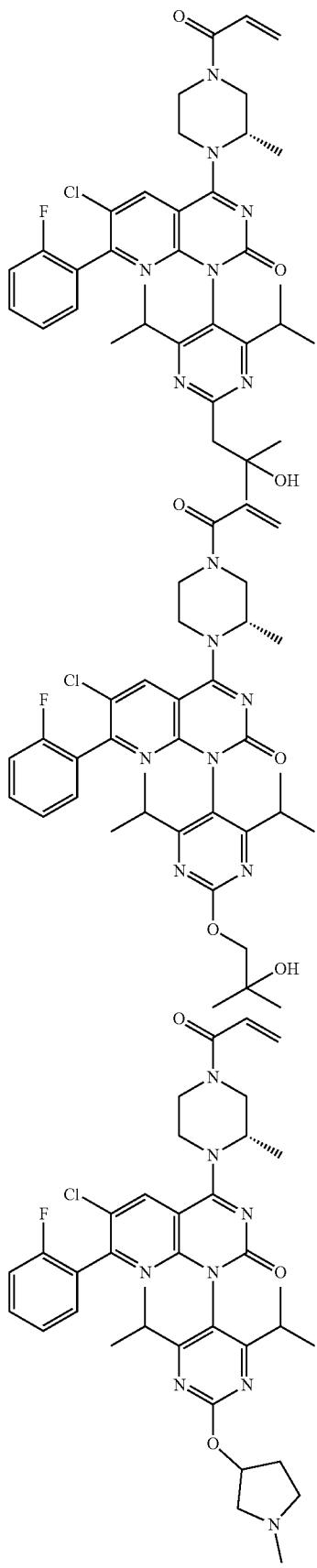

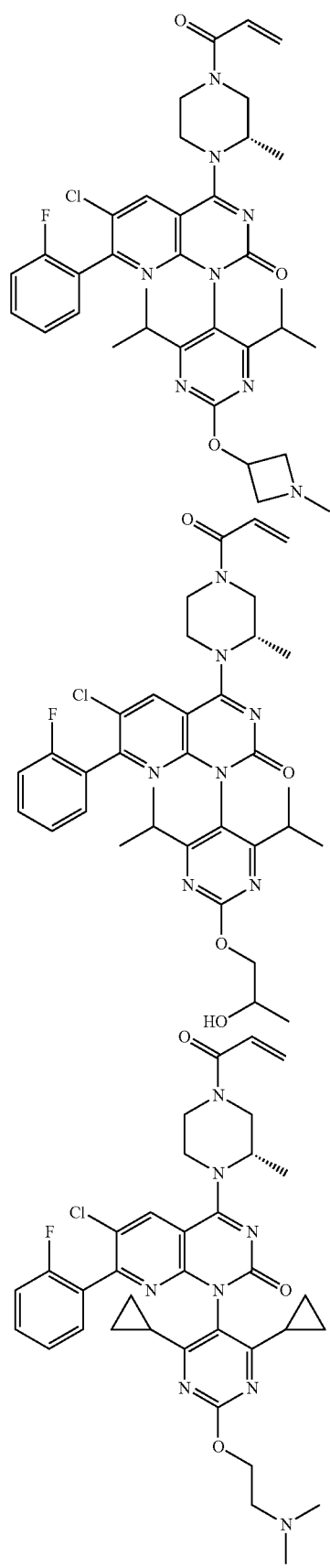

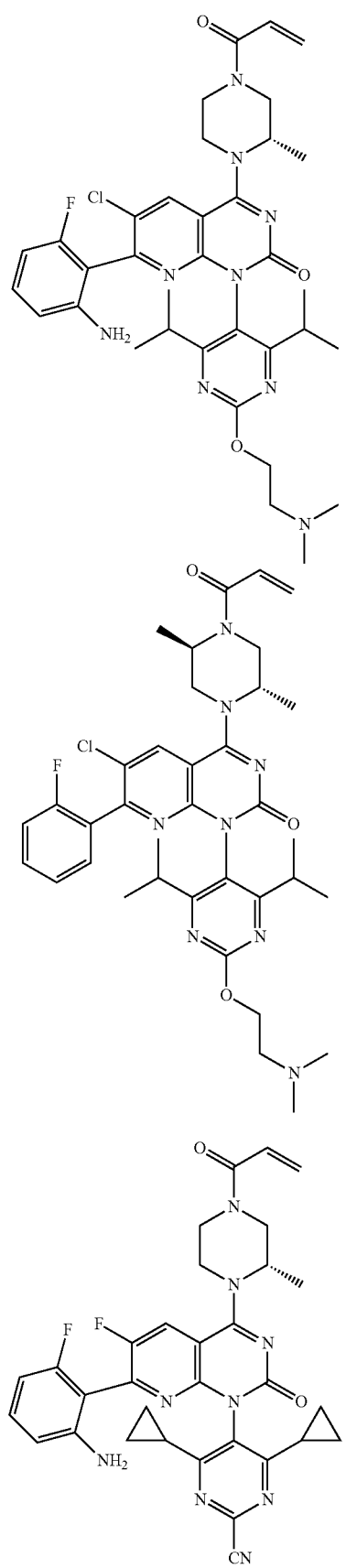
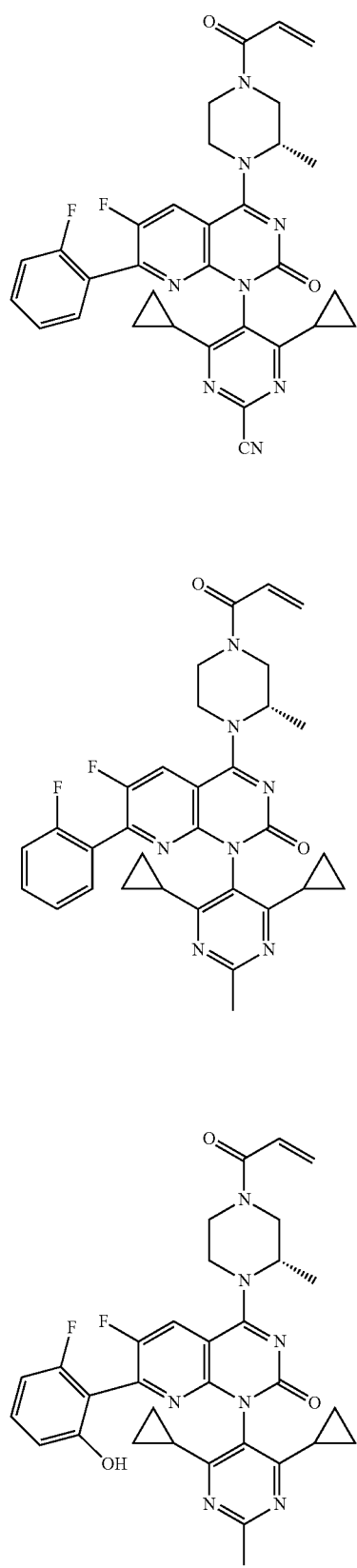

29
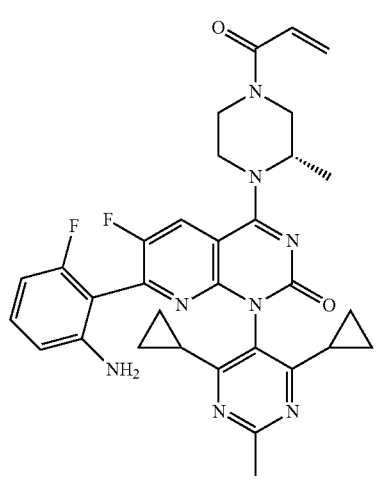
30
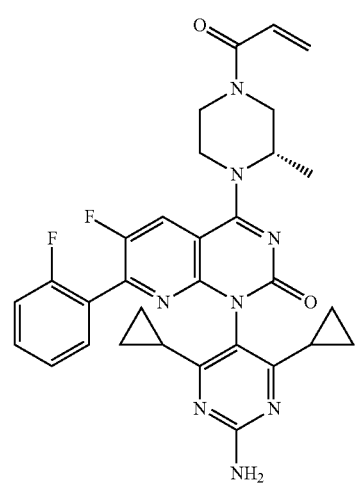
31
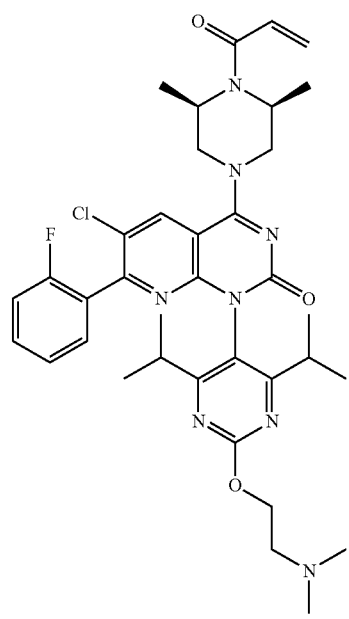
32
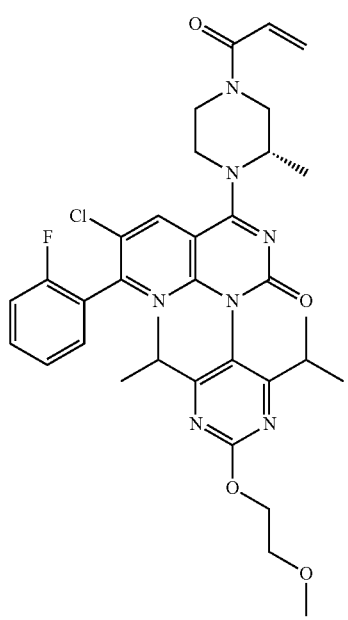
33
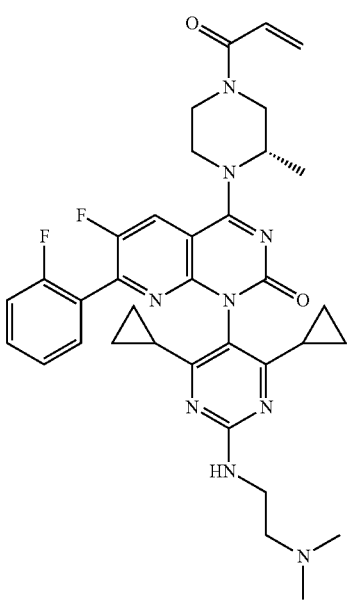

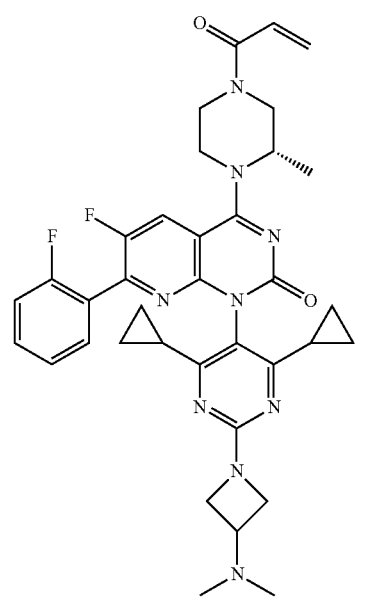
34
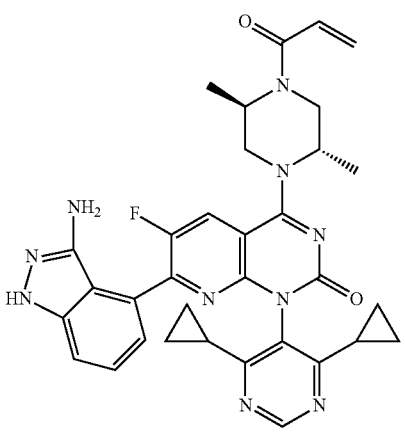
37
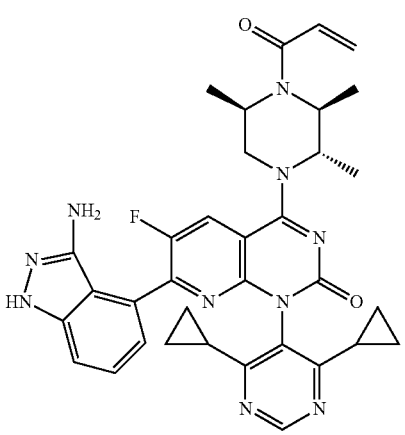
38
35
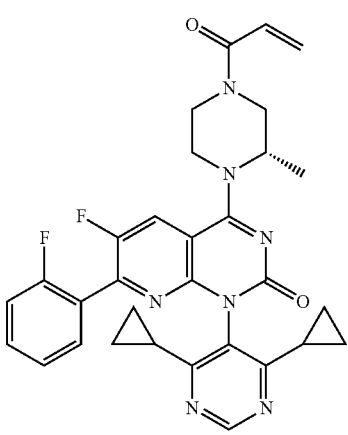
36
39

40
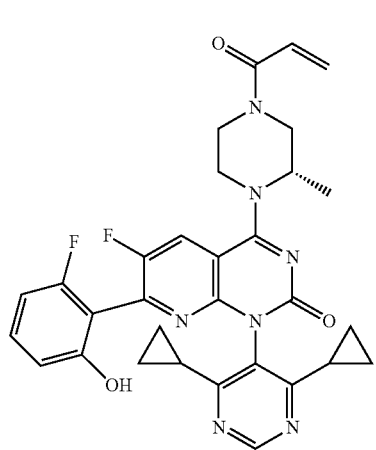
41
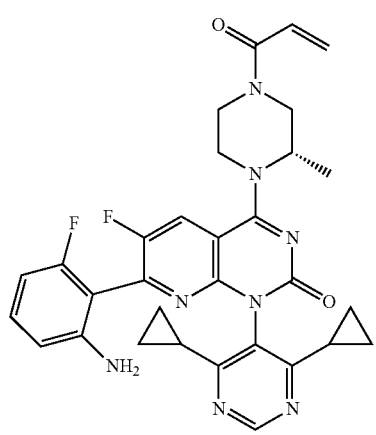
42
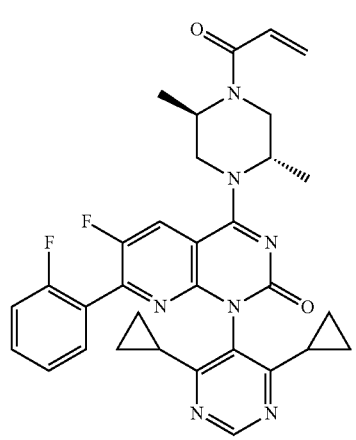
43
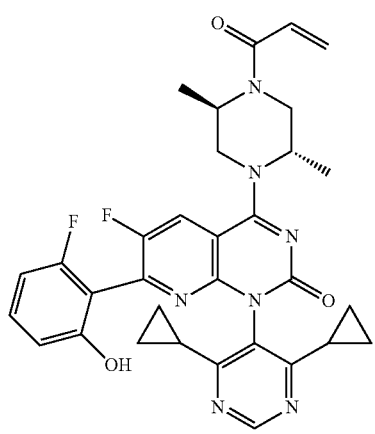
44
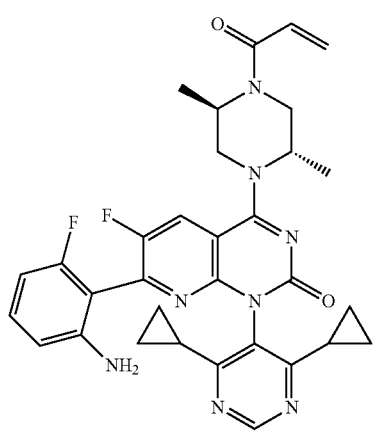
45
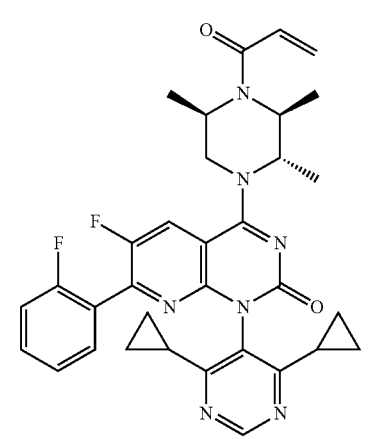

46 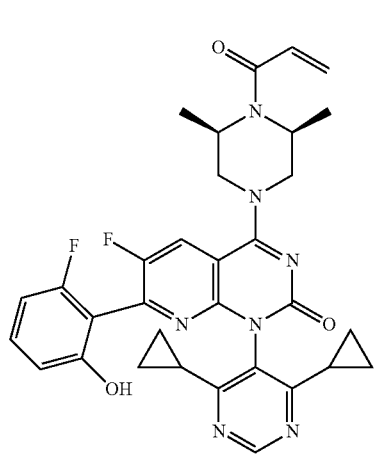
47 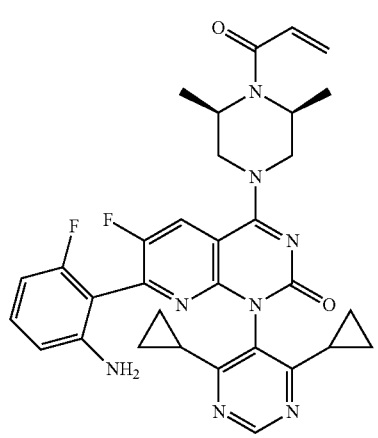
48 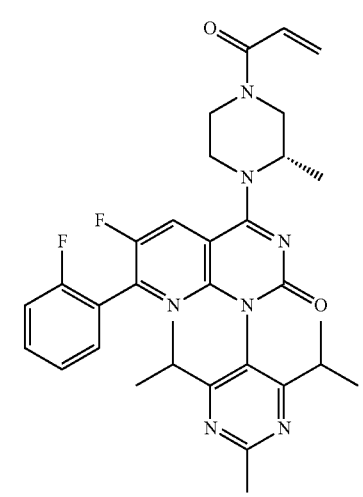
49 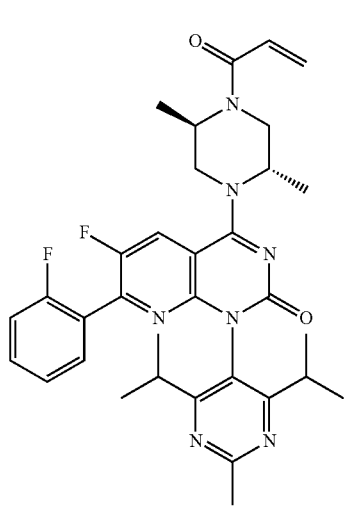
50 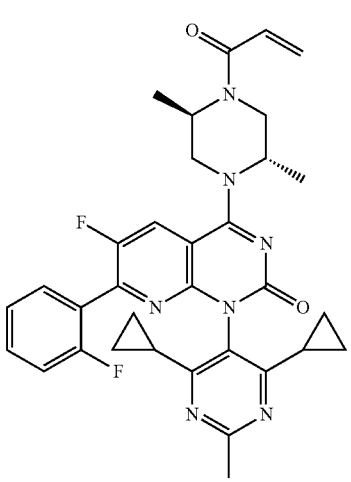
51 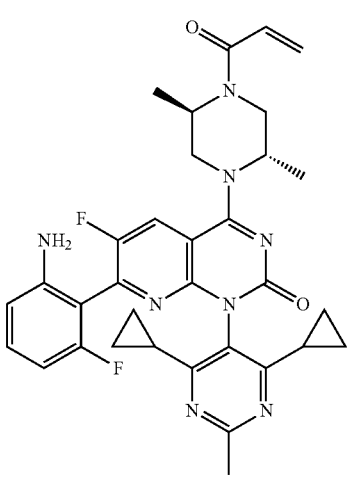

52
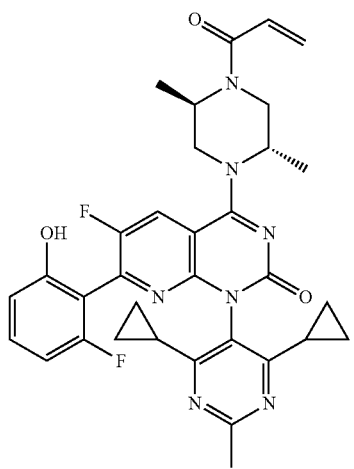
53
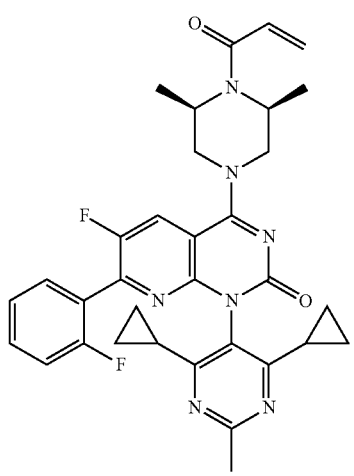
54
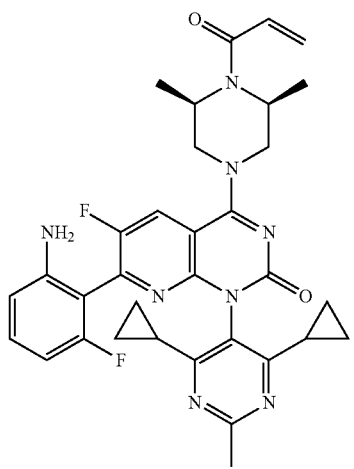
55
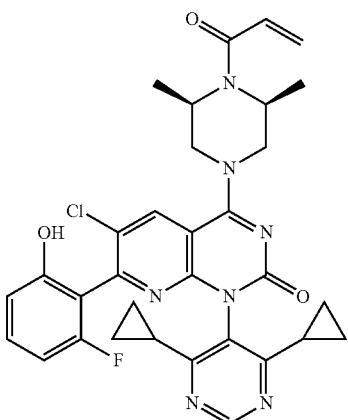
56
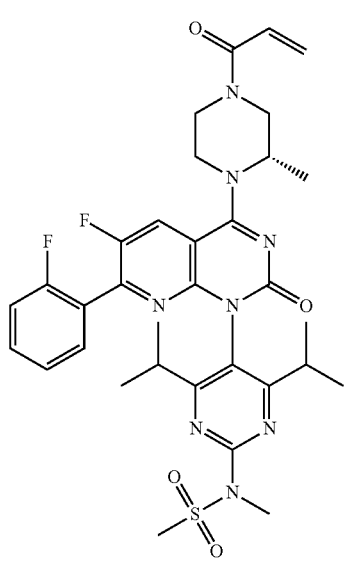
57
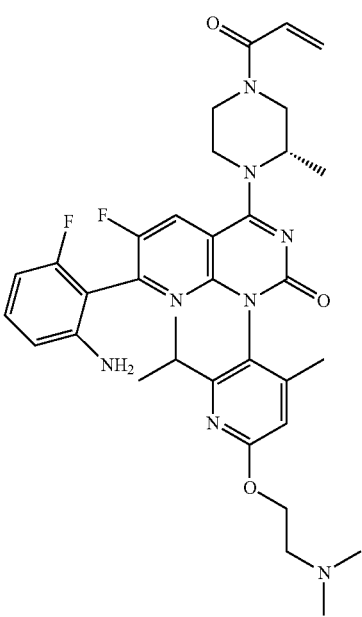

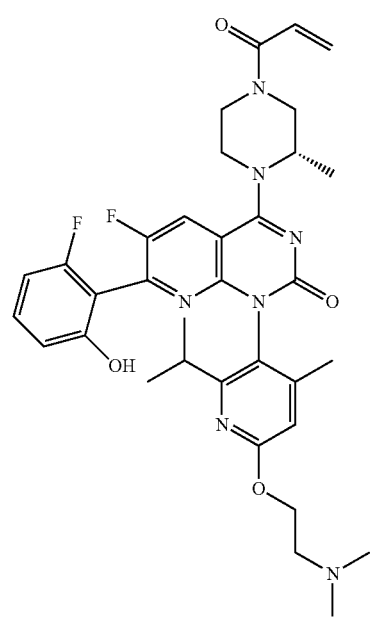
58
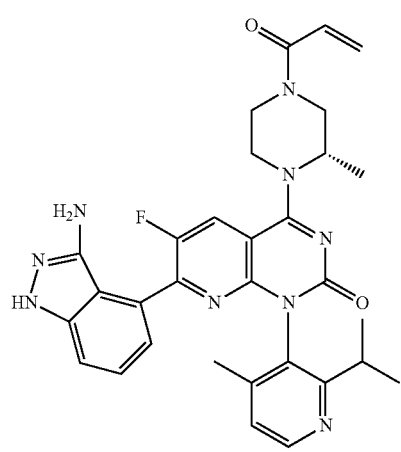
59
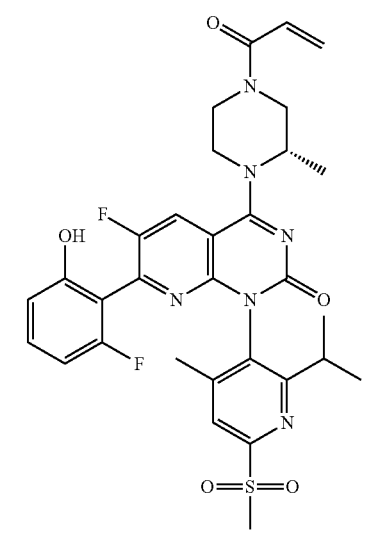
60
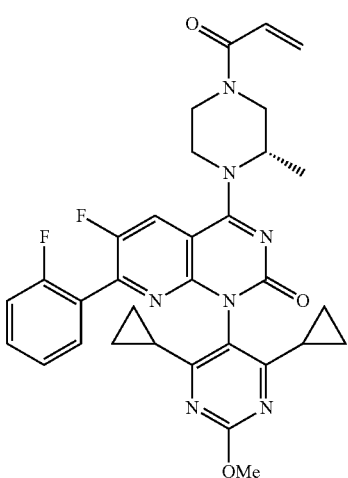
61
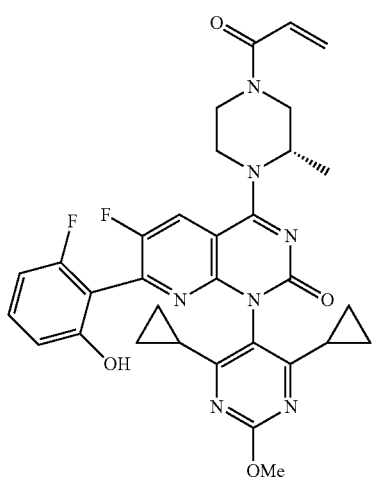
62
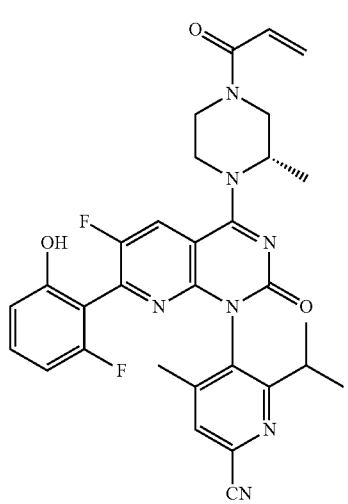
63

64
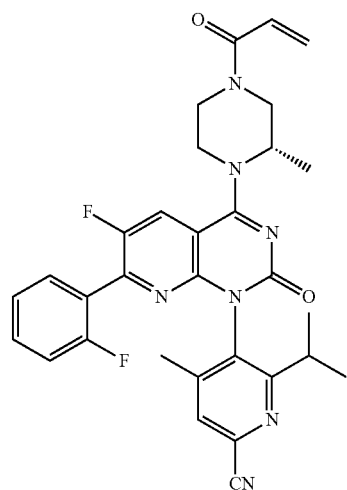
65
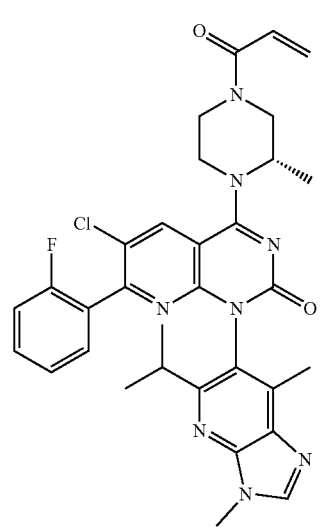
66
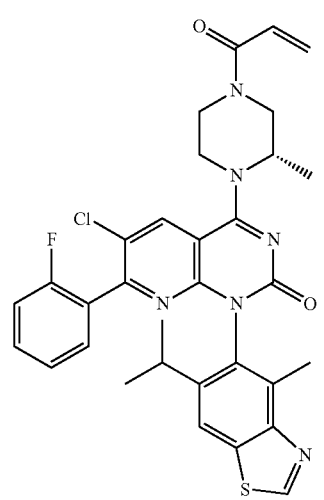
67
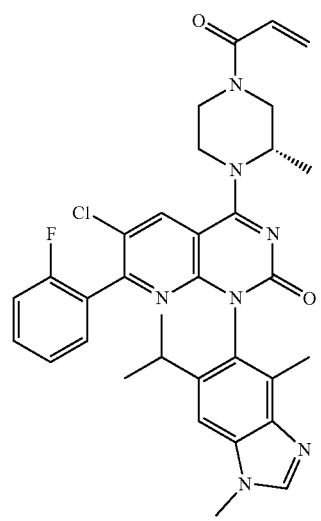
68
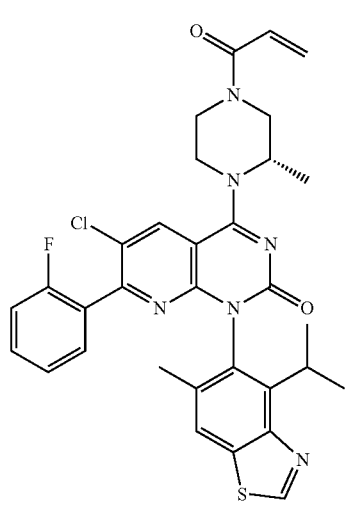
69
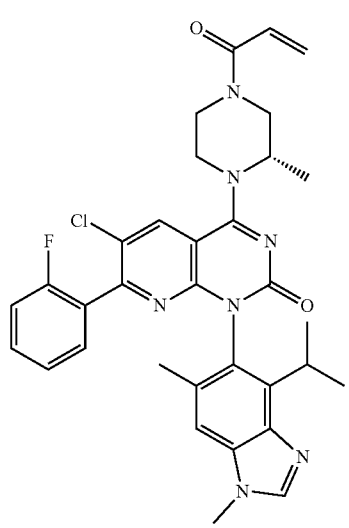

70
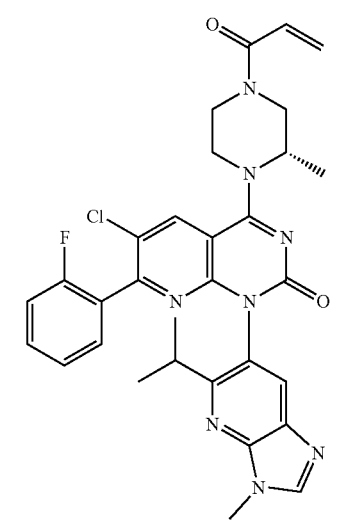
71
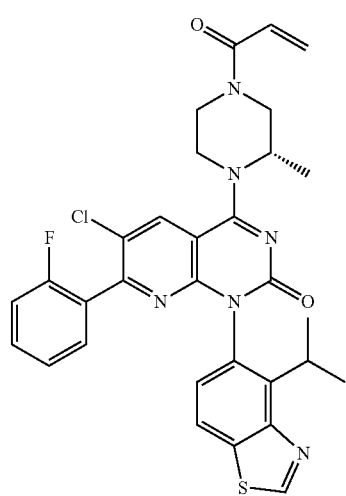
72
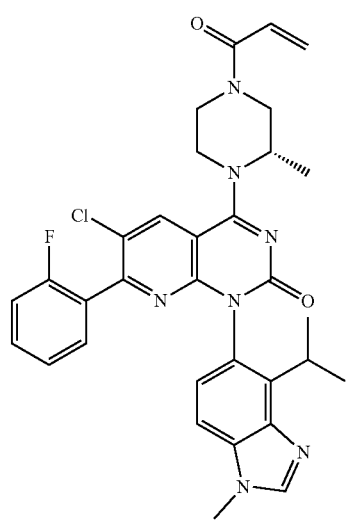
73
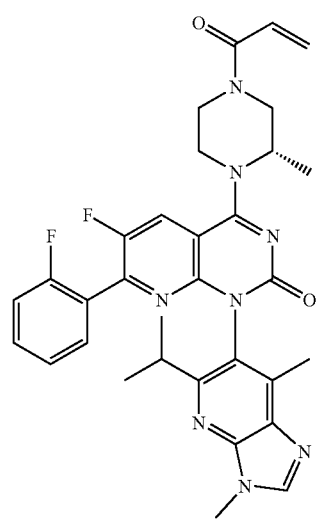
74
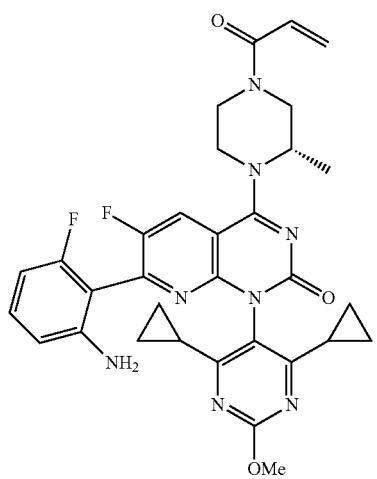
75
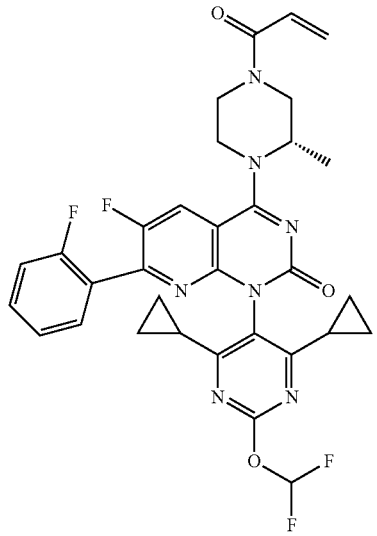

65
-continued
76
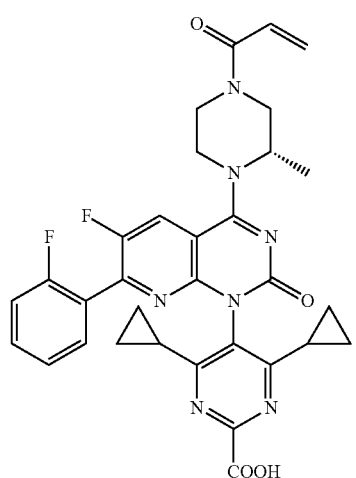
77
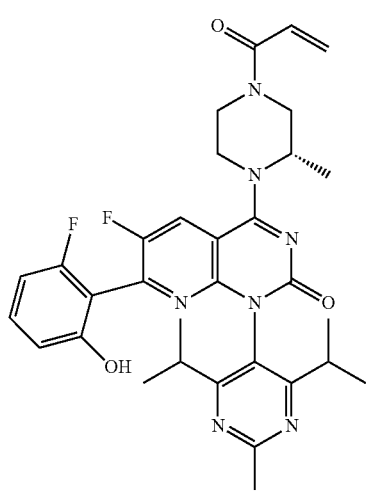
78
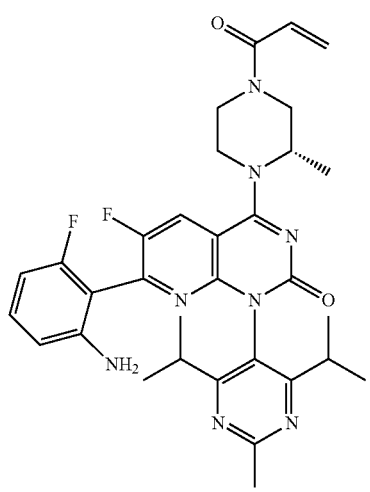
66
-continued
79
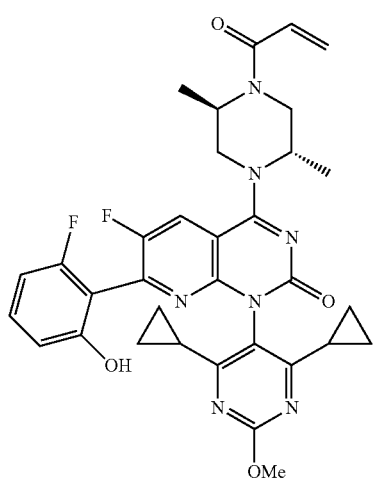
80
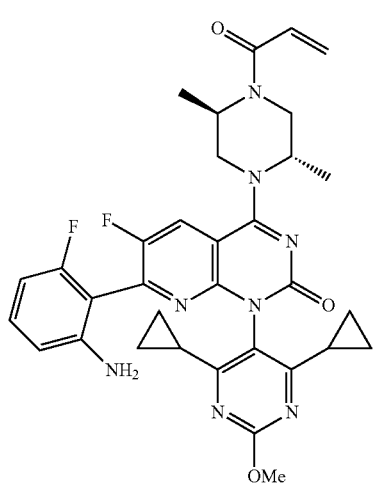
81
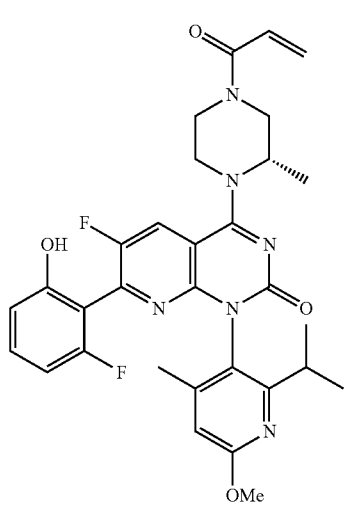

67
-continued
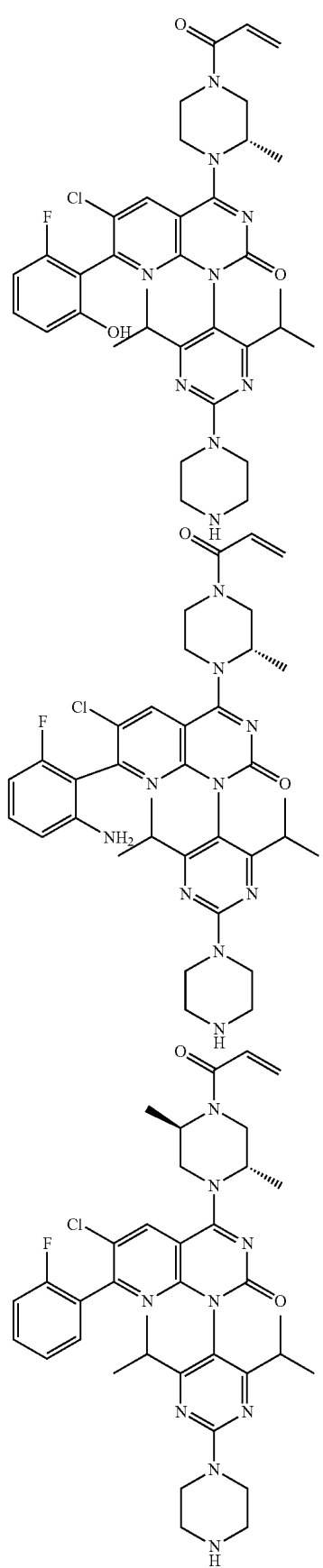
82
83
84
68
-continued
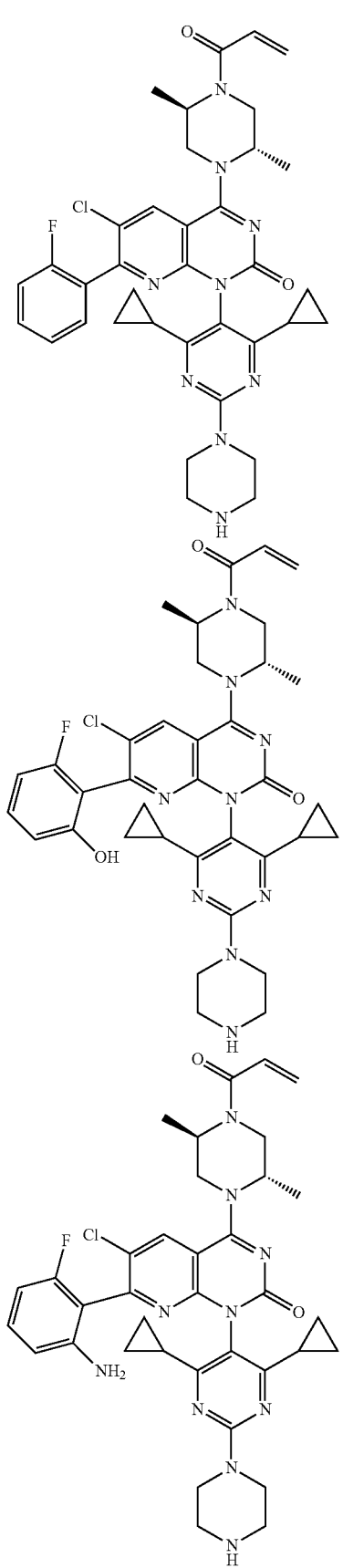
85
86
87

88
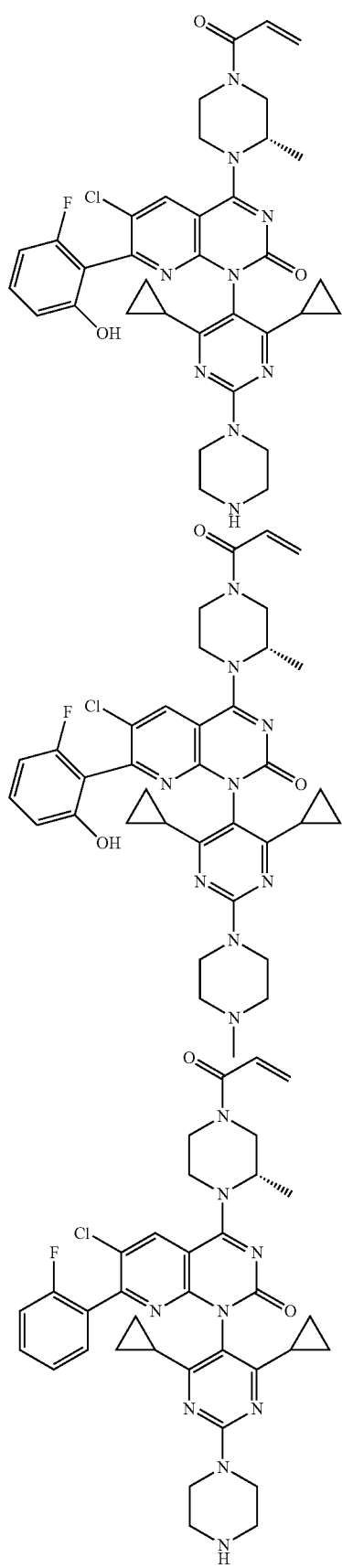
89
90
91
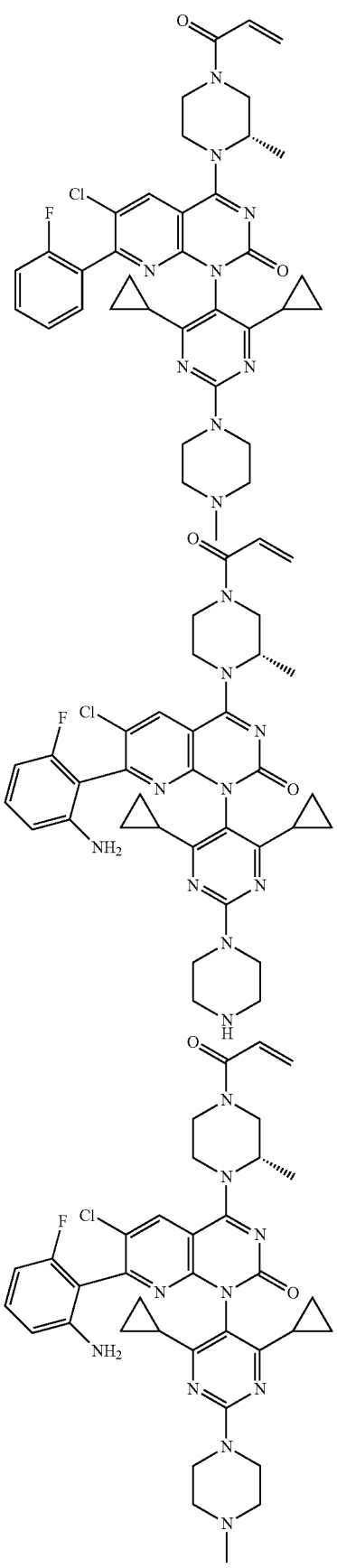
92
93

94
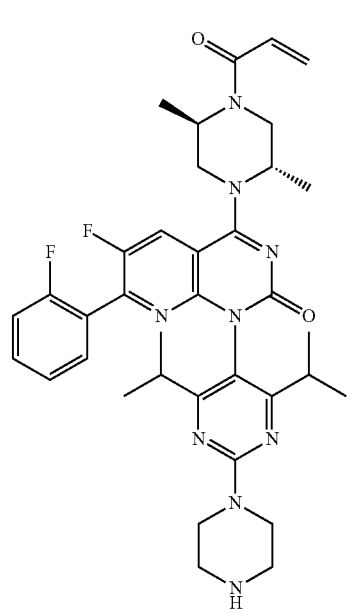
95
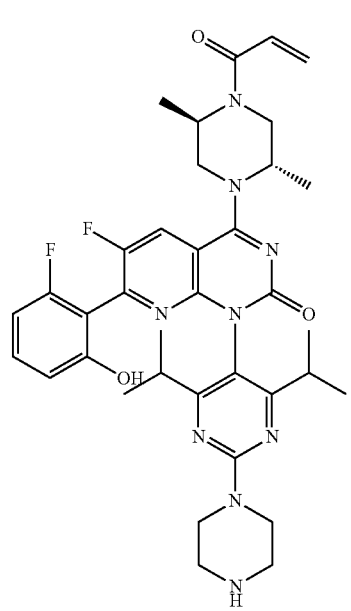
96
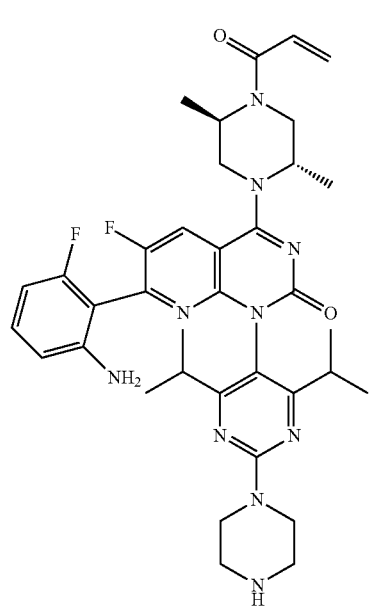
97
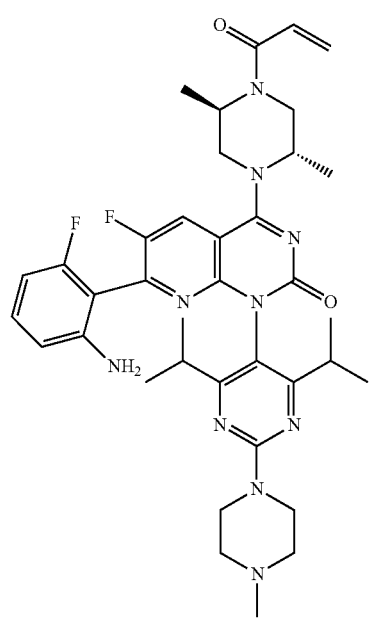

73
-continued
98
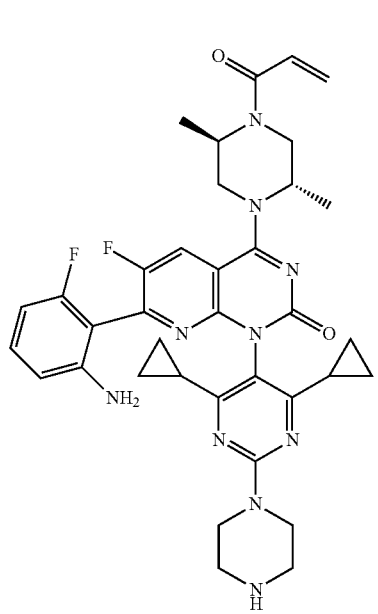
99
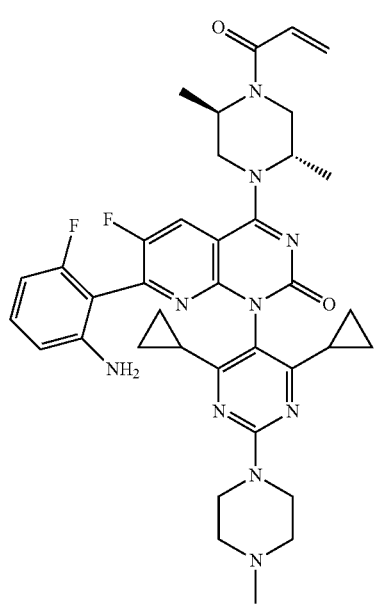
74
-continued
100
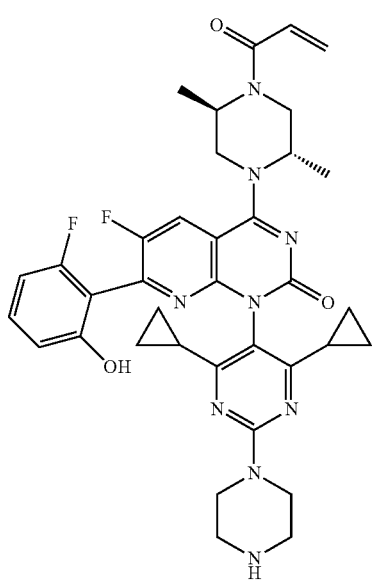
101
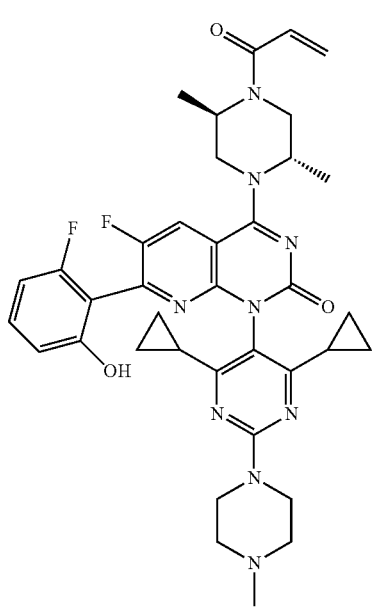

102
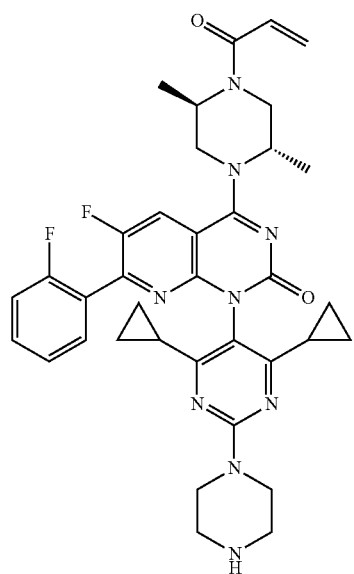
103
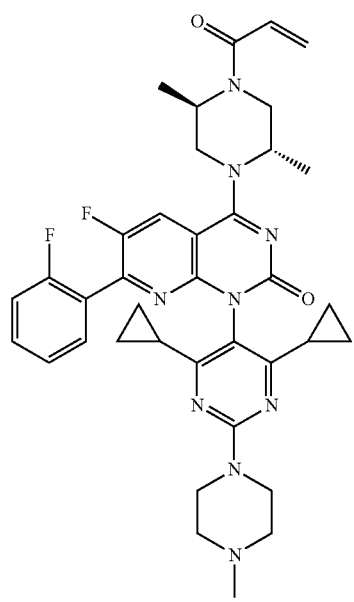
104
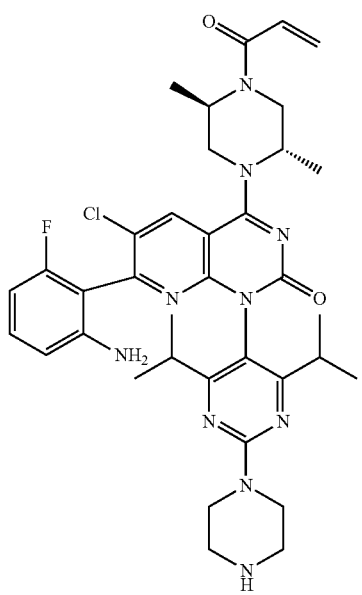
105
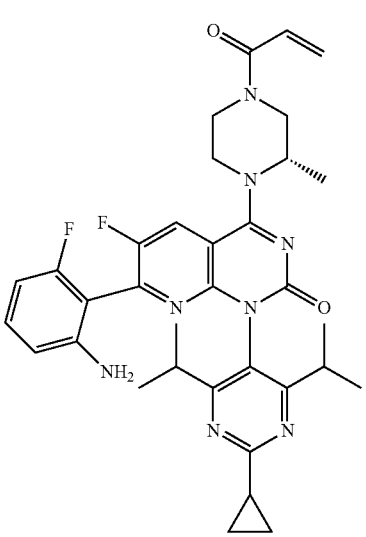
106
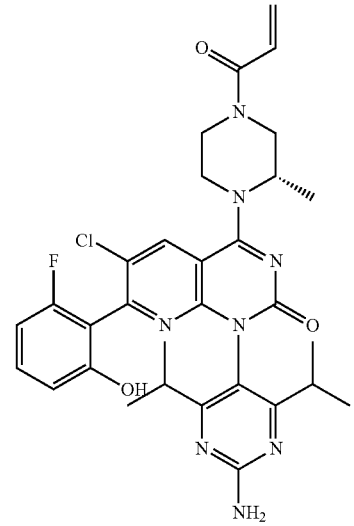

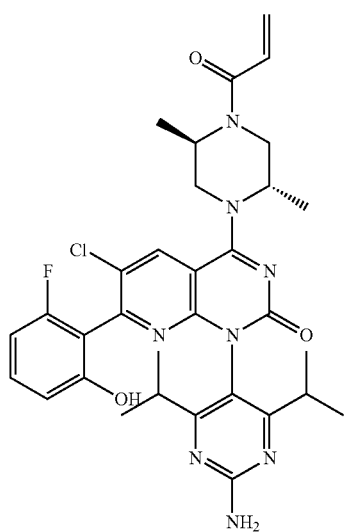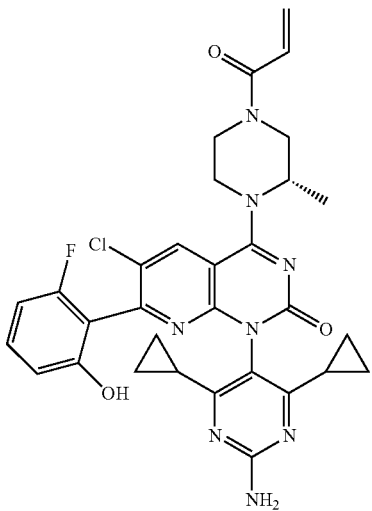

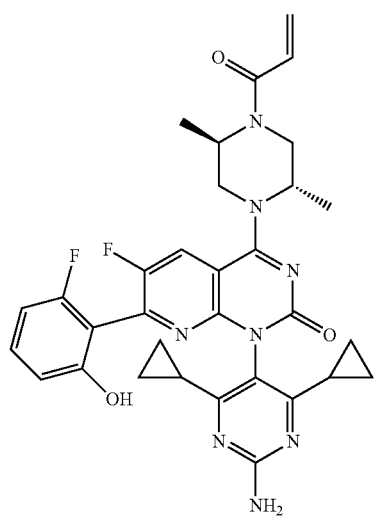
113
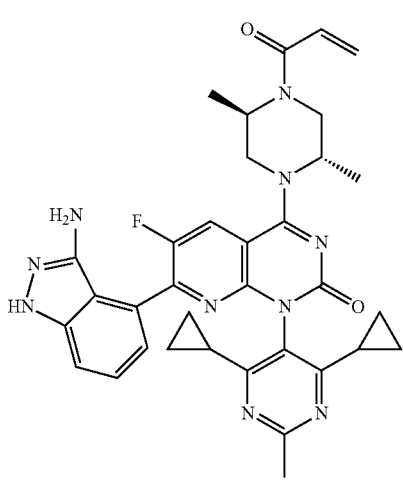
114
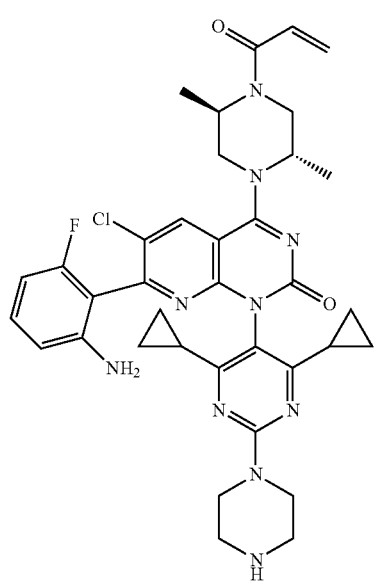
115
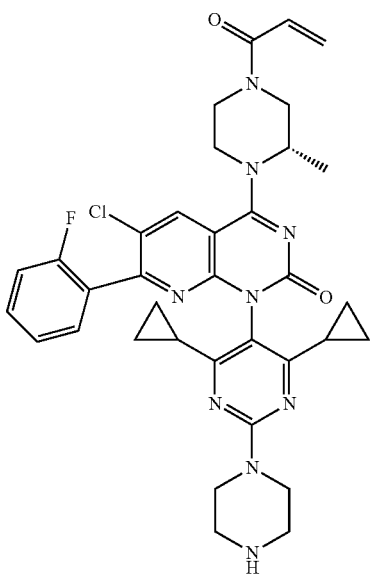
116
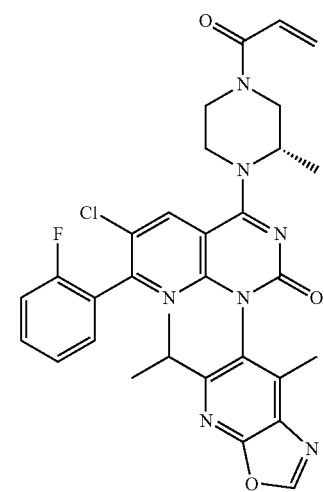
117
118

81
-continued
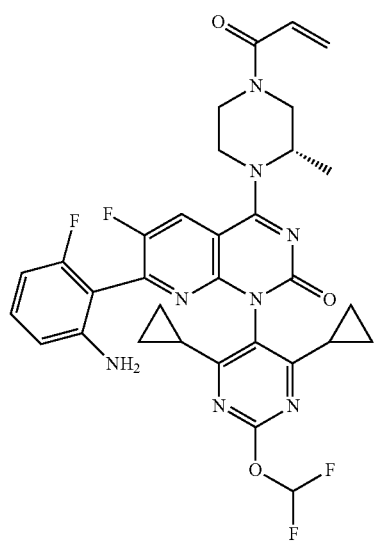
119
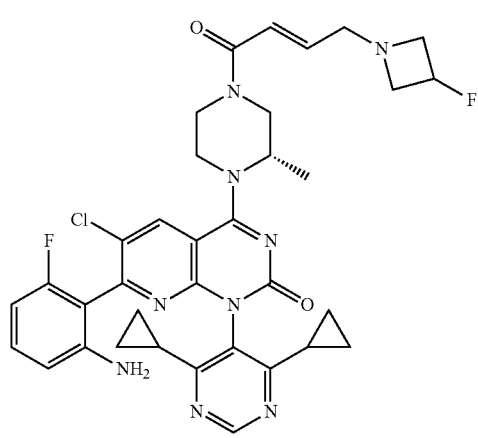
120
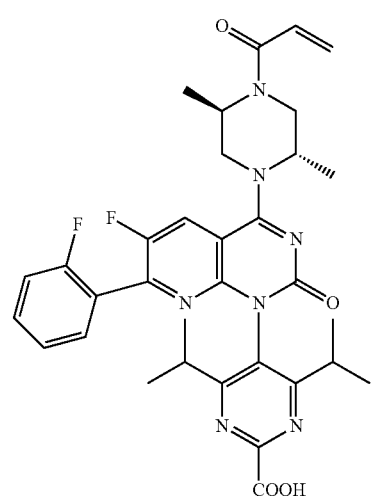
121
82
-continued
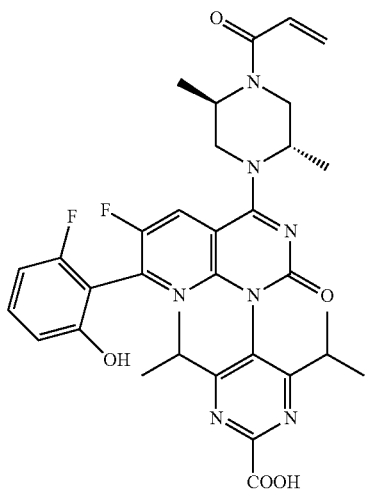
122
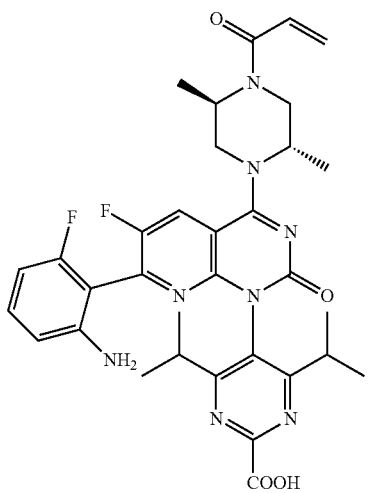
123
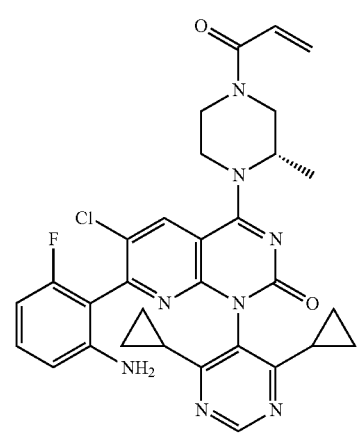
124

125 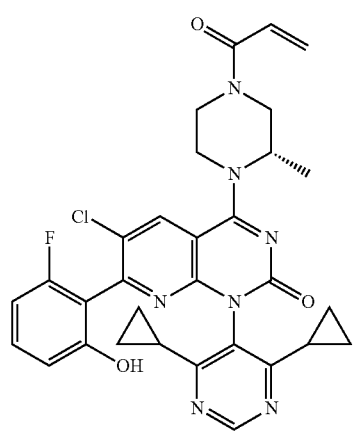
126 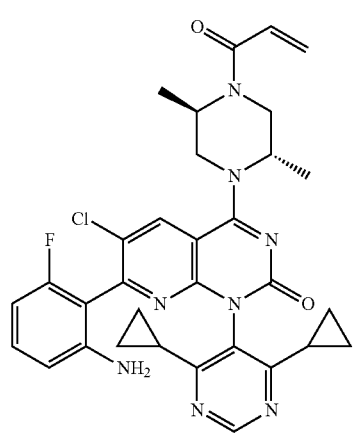
127 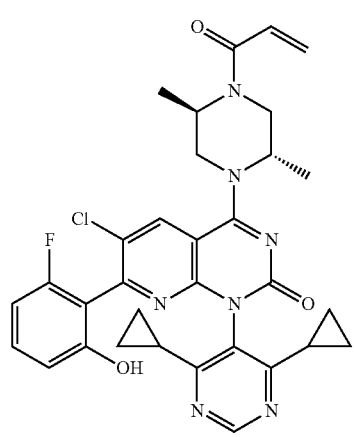
128 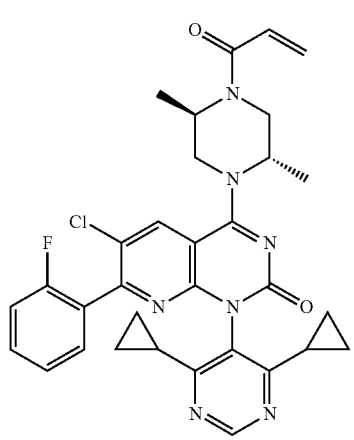
129 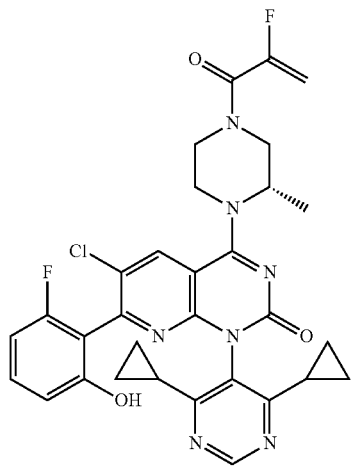
130 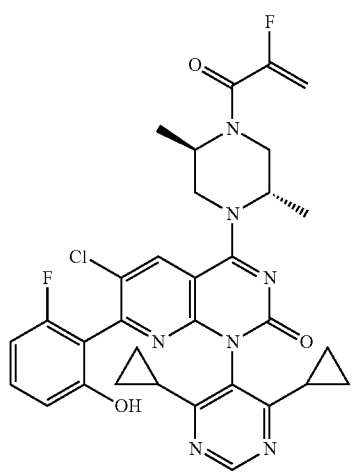

131
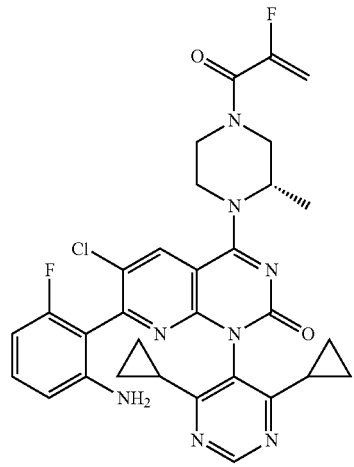
132
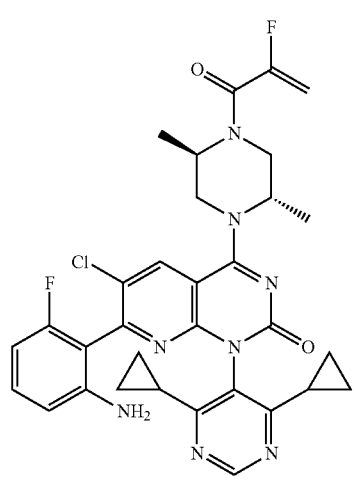
133
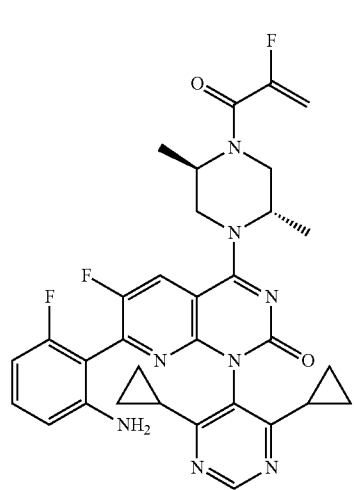
134
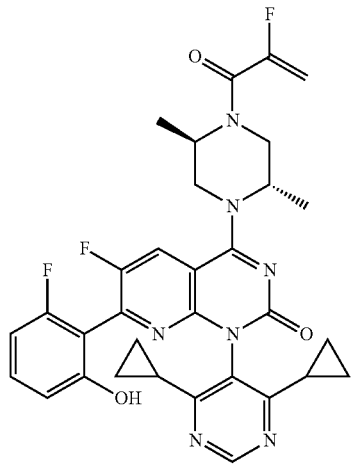
135
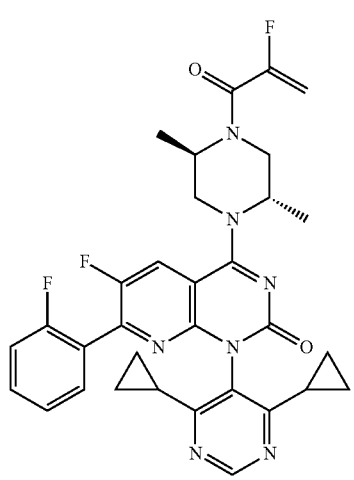
136
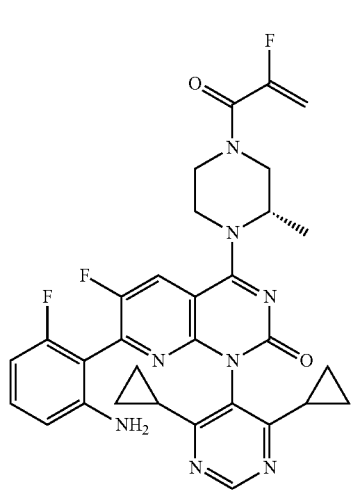

87
-continued
88
-continued
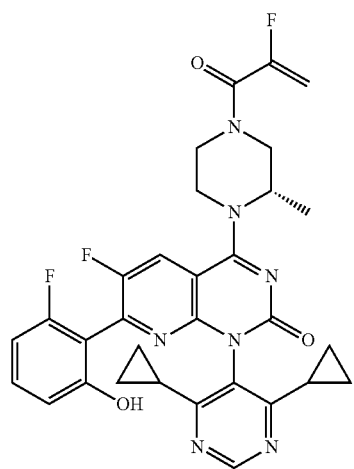
137
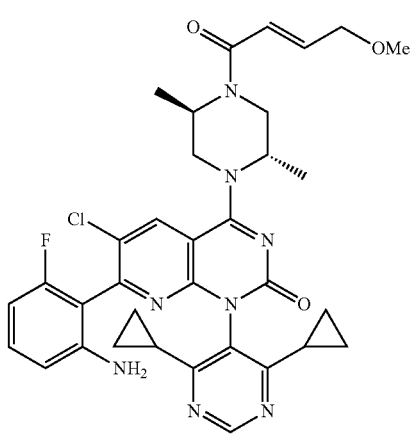
140
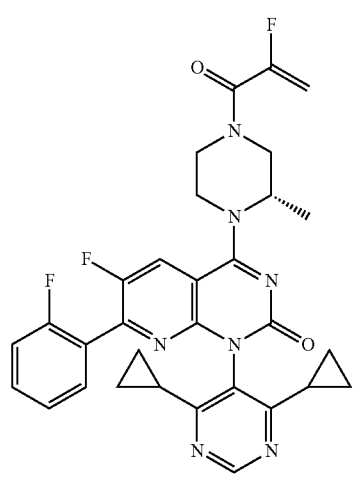
138
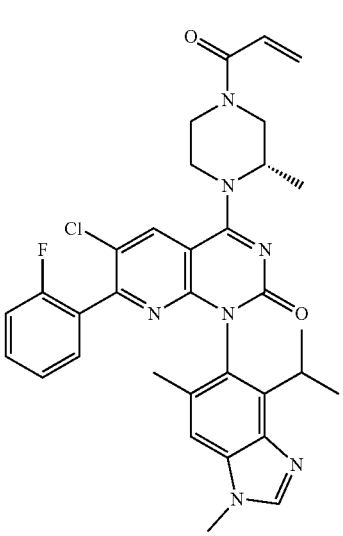
141
atropisomer 1
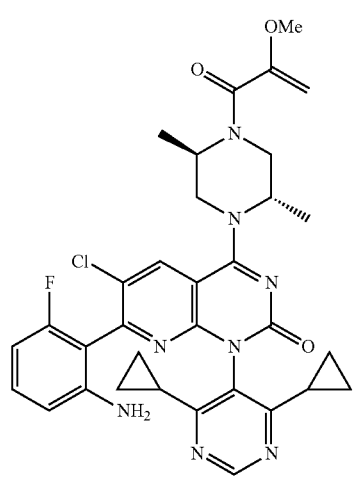
139
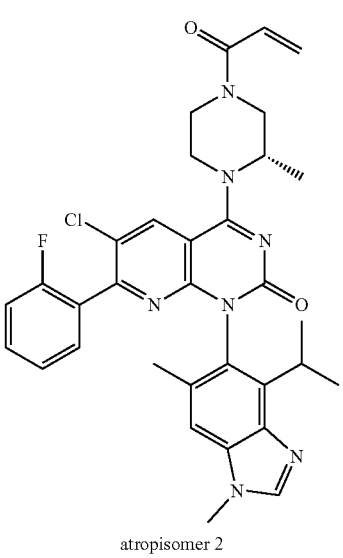
142
atropisomer 2

143
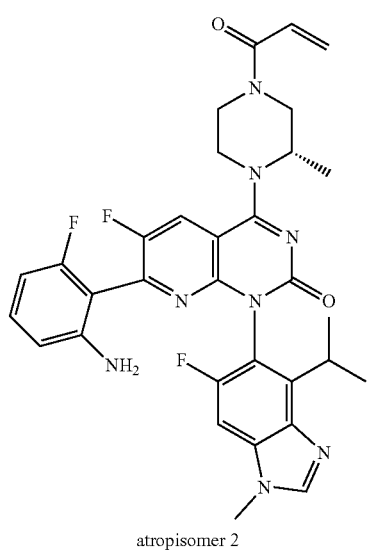
atropisomer 2
144
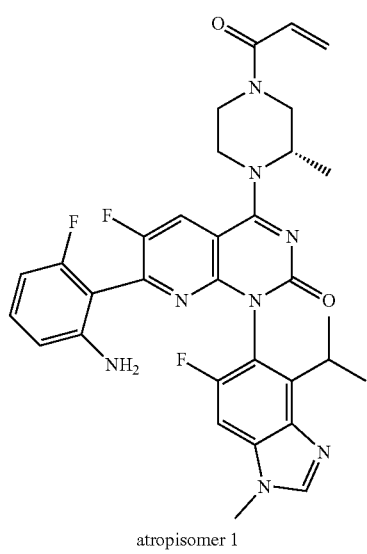
atropisomer 1
145
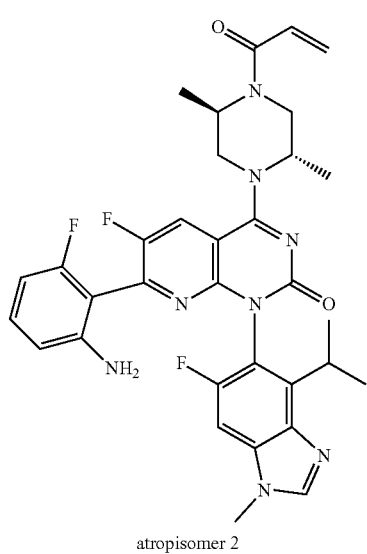
atropisomer 2
146
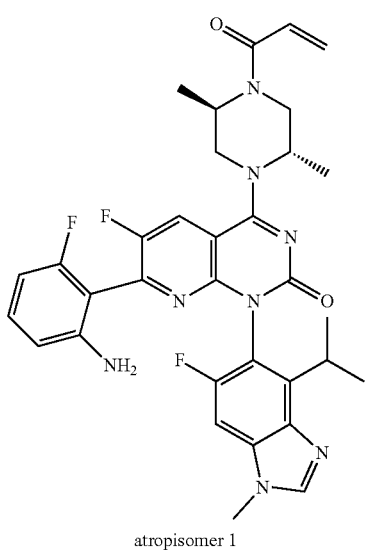
atropisomer 1
147
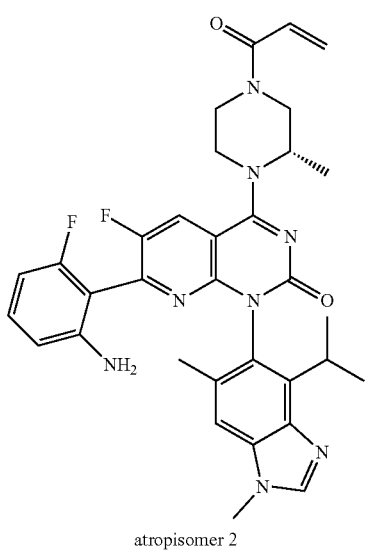
atropisomer 2
148
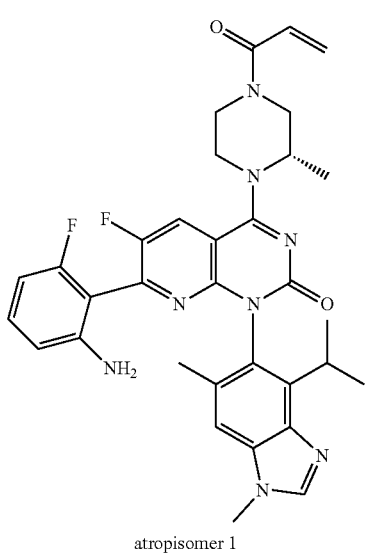
atropisomer 1

149
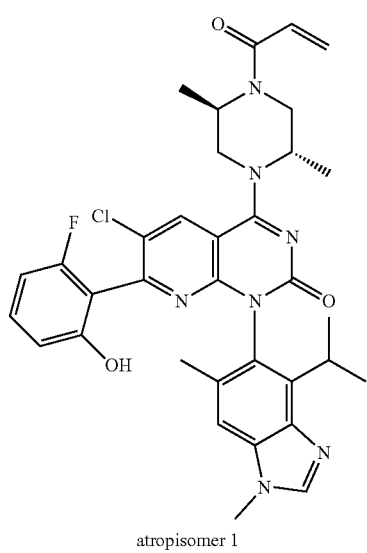
atropisomer 1
150
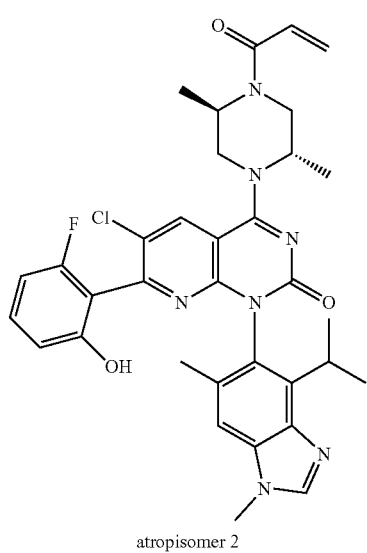
atropisomer 2
151
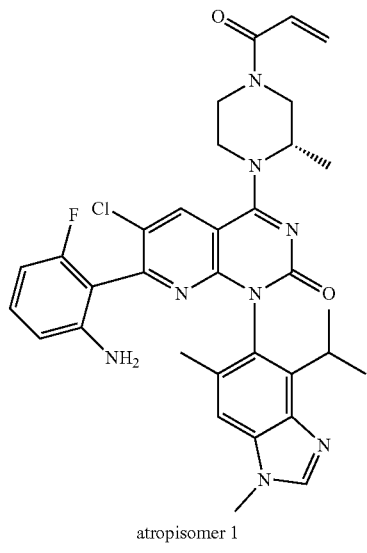
atropisomer 1
152
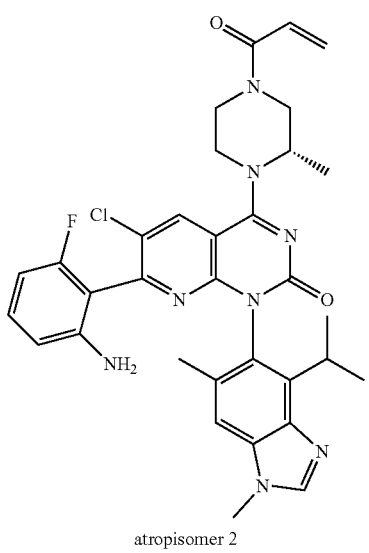
atropisomer 2
153
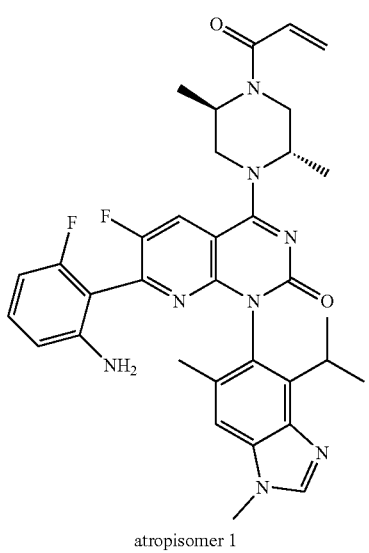
atropisomer 1
154
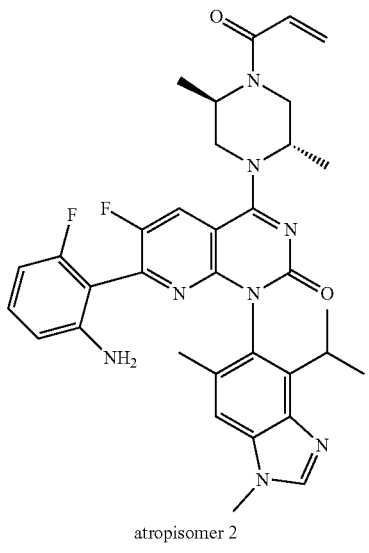
atropisomer 2

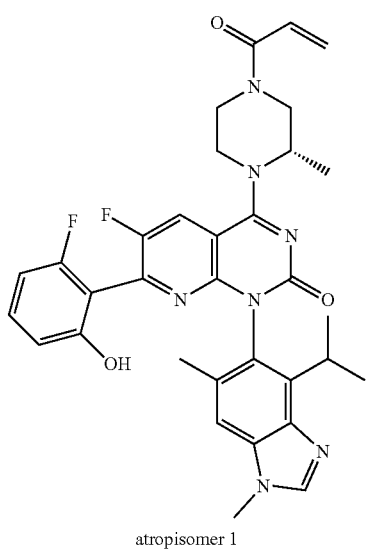
155
atropisomer 1
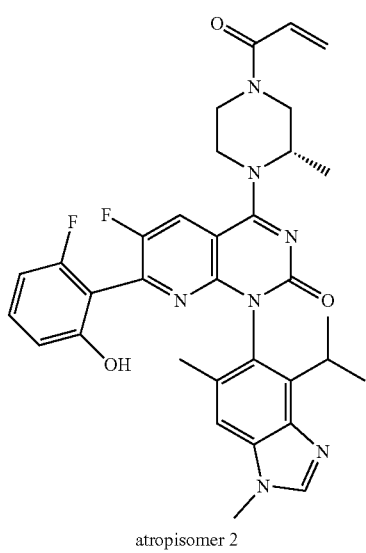
156
atropisomer 2
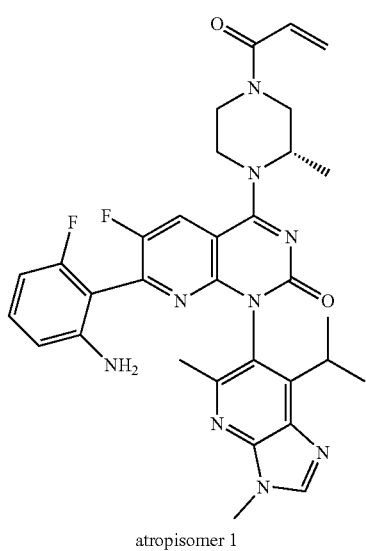
157
atropisomer 1
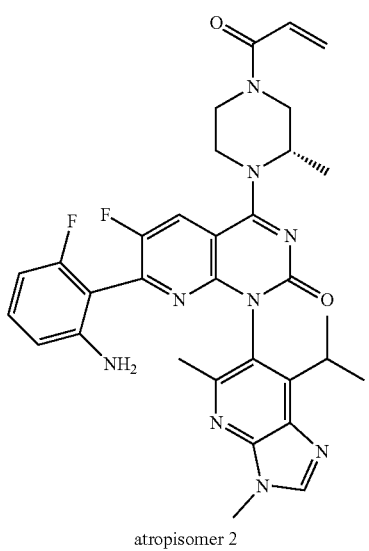
158
atropisomer 2
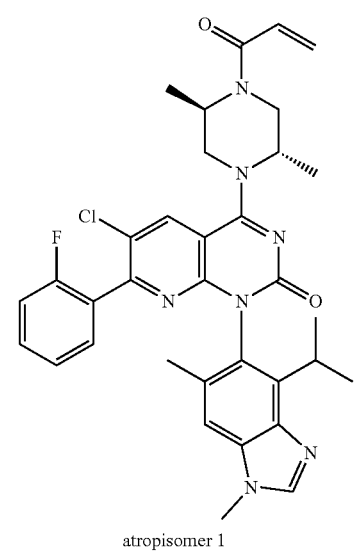
159
atropisomer 1
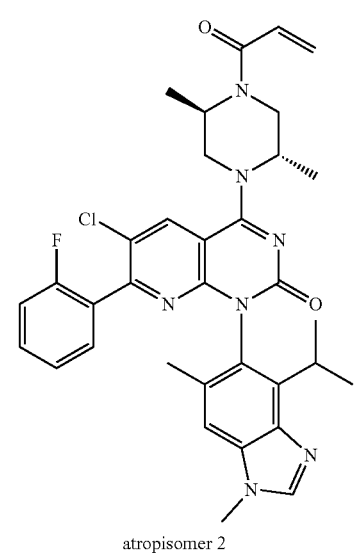
160
atropisomer 2

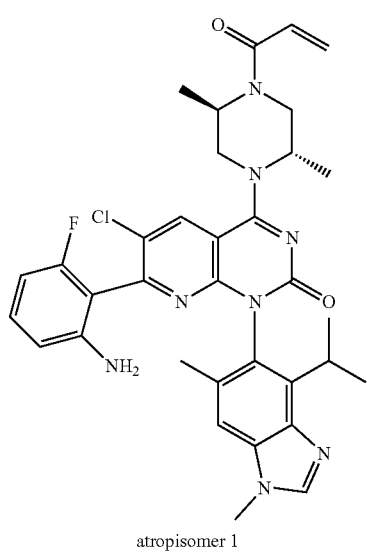
161
atropisomer 1
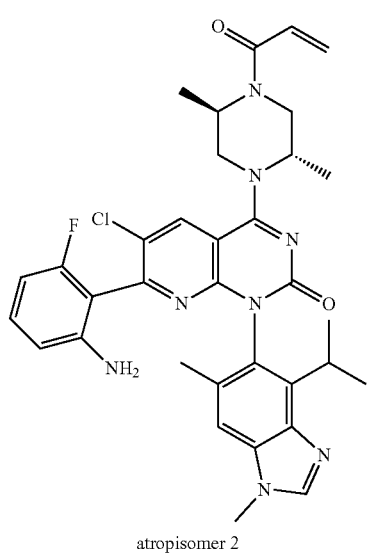
162
atropisomer 2
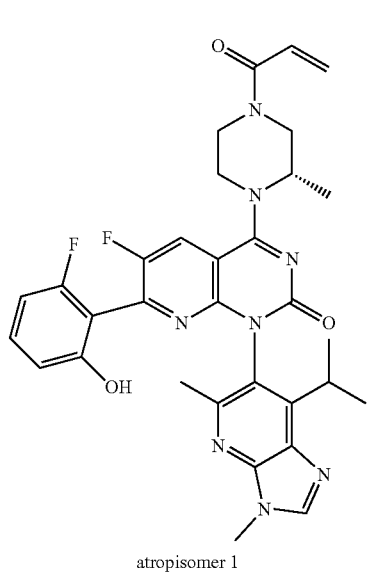
163
atropisomer 1
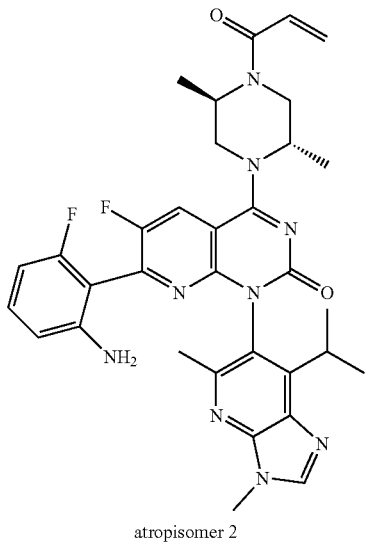
164
atropisomer 2
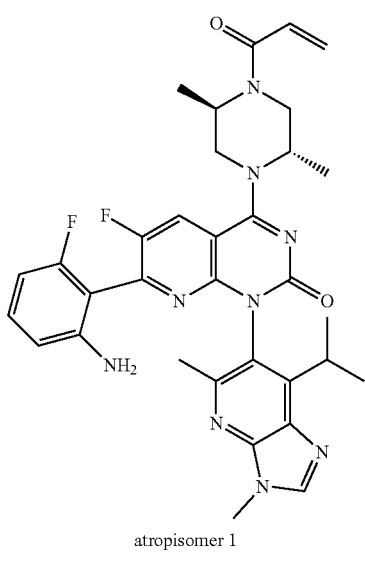
165
atropisomer 1
166

167
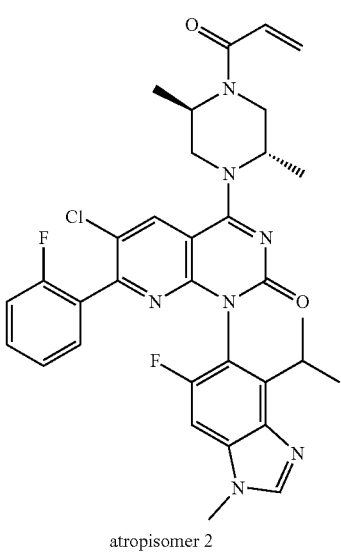
atropisomer 2
168
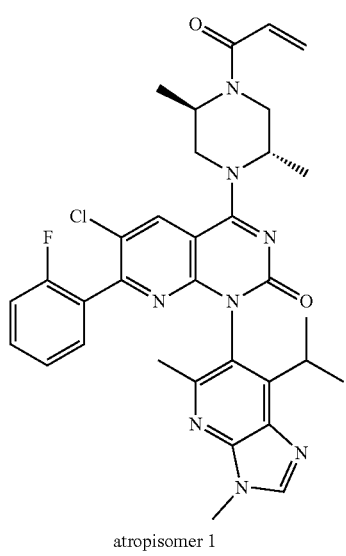
atropisomer 1
169
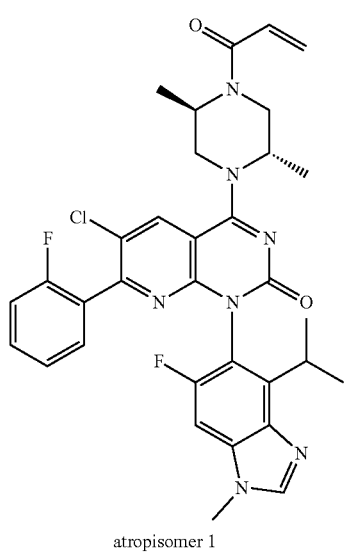
atropisomer 1
170
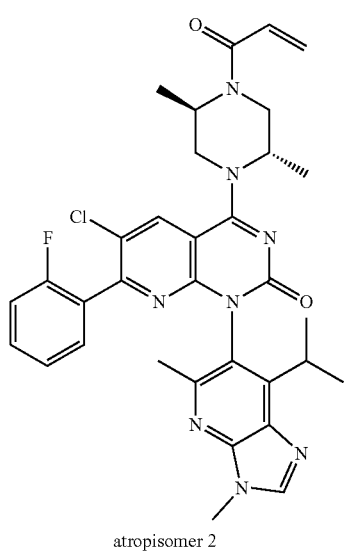
atropisomer 2
171
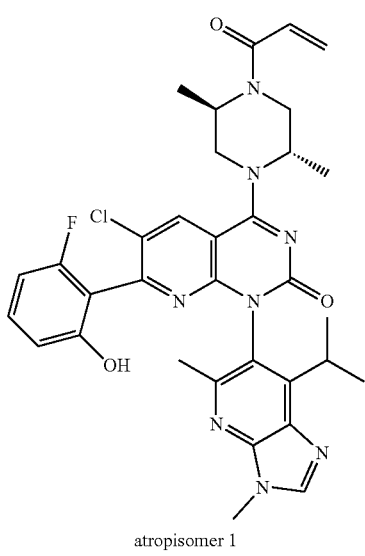
atropisomer 1
172
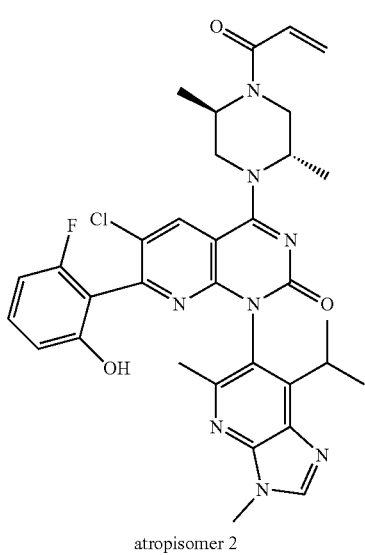
atropisomer 2

173
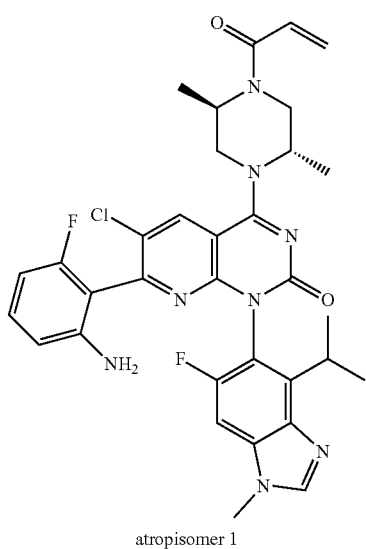
atropisomer 1
174
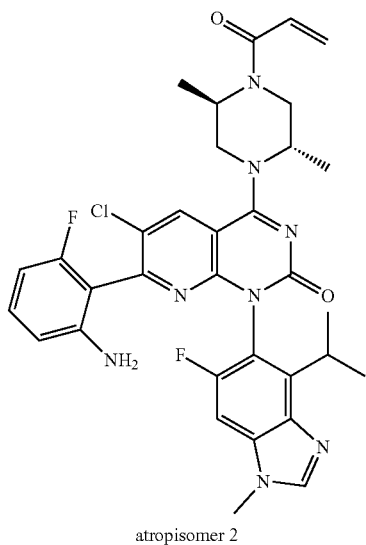
atropisomer 2
175
176
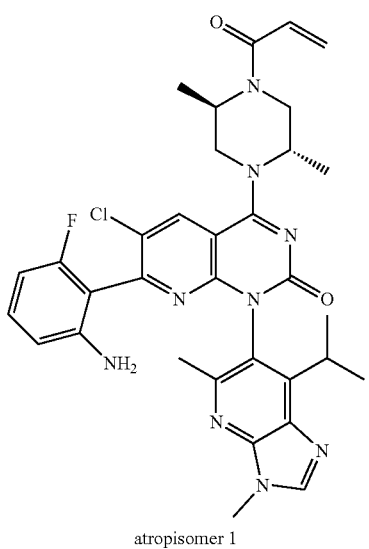
atropisomer 1
177
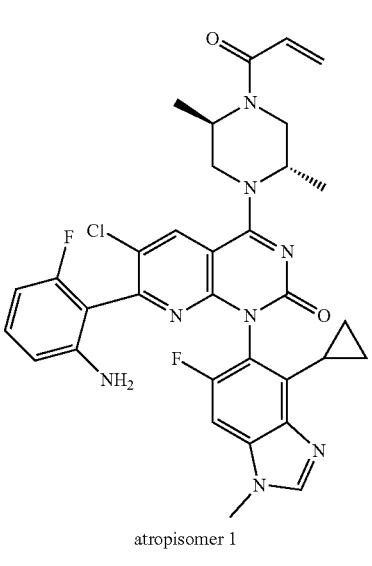
atropisomer 1
178
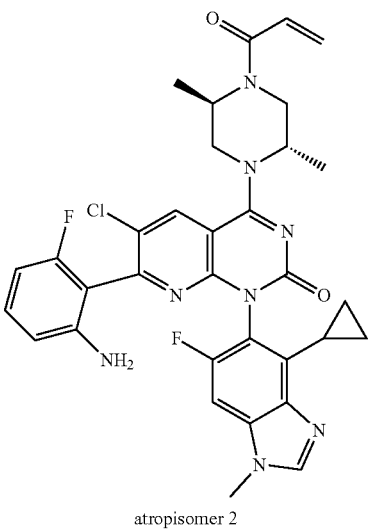
atropisomer 2

179
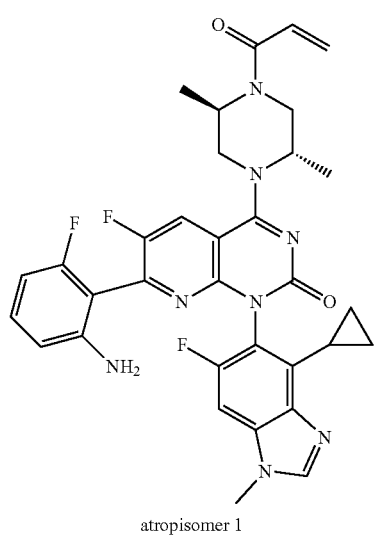
atropisomer 1
180
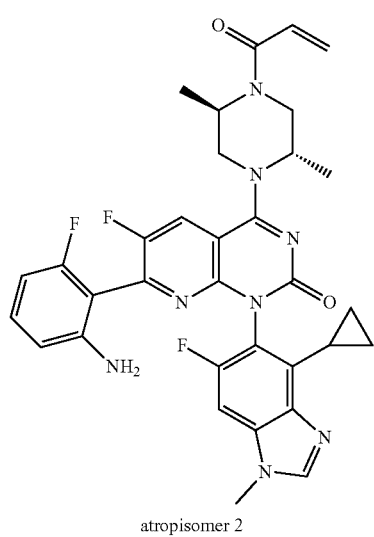
atropisomer 2
181
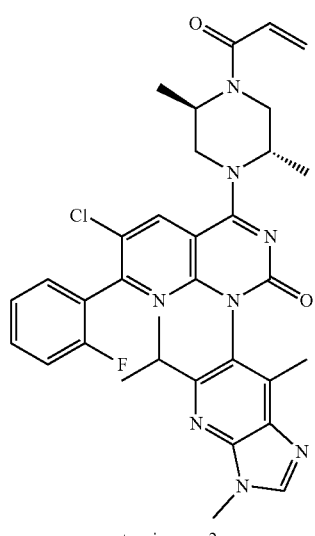
atropisomer 1
182
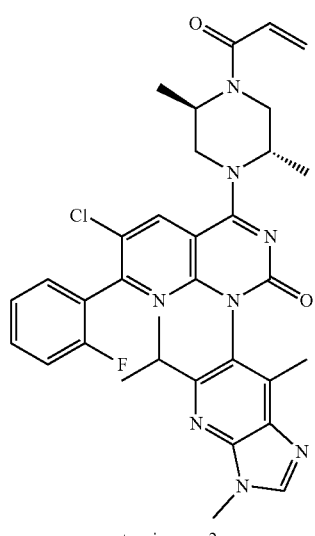
atropisomer 2
183
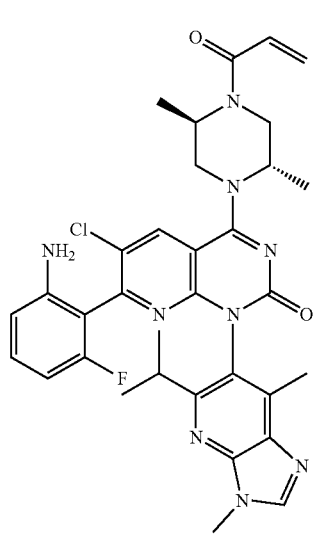
atropisomer 1
184
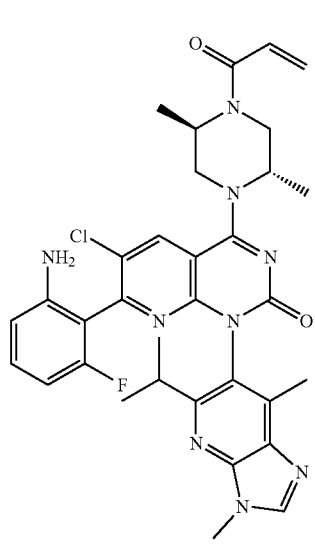
atropisomer 2

185

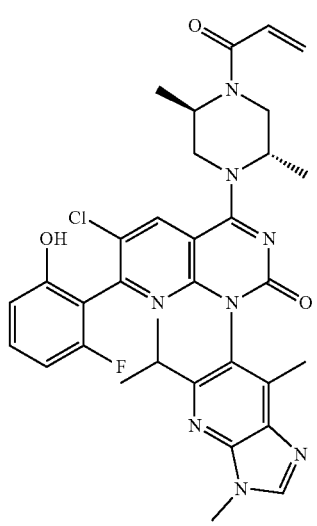

atropisomer 1

186

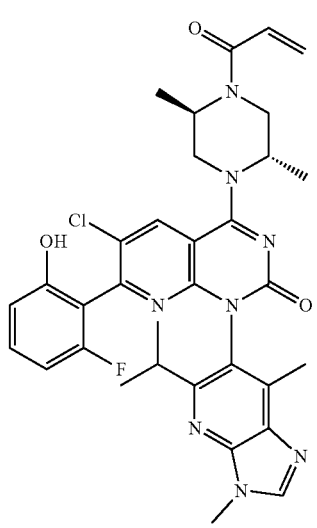

atropisomer 2

In some embodiments, the present disclosure also provides a compound selected from any of Compound Nos 1, 6, 8, 13, 20, 26, 33, 42, 44, 65, 68, 69, 70, 71, 72, 117, 124, 126, 127, 145, 146, 151, 152, 157, 158, 179, and 180, or a pharmaceutically acceptable salt thereof. In any of the embodiments described herein, unless specified or contradictory from context, the compound of the present disclosure can be Compound No. 44, 126, or 145, or a pharmaceutically acceptable salt thereof.

In some embodiments, to the extent applicable, the genus of compounds in the present disclosure also excludes any of the compounds specifically prepared and disclosed in WO2019/213516.

Additional Exemplary Embodiments

In some embodiments, the present disclosure provides the following additional exemplary embodiments.

Embodiment 1. A compound of Formula I-3A-1, I-3B-1, I-3C-1, I-4A-1, I-4B-1, or I-4C-1, or a pharmaceutically acceptable salt thereof:

Formula I-3A-1

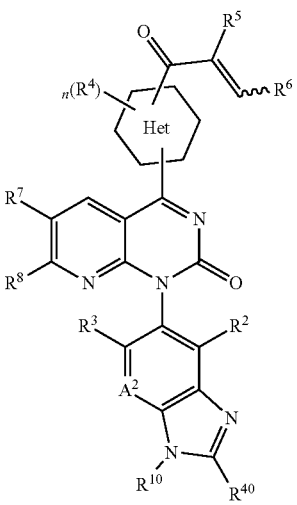

Formula I-3B-1

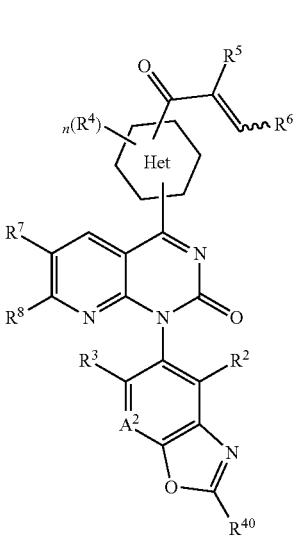

Formula I-3C-1

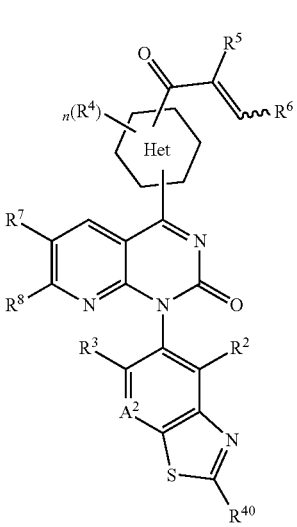

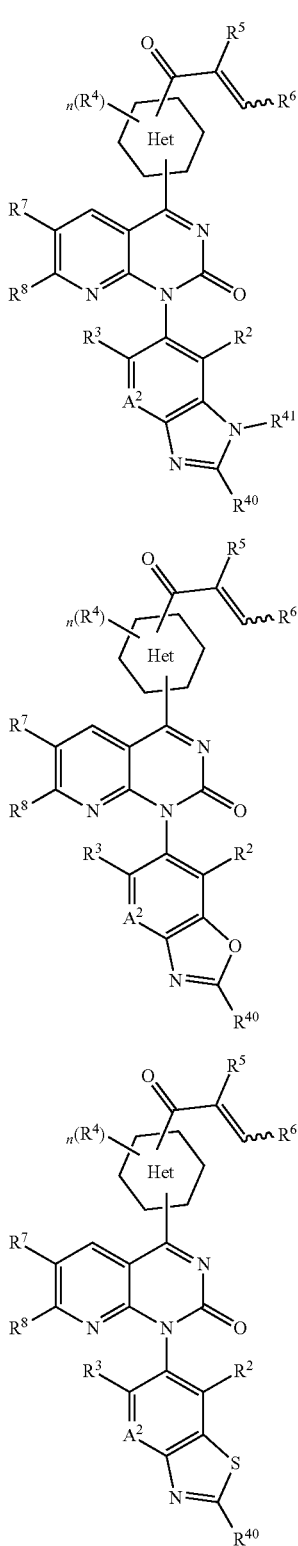

Formula I-4A-1

Formula I-4B-1

Formula I-4C-1 wherein in each formula as applicable:
A² is CH or N;
R² and R³ are each independently hydrogen, halogen, —OH, —CN, optionally substituted $C_{1-4}$ alkyl, optionally substituted $C_{2-4}$ alkenyl, optionally substituted $C_{2-4}$ alkynyl, optionally substituted $C_{3-6}$ carbocyclic ring, optionally substituted 4 to 7 membered heterocyclic ring, or optionally substituted $C_{1-4}$ alkoxy;

Het is a 4-10 membered heterocyclic ring, optionally substituted with independently selected R⁴ group(s), $(R^4)_n$, wherein n is 0, 1, 2, or 3, and R⁴ at each occurrence is independently $C_{1-4}$ alkyl, $C_{2-4}$ alkenyl, $C_{2-4}$ alkynyl, 3 or 4 membered ring (e.g., cyclopropyl), fluorine substituted $C_{1-4}$ alkyl, hydroxyl substituted $C_{1-4}$ alkyl, or cyano substituted $C_{1-4}$ alkyl; or two R⁴ groups can join together to form a 3-6 membered ring structure;

R⁵ and R⁶ are each independently hydrogen, halogen, —CN, —COOR²³ᴬ, —CONR²¹ᴬR²²ᴬ, optionally substituted $C_{1-6}$ alkyl, optionally substituted $C_{2-6}$ alkenyl, optionally substituted $C_{2-6}$ alkynyl, optionally substituted $C_{3-6}$ carbocyclic ring, optionally substituted phenyl, optionally substituted 5 or 6 membered heteroaryl, or optionally substituted 4 to 7 membered heterocyclic ring, or R⁵ and R⁶ can join together to form an optionally substituted $C_{3-6}$ carbocyclic ring, or optionally substituted 4 to 7 membered heterocyclic ring, wherein each of R²¹ᴬ and R²²ᴬ at each occurrence is independently hydrogen, an optionally substituted $C_{1-4}$ alkyl, optionally substituted $C_{2-4}$ alkenyl, optionally substituted $C_{2-4}$ alkynyl, optionally substituted $C_{1-4}$ heteroalkyl, optionally substituted $C_{3-6}$ carbocyclic ring, optionally substituted 4 to 7 membered heterocyclic ring, or a nitrogen protecting group; and R²³ᴬ at each occurrence is independently hydrogen, an optionally substituted $C_{1-4}$ alkyl, optionally substituted $C_{2-4}$ alkenyl, optionally substituted $C_{2-4}$ alkynyl, optionally substituted $C_{1-4}$ heteroalkyl, optionally substituted $C_{3-6}$ carbocyclic ring, optionally substituted 4 to 7 membered heterocyclic ring, or an oxygen protecting group;

R⁷ is hydrogen, halogen, CN, a 3-4 membered ring, (e.g., cyclopropyl), optionally substituted $C_{1-4}$ alkyl, optionally substituted $C_{2-4}$ alkenyl, optionally substituted $C_{2-4}$ alkynyl, or optionally substituted $C_{1-4}$ alkoxyl;

R⁸ is an optionally substituted aryl or optionally substituted heteroaryl;

R¹⁰ is hydrogen, an optionally substituted $C_{1-4}$ alkyl, optionally substituted $C_{2-4}$ alkenyl, optionally substituted $C_{2-4}$ alkynyl, optionally substituted $C_4$ heteroalkyl, optionally substituted $C_{3-6}$ carbocyclic ring, optionally substituted 4 to 7 membered heterocyclic ring, or a nitrogen protecting group; and each of R⁴⁰ and R⁴¹ at each occurrence is independently hydrogen, OH, CN, halogen, an optionally substituted $C_{1-4}$ alkyl, optionally substituted $C_{2-4}$ alkenyl, optionally substituted $C_2$-4 alkynyl, an optionally substituted $C_{1-4}$ alkoxy, optionally substituted $C_{1-4}$ heteroalkyl, optionally substituted $C_{3-6}$ carbocyclic ring, or optionally substituted 4 to 7 membered heterocyclic ring.

Embodiment 2. The compound of Embodiment 1, or a pharmaceutically acceptable salt thereof, wherein in each formula, A² is CH.

Embodiment 3. The compound of Embodiment 1, or a pharmaceutically acceptable salt thereof, wherein in each formula, A² is N.

Embodiment 4. The compound of any one of Embodiments 1-3, or a pharmaceutically acceptable salt thereof, wherein in each formula, R² and R³ are independently selected from hydrogen, $C_{1-4}$ alkyl optionally substituted with 1-3 fluorine, $C_{3-6}$ cycloalkyl, and halogen.

Embodiment 5. The compound of any one of Embodiments 1-3, or a pharmaceutically acceptable salt thereof, wherein in each formula, R² and R³ are independently selected from hydrogen, methyl, ethyl, isopropyl, tert-butyl, cyclopropyl, F, and Cl.

Embodiment 6. The compound of any one of Embodiments 1-3, or a pharmaceutically acceptable salt thereof, wherein in each formula, $R^2$ and $R^3$ are both isopropyl or both cyclopropyl.

Embodiment 7. The compound of any one of Embodiments 1-3, or a pharmaceutically acceptable salt thereof, wherein in each formula, one of $R^2$ and $R^3$ is hydrogen, F or methyl, and the other of $R^2$ and $R^3$ is isopropyl or cyclopropyl.

Embodiment 8. The compound of any one of Embodiments 1-3, or a pharmaceutically acceptable salt thereof, wherein in each formula, one of $R^2$ and $R^3$ is F, and the other of $R^2$ and $R^3$ is isopropyl or cyclopropyl, e.g., $R^2$ is F and $R^3$ is isopropyl or cyclopropyl; or $R^3$ is F and $R^2$ is isopropyl or cyclopropyl.

Embodiment 9. The compound of any one of Embodiments 1-3, or a pharmaceutically acceptable salt thereof, wherein in each formula, one of $R^2$ and $R^3$ is methyl, and the other of $R^2$ and $R^3$ is isopropyl or cyclopropyl, e.g., $R^2$ is methyl and $R^3$ is isopropyl or cyclopropyl; or $R^3$ is methyl and $R^2$ is isopropyl or cyclopropyl.

Embodiment 10. The compound of any one of Embodiments 1-9, or a pharmaceutically acceptable salt thereof, wherein in each formula as applicable, the compound exists as an isolated individual atropisomer substantially free (e.g., with less than 20%, less than 10%, less than 5%, less than 1%, by weight, by HPLC area, or both, or with a non-detectable amount) of the other atropisomer.

Embodiment 11. The compound of any one of Embodiments 1-10, or a pharmaceutically acceptable salt thereof, wherein in each formula as applicable, $R^{10}$, $R^{40}$ and $R^{41}$ are independently selected from hydrogen and $C_{1-4}$ alkyl.

Embodiment 12. The compound of any one of Embodiments 1-11, or a pharmaceutically acceptable salt thereof, wherein in each formula, $R^{40}$ is hydrogen.

Embodiment 13. The compound of any one of Embodiments 1-12, or a pharmaceutically acceptable salt thereof, wherein in each formula as applicable, $R^{10}$ is a $C_{1-4}$ alkyl, preferably, methyl.

Embodiment 14. The compound of any one of Embodiments 1-13, or a pharmaceutically acceptable salt thereof, wherein in each formula, Het, together with $(R^4)_n$ and

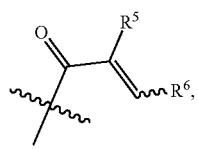

is represented by

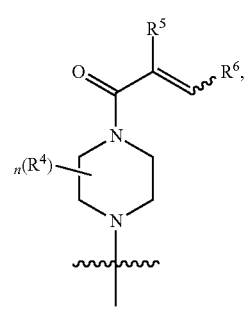

wherein n is 0, 1, or 2, wherein when n is 1 or 2, $R^4$ at each occurrence is independently methyl, ethyl, —$CF_3$, —$CF_2H$, —$CH_2OH$, or —$CH_2CN$.

Embodiment 15. The compound of any one of Embodiments 1-13, or a pharmaceutically acceptable salt thereof, wherein in each formula, Het, together with $(R^4)_n$ and

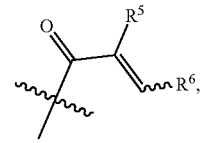

is represented by

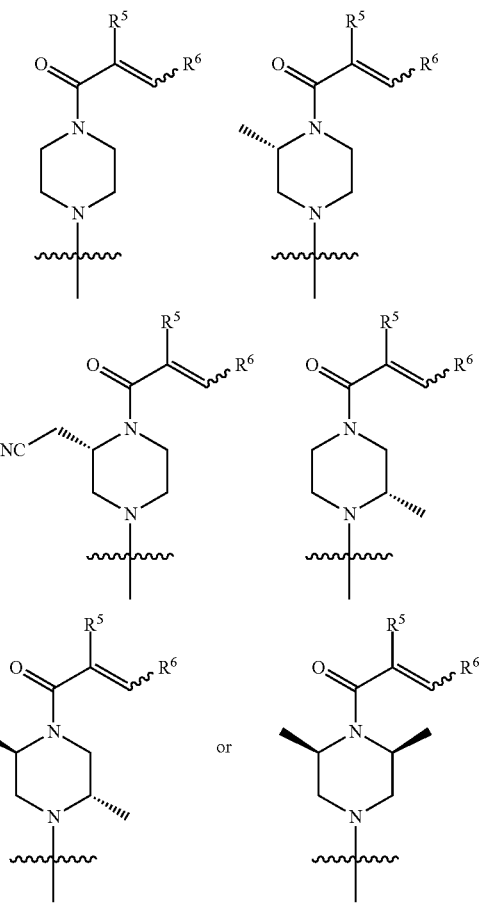

or.

Embodiment 16. The compound of any one of Embodiments 1-13, or a pharmaceutically acceptable salt thereof, wherein in each formula, Het, together with $(R^4)_n$ and

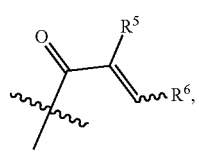

is represented by

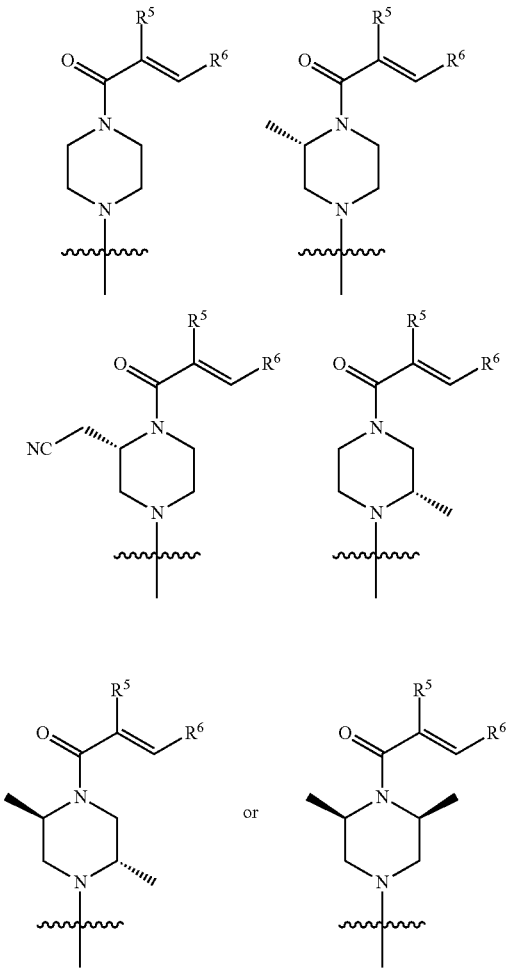

Embodiment 17. The compound of any one of Embodiments 1-16, or a pharmaceutically acceptable salt thereof, wherein in each formula, both of $R^5$ and $R^6$ are hydrogen.

Embodiment 18. The compound of any one of Embodiments 1-16, or a pharmaceutically acceptable salt thereof, wherein in each formula, $R^5$ is F or OMe, and $R^6$ is hydrogen.

Embodiment 19. The compound of any one of Embodiments 1-16, or a pharmaceutically acceptable salt thereof, wherein in each formula, $R^5$ is hydrogen, and $R^6$ is —CH$_2$—OMe or

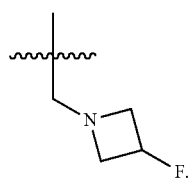 [SMILES: *CN1CC(F)C1]

Embodiment 20. The compound of any one of Embodiments 1-13, or a pharmaceutically acceptable salt thereof, wherein in each formula, Het, together with $(R^4)_n$ and

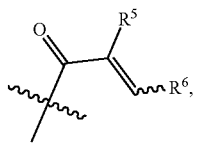

is represented by

[structures on right side of page]

Embodiment 21. The compound of any one of Embodiments 1-20, or a pharmaceutically acceptable salt thereof, wherein in each formula, $R^7$ is hydrogen, F, Cl, methyl, or —CF$_3$.

Embodiment 22. The compound of any one of Embodiments 1-20, or a pharmaceutically acceptable salt thereof, wherein in each formula, $R^7$ is F.

Embodiment 23. The compound of any one of Embodiments 1-20, or a pharmaceutically acceptable salt thereof, wherein in each formula, $R^7$ is Cl.

Embodiment 24. The compound of any one of Embodiments 1-23, or a pharmaceutically acceptable salt thereof, wherein in each formula, $R^8$ is a phenyl optionally substituted with 1-3 groups each independently selected from F, Cl, —OH, NH$_2$, protected hydroxyl group, protected amino group, C$_{1-4}$ alkyl, C$_{2-4}$ alkenyl, C$_{2-4}$ alkynyl, 3 or 4 membered ring (e.g., cyclopropyl), C$_{1-4}$ alkoxy, fluorine substituted C$_{1-4}$ alkyl, and fluorine substituted C$_{1-4}$ alkoxy. Embodiment 24. The compound of any one of Embodiments 1-23, or a pharmaceutically acceptable salt thereof, wherein $R^8$ is a bicyclic heteroaryl (e.g., indazolyl) optionally substituted with 1-3 groups each independently selected from F, Cl, —OH, —NH$_2$, protected hydroxyl group, protected amino group, C$_{1-4}$ alkyl, C$_{2-4}$ alkenyl, C$_{2-4}$ alkynyl, 3 or 4 membered ring (e.g., cyclopropyl), C$_{1-4}$ alkoxy, fluorine substituted C$_{1-4}$ alkyl, and fluorine substituted C$_{1-4}$ alkoxy.

Embodiment 25. The compound of any one of Embodiments 1-23, or a pharmaceutically acceptable salt thereof, wherein in each formula, $R^8$ is selected from:

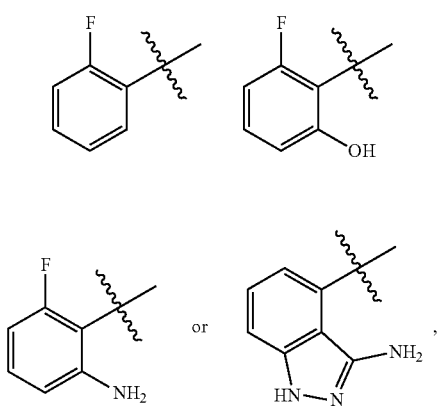

preferably,

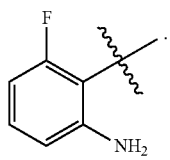

Embodiment 26. A pharmaceutical composition comprising the compound of any one of Embodiments 1-25, or a pharmaceutically acceptable salt thereof, and a pharmaceutically acceptable excipient.

Embodiment 27. A method of inhibiting KRAS G12C mutant protein in a cell, the method comprising contacting the cell with the compound of any one of Embodiments 1-25, or a pharmaceutically acceptable salt thereof.

Embodiment 28. A method of treating cancer in a subject, the method comprising administering to the subject a therapeutically effective amount of the compound of any one of Embodiments 1-25, or a pharmaceutically acceptable salt thereof, or the pharmaceutical composition of embodiment 26.

Embodiment 29. The method of Embodiment 28, wherein the cancer is a hematologic malignancy, lung cancer (e.g., non-small cell lung cancer), pancreatic cancer, endometrial cancer, gall bladder cancer, thyroid cancer, bile duct cancer, and/or colorectal cancer.

Embodiment 30. The method of Embodiment 28 or 29, further comprising treating the subject with an additional therapy.

Embodiment 31. The method of Embodiment 30, wherein the additional therapy is a chemotherapeutic agent, therapeutic antibody, radiation, cell therapy, or immunotherapy.

Embodiment 32. The method of any one of Embodiments 28-31, wherein the subject has a G12C mutation of KRAS, HRAS and/or NRAS.

Method of Synthesis

The compounds of the present disclosure can be readily synthesized by those skilled in the art in view of the present disclosure. Exemplified synthesis are also shown in the Examples section.

The following synthetic process of Formula I is illustrative, which can be applied similarly by those skilled in the art for the synthesis of compounds of Formula II, by replacing the starting material or intermediate with an —X—$R^1$ group with the corresponding starting material or intermediate with a $G^1$ group. Compounds of Formula III or IV can also be prepared similarly. In some embodiments, the present disclosure also provides synthetic methods and synthetic intermediates for preparing the compounds of Formula I, II, III, or IV, as represented by the schemes herein.

As shown in Scheme 1, in some embodiments, compounds of Formula I can be prepared by reacting an intermediate S-2 with a heterocyclic compound S-1 under suitable conditions, wherein $Lg^1$ is a leaving group such as a halide or a sulfonate leaving group such as triflate ($CF_3SO_3$—) or tosylate etc. In some embodiments, S-1 can react with S-2 with a base such as an amine base (e.g., diisopropylethyl amine), or an inorganic base such as a carbonate base, in a suitable solvent. In some embodiments, $R^{8A}$ is the same as $R^8$. In some embodiments, however, $R^{8A}$ can also be different from the $R^8$, and the method of synthesis can include converting $R^{8A}$ into $R^8$. For example, in some embodiments, $R^{8A}$ can be a leaving group, such as a halide or a sulfonate leaving group, and the reaction product of S-1 and S-2 can be coupled with a suitable partner to introduce the desired $R^8$ group, either through one step or multiple steps. Typically, when applicable, the introduction of $R^8$ group can be mediated by a metal catalyzed coupling reaction, such as a palladium catalyzed coupling reaction as exemplified herein. Useful reagents and reaction conditions for palladium catalyzed coupling reactions are generally known, see for examples WO2019/051291, WO 2018/119183, and WO2018/217651. In some embodiments, the suitable partner can be a boronic acid or ester compound such as $R^8$—$B(OH)_2$. In some embodiments, $R^{8A}$ can be converted into boronic acid or ester and then couple with $R^8$-$Lg^2$, wherein $Lg^2$ is a leaving group, such as a halide or a sulfonate leaving group. Other suitable coupling reactions such as Stille or Negishi coupling, are known in the art and can be adapted for the synthesis of the compounds herein in view of this disclosure. Example 4 shows an example of reaction of S-1 and S-2, where $A^3$ is N, and $Lg^1$ is Cl. Other compounds of Formula I can be prepared similarly. The variables X, $R^1$, $R^2$, $R^3$, $R^4$, $R^7$, $R^8$, Het, n, U, $A^1$, $A^2$, $A^3$, $A^4$, and $A^5$ in Scheme 1 can be any of those defined herein.

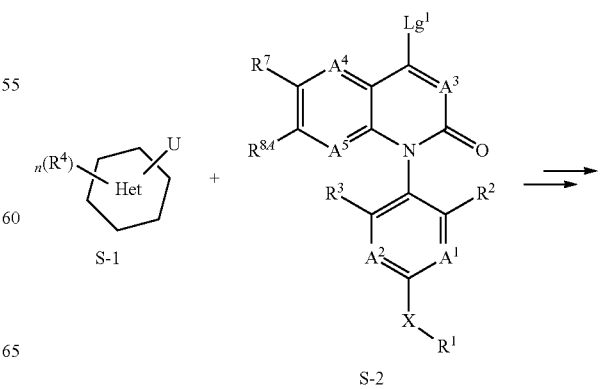

Scheme 1

Scheme 2

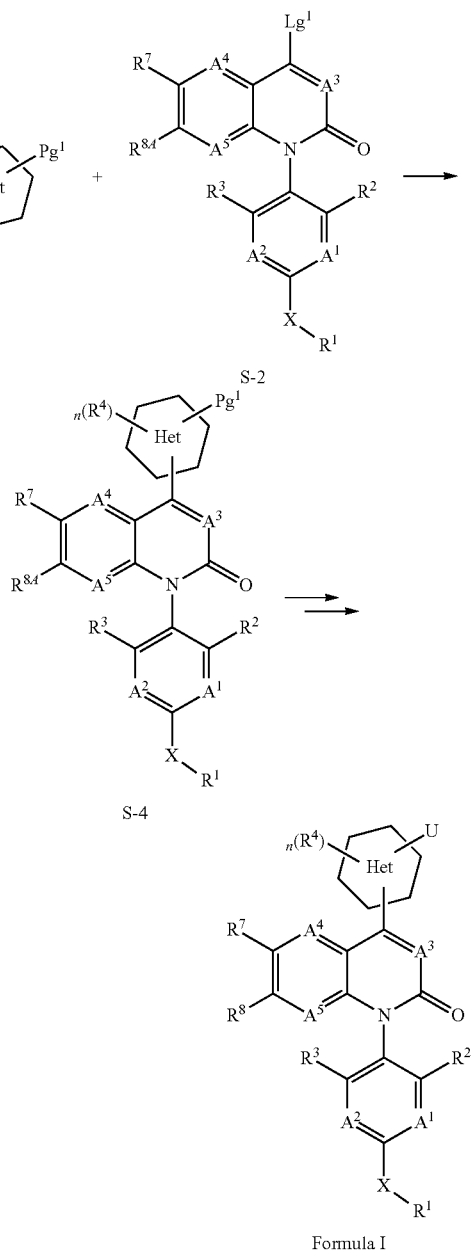

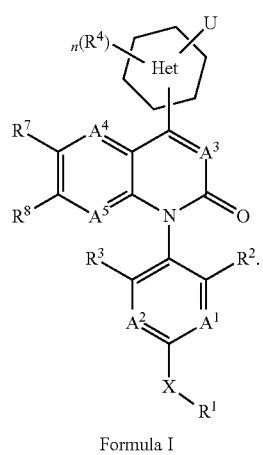

Formula I

In some cases, introducing $R^8$ and/or the U group can proceed after incorporation of a heterocyclic ring without U group. For example, as shown in Scheme 2, a heterocycle of S-3 can react with S-2 to form an intermediate S-4. $Pg^1$ in S-3 is typically hydrogen or a nitrogen protecting group such as Boc. Typically, to introduce the U group, S-4 can be deprotected under suitable conditions. This deprotection step can then generate an NH moiety which can react with a suitable U group donor to provide Formula I. Generally, such U group donor can have a formula of U-$Lg^3$, wherein $Lg^3$ is OH, Cl, or other suitable leaving group, exemplary U group donor can be a molecule of

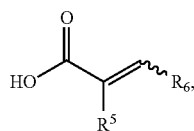

or an activated form, such as an acyl chloride,

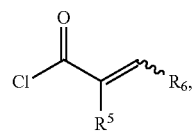

wherein $R^5$ and $R^6$ can be any of those defined herein. As with Scheme 1, $R^{8A}$ can be the same as or different from $R^8$. In cases when $R^{8A}$ is different from the $R^8$, and the method of synthesis also includes converting $R^{8A}$ into $R^8$. As discussed above, $R^{8A}$ can be a leaving group, such as a halide or a sulfonate leaving group, and can be coupled with a suitable partner to introduce the desired $R^8$ group, either through one step or multiple steps. When applicable, the conversion of $R^{8A}$ to $R^8$ can occur either prior to or after the introduction of the heterocyclic ring of S-3 and/or the U group. The variables X, $R^1$, $R^2$, $R^3$, $R^4$, $R^7$, $R^8$, Het, n, U, $A^1$, $A^2$, $A^3$, $A^4$, and $A^5$ in Scheme 2 can be any of those defined herein.

In some embodiments, the —X—$R^1$ group of Formula I can be derived from other compounds of Formula I. For example, in some embodiments, —X—$R^1$ group in some compounds of Formula I can be —$SO_2$Me, and such compounds can be prepared from corresponding compounds of Formula I where the —X—$R^1$ group is —S-Me through an oxidation process. Compounds of Formula I where the —X—$R^1$ group is —$SO_2$Me can also serve as starting material for the synthesis of other compounds of Formula I. As will be apparent to those skilled in the art, such transformation can be carried out in any of the suitable intermediates described herein. Other derivatizations of —X—$R^1$ group of Formula I are also possible and can be used in some cases for the preparation of compounds of the present disclosure.

Intermediate compounds of S-2 can be typically prepared by methods including forming the 6,6-bicyclic ring. For example, Scheme 3 shows a typical process of preparing compounds of S-2 with $A^3$ and $A^5$ being N. Thus, a compound of S-5 can couple with S-6 through a carbonyl donor, such as oxalyl chloride to form an intermediate S-7, wherein $Lg^4$ is a leaving group such as a halide (e.g., Cl) or a sulfonate leaving group. S-7 can then cyclize to form a compound of S-8, typically mediated by a base. S-8 can then be converted into a compound of S-9, e.g., though reacting with $POCl_3$ or other suitable reagents. Exemplary synthesis of various compounds of S-5 are shown in the Examples section. Other compounds of S-5 can be synthesized similarly in light of this disclosure. Compounds of S-6 can sometimes be commercially available or otherwise prepared by those skilled in the art. The variables X, $R^1$, $R^2$, $R^3$, $R^7$, $R^{8A}$, $A^1$, $A^2$, and $A^4$ in Scheme 3 can be any of those defined herein.

Fieser's Reagents for Organic Synthesis, Volumes 1-15 (John Wiley and Sons, 1991), Rodd's Chemistry of Carbon Compounds, Volumes 1-5 and Supplemental (Elsevier Science Publishers, 1989), Organic Reactions, Volumes 1-40 (John Wiley and Sons, 1991), March's Advanced Organic Chemistry, (Wiley, $7^{th}$ Edition), and Larock's Comprehensive Organic Transformations (Wiley-VCH, 1999), and any of available updates as of this filing.

Pharmaceutical Compositions

Certain embodiments are directed to a pharmaceutical composition comprising one or more of the compounds of the present disclosure.

The pharmaceutical composition can optionally contain a pharmaceutically acceptable excipient. In some embodiments, the pharmaceutical composition comprises a compound of the present disclosure (e.g., a compound of Formula I (e.g., Formula I-1, I-2, I-3A, I-3A-1, I-3A-C, I-3A-N, I-3B, I-3C, I-4A, I-4B, I-4C, I-3B-1, I-3C-1, I-4A-1, I-4B-1,

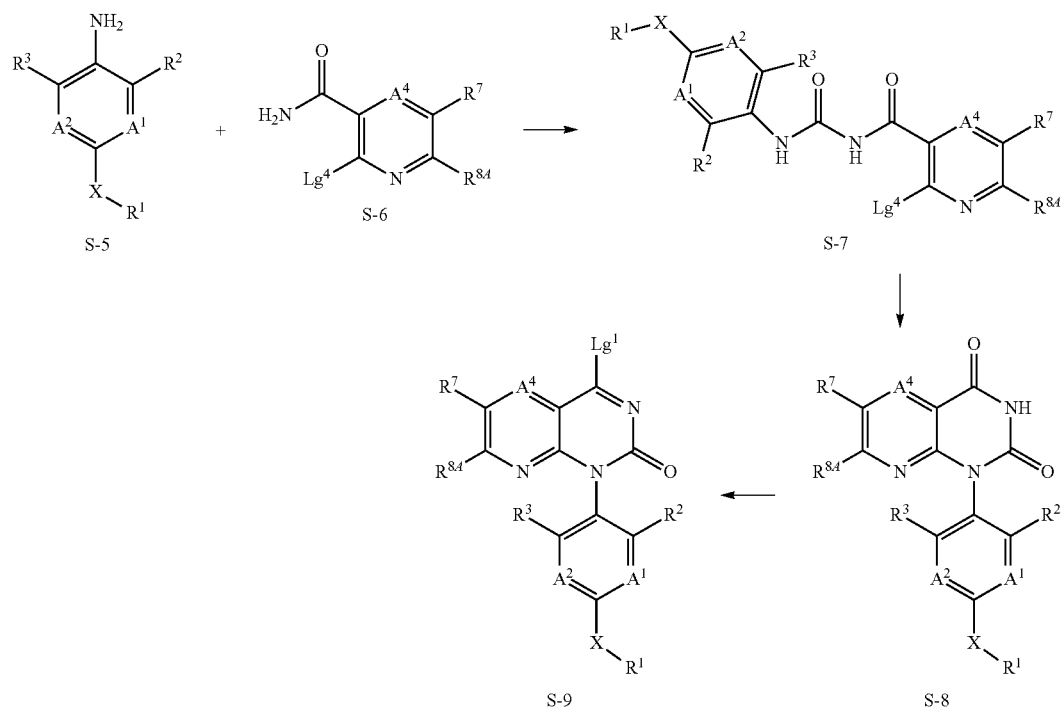

Scheme 3

I-4C-1, I-5, I-6, I-7, or I-8), Formula II, Formula III, Formula IV, any of compound Nos. 1-186, or a pharmaceutically acceptable salt thereof) and a pharmaceutically acceptable excipient. Pharmaceutically acceptable excipients are known in the art. Non-limiting suitable excipients include, for example, encapsulating materials or additives such as absorption accelerators, antioxidants, binders, buffers, carriers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. See also Remington's The Science and Practice of Pharmacy, 21st Edition, A. R. Gennaro (Lippincott, Williams & Wilkins, Baltimore, Md., 2005; incorporated herein by reference), which discloses various excipients used in formulating pharmaceutical compositions and known techniques for the preparation thereof.

As will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in "Protective Groups in Organic Synthesis", $4^{th}$ ed. P. G. M. Wuts; T. W. Greene, John Wiley, 2007, and references cited therein. The reagents for the reactions described herein are generally known compounds or can be prepared by known procedures or obvious modifications thereof. For example, many of the reagents are available from commercial suppliers such as Aldrich Chemical Co. (Milwaukee, Wis., USA), Sigma (St. Louis, Mo., USA). Others may be prepared by procedures, or obvious modifications thereof, described in standard reference texts such as Fieser and The pharmaceutical composition can include any one or more of the compounds of the present disclosure. For example, in some embodiments, the pharmaceutical composition comprises a compound of Formula I (e.g., Formula I-1, I-2, I-3A, I-3A-1, I-3A-C, I-3A-N, I-3B, I-3C, I-4A, I-4B, I-4C, I-3B-1, I-3C-1, I-4A-1, I-4B-1, I-4C-1, I-5, I-6, I-7, or I-8), Formula II, Formula III, Formula IV, any of compound Nos. 1-186, or a pharmaceutically acceptable salt thereof), e.g., in a therapeutically effective amount. In any of the embodiments described herein, the pharmaceutical composition can comprise a therapeutically effective amount of a compound selected from compound Nos. 1-186, or a pharmaceutically acceptable salt thereof.

The pharmaceutical composition can also be formulated for delivery via any of the known routes of delivery, which include but are not limited to oral, parenteral, inhalation, etc.

In some embodiments, the pharmaceutical composition can be formulated for oral administration. The oral formulations can be presented in discrete units, such as capsules, pills, cachets, lozenges, or tablets, each containing a predetermined amount of the active compound; as a powder or granules; as a solution or a suspension in an aqueous or non-aqueous liquid; or as an oil-in-water or water-in-oil emulsion. Excipients for the preparation of compositions for oral administration are known in the art. Non-limiting suitable excipients include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof.

In some embodiments, the pharmaceutical composition is formulated for parenteral administration (such as intravenous injection or infusion, subcutaneous or intramuscular injection). The parenteral formulations can be, for example, an aqueous solution, a suspension, or an emulsion. Excipients for the preparation of parenteral formulations are known in the art. Non-limiting suitable excipients include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof.

In some embodiments, the pharmaceutical composition is formulated for inhalation. The inhalable formulations can be, for example, formulated as a nasal spray, dry powder, or an aerosol administrable through a metered-dose inhaler. Excipients for preparing formulations for inhalation are known in the art. Non-limiting suitable excipients include, for example, lactose, talc, silicic acid, aluminum hydroxide, calcium silicates and polyamide powder, and mixtures of these substances. Sprays can additionally contain propellants, such as chlorofluorohydrocarbons and volatile unsubstituted hydrocarbons, such as butane and propane.

The pharmaceutical composition can include various amounts of the compounds of the present disclosure, depending on various factors such as the intended use and potency and selectivity of the compounds. In some embodiments, the pharmaceutical composition comprises a therapeutically effective amount of a compound of the present disclosure (e.g., a compound of Formula I (e.g., Formula I-1, I-2, I-3A, I-3A-1, I-3A-C, I-3A-N, I-3B, I-3C, I-4A, I-4B, I-4C, I-3B-1, I-3C-1, I-4A-1, I-4B-1, I-4C-1, I-5, I-6, I-7, or I-8), Formula II, Formula III, Formula IV, any of compound Nos. 1-186, or a pharmaceutically acceptable salt thereof). In some embodiments, the pharmaceutical composition comprises a therapeutically effective amount of the compound of the present disclosure and a pharmaceutically acceptable excipient. As used herein, a therapeutically effective amount of a compound of the present disclosure is an amount effective to treat a disease or disorder as described herein, which can depend on the recipient of the treatment, the disease or disorder being treated and the severity thereof, the composition containing the compound, the time of administration, the route of administration, the duration of treatment, the compound potency (e.g., for inhibiting KRAS G12C), its rate of clearance and whether or not another drug is co-administered.

For veterinary use, a compound of the present disclosure can be administered as a suitably acceptable formulation in accordance with normal veterinary practice. The veterinarian can readily determine the dosing regimen and route of administration that is most appropriate for a particular animal.

In some embodiments, all the necessary components for the treatment of KRAS-related disorder using a compound of the present disclosure either alone or in combination with another agent or intervention traditionally used for the treatment of such disease can be packaged into a kit. Specifically, in some embodiments, the present invention provides a kit for use in the therapeutic intervention of the disease comprising a packaged set of medicaments that include the compound disclosed herein as well as buffers and other components for preparing deliverable forms of said medicaments, and/or devices for delivering such medicaments, and/or any agents that are used in combination therapy with the compound of the present disclosure, and/or instructions for the treatment of the disease packaged with the medicaments. The instructions may be fixed in any tangible medium, such as printed paper, or a computer readable magnetic or optical medium, or instructions to reference a remote computer data source such as a world wide web page accessible via the internet.

Method of Treatment

Compounds of the present disclosure are useful as therapeutic active substances for the treatment and/or prophylaxis of diseases or disorders that are associated with RAS, e.g., KRAS G12C.

In some embodiments, the present disclosure provides a method of inhibiting RAS-mediated cell signaling comprising contacting a cell with an effective amount of one or more compounds of the present disclosure (e.g., a compound of Formula I (e.g., Formula I-1, I-2, I-3A, I-3A-1, I-3A-C, I-3A-N, I-3B, I-3C, I-4A, I-4B, I-4C, I-3B-1, I-3C-1, I-4A-1, I-4B-1, I-4C-1, I-5, I-6, I-7, or I-8), Formula II, Formula III, Formula IV, any of compound Nos. 1-186, or a pharmaceutically acceptable salt thereof). Inhibition of RAS-mediated signal transduction can be assessed and demonstrated by a wide variety of ways known in the art. Non-limiting examples include a showing of (a) a decrease in GTPase activity of RAS; (b) a decrease in GTP binding affinity or an increase in GDP binding affinity; (c) an increase in $K_{off}$ of GTP or a decrease in $K_{off}$ of GDP; (d) a decrease in the levels of signaling transduction molecules downstream in the RAS pathway, such as a decrease in pMEK, pERK, or pAKT levels; and/or (e) a decrease in binding of RAS complex to downstream signaling molecules including but not limited to Raf. Kits and commercially available assays can be utilized for determining one or more of the above.

In some embodiments, the present disclosure provides a method of inhibiting KRAS, HRAS, and/or NRAS G12C in a cell, the method comprising contacting the cell with an effective amount of one or more compounds of the present disclosure (e.g., a compound of Formula I (e.g., Formula I-1, I-2, I-3A, I-3A-1, I-3A-C, I-3A-N, I-3B, I-3C, I-4A, I-4B, I-4C, I-3B-1, I-3C-1, I-4A-1, I-4B-1, I-4C-1, I-5, I-6, I-7, or I-8), Formula II, Formula III, Formula IV, any of compound Nos. 1-186, or a pharmaceutically acceptable salt thereof).

In some embodiments, the present disclosure provides a method of treating a disease or disorder, e.g., a cancer associated with G12C mutation of KRAS, HRAS and/or NRAS, such as a cancer associated with KRAS G12C, in a subject in need thereof. In some embodiments, the method comprises administering to the subject a therapeutically effective amount of a compound of the present disclosure (e.g., a compound of Formula I (e.g., Formula I-1, I-2, I-3A, I-3A-1, I-3A-C, I-3A-N, I-3B, I-3C, I-4A, I-4B, I-4C, I-3B-1, I-3C-1, I-4A-1, I-4B-1, I-4C-1, I-5, I-6, I-7, or I-8), Formula II, Formula III, Formula IV, any of compound Nos. 1-186, or a pharmaceutically acceptable salt thereof) or a therapeutically effective amount of a pharmaceutical composition described herein.

In some embodiments, a method for treatment of cancer is provided, the method comprising administering to a subject in need thereof an effective amount of any of the compound of the present disclosure (e.g., a compound of Formula I (e.g., Formula I-1, I-2, I-3A, I-3A-1, I-3A-C, I-3A-N, I-3B, I-3C, I-4A, I-4B, I-4C, I-3B-1, I-3C-1, I-4A-1, I-4B-1, I-4C-1, I-5, I-6, I-7, or I-8), Formula II, Formula III, Formula IV, any of compound Nos. 1-186, or a pharmaceutically acceptable salt thereof) or a pharmaceutical composition comprising the compound of the present disclosure. In some embodiments, the cancer comprises a G12C mutation of KRAS, HRAS and/or NRAS, e.g., a KRAS G12 mutation. Determining whether a tumor or cancer comprises a G12C mutation of KRAS, HRAS and/or NRAS is known in the art, for example, as described in US2018/0334454. In various embodiments, the cancer can be pancreatic cancer, endometrial cancer, colorectal cancer or lung cancer (e.g., non-small cell lung cancer). In some embodiments, the cancer is a hematological cancer (e.g., described herein). In some embodiments, the cancer is MYH associated polyposis. In some embodiments, the cancer is gall bladder cancer, thyroid cancer, or bile duct cancer. Non-limiting examples of cancer also include acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, Burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myeloproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplasia syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or viral-induced cancer.

In some embodiments the present disclosure provides a method of treating a disease or disorder (e.g., a cancer described herein) in a subject in need thereof, wherein the method comprises determining if the subject has a G12C mutation of KRAS, HRAS and/or NRAS, e.g., KRAS G12C mutation, and if the subject is determined to have the KRAS, HRAS and/or NRAS G12C mutation, e.g., KRAS G12C mutation, then administering to the subject a therapeutically effective dose of at least one compound of the present disclosure (e.g., a compound of Formula I (e.g., Formula I-1, I-2, I-3A, I-3A-1, I-3A-C, I-3A-N, I-3B, I-3C, I-4A, I-4B, I-4C, I-3B-1, I-3C-1, I-4A-1, I-4B-1, I-4C-1, I-5, I-6, I-7, or I-8), Formula II, Formula III, Formula IV, any of compound Nos. 1-186, or a pharmaceutically acceptable salt thereof) or a pharmaceutical composition comprising the at least one compound of the present disclosure.

G12C mutation of KRAS, HRAS and/or NRAS has also been identified in hematological malignancies (e.g., cancers that affect blood, bone marrow and/or lymph nodes). Accordingly, certain embodiments are directed to a method of treating hematological malignancy in a subject in need thereof, the method typically comprises administration of a compound of the present disclosure (e.g., in the form of a pharmaceutical composition) to the subject. Such malignancies include, but are not limited to leukemias and lymphomas, such as Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AMoL) and/or other leukemias. In some embodiments, the hematological malignancy can also include lymphomas such as Hodgkins lymphoma or non-Hodgkins lymphoma, plasma cell malignancies such as multiple myeloma, mantle cell lymphoma, and Waldenstrom's macroglubunemia.

Compounds of the present disclosure can be used as a monotherapy or in a combination therapy. In some embodiments, the combination therapy includes treating the subject with a chemotherapeutic agent, therapeutic antibody, radiation, cell therapy, or immunotherapy. In some embodiments, compounds of the present disclosure can also be co-administered with an additional pharmaceutically active compound, either concurrently or sequentially in any order, to a subject in need thereof (e.g., a subject having a cancer associated with KRAS G12C mutation as described herein). In some embodiments, the additional pharmaceutically active compound can be a chemotherapeutic agent, a therapeutic antibody, etc. Any of the known chemotherapeutics can be used in combination with the compounds of the present disclosure. In some embodiments, compounds of the present disclosure can also be used in combination with a radiation therapy, hormone therapy, cell therapy, surgery and immunotherapy, which therapies are well known to those skilled in the art.

Many chemotherapeutics are presently known in the art and can be used in combination with the compounds of the present disclosure. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (Imatinib Mesylate), Kyprolis® (carfilzomib), Velcade® (bortezomib), Casodex (bicalutamide), Iressa® (gefitinib), venetoclax, and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel and docetaxel; retinoic acid; esperamicins; capecitabine; and pharmaceutically acceptable salts, acids or derivatives of any of the above.

Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO).

Where desired, the compounds or pharmaceutical composition of the present disclosure can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

The compounds of the present disclosure may also be used in combination with an additional pharmaceutically active compound that disrupts or inhibits RAS-RAF-ERK or PI3K-AKT-TOR signaling pathways. In other such combinations, the additional pharmaceutically active compound is a PD-1 and PD-L1 antagonist. The compounds or pharmaceutical compositions of the disclosure can also be used in combination with an amount of one or more substances selected from EGFR inhibitors, MEK inhibitors, PI3K inhibitors, AKT inhibitors, TOR inhibitors, Mcl-1 inhibitors, BCL-2 inhibitors, SHP2 inhibitors, proteasome inhibitors, and immune therapies, including monoclonal antibodies, immunomodulatory imides (IMiDs), anti-PD-1, anti-PDL-1, anti-CTLA4, anti-LAG1, and anti-OX40 agents, GITR agonists, CAR-T cells, and BiTEs.

Exemplary anti-PD-1 or anti-PDL-1 antibodies and methods for their use are described by Goldberg et al., Blood 110(1):186-192 (2007), Thompson et al., Clin. Cancer Res. 13(6):1757-1761 (2007), and Korman et al., International Application No. PCT/JP2006/309606 (publication no. WO 2006/121168 A1), each of which are expressly incorporated by reference herein, include: pembrolizumab (Keytruda®), nivolumab (Opdivo®), Yervoy™ (ipilimumab) or Tremelimumab (to CTLA-4), galiximab (to B7.1), M7824 (a bifunctional anti-PD-L1/TGF-β Trap fusion protein), AMP224 (to B7DC), BMS-936559 (to B7-H1), MPDL3280A (to B7-H1), MEDI-570 (to ICOS), AMG 404, AMG557 (to B7H2), MGA271 (to B7H3), IMP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuzumab (to CD40), Muromonab-CD3 (to CD3), Ipilumumab (to CTLA-4). Immune therapies also include genetically engineered T-cells (e.g., CAR-T cells) and bispecific antibodies (e.g., BiTEs). Non-limiting useful additional agents also include anti-EGFR antibody and small molecule EGFR inhibitors such as cetuximab (Erbitux), panitumumab (Vectibix), zalutumumab, nimotuzumab, matuzumab, gefitinib, erlotinib (Tarceva), lapatinib (TykerB), etc. Non-limiting useful additional agents also include CDK inhibitors such as CDK4/6 inhibitors, such as seliciclib, UCN-01, P1446A-05, palbociclib (PD-0332991), abemaciclib, dinaciclib, P27-00, AT-7519, RGB286638, and SCH727965, etc. Non-limiting useful additional agents also include MEK inhibitors such as trametinib (Mekinist®), CI-1040, AZD6244, PD318088, PD98059, PD334581, RDEA119, ARRY-142886, ARRY-438162, and PD-325901. WO 2019/213516 describes a list of additional agents that can be used in combination with KRAS G12C inhibitors. These additional agents can also be used in combination with the compounds of the present disclosure.

As shown in the Examples section, the combination of Compound Nos. 44, 126, and 145 with various agents including platinum based drugs (cisplatin or carboplatin), a SHP2 inhibitor (RMC-4550, (3-((3S,4S)-4-amino-3-methyl-2-oxa-8-azaspiro[4.5]decan-8-yl)-6-(2,3-dichlorophenyl)-5-methylpyrazin-2-yl)methanol), a MEK inhibitor (trametinib), were shown to provide synergistic effect in reducing tumor volume in several animal models. Thus, in some embodiments, compounds of the present disclosure (e.g., compound 44, 126, or 145) can be used in combination with a platinum based drug (e.g., cisplatin or carboplatin), a SHP2 inhibitor (such as RMC-4550, RMC-4630, TNO155), and/or a MEK inhibitor (such as trametinib).

The administering herein is not limited to any particular route of administration. For example, in some embodiments, the administering can be orally, nasally, transdermally, pulmonary, inhalationally, buccally, sublingually, intraperitoneally, subcutaneously, intramuscularly, intravenously, rectally, intrapleurally, intrathecally and parenterally. In some embodiments, the administering is orally.

Dosing regimen including doses can vary and can be adjusted, which can depend on the recipient of the treatment, the disease or disorder being treated and the severity thereof, the composition containing the compound, the time of administration, the route of administration, the duration of treatment, the compound potency, its rate of clearance and whether or not another drug is co-administered.

Definitions

It is meant to be understood that proper valences are maintained for all moieties and combinations thereof.

It is also meant to be understood that a specific embodiment of a variable moiety herein can be the same or different as another specific embodiment having the same identifier.

Suitable atoms or groups for the variables herein are independently selected. The definitions of the variables can be combined. Using Formula I as an example, any of the definitions of one of X, $R^1$, $R^2$, $R^3$, $R^4$, $R^7$, $R^8$, Het, n, U, $A^1$, $A^2$, $A^3$, $A^4$, and $A^5$ in Formula I can be combined with any of the definitions of the others of X, $R^1$, $R^2$, $R^3$, $R^4$, $R^7$, $R^8$, Het, n, U, $A^1$, $A^2$, $A^3$, $A^4$, and $A^5$ in Formula I. Such combination is contemplated and within the scope of the present invention.

Definitions of specific functional groups and chemical terms are described in more detail below. The chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987. The disclosure is not intended to be limited in any manner by the exemplary listing of substituents described herein.

Compounds of the present disclosure can comprise one or more asymmetric centers and/or axial chirality, and thus can exist in various isomeric forms, e.g., enantiomers and/or diastereomers. For example, the compounds described herein can be in the form of an individual enantiomer, diastereomer, atropisomer, or geometric isomer, or can be in the form of a mixture of stereoisomers, including racemic mixtures and mixtures enriched in one or more stereoisomer. Isomers can be isolated from mixtures by methods known to those skilled in the art, including chiral high performance liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, Tables of *Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers including racemic mixtures. When a stereochemistry is specifically drawn, it should be understood that with respect to that particular chiral center or axial chirality, the compound exists predominantly as the as-drawn stereoisomer, such as with less than 20%, less than 10%, less than 5%, less than 1%, by weight, by HPLC area, or both, or with a non-detectable amount of the other stereoisomer(s). The presence and/or amounts of stereoisomers can be determined by those skilled in the art in view of the present disclosure, including through the use of chiral HPLC.

Compounds of the present disclosure can have atropisomers. In any of the embodiments described herein, when applicable, the compound of the present disclosure can exist as a mixture of atropisomers in any ratio. In some embodiments, when applicable, the compound can exist as an isolated individual atropisomer substantially free (e.g., with less than 20%, less than 10%, less than 5%, less than 1%, by weight, by HPLC area, or both, or with a non-detectable amount) of the other atropisomer(s). The Examples section shows some exemplary isolated atropisomers of compounds of the present disclosure. As understood by those skilled in the art, when the rotation is restricted around a single bond, e.g., a biaryl single bond, a compound may exist in a mixture of atropisomers with each individual atropisomer isolable.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

As used herein, the term "compound(s) of the present disclosure" or "compound(s) of the present invention" refers to any of the compounds described herein according to Formula I (e.g., Formula I-1, I-2, I-3A, I-3A-1, I-3A-C, I-3A-N, I-3B, I-3C, I-4A, I-4B, I-4C, I-3B-1, I-3C-1, I-4A-1, I-4B-1, I-4C-1, I-5, I-6, I-7, or I-8), Formula II, Formula III, Formula IV, any of compound Nos. 1-186, isotopically labeled compound(s) thereof (such as a deuterated analog wherein one of the hydrogen atoms is substituted with a deuterium atom with an abundance above its natural abundance), possible stereoisomers thereof (including diastereoisomers, enantiomers, and racemic mixtures), geometric isomers thereof, atropisomers thereof, tautomers thereof, conformational isomers thereof, and/or pharmaceutically acceptable salts thereof (e.g., acid addition salt such as HCl salt or base addition salt such as Na salt). For the avoidance of doubt, Compound Nos. 1-186 or Compounds 1-186 refers to the compounds described herein labeled as integers 1, 2, 3, . . . , 186, see for example the title compounds of Examples 1-23 and Table 1. Hydrates and solvates of the compounds of the present disclosure are considered compositions of the present disclosure, wherein the compound(s) is in association with water or solvent, respectively.

Compounds of the present disclosure can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^2H$, $^3H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

As used herein, the phrase "administration" of a compound, "administering" a compound, or other variants thereof means providing the compound or a prodrug of the compound to the individual in need of treatment.

As used herein, the term "alkyl" as used by itself or as part of another group refers to a straight- or branched-chain aliphatic saturated hydrocarbon. In some embodiments, the alkyl which can include one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is a straight chain $C_{1-10}$ alkyl group. In another embodiment, the alkyl group is a branched chain $C_{3-10}$ alkyl group. In another embodiment, the alkyl group is a straight chain $C_{1-6}$ alkyl group. In another embodiment, the alkyl group is a branched chain $C_{3-6}$ alkyl group. In another embodiment, the alkyl group is a straight chain $C_{1-4}$ alkyl group. For example, a $C_{1-4}$ alkyl group as used herein refers to a group selected from methyl, ethyl, propyl (n-propyl), isopropyl, butyl (n-butyl), sec-butyl, tert-butyl, and isobutyl. An optionally substituted $C_{1-4}$ alkyl group refers to the $C_{1-4}$ alkyl group as defined, optionally substituted with one or more permissible substituents as described herein. As used herein, the term "alkylene" as used by itself or as part of another group refers to a divalent radical derived from an alkyl group. For example, non-limiting straight chain alkylene groups include —$CH_2$—$CH_2$—$CH_2$—$CH_2$—, —$CH_2$—$CH_2$—$CH_2$—, —$CH_2$—$CH_2$—, and the like.

As used herein, the term "heteroalkyl" refers to an alkyl group as defined above, with one or more carbon being replaced with a heteroatom, such as O or N. A heteroalkyl can be designated by its number of carbons. For example, a $C_{1-4}$ heteroalkyl refers to a heteroalkyl group containing 1-4 carbons. When optionally substituted, either the heteroatom or the carbon atom of the heteroalkyl group can be substituted with a permissible substituent. As used herein, the term "heteroalkylene" as used by itself or as part of another group refers to a divalent radical derived from a heteroalkyl group.

As used herein, the term "alkenyl" as used by itself or as part of another group refers to an alkyl group as defined above containing one, two or three carbon-to-carbon double bonds. In one embodiment, the alkenyl group is a $C_{2-6}$ alkenyl group. In another embodiment, the alkenyl group is a $C_{2-4}$ alkenyl group. Non-limiting exemplary alkenyl groups include ethenyl, propenyl, isopropenyl, butenyl, sec-butenyl, pentenyl, and hexenyl.

As used herein, the term "alkynyl" as used by itself or as part of another group refers to an alkyl group as defined above containing one to three carbon-to-carbon triple bonds. In one embodiment, the alkynyl has one carbon-carbon triple bond. In one embodiment, the alkynyl group is a $C_{2-6}$ alkynyl group. In another embodiment, the alkynyl group is a $C_{2-4}$ alkynyl group. Non-limiting exemplary alkynyl groups include ethynyl, propynyl, butynyl, 2-butynyl, pentynyl, and hexynyl groups.

As used herein, the term "alkoxy" as used by itself or as part of another group refers to a radical of the formula $OR^{a1}$, wherein $R^{a1}$ is an alkyl.

As used herein, the term "haloalkyl" as used by itself or as part of another group refers to an alkyl substituted with one or more fluorine, chlorine, bromine and/or iodine atoms. In preferred embodiments, the haloalkyl is an alkyl group substituted with one, two, or three fluorine atoms. In one embodiment, the haloalkyl group is a $C_{1-10}$ haloalkyl group. In one embodiment, the haloalkyl group is a $C_{1-6}$ haloalkyl group. In one embodiment, the haloalkyl group is a $C_{1-4}$ haloalkyl group.

"Carbocyclyl" or "carbocyclic" as used by itself or as part of another group refers to a radical of a non-aromatic cyclic hydrocarbon group having from 3 to 10 ring carbon atoms ("$C_{3-10}$ carbocyclyl") and zero heteroatoms in the non-aromatic ring system. The carbocyclyl group can be either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Non-limiting exemplary carbocyclyl groups include cyclopropyl, cyclobutyl, cyclopentyl, cyclohexyl, cycloheptyl, cyclooctyl, norbornyl, decalin, adamantyl, cyclopentenyl, and cyclohexenyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl").

"Heterocyclyl" or "heterocyclic" as used by itself or as part of another group refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" as used by itself or as part of another group refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{1-4}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system.

"Aralkyl" as used by itself or as part of another group refers to an alkyl substituted with one or more aryl groups, preferably, substituted with one aryl group. Examples of aralkyl include benzyl, phenethyl, etc. When an aralkyl is said to be optionally substituted, either the alkyl portion or the aryl portion of the aralkyl can be optionally substituted.

"Heteroaryl" as used by itself or as part of another group refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" as used by itself or as part of another group refers to an alkyl substituted with one or more heteroaryl groups, preferably, substituted with one heteroaryl group. When a heteroaralkyl is said to be optionally substituted, either the alkyl portion or the heteroaryl portion of the heteroaralkyl can be optionally substituted.

As commonly understood by those skilled in the art, alkylene, alkenylene, alkynylene, carbocyclylene, heterocyclylene, arylene, and heteroarylene refer to the corresponding divalent radicals of alkyl, alkenyl, alkynyl, carbocyclyl, heterocyclyl, aryl, and heteroaryl groups, respectively.

An "optionally substituted" group, such as an optionally substituted alkyl, optionally substituted alkenyl, optionally substituted alkynyl, optionally substituted carbocyclyl, optionally substituted heterocyclyl, optionally substituted aryl, and optionally substituted heteroaryl groups, refers to the respective group that is unsubstituted or substituted. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent can be the same or different at each position. Typically, when substituted, the optionally substituted groups herein can be substituted with 1-5 substituents. Substituents can be a carbon atom substituent, a nitrogen atom substituent, an oxygen atom substituent or a sulfur atom substituent, as applicable.

Unless expressly stated to the contrary, combinations of substituents and/or variables are allowable only if such combinations are chemically allowed and result in a stable compound. A "stable" compound is a compound that can be prepared and isolated and whose structure and properties remain or can be caused to remain essentially unchanged for a period of time sufficient to allow use of the compound for the purposes described herein (e.g., therapeutic administration to a subject).

In some embodiments, the "optionally substituted" non-aromatic group herein can be unsubstituted or substituted with 1, 2, or 3 substituents independently selected from F, Cl, —OH, oxo (as applicable), $C_{1-4}$ alkyl, $C_{2-4}$ alkenyl, $C_{2-4}$ alkynyl, $C_{1-4}$ alkoxy, $C_{3-6}$ cycloalkyl, $C_{3-6}$ cycloalkoxy, phenyl, 5 or 6 membered heteroaryl containing 1 or 2 ring heteroatoms independently selected from O, S, and N, 4-7 membered heterocyclyl containing 1 or 2 ring heteroatoms independently selected from O, S, and N, wherein each of the alkyl, alkenyl, alkynyl, alkoxy, cycloalkyl, cycloalkoxy phenyl, heteroaryl, and heterocyclyl, is optionally substituted with 1, 2, or 3 substituents independently selected from F, —OH, oxo (as applicable), $C_{1-4}$ alkyl, fluoro-substituted $C_{1-4}$ alkyl (e.g., $CF_3$), $C_{1-4}$ alkoxy and fluoro-substituted $C_{1-4}$ alkoxy. In some embodiments, the "optionally substituted" aromatic group (including aryl and heteroaryl groups) herein can be unsubstituted or substituted with 1, 2, or 3 substituents independently selected from F, Cl, —OH, —CN, $C_{1-4}$ alkyl, $C_{2-4}$ alkenyl, $C_{2-4}$ alkynyl, $C_{1-4}$ alkoxy, $C_{3-6}$ cycloalkyl, $C_{3-6}$ cycloalkoxy, phenyl, 5 or 6 membered heteroaryl containing 1 or 2 ring heteroatoms independently selected from O, S, and N, 4-7 membered heterocyclyl containing 1 or 2 ring heteroatoms independently selected from O, S, and N, wherein each of the alkyl, alkenyl, alkynyl, alkoxy, cycloalkyl, cycloalkoxy, phenyl, heteroaryl, and heterocyclyl, is optionally substituted with 1, 2, or 3 substituents independently selected from F, —OH, oxo (as applicable), $C_{1-4}$ alkyl, fluoro-substituted $C_{1-4}$ alkyl, $C_{1-4}$ alkoxy and fluoro-substituted $C_{1-4}$ alkoxy.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_2$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{bb})N(R^{bb})_2$, —$NR^{bb}C(=NR^{bb})N(R^{bb})_2$, —$C(=O)NR^{bb}SO_2R^{aa}$, —$NR^{bb}SO_2R^{aa}$, —$SO_2N(R^{bb})_2$, —$SO_2R^{aa}$, —$SO_2OR$—, —$OSO_2R^{aa}$, —$S(=O)R^{aa}$, —$OS(=O)R^{aa}$, —$Si(R^{aa})_3$, —$OSi(R^{aa})_3$ —$C(=S)N(R^{bb})_2$, —$C(=O)SR^{aa}$, —$C(=S)SR^{aa}$, —$SC(=S)SR^{aa}$, —$SC(=O)SR^{aa}$, —$OC(=O)SR^{aa}$, —$SC(=O)OR^{aa}$, —$SC(=O)R^{aa}$, —$P(=O)(R^{aa})_2$, —$P(=O)(OR^{cc})_2$, —$OP(=O)(R^{aa})_2$, —$OP(=O)(OR^{cc})_2$, —$P(=O)(N(R^{bb})_2)_2$, —$OP(=O)(N(R^{bb})_2)_2$, —$NR^{bb}P(=O)(R^{aa})_2$, —$NR^{bb}P(=O)(OR^{cc})_2$, —$NR^{bb}P(=O)(N(R^{bb})_2)_2$, —$P(R^{cc})_2$, —$P(OR^{cc})_2$, —$P(R^{cc})_3^+X^-$, —$P(OR^{cc})_3^+X^-$, —$P(R^{cc})_4$, —$P(OR^{cc})_4$, —$OP(R^{cc})_2$, —$OP(R^{cc})_3^+X^-$, —$OP(OR^{cc})_2$, —$OP(OR^{cc})_3^+X^-$, —$OP(R^{cc})_4$, —$OP(OR^{cc})_4$, —$B(R^{aa})_2$, —$B(OR^{cc})_2$, —$BR^{aa}(OR^{cc})$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups; wherein $X^-$ is a counterion; or two geminal hydrogens on a carbon atom are replaced with the group =O, =S, =NN$(R^{bb})_2$, =$NNR^{bb}C(=O)R^{aa}$, =$NNR^{bb}C(=O)OR^{aa}$, $NNR^{bb}S(=O)_2R^{aa}$, =$NR^{bb}$, or =$NOR^{cc}$; each instance of $R^{aa}$ is, independently, selected from $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;
each instance of $R^{bb}$ is, independently, selected from hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(Re)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ haloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X is a counterion;

each instance of R$^{ee}$ is, independently, selected from C$_{1-6}$ alkyl, C$_{1-6}$ haloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ haloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-4}$ alkyl, —SS(C$_{1-6}$ alkyl), —C(=O)(C$_{1-6}$alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-4}$ alkyl), —N(C$_{1-6}$ alkyl)C(=O)(C$_{1-4}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$alkyl)$_3$, —OSi(C$_{1-6}$ alkyl)$_3$-C(=S)N(C$_{1-6}$alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-4}$ alkyl, C$_{1-6}$haloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$]$^-$, BPh$_4$$^-$, Al(OC(CF$_3$)$_3$)$_4$$^-$, and a carborane anion (e.g., CB$_{11}$H$_{12}$$^-$ or (HCB$_{11}$Me$_5$Br$_6$)$^-$). Exemplary counterions which may be multivalent include CO$_3$$^{2-}$, HPO$_4$$^{2-}$, PO$_4$$^{3-}$, B$_4$O$_7$$^{2-}$, SO$_4$$^{2-}$, S$_2$O$_3$$^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$—, —C(=NR$^{bb}$)N(R$^{bb}$)$_2$, —C(=O)NR$^{bb}$SO$_2$R—, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rd groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl, ar-C$_{1-10}$ alkyl, heteroar-C$_{1-10}$ alkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protective Groups in Organic Synthesis*, T. W. Greene and P. G. M. Wuts, 3$^{rd}$ edition, John Wiley & Sons, 1999, incorporated by reference herein.

Exemplary oxygen atom substituents include, but are not limited to, —R$^{aa}$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protective Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, alkyl ethers or substituted alkyl ethers such as methyl, allyl, benzyl, substituted benzyls such as 4-methoxybenzyl, methoxylmethyl (MOM), benzyloxymethyl (BOM), 2-methoxyethoxymethyl (MEM), etc., silyl ethers such as trymethylsilyl (TMS), triethylsilyl (TES), triisopropylsilyl (TIPS), t-butyldimethylsilyl (TBDMS), etc., acetals or ketals, such as tetrahydropyranyl (THP), esters such as formate, acetate, chloroacetate, dichloroacetate, trichloroacetate, trifluoroacetate, methoxyacetate, etc., carbonates, sulfonates such as methanesulfonate (mesylate), benzylsulfonate, and tosylate (Ts), etc.

The term "leaving group" is given its ordinary meaning in the art of synthetic organic chemistry, for example, it can refer to an atom or a group capable of being displaced by a nucleophile. See, for example, Smith, *March Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art.

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

The term "subject" (alternatively referred to herein as "patient") as used herein, refers to an animal, preferably a mammal, most preferably a human, who has been the object of treatment, observation or experiment.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound described herein to a subject in need of such treatment.

EXAMPLES

The various starting materials, intermediates, and compounds of the preferred embodiments can be isolated and purified where appropriate using conventional techniques such as precipitation, filtration, crystallization, evaporation, distillation, and chromatography. Characterization of these compounds can be performed using conventional methods such as by melting point, mass spectrum, nuclear magnetic resonance, and various other spectroscopic analyses. Exemplary embodiments of steps for performing the synthesis of products described herein are described in greater detail infra.

Example 1. Synthesis of Compound 1

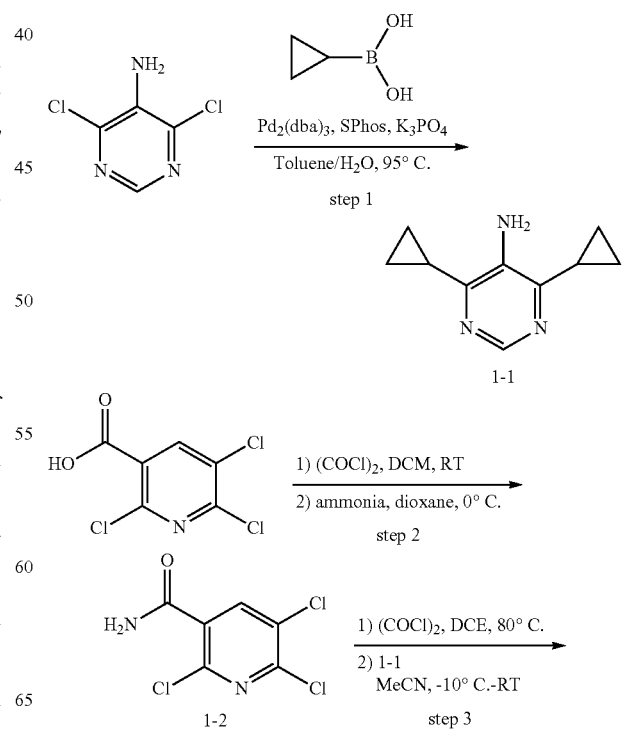

-continued

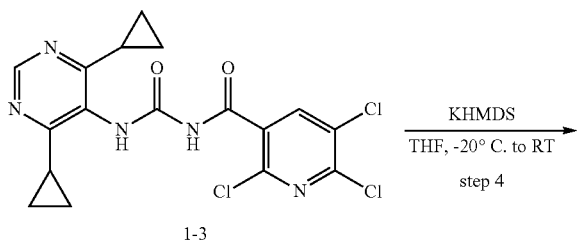

1-3

KHMDS
THF, -20° C. to RT
step 4

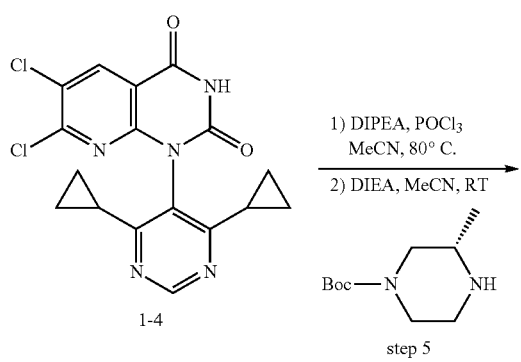

1-4

1) DIPEA, POCl₃
MeCN, 80° C.

2) DIEA, MeCN, RT step 5

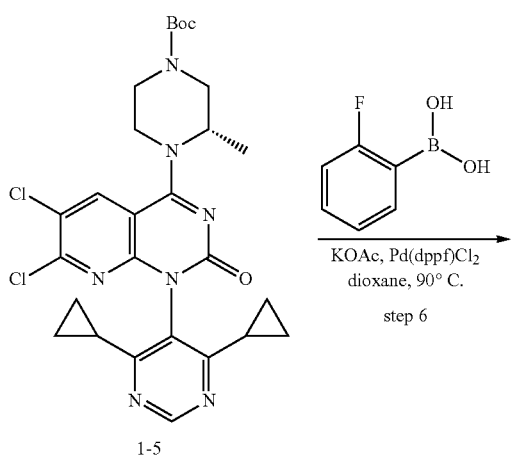

1-5

KOAc, Pd(dppf)Cl₂
dioxane, 90° C.

step 6

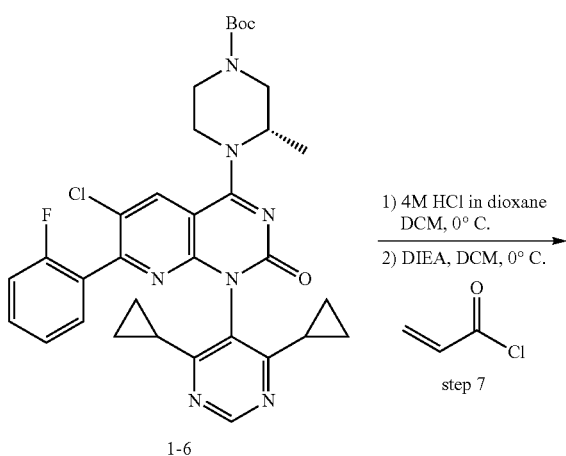

1-6

1) 4M HCl in dioxane
DCM, 0° C.

2) DIEA, DCM, 0° C.

step 7

-continued

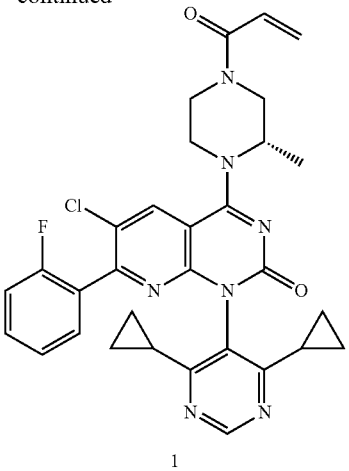

1

Step 1:

A mixture of 4.6-dichloropyrimidin-5-amine (8.15 g, 50 mmol), cyclopropylboronic acid (21.5 g, 250 mmol), K₃PO₄ (31.8 g, 150 mmol), Pd₂(dba)₃ (4.6 g, 5 mmol) and Sphos (4.1 g, 10 mmol) in toluene (180 mL) and water (20 mL) was stirred at 95° C. under nitrogen for 30 minutes. The reaction was cooled to room temperature and then washed with water. The mixture was extracted with ethyl acetate. The organic layer was dried over anhydrous sodium sulfate, filtered and concentrated. The residue was purified by flash column chromatography on silica gel (petroleum ether to petroleum ether/ethyl acetate=4/1) to afford 1-1.

Step 2: To a suspension of 2,5,6-trichloronicotinic acid (10 g, 44 mmol) in dichloromethane (100 mL) at room temperature was added oxalyl chloride (11 g, 88 mmol) and 15 drops of dry DMF. After 30 minutes, the resulting solution was concentrated to give a residue which was dissolved in dioxane (40 mL). 100 mL of ammonia (28% NH₃ in water) was added dropwise at 0° C., and the reaction mixture was allowed to stir for an additional 10 minutes, filtered, and washed with water. The filter cake was collected and freeze-dried to afford 1-2.

Step 3: A solution of 1-2 (550 mg, 2.44 mmol) in DCE (5 mL) was treated with oxalyl chloride (464.5 mg, 3.66 mmol). The mixture was stirred for 45 minutes at 80° C. and then concentrated. The residue was dissolved in acetonitrile (5 mL) and cooled to −10° C., and a solution of 1-1 (1 g, 5.86 mmol) in acetonitrile (5 mL) was added. The resulting solution was stirred at room temperature overnight and then concentrated. The residue was purified by flash column chromatography on silica gel (ethyl acetate/petroleum ether=1/9 to 1/3) to afford 1-3.

Step 4: To a stirred solution of 1-3 (845 mg, 1.98 mmol) in THF (40 mL) at −20° C. was added KHMDS (5 mL, 1 M in THF, 5.0 mmol). The resulting mixture was then stirred at room temperature for 2 hours. The reaction was quenched with sat. NH₄Cl(aq.). and extracted with ethyl acetate. The combined organic layers were dried over anhydrous sodium sulfate and concentrated. The residue was purified by flash column chromatography on silica gel (ethyl acetate/petroleum ether=1/9 to 2/1) to afford 1-4.

Step 5: A mixture of 1-4 (250 mg, 0.64 mmol), DIEA (107.6 mg, 0.83 mmol) and POCl₃ (117.9 mg, 0.77 mmol) in MeCN (3 mL) was stirred at 80° C. for 30 minutes. The reaction mixture was cooled to −10° C. and DIEA (248.4 mg, 1.92 mmol) was added, followed by addition of a solution of tert-butyl (3S)-3-methylpiperazine-1-carboxylate (384.9 mg, 1.92 mmol) in MeCN (1 mL) dropwise. The resulting solution was stirred at room temperature for 1 hour. The reaction was quenched with ice and extracted with ethyl acetate. The combined organic layers were dried over anhydrous sodium sulfate and concentrated. The residue was purified by flash column chromatography on silica gel (ethyl acetate/petroleum ether=1/4 to 1/1) to afford 1-5.

Step 6: A mixture of 1-5 (100 mg, 0.18 mmol), 2-fluorophenylboronic acid (48.9 mg, 0.35 mmol), KOAc (85.7 mg, 0.87 mmol) and Pd(dppf)Cl$_2$ (12.8 mg, 0.017 mmol) in 1,4-dioxane (2 mL) and H$_2$O (3 drops) was stirred at 90° C. for 1.5 h under N$_2$. The mixture was cooled and extracted with EtOAc. The combined organic layers were dried over anhydrous Na$_2$SO$_4$ and concentrated. The residue was purified by a prep-TLC (CH$_2$Cl$_2$/MeOH=15/1) to afford 1-6.

Step 7: A solution of 1-6 (70 mg, 0.11 mmol) and HCl in 1,4-dioxane (4 M, 1 mL, 4 mmol) in DCM (2 mL) was stirred at 0° C. for 2 h. The mixture was then concentrated to give a residue which was dissolved in DCM (3 mL). DIEA (171.7 mg, 1.33 mmol) was added at 0° C. followed by addition of acryloyl chloride (10.2 mg, 0.11 mmol) in DCM (1 mL) dropwise. The mixture was stirred at 0° C. for 10 minutes, and was then concentrated to give a residue which was purified by a prep-HPLC (aqueous NH$_4$HCO$_3$ (10 mM) with acetonitrile (30%-54%)) to afford compound 1 (30 mg). LCMS (ESI, m/z): [M+H]$^+$=586.3; HNMR (300 MHz, DMSO-d$_6$, ppm): δ 8.73 (s, 1H), 8.47 (s, 1H), 7.55 (m, 1H), 7.40-7.28 (m, 3H), 6.87 (m, 1H), 6.24-6.18 (m, 1H), 5.78 (dd, J=10.4, 2.4 Hz, 1H), 4.98 (brs, 1H), 4.43-4.03 (m, 3H), 3.90-3.70 (m, 1H), 3.66-3.44 (m, 1H), 3.27-3.08 (m, 1H), 1.85-1.68 (m, 2H), 1.35 (d, J=6.7 Hz, 3H), 0.97-0.81 (m, 8H). FNMR (282 MHz, DMSO-d$_6$, ppm): δ −113.10 (1F).

Example 2 Synthesis of Compound 42

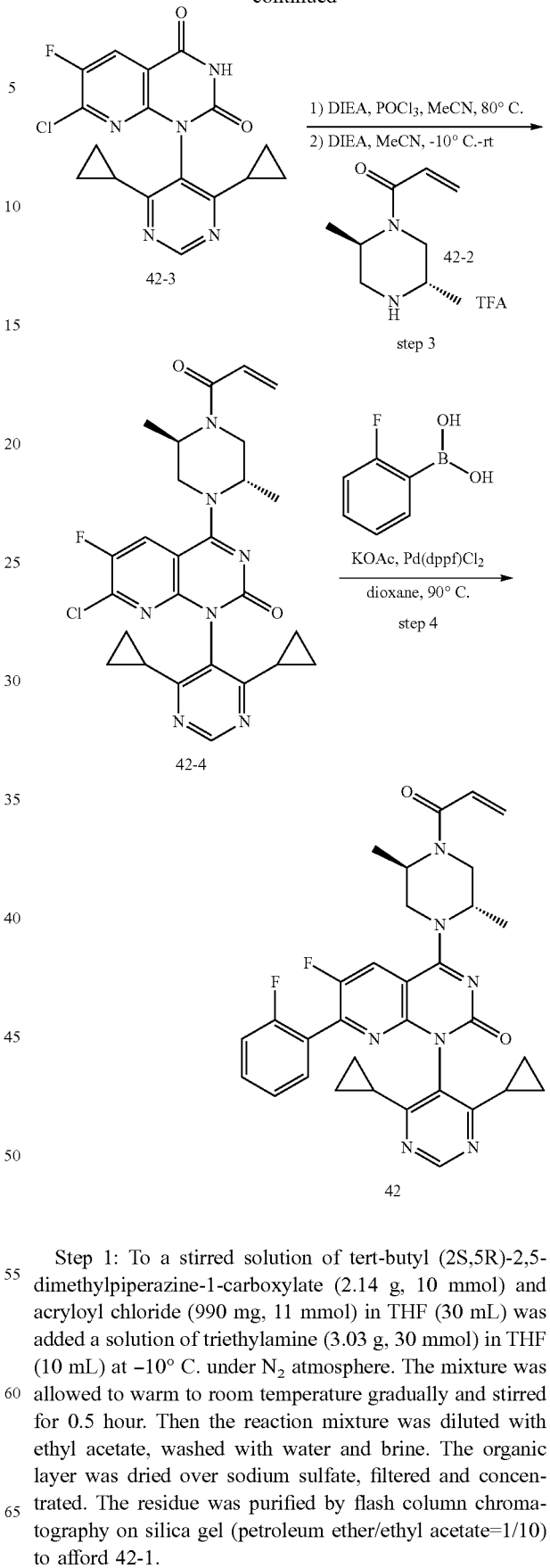

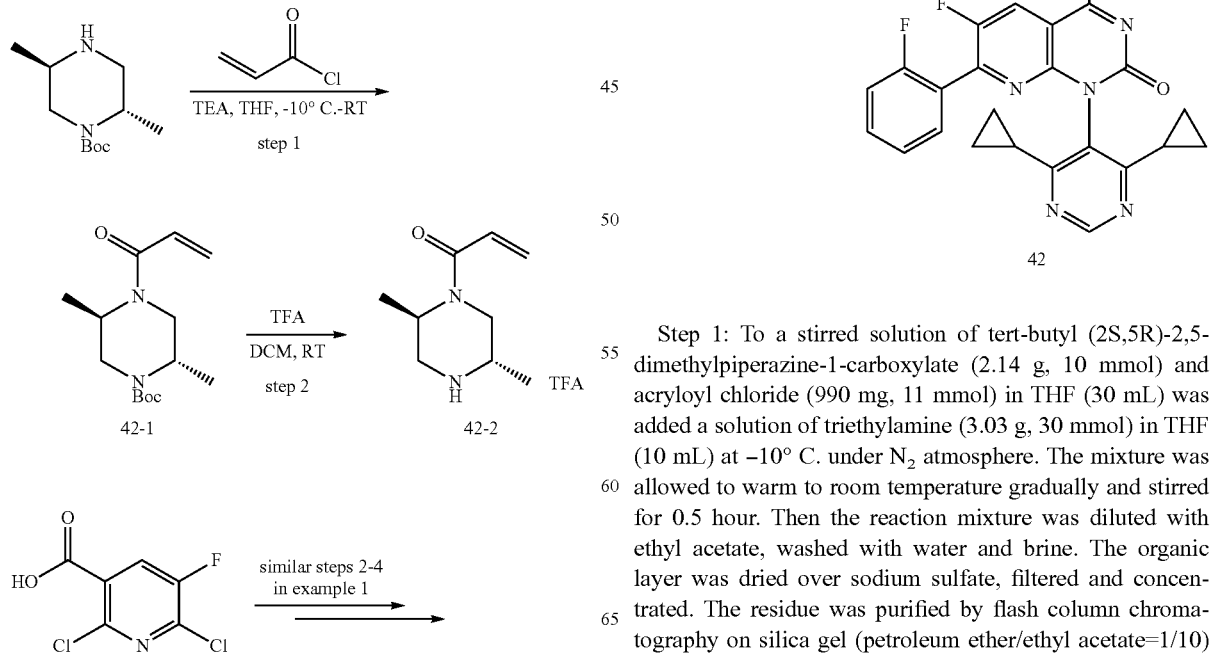

Step 1: To a stirred solution of tert-butyl (2S,5R)-2,5-dimethylpiperazine-1-carboxylate (2.14 g, 10 mmol) and acryloyl chloride (990 mg, 11 mmol) in THF (30 mL) was added a solution of triethylamine (3.03 g, 30 mmol) in THF (10 mL) at −10° C. under N$_2$ atmosphere. The mixture was allowed to warm to room temperature gradually and stirred for 0.5 hour. Then the reaction mixture was diluted with ethyl acetate, washed with water and brine. The organic layer was dried over sodium sulfate, filtered and concentrated. The residue was purified by flash column chromatography on silica gel (petroleum ether/ethyl acetate=1/10) to afford 42-1.

Step 2: To a solution of 42-1 (804 mg, 3 mmol) in DCM (5 mL) was added trifluoroacetic acid (2 mL). The mixture was stirred at room temperature for 1.5 hours and then concentrated to afford 42-2.

Step 3: To a solution of 42-3 (746 mg, 2 mmol) and DIEA (387 mg, 3 mmol) in acetonitrile (20 mL) was added $POCl_3$ (367 mg, 2.4 mmol) dropwise at room temperature. The mixture was stirred at 80° C. for 2 hours. Then the mixture was cooled to −10° C. and treated with DIEA (3.87 g, 30 mmol), followed by addition of a solution of 42-2 (1.58 g, 4 mmol) in acetonitrile (10 mL). The mixture was stirred at room temperature for 1 hour, then diluted with ethyl acetate, washed with water and brine. The organic layer was dried over sodium sulfate, filtered and concentrated. The residue was purified by column chromatography on silica gel (DCM to DCM/MeOH=10/1) to afford 42-4.

Step 4: A mixture of 42-4 (104 mg, 0.2 mmol), (2-fluorophenyl)boronic acid (42 mg, 0.3 mmol), potassium acetate (157 mg, 1.6 mmol), and [1,1'-bis(diphenylphosphino)ferrocene]dichloro-palladium (II) (15 mg, 0.02 mmol) in 1,4-dioxane (3 mL) and water (3 drops) was stirred at 90° C. for 3 hours under nitrogen atmosphere. The reaction mixture was filtered and the filtrate was purified by a prep-HPLC (acetonitrile with 0.05% TFA in water: 25% to 95%) to afford compound 42 (58 mg). LCMS (ESI, m/z): $[M+H]^+$ =584.1; HNMR (400 MHz, DMSO-$d_6$, ppm): δ 8.73 (s, 1H), 8.33-29 (m, 1H), 7.58-7.51 (m, 1H), 7.40-7.29 (m, 3H), 6.87-6.74 (m, 1H), 6.17-6.13 (m, 1H), 5.74-5.69 (m, 1H), 4.91-4.72 (m, 1.5H), 4.51-4.43 (m, 0.5H), 4.20-4.12 (m, 1.5H), 3.82-3.77 (m, 2H), 3.49-3.45 (m, 0.5H), 1.73-1.66 (m, 2H), 1.30-1.15 (m, 6H), 0.99-0.72 (m, 8H). FNMR (376 MHz, DMSO-$d_6$, ppm): δ −113.32 (1F), −128.68 (1F).

Example 3 Synthesis of Compound 13

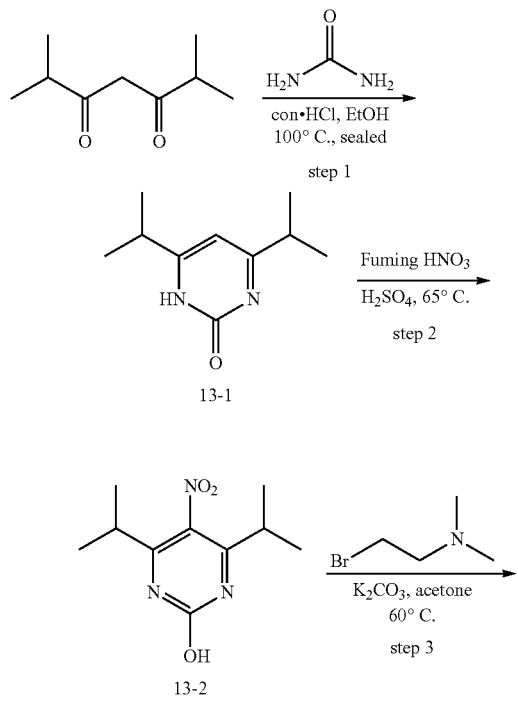

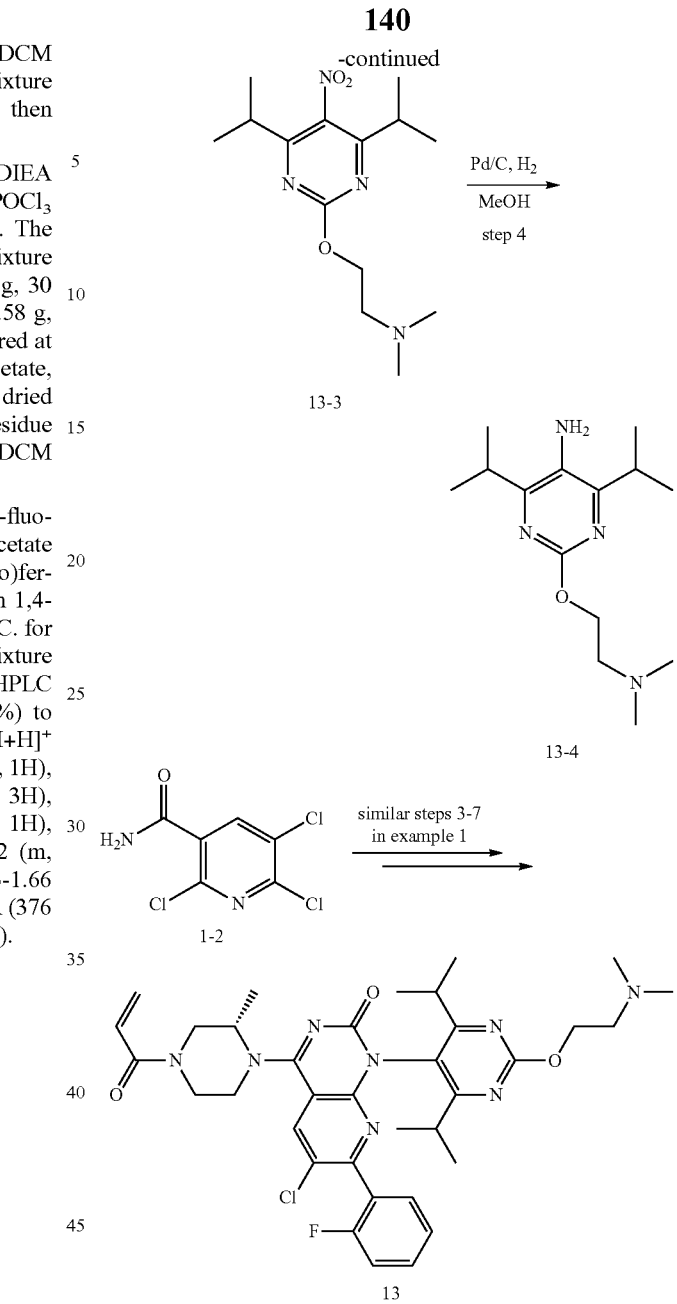

Step 1: To a 250 mL sealed tube was added 2,6-dimethylheptane-3,5-dione (10 g, 64.0 mmol), urea (7.69 g, 128.0 mmol), EtOH (120 mL) and con. HCl (50 mL) at room temperature. The resulting mixture was stirred at 100° C. for 18 hours. The mixture was cooled to room temperature and concentrated. Water and ethyl acetate were added, and the organic layer was separated, dried over anhydrous $Na_2SO_4$, filtered and concentrated to afford 13-1.

Step 2: To a stirred solution of 13-1 (8.40 g, 46.6 mmol) in con. $H_2SO_4$ (100 mL) was added fuming $HNO_3$ (11.75 g, 186.4 mmol) dropwise at room temperature. The resulting mixture was stirred at 65° C. for 6 hours. The mixture was cooled to room temperature, diluted with water, and extracted with ethyl acetate. The combined organic layers were washed with brine, dried over anhydrous $Na_2SO_4$, filtered and concentrated to afford 13-2.

Step 3: To a stirred solution of 13-2 (4 g, 17.8 mmol) and $K_2CO_3$ (4.9 g, 35.5 mmol) in acetone (80 mL) was added 2-bromo-N,N-dimethylethan-1-amine hydrobromide (4.96 g, 21.3 mmol) in portions at room temperature. The resulting mixture was stirred at 60° C. for 16 hours under nitrogen atmosphere, cooled to room temperature, and concentrated. The residue was diluted with water and extracted with DCM/MeOH (10/1). The combined organic layers were dried over anhydrous Na$_2$SO$_4$, filtered and concentrated to afford 13-3.

Step 4: A mixture of 13-3 (300 mg, 1.0 mmol), 10% Pd/C (38.1 mg) and MeOH (10 mL) was stirred at room temperature under H$_2$ atmosphere for overnight. The resulting mixture was filtered, and the filtrate was concentrated to afford 13-4.

Followed similar steps in example 1 to synthesize 13. LCMS (ESI, m/z): [M+H]$^+$=677.4; HNMR (400 MHz, DMSO-d$_6$, ppm): δ 8.48 (s, 1H), 7.60-7.44 (m, 1H), 7.32 (m, 2H), 7.20 (t, J=6.7 Hz, 1H), 6.98-6.79 (m, 1H), 6.22 (d, J=15.6 Hz, 1H), 5.78 (d, J=10.2 Hz, 1H), 4.98 (brs, 1H), 4.50-4.28 (m, 4H), 4.21-4.03 (m, 1H), 3.90-3.60 (m, 2H), 3.30-3.20 (m, 1H), 2.71-2.59 (m, 4H), 2.21 (s, 6H), 1.35 (d, J=6.6 Hz, 3H), 1.06 (d, J=6.5 Hz, 6H), 0.91 (d, J=6.4 Hz, 6H). FNMR (282 MHz, DMSO-d$_6$, ppm): δ −114.70 (1F).

Example 4 Synthesis of Compound 8

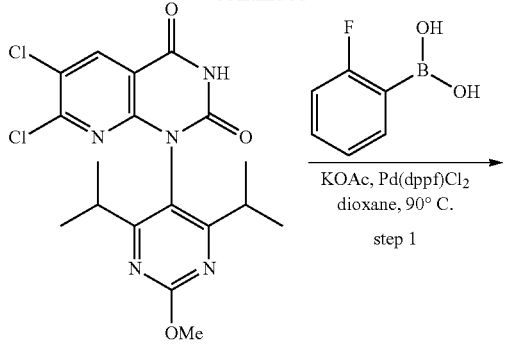

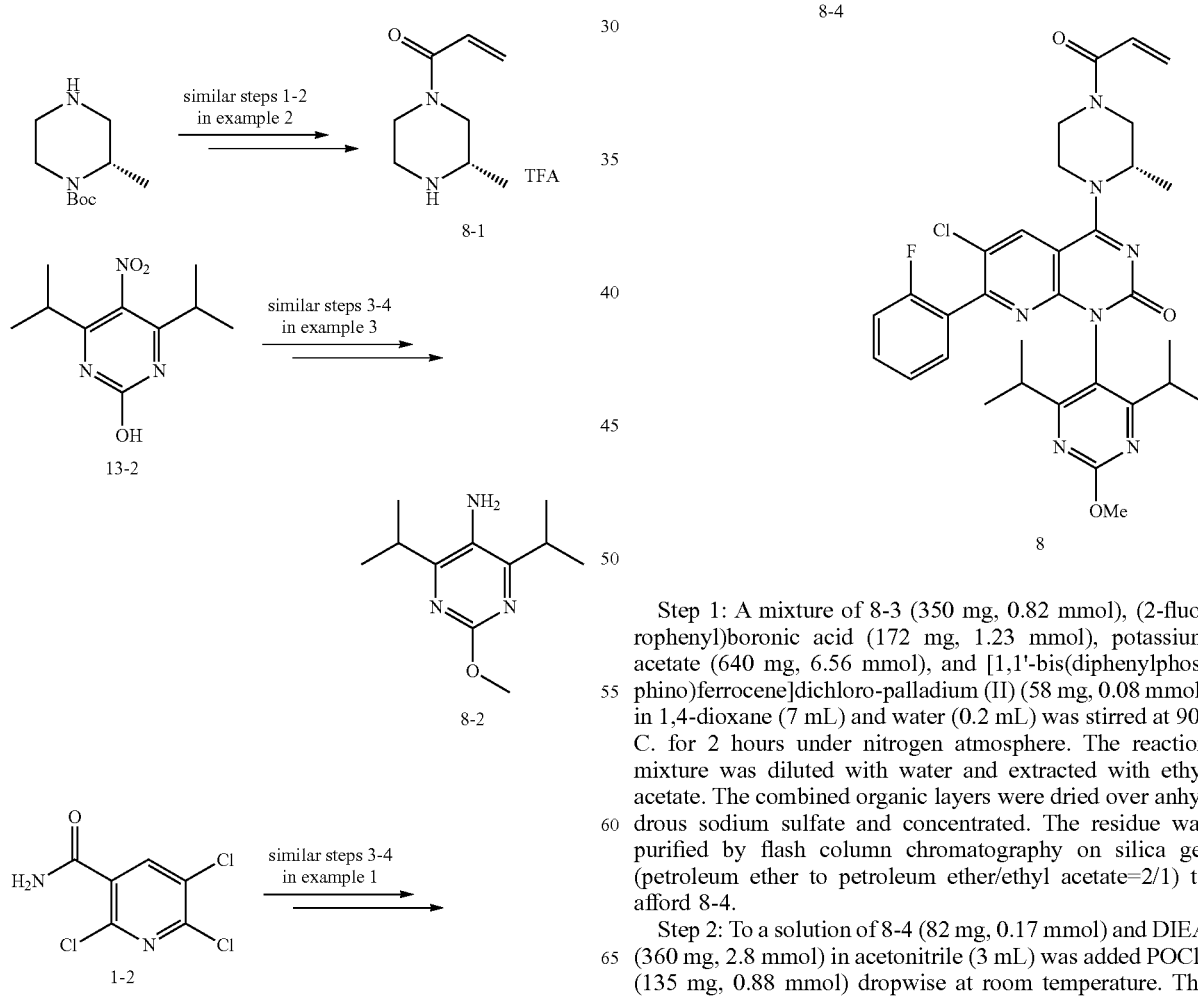

Step 1: A mixture of 8-3 (350 mg, 0.82 mmol), (2-fluorophenyl)boronic acid (172 mg, 1.23 mmol), potassium acetate (640 mg, 6.56 mmol), and [1,1'-bis(diphenylphosphino)ferrocene]dichloro-palladium (II) (58 mg, 0.08 mmol) in 1,4-dioxane (7 mL) and water (0.2 mL) was stirred at 90° C. for 2 hours under nitrogen atmosphere. The reaction mixture was diluted with water and extracted with ethyl acetate. The combined organic layers were dried over anhydrous sodium sulfate and concentrated. The residue was purified by flash column chromatography on silica gel (petroleum ether to petroleum ether/ethyl acetate=2/1) to afford 8-4.

Step 2: To a solution of 8-4 (82 mg, 0.17 mmol) and DIEA (360 mg, 2.8 mmol) in acetonitrile (3 mL) was added POCl$_3$ (135 mg, 0.88 mmol) dropwise at room temperature. The reaction mixture was heated at 80° C. for 30 minutes, cooled to −10° C. and DIEA (129 mg, 1 mmol) was added, followed by addition of a solution of 8-1 (118 mg, 0.26 mmol) in acetonitrile (2 mL). The mixture was stirred at room temperature for 1 hour, diluted with ice-water and extracted with ethyl acetate. The organic layer was dried over anhydrous sodium sulfate and concentrated. The residue was purified by a prep-HPLC (acetonitrile with 0.05% of TFA in water: 5% to 65%) to afford compound 8 (26.2 mg). LCMS (ESI, m/z): [M+H]$^+$=620.1; HNMR (400 MHz, DMSO-$d_6$, ppm): δ 8.44-8.42 (m, 1H), 7.52-7.46 (m, 1H), 7.31-7.25 (m, 2H), 7.18-7.14 (m, 1H), 6.85-6.81 (m, 1H), 6.20-6.16 (m, 1H), 5.73 (dd, J=10.4, 2.4 Hz, 1H), 4.94 (brs, 1H), 4.34-4.24 (m, 2H), 4.12-3.99 (m, 1H), 3.84 (s, 3H), 3.55-3.43 (m, 2H), 3.24-3.08 (m, 1H), 2.60-2.58 (m, 2H), 1.31 (d, J=6.4 Hz, 3H), 1.02 (d, J=6.8 Hz, 6H), 0.87 (d, J=6.4 Hz, 6H). FNMR (376 MHz, DMSO-$d_6$, ppm): δ −114.78 (1F).

Example 5 Synthesis of Compound 6

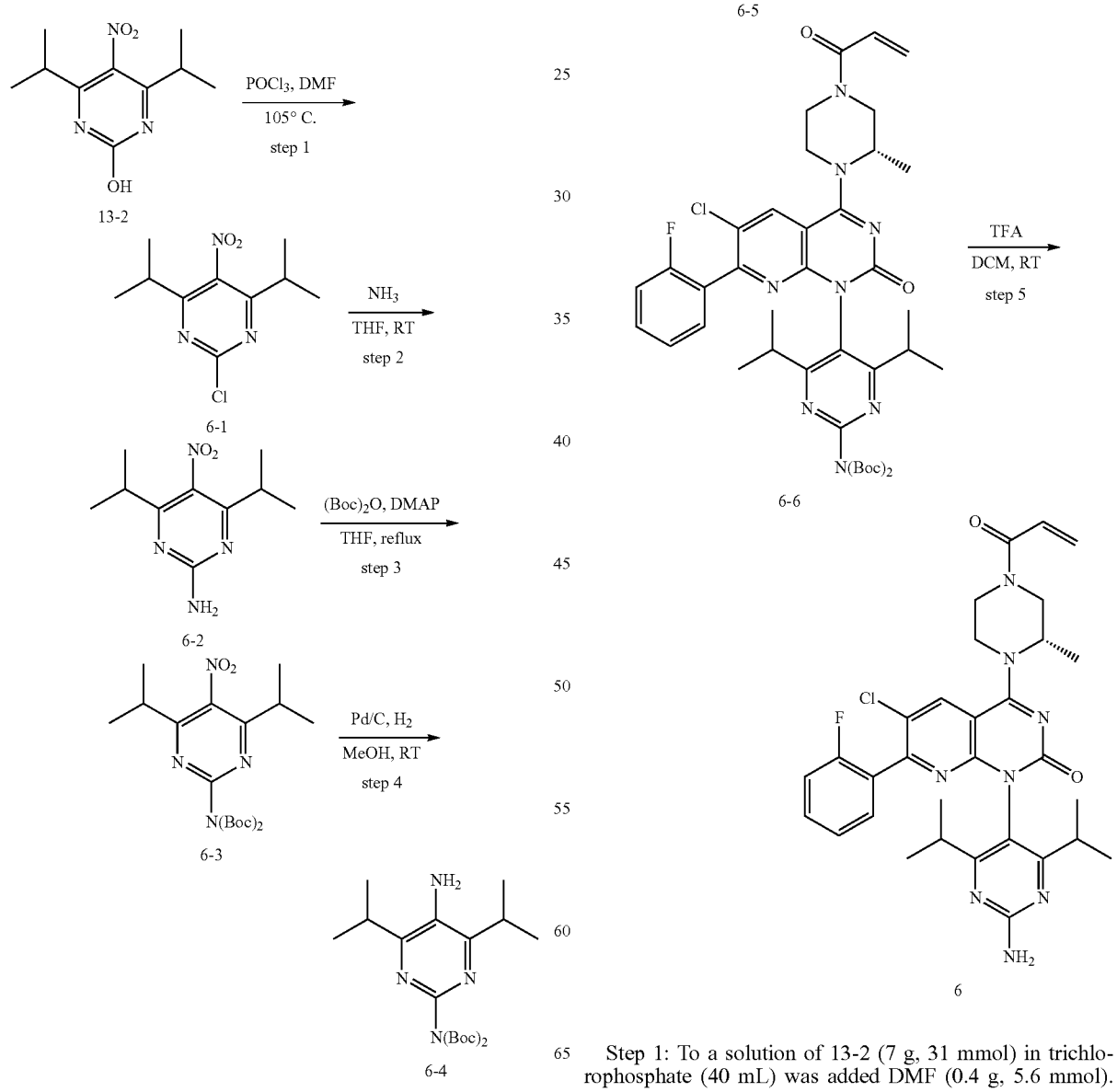

Step 1: To a solution of 13-2 (7 g, 31 mmol) in trichlorophosphate (40 mL) was added DMF (0.4 g, 5.6 mmol). The mixture was stirred at 105° C. for 0.5 hour, cooled, and concentrated. The crude residue was diluted with ethyl acetate and ice-water. The organic layer was separated and dried over sodium sulfate, filtered and concentrated. The residue was purified by flash column chromatography on silica gel (petroleum ether to petroleum ether/ethyl acetate=10/1) to afford 6-1.

Step 2: A mixture of 6-1 (0.95 g, 3.7 mmol) and ammonia (8 mL) in tetrahydrofuran (40 mL) was stirred at room temperature for 20 hours. The reaction mixture was diluted with ethyl acetate, and washed with water and brine. The organic layer was dried over sodium sulfate, filtered and concentrated to afford 6-2.

Step 3: A mixture of 6-2 (1.1 g, 4.9 mmol), di-tert-butyl dicarbonate (3.2 g, 14.7 mmol) and 4-dimethylaminopyridine (0.6 g, 4.9 mmol) in tetrahydrofuran (30 mL) was refluxed for 0.5 hour. The reaction mixture was diluted with ethyl acetate, and washed with water and brine. The organic layer was dried over sodium sulfate, filtered and concentrated. The residue was purified by flash column chromatography on silica gel (petroleum ether to petroleum ether/ethyl acetate=10/1) to afford 6-3.

Step 4: A mixture of 6-3 (1.7 g, 4 mmol), ammonia (0.05 mL) and 10% Pd/C (400 mg) in methanol (40 mL) was stirred at room temperature under hydrogen atmosphere for 16 hours. The reaction mixture was filtered through Celite and the filtrate was concentrated to afford 6-4.

Step 5: To a solution of 6-6 (50 mg, 0.062 mmol) in dichloromethane (1.5 mL) was added trifluoroacetic acid (0.5 mL) at room temperature. The mixture was stirred for 1 hour, concentrated, and purified by a prep-HPLC (acetonitrile with 0.05% of TFA in water: 25% to 95%) to afford compound 6 (17.8 mg). LCMS (ESI, m/z): [M+H]$^+$=605.1; HNMR (400 MHz, DMSO-d$_6$, ppm): δ 8.41-8.39 (m, 1H), 7.53-7.47 (m, 1H), 7.32-7.26 (m, 2H), 7.21-7.17 (m, 1H), 6.85-6.81 (m, 1H), 6.20-6.15 (m, 1H), 5.73 (dd, J=10.4, 2.4 Hz, 1H), 4.92 (brs, 1H), 4.34-4.23 (m, 2H), 4.13-3.98 (m, 1H), 3.58-3.43 (m, 2H), 3.24-3.08 (m, 1H), 2.50-2.48 (m, 2H), 1.29 (d, J=6.8 Hz, 3H), 0.98 (d, J=6.4 Hz, 6H), 0.83 (d, J=6.8 Hz, 6H). FNMR (376 MHz, DMSO-d$_6$, ppm): δ −114.67 (1F).

Example 6 Synthesis of Compound 20

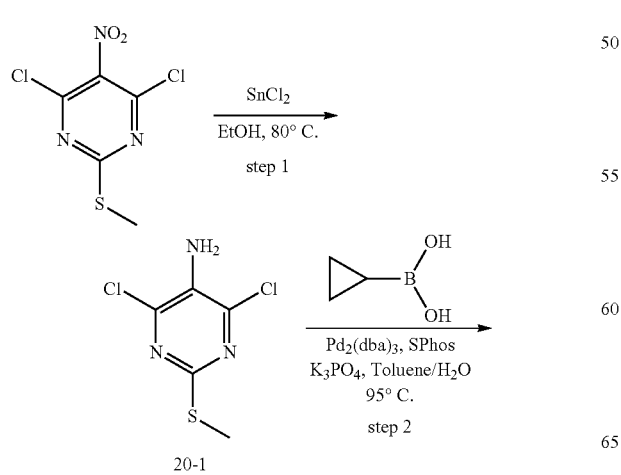

Step 1: To a solution of 4,6-dichloro-2-(methylthio)-5-nitropyrimidine (2.4 g, 12.5 mmol) in ethanol (50 mL) was added stannous chloride (8.3 g, 43.7 mmol), and the reaction mixture was heated at 80° C. for 4 hours. The reaction was quenched with a saturated sodium carbonate solution and extracted with ethyl acetate. The combined organic layers were washed with brine, dried over sodium sulfate, filtered and concentrated. The residue was purified by flash column chromatography on silica gel (petroleum ether to petroleum ether/ethyl acetate=5/1) to afford 20-1.

Step 2: To a mixture of 20-1 (1.8 g, 8.6 mmol), cyclopropylboronic acid (3.7 g, 42.8 mmol), potassium phosphate (6.5 g, 30.2 mmol) and 2-dicyclohexylphosphino-2',6'-dimethoxybiphenyl (705 mg, 1.72 mmol) in toluene (60 mL) and H₂O (20 mL) was added tris(dibenzylideneacetone)-dipalladium (789 mg, 0.86 mmol) under N₂ atmosphere. The reaction mixture was stirred at 95° C. for 3 hours, cooled to room temperature, diluted with water and extracted with ethyl acetate. The combined organic layers were washed with brine, dried over sodium sulfate, filtered and concentrated. The residue was purified by flash column chromatography on silica gel (petroleum ether to petroleum ether/ethyl acetate=5/1) to afford 20-2.

Step 3: To a solution of 20-2 (1.4 g, 6.3 mmol) in dichloromethane (70 mL) was added 3-chloroperoxybenzoic acid (3.3 g, 19.0 mmol) at 0° C., and the reaction mixture was stirred at room temperature for 2 hours. The mixture was filtered and the filtrate was concentrated. The residue was purified by flash column chromatography on silica gel (petroleum ether to petroleum ether/ethyl acetate=2/1) to afford 20-3.

Step 4: To a solution of 2-(dimethylamino)ethanol (1.5 g, 18 mmol) in tetrahydrofuran (50 mL) was added sodium hydride (1.4 g, 36 mmol) at 0° C. The reaction mixture was stirred at 0° C. for 15 minutes, and 20-3 (1.4 g, 5.5 mmol) was added. After stirring for 3 hours at room temperature, the mixture was quenched with water and concentrated. The residue was purified by a prep-HPLC (acetonitrile with 0.05% of TFA in water: 5% to 25%) to afford 20-4 as a TFA salt.

Followed similar steps in example 1 and example 4 to synthesize 20. LCMS (ESI, m/z): [M+H]⁺=673.1; HNMR (400 MHz, DMSO-d₆, ppm): δ 9.46 (brs, 1H), 8.42 (s, 1H), 7.54-7.52 (m, 1H), 7.34-7.29 (m, 3H), 6.85-6.78 (m, 1H), 6.17 (d, J=16.8 Hz, 1H), 5.74 (dd, J=10.8, 2.0 Hz, 1H), 4.92 (brs, 1H), 4.52-4.46 (m, 2H), 4.38-3.98 (m, 3H), 3.78-3.57 (m, 2H), 3.44-3.32 (m, 3H), 2.80 (d, J=4.4 Hz, 6H), 1.71-1.67 (m, 2H), 1.31 (d, J=6.8 Hz, 3H), 1.08-0.80 (m, 8H). FNMR (376 MHz, DMSO-d₆, ppm): δ −113.43 (1F).

Example 7 Synthesis of Compound 33

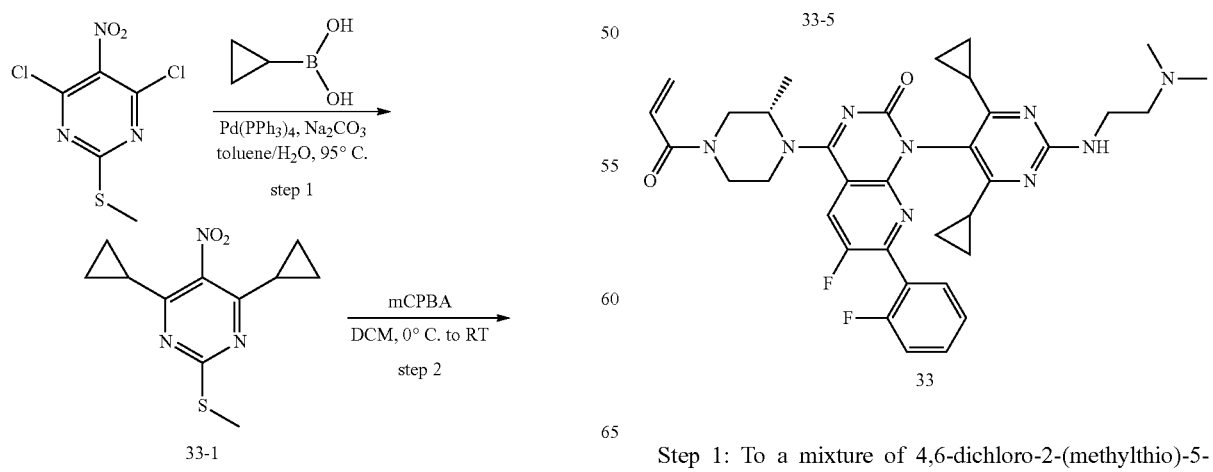

Step 1: To a mixture of 4,6-dichloro-2-(methylthio)-5-nitropyrimidine (2.4 g, 10 mmol), cyclopropyl-boronic acid (3.7 g, 42.8 mmol), sodium carbonate (3.2 g, 30.2 mmol) in toluene (60 mL) and H₂O (20 mL) was added Pd(PPh₃)₄ (1.1 g, 1.0 mmol) under N₂ atmosphere. The reaction mixture was stirred at 95° C. for 3 hours. Then the reaction mixture was cooled, diluted with water and extracted with ethyl acetate. The combined organic layers were dried over sodium sulfate, filtered and concentrated. The residue was purified by flash column chromatography on silica gel (petroleum ether to petroleum ether/ethyl acetate=6/1) to afford 33-1.

Step 2: To a solution of 33-1 (2.0 g, 8.0 mmol) in dichloromethane (80 mL) was added 3-chloroperoxy-benzoic acid (3.5 g, 20.0 mmol) at 0° C., and the reaction mixture was stirred at room temperature for 2 hours. The mixture was filtered and the filtrate was concentrated. The residue was purified by flash column chromatography on silica gel (petroleum ether to petroleum ether/ethyl acetate=4/1) to afford 33-2.

Step 3: To a solution of 33-2 (940 mg, 5.0 mmol) and DIEA (1.29 g, 10.0 mmol) in tetrahydrofuran (12 mL) was added N,N-dimethylethylenediamine (510 mg, 5.8 mmol), and the mixture was stirred at room temperature for 2 hours. Then the reaction solution was concentrated, and the residue was purified by flash column chromatography on silica gel (petroleum ether to petroleum ether/ethyl acetate=2/1) to afford 33-3.

Step 4: A mixture of 33-3 (700 mg, 3.6 mmol) and Zn powder (1.3 g, 20.0 mmol) in ethanol (20 mL) and saturated NH₄Cl solution (3.0 mL) was stirred at 85° C. for 4 hours. The reaction mixture was filtered and the filtrate was concentrated. The residue was purified by flash column chromatography on silica gel (petroleum ether to petroleum ether/ethyl acetate=1/1) to afford 33-4.

Followed similar steps in example 1 and example 4 to synthesize 33. LCMS (ESI, m/z): [M+H]⁺=656.2; HNMR (400 MHz, methanol-d₄, ppm): δ 8.25-8.20 (m, 1H), 7.53-7.51 (m, 1H), 7.48-7.44 (m, 1H), 7.27-7.19 (m, 2H), 6.83-6.81 (m, 1H), 6.26 (dd, J=16.8, 3.2 Hz, 1H), 5.79 (dd, J=10.8, 1.6 Hz, 1H), 5.10-5.00 (m, 1H), 4.49-4.43 (m, 2H), 4.20-4.04 (m, 1H), 3.82-3.80 (m, 1H), 3.73-3.65 (m, 2H), 3.64-3.52 (m, 1H), 3.41-3.31 (m, 3H), 2.89 (s, 6H), 1.62-1.50 (m, 2H), 1.45 (d, J=6.0 Hz, 3H), 1.05-1.01 (m, 4H), 0.88-0.73 (m, 4H). FNMR (376 MHz, methanol-d₄, ppm): δ −115.0 (1F), −129.2 (1F).

Example 8 Synthesis of Compound 26

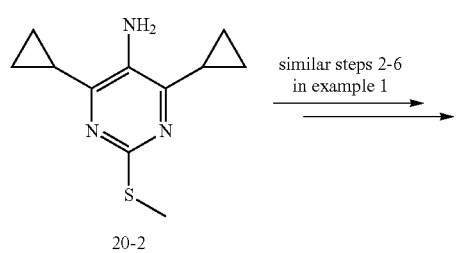

20-2

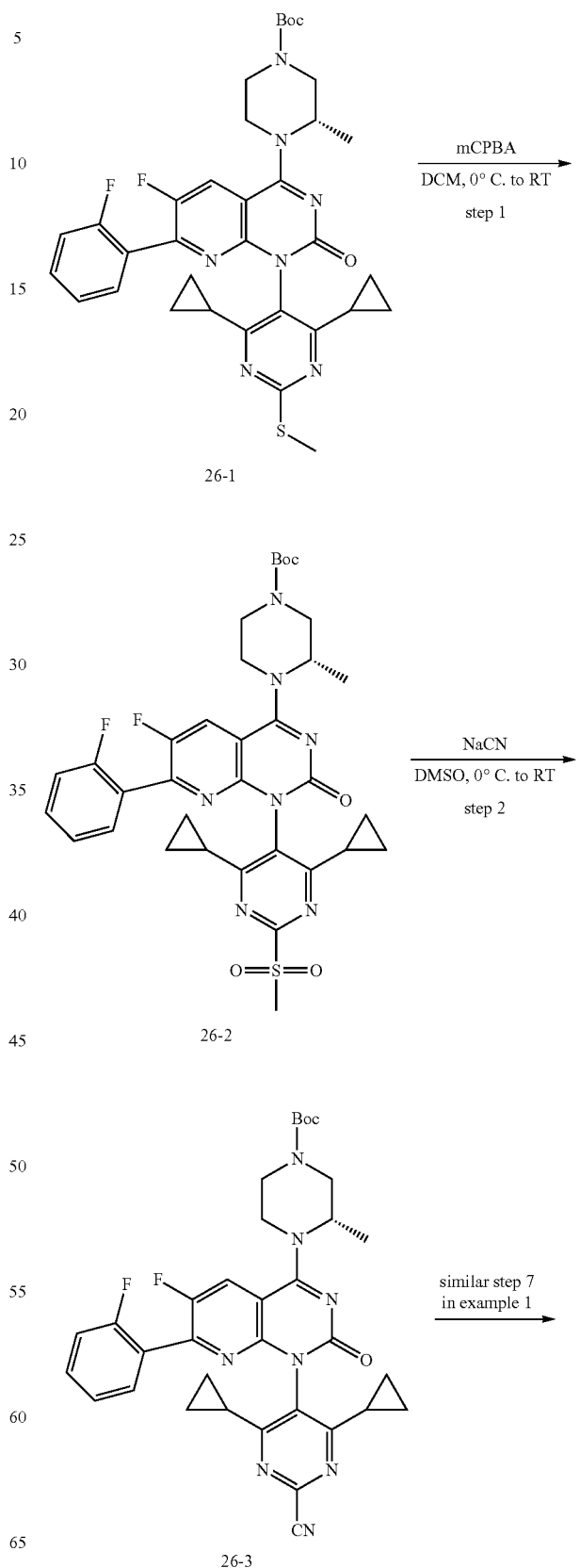

-continued

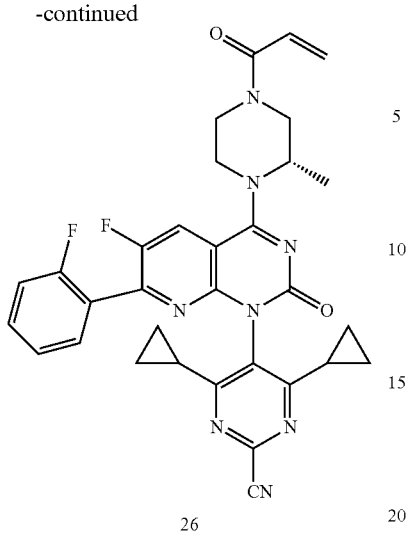

26

Followed similar steps in example 1 to synthesize 26-1.

Step 1: To a solution of 26-1 (500 mg, 0.75 mmol) in dichloromethane (8 mL) was added 3-chloroperoxybenzoic acid (260 mg, 1.5 mmol) at 0° C., and the reaction mixture was stirred at room temperature for 2 hours. The mixture was filtered and the filtrate was concentrated. The residue was purified by flash column chromatography on silica gel (ethyl acetate/dichloromethane=1/1 to ethyl acetate) to afford 26-2.

Step 2: To a solution of 26-2 (300 mg, 0.43 mmol) in DMSO (4 mL) was added NaCN (106 mg, 2.2 mmol) at 0° C., and the reaction mixture was stirred at room temperature for 18 hours. Then the reaction mixture was diluted with water and extracted with ethyl acetate. The combined organic layers were dried over sodium sulfate, filtered and concentrated. The residue was purified by flash column chromatography on silica gel (petroleum ether/ethyl acetate=1/1) to afford 26-3.

Followed similar step in example 1 to synthesize 26. LCMS (ESI, m/z): [M+H]$^+$=595.3; HNMR (300 MHz, DMSO-$d_6$, ppm): δ 8.43-8.35 (m, 1H), 7.62-7.57 (m, 1H), 7.44-7.27 (m, 3H), 6.95-6.81 (m, 1H), 6.21 (d, J=17.0 Hz, 1H), 5.78 (dd, J=10.4, 2.4 Hz, 1H), 4.98 (brs, 1H), 4.39-4.32 (m, 2H), 4.19-4.03 (m, 1H), 3.85-3.78 (m, 1H), 3.70-3.42 (m, 1H), 3.25-3.11 (m, 1H), 1.98-1.85 (m, 2H), 1.35 (d, J=6.7 Hz, 3H), 1.15-0.90 (m, 8H). FNMR (282 MHz, DMSO-$d_6$, ppm): δ −113.63 (1F), −128.34 (1F).

Example 9 Synthesis of Compound 71

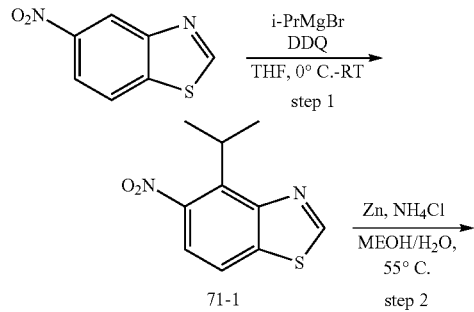

-continued

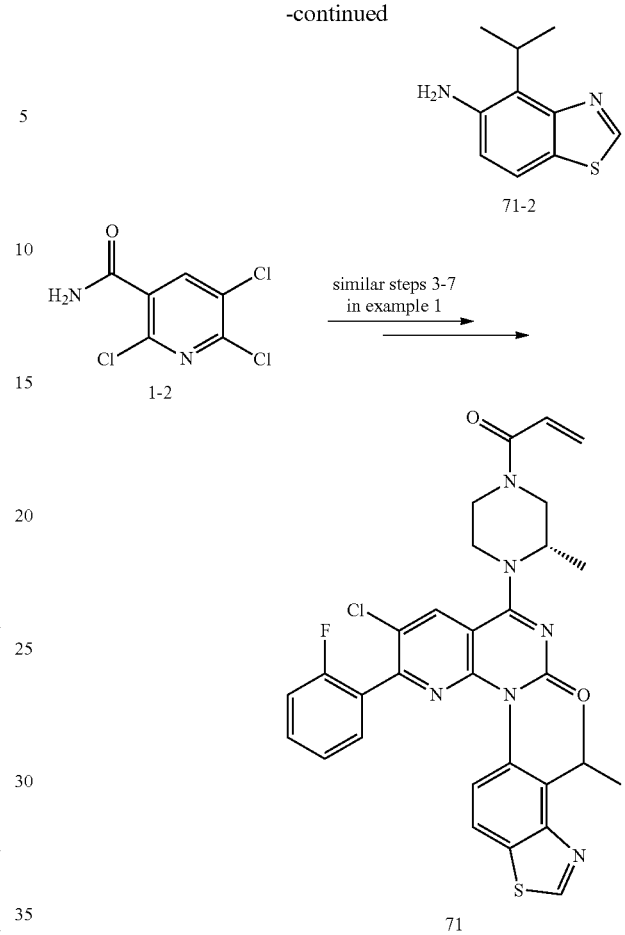

Step 1: To a solution of 5-nitro-1,3-benzothiazole (8.0 g, 44.4 mmol) in tetrahydrofuran (50 mL) was added a solution of isopropylmagnesium bromide in tetrahydrofuran (2 M, 24.4 mL, 48.8 mmol) at 0° C. The mixture was stirred at 0° C. for 0.5 hour. Then DDQ (12.1 g, 53.2 mmol) in tetrahydrofuran (10 mL) was added thereto. The resulting mixture was stirred at 0° C. for 1 hour and at room temperature for another 2 hours. The mixture was purified by flash column chromatography on silica gel (petroleum ether/ethyl acetate=20/1) to afford 71-1.

HNMR (300 MHz, DMSO-$d_6$, ppm): δ 9.62 (s, 1H), 8.27 (d, J=6.0 Hz, 1H), 7.84 (d, J=9.0 Hz, 1H), 3.56-3.47 (m, 1H), 1.54 (d, J=6.9 Hz, 6H).

Step 2: A mixture of 71-1 (79 mg, 0.35 mmol), NH$_4$Cl (189 mg, 3.5 mmol), Zn (231 mg, 3.5 mmol) in MeOH (100 mL) and H$_2$O (10 mL) was stirred at 55° C. for 2 hours. The resulting mixture was filtered, the filter cake was washed with ethyl acetate. The combined organic layers were concentrated to give a residue which was purified by flash column chromatography on silica gel (petroleum ether/ethyl acetate=20/1) to afford 71-2.

Followed similar steps in example 1 to synthesize 71. LCMS (ESI, m/z): [M+H]$^+$=603.3; HNMR (300 MHz, DMSO-$d_6$, ppm): δ 9.42 (s, 1H), 8.46-8.42 (m, 1H), 8.05 (d, J=8.4 Hz, 1H), 7.52-7.42 (m, 1H), 7.32-7.12 (m, 4H), 6.97-6.81 (m, 1H), 6.25-6.19 (d, J=17.4 Hz, 1H), 5.79 (dd, J=10.2, 2.4 Hz, 1H), 5.05-4.85 (m, 1H), 4.45-4.00 (m, 3H), 3.90-3.40 (m, 2H), 3.00-3.30 (m, 1H), 2.99-2.85 (m, 1H), 1.44-1.26 (m, 9H). FNMR (282 MHz, DMSO-$d_6$, ppm): δ −114.01 (1F).

Example 10 Synthesis of Compound 68

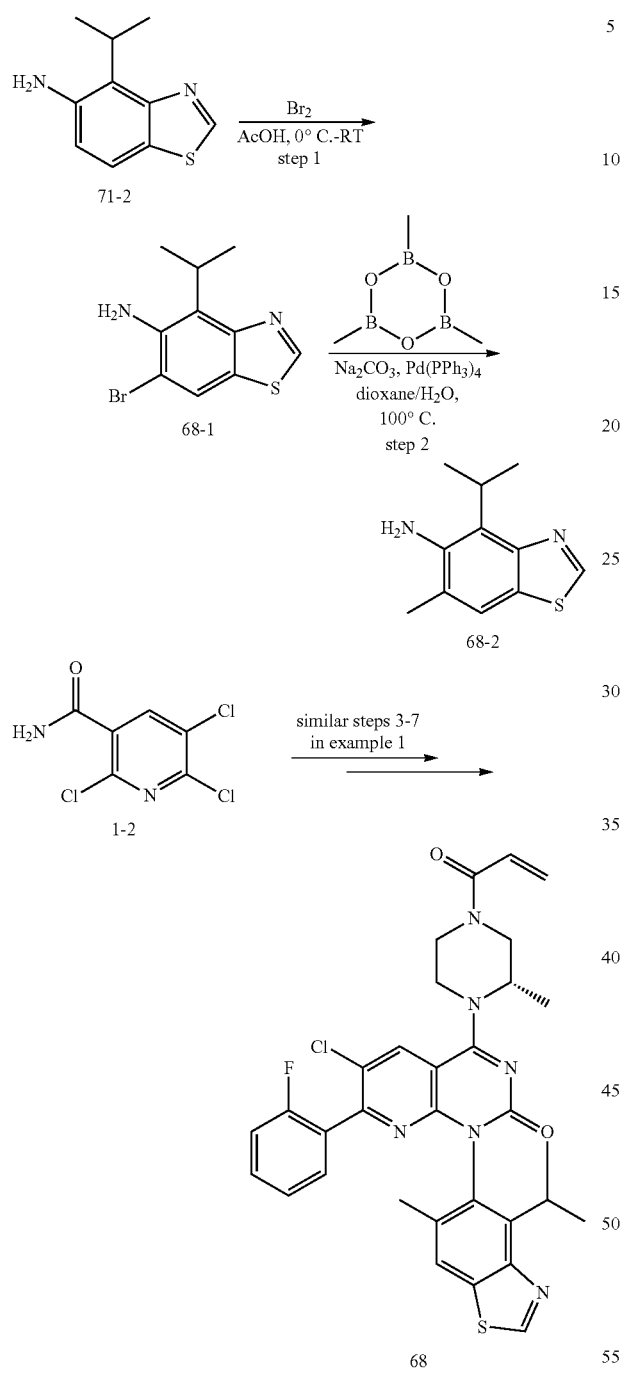

Example 11 Synthesis of Compound 70

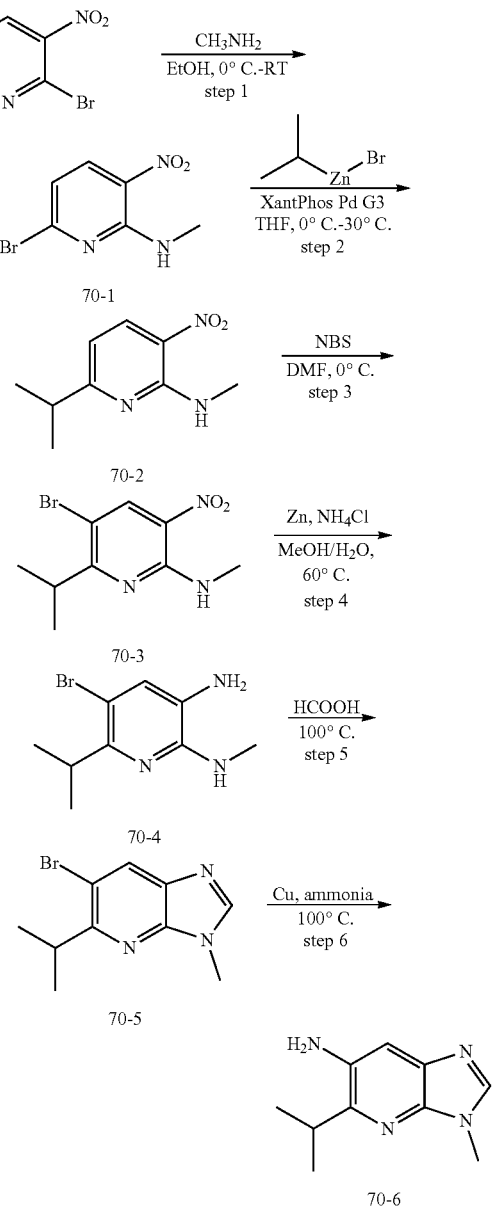

mixture was stirred at 100° C. for 5 hours under N2 atmosphere. After cooling to room temperature, the mixture was washed with water and then extracted with ethyl acetate. The organic layer was washed with brine, dried over MgSO4. concentrated and purified by preparative TLC (petroleum ether/ethyl acetate=5/1) to afford 68.

Followed similar steps in example 1 to synthesize 68. LCMS (ESI, m/z): [M+H]$^+$=617.1; HNMR (300 MHz, DMSO-d$_6$, ppm): δ 9.33 (s, 1H), 8.49 (s, 1H), 7.95 (d, J=0.9 Hz, 1H), 7.51-7.44 (m, 1H), 7.31-7.16 (m, 3H), 6.98-6.81 (m, 1H), 6.22 (d, J=16.7 Hz, 1H), 5.78 (dd, J=10.2, 2.4 Hz, 1H), 4.97 (brs, 1H), 4.49-4.28 (m, 2H), 4.25-4.02 (m, 1H), 3.87-3.45 (m, 2H), 3.22-3.05 (m, 1H), 3.02-2.88 (m, 1H), 2.05-1.98 (m, 1H), 1.42-1.32 (m, 6H), 1.27 (dd, J=6.9, 1.8 Hz, 3H). FNMR (282 MHz, DMSO-d$_6$, ppm): δ −114.35 (1F).

Step 1: A solution of 71-2 (2.0 g, 10.6 mmol) in HOAc (40 mL) was added Br$_2$ (1.7 g, 10.6 mmol) at 0° C. The resulting mixture was stirred for 2 hours at room temperature. The mixture was purified by flash column chromatography on silica gel (petroleum ether/ethyl acetate=99/1) to afford 68-1.

Step 2: To a solution of 71-2 (2.4 g, 8.8 mmol) in 20 mL of 1,4-dioxane/H$_2$O (5/1) was added trimethyl-1,3,5,2,4,6-trioxatriborinane (2.2 g, 17.6 mmol) and Na$_2$CO$_3$ (2.35 g, 22.1 mmol) and Pd(PPh$_3$)$_4$ (1.0 g, 0.89 mmol). The resulting

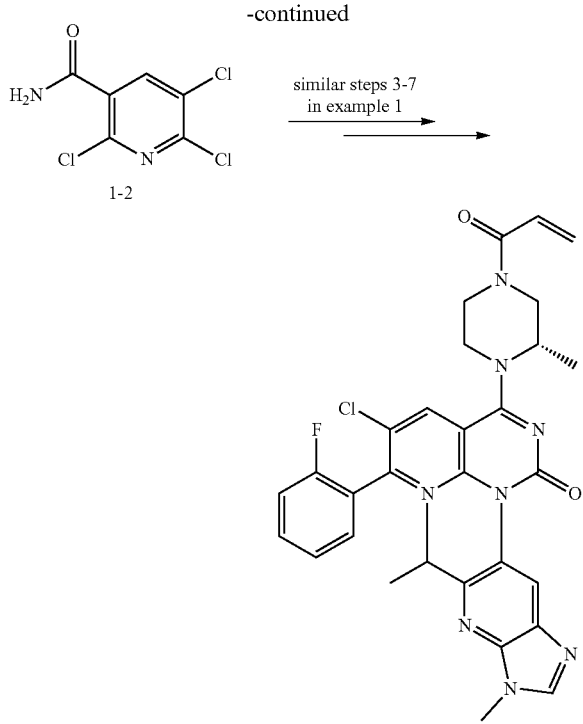

Step 1: To a stirred mixture of 2,6-dibromo-3-nitropyridine (50 g, 177 mmol) and Na$_2$CO$_3$ (37.6 g, 355 mmol) in EtOH (500 mL) was added a solution of CH$_3$NH$_2$ in THF (107 mL, 214 mmol) dropwise at 0° C. The resulting mixture was stirred at room temperature overnight. The resulting mixture was filtered, the filter cake was washed with ethyl acetate. The filtrate was concentrated to give a solid which was re-crystallized from ethyl acetate/petroleum ether (10/1) to afford 70-1.

Step 2: To a solution of 70-1 (10 g, 43 mmol) and XantPhos Pd G3 (408 mg, 0.43 mmol) in THF (100 mL) was added a solution of isopropylzinc bromide in THF (0.5 M, 33 mL, 66 mmol) dropwise at room temperature. The resulting mixture was stirred at 30° C. for 3 hours under argon atmosphere. The reaction was quenched with sat. aqueous NH$_4$Cl solution at room temperature. The resulting mixture was extracted with ethyl acetate. The combined organic layers were washed with brine, dried over anhydrous Na$_2$SO$_4$, concentrated and purified by flash column chromatography on silica gel (petroleum ether/ethyl acetate=20/1) to afford 70-2.

Step 3: To a solution of 70-2 (1.5 g, 7.7 mmol) in DMF (15 mL) was added NBS (1.64 g, 9.2 mmol) in DMF (15 mL) dropwise at 0° C. The resulting mixture was stirred at 0° C. for 2 hours, diluted with water and extracted with ethyl acetate. The combined organic layers were washed with brine and dried over anhydrous Na$_2$SO$_4$. After filtration, the filtrate was concentrated to give a residue which was purified by flash column chromatography on silica gel (petroleum ether/ethyl acetate=10/1) to afford 70-3.

Step 4: A mixture of 70-3 (1.5 g, 5.5 mmol), NH$_4$Cl (2.34 g, 43.7 mmol) and Zn (1.8 g, 27.4 mmol) in methanol (15 mL)/H$_2$O (8 mL) was stirred at 60° C. for 2 hours. The mixture was filtered, concentrated to remove methanol and extracted with ethyl acetate. The combined organic layers were washed with brine, dried over anhydrous Na$_2$SO$_4$, filtered and concentrated to afford 70-4.

Step 5: A solution of 70-4 (1.2 g, 4.9 mmol) in formic acid (10 mL) was stirred at 100° C. overnight. Then cooled, diluted with water and neutralized to pH=7 with NaOH. The resulting mixture was extracted with EtOAc. The combined organic layers were washed with brine, dried over anhydrous Na$_2$SO$_4$, and concentrated to afford 70-5.

Step 6: A mixture of 70-5 (2.9 g, 11.4 mmol) and Cu (362 mg, 5.7 mmol) in ammonia (40 mL) was stirred at room temperature for 0.5 hour and then stirred at 100° C. overnight. The resulting mixture was extracted with ethyl acetate, dried over anhydrous Na$_2$SO$_4$, concentrated and purified by flash column chromatography on silica gel (petroleum ether/ethyl acetate=3/1) to afford 70-6.

Followed similar steps in example 1 to synthesize 70. LCMS (ESI, m/z): [M+H]$^+$=601.4; HNMR (400 MHz, DMSO-d$_6$, ppm): δ 8.51-8.39 (m, 2H), 7.92-7.88 (m, 1H), 7.53-7.45 (m, 1H), 7.35-7.12 (m, 3H), 6.94-6.81 (m, 1H), 6.23 (d, J=16.4 Hz, 1H), 5.78 (dd, J=10.4, 2.4 Hz, 1H), 5.10-4.85 (m, 1H), 4.45-4.00 (m, 3H), 3.83 (s, 3H), 3.73-3.60 (m, 1H), 3.55-3.40 (m, 1H), 3.15-3.05 (m, 1H), 2.85-2.75 (m, 1H), 1.35 (dd, J=13.1, 6.6 Hz, 3H), 1.16 (d, J=6.7 Hz, 3H), 1.06 (dd, J=6.7, 2.3 Hz, 3H). FNMR (376 MHz, DMSO-d$_6$, ppm): δ −114.16 (1F).

Example 12 Synthesis of Compound 65

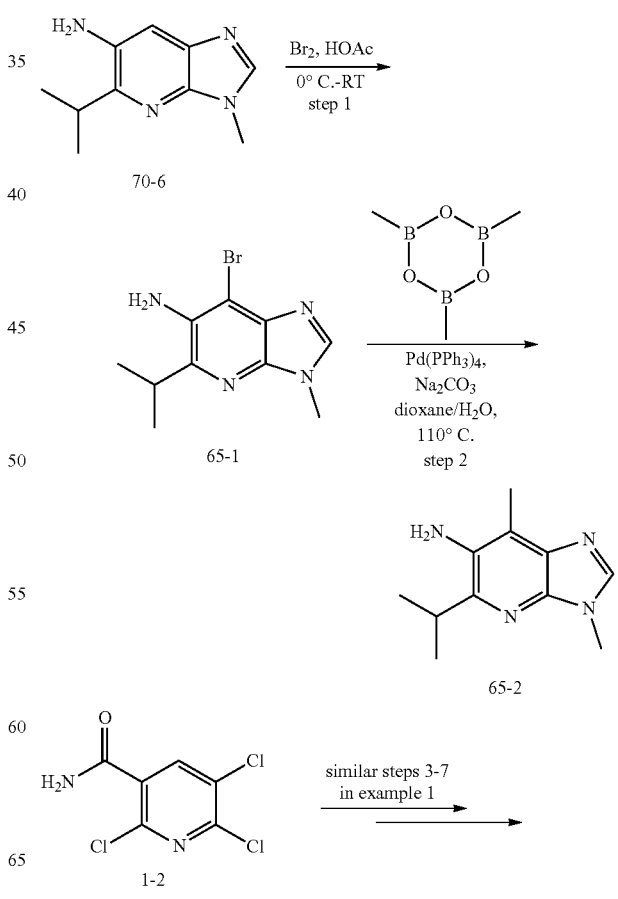

157

-continued

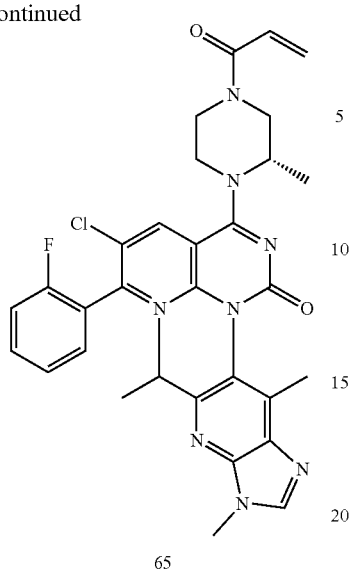

65

Step 1: To a solution of 70-6 (30 mg, 1.57 mmol) in HOAc (15 mL) and CHCl₃ (6 mL) was added Br₂ (252 mg, 1.57 mmol) in HOAc (1 mL) dropwise at 0° C. The mixture was stirred at room temperature for 0.5 hour and then quenched with sat. NaHCO₃ solution. The resulting mixture was extracted with ethyl acetate. The combined organic layers were washed with brine, dried over anhydrous Na₂SO₄, concentrated and purified by flash column chromatography on silica gel (petroleum ether/ethyl acetate=1/9) to afford 65-1.

Step 2: A mixture of 65-1 (200 mg, 0.74 mmol), trimethyl-1,3,5,2,4,6-trioxatriborinane (559 mg, 4.45 mmol), Pd(PPh₃)₄ (85 mg, 0.074 mmol), Na₂CO₃ (196 mg, 1.85 mmol) and in dioxane/H₂O (5/1, 2 mL) was stirred at 110° C. for 3 hours under nitrogen atmosphere. The residue was purified by flash column chromatography on silica gel (petroleum ether/ethyl acetate=1/1) to afford 65-2.

Followed similar steps in example 1 to synthesize 65. LCMS (ESI, m/z): [M+H]⁺=615.3; HNMR (400 MHz, DMSO-d₆, ppm): δ 8.48-8.47 (m, 1H), 8.33 (s, 1H), 7.49-7.46 (m, 1H), 7.30-7.17 (m, 3H), 6.94-6.83 (m, 1H), 6.24-6.19 (m, 1H), 5.79-5.76 (m, 1H), 4.97 (brs, 1H), 4.44-4.32 (m, 2H), 4.19-4.04 (m, 1H), 3.90-3.46 (m, 5H), 3.16-3.10 (m, 1H), 2.78-2.76 (m, 1H), 2.21-2.15 (m, 3H), 1.35 (d, J=6.8 Hz, 3H), 1.14 (d, J=6.8 Hz, 3H), 1.02 (dd, J=6.4, 1.8 Hz, 3H). FNMR (376 MHz, DMSO-d₆, ppm): δ −114.52 (1F).

Example 13 Synthesis of Compound 72

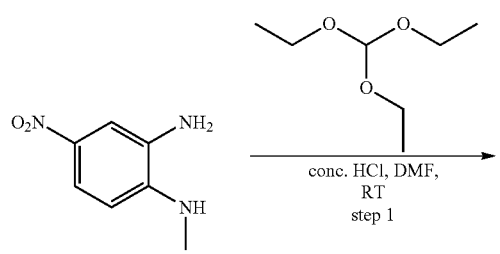

158

-continued

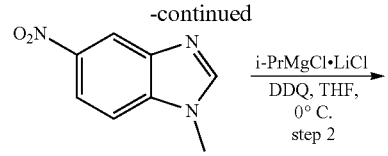

72-1

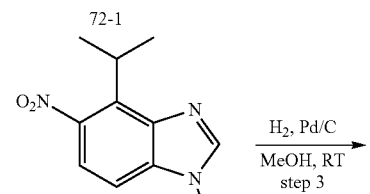

72-2

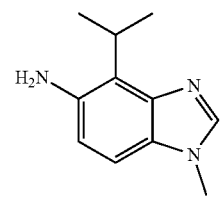

72-3

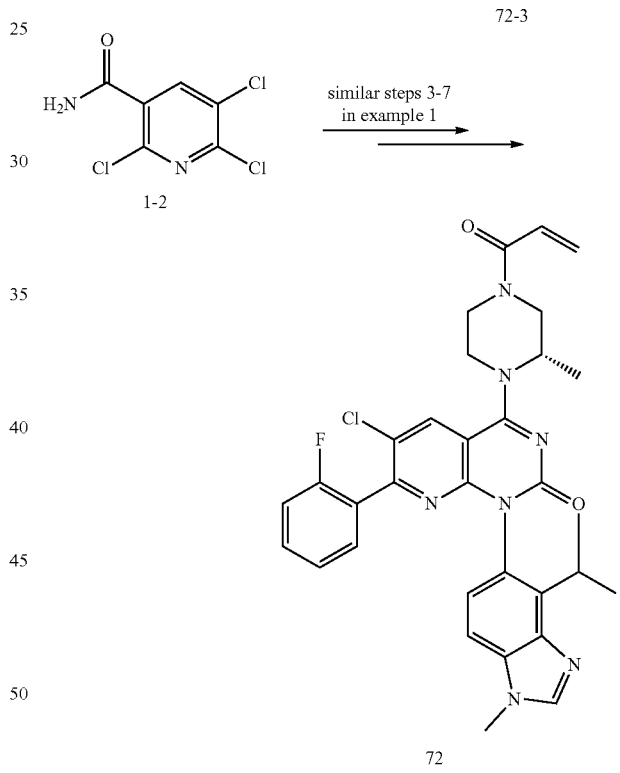

1-2

72

Step 1: To a solution of N¹-methyl-4-nitrobenzene-1,2-diamine (25 g, 149 mmol) and trimethyl orthoformate (200 mL) in DMF (300 mL) was added conc. HCl (16 mL) dropwise at room temperature. After stirring at room temperature overnight, the mixture was concentrated. The residue was dissolved in ethyl acetate. The mixture was basified with Et₃N. The organic layer was dried over anhydrous Na₂SO₄ and concentrated to give a residue which was purified by flash column chromatography on silica gel (dichloromethane/methanol=12/1) to afford 72-1.

Step 2: To a solution of 72-1 (32 g, 180 mmol) in tetrahydrofuran (80 mL) was added i-PrMgCl.LiCl (210 mL, 1.3 M in THF, 271 mmol) at 0° C. The mixture was stirred at 0° C. for 0.5 hour. Then DDQ (49.2 g, 216 mmol) in tetrahydrofuran (40 mL) was added. The mixture was stirred at 0° C. for 1 hour. The reaction was quenched with water at 0° C. The resulting mixture was extracted with ethyl acetate. The combined organic layers were washed with brine, dried over anhydrous $Na_2SO_4$ and concentrated. The residue was purified by silica gel column chromatography to afford 72-2.

Step 3: A mixture of 72-2 (7.0 (petroleum ether/ethyl acetate=4/1) g, 31.9 mmol) and 10% Pd/C (3.4 g) in methanol (30 mL) was stirred at room temperature overnight under hydrogen atmosphere. The resulting mixture was filtered, the filter cake was washed with MeOH. The filtrate was concentrated to afford 72-3.

Followed similar steps in example 1 to synthesize 72. LCMS (ESI, m/z): $[M+H]^+$=600.4; HNMR (300 MHz, DMSO-$d_6$, ppm): δ 8.44-8.36 (m, 1H), 8.15 (s, 1H), 7.48-7.43 (m, 1H), 7.41-7.38 (d, J=8.4 Hz, 1H), 7.27-7.14 (m, 3H), 7.02-6.98 (dd, J=10.5, 2.1 Hz, 1H), 6.91-6.85 (m, 1H), 6.24-6.19 (d, J=16.2 Hz, 1H), 5.79-5.75 (dd, J=12.9, 2.4 Hz, 1H), 4.95-4.85 (m, 1H), 4.36-4.05 (m, 3H), 3.81 (s, 3H), 3.67-3.40 (m, 2H), 3.20-2.90 (m, 1H), 2.75-2.70 (m, 1H), 1.39-1.29 (m, 9H). FNMR (282 MHz, DMSO-$d_6$, ppm): δ −114.19 (1F).

Example 14 Synthesis of Compound 69

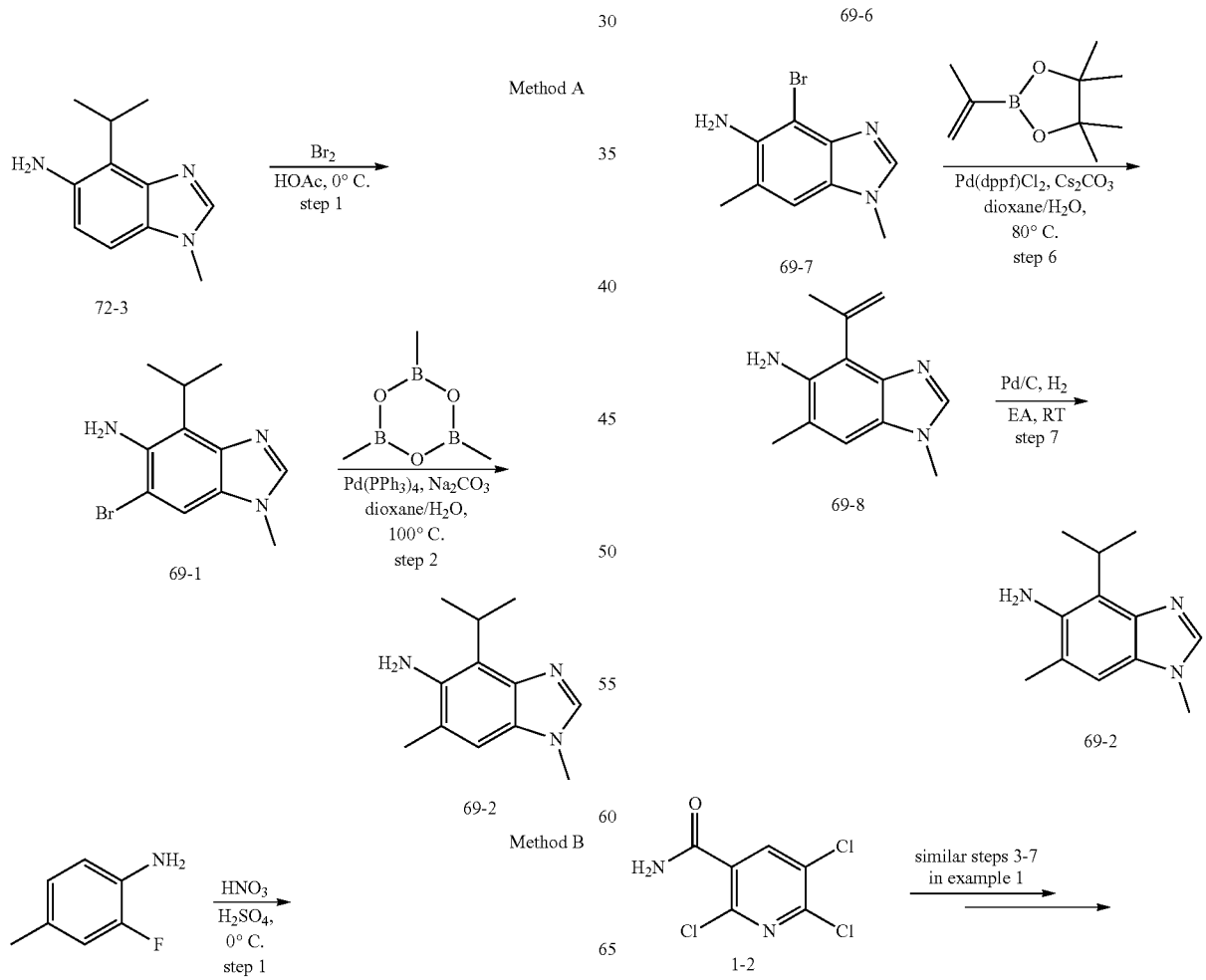

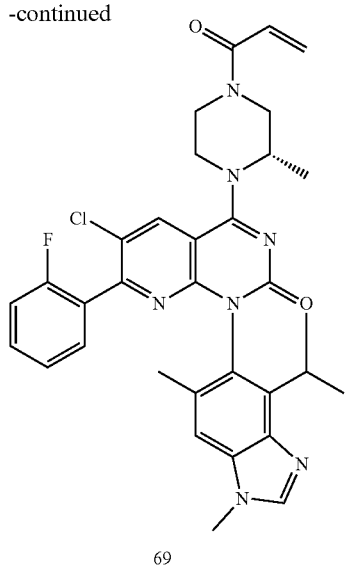

69

Method A

Step 1: To a solution of 4-isopropyl-1-methyl-1,3-benzodiazol-5-amine (6.0 g, 31.7 mmol) in HOAc (20 mL) was added $Br_2$ (5.1 g, 31.7 mmol) in HOAc (2 mL) dropwise at 0° C. After stirring for 1 hour, the mixture was concentrated. The residue was partitioned between ethyl acetate and 2 M NaOH. The organic layer was washed with brine, dried over anhydrous $Na_2SO_4$ and concentrated. The residue was purified by silica gel column chromatography (petroleum ether/ethyl acetate=4/1) to afford 69-1.

Step 2: A mixture of 69-1 (3.8 g, 14.2 mmol), trimethyl-1,3,5,2,4,6-trioxatriborinane (3.6 g, 28.4 mmol), $Na_2CO_3$ (3.0 g, 28.4 mmol) and $Pd(PPh_3)_4$ (1.64 g, 1.42 mmol) in 30 mL of dioxane/$H_2O$ (5/1) was stirred at 100° C. for 5 hours under $N_2$ atmosphere. After cooling to room temperature, water was added and the mixture was extracted with ethyl acetate. The combined organic layers were washed with brine, dried over $MgSO_4$ and concentrated. The residue was purified by a preparative TLC (petroleum ether/ethyl acetate=1/1) to afford 69-2.

Method B

Step 1: To a solution of 2-fluoro-4-methylaniline (10.0 g, 79.9 mmol) in $H_2SO_4$ (100 mL) was added a solution of conc. $HNO_3$ (5.66 g, 87.9 mmol) in $H_2SO_4$ (11.2 mL) dropwise at 0° C. After stirring for 3 hours at 0° C., the reaction mixture was poured into ice water (600 mL) and the resulting mixture was basified by slow addition of an NaOH solution (180 g dissolved in 240 mL water). Then filtered and dried to afford 69-3.

Step 2: To a solution of 69-3 (5 g, 29.4 mmol) in DMSO (35 mL) was added $Cs_2CO_3$ (47.88 g, 146.9 mmmol) and methylamine hydrochloride (5.95 g, 88.2 mmol). The mixture was stirred at 120° C. overnight. The mixture was poured into water, and the solution was extracted with ethyl acetate. The combined organic layers were dried over $Na_2SO_4$, filtered and concentrated to give a residue which was purified by silica gel chromatography (petroleum ether/ethyl acetate=1/1 to 1/4) to afford 69-4.

Step 3: To a solution of 69-4 (3.2 g, 15.9 mmol) in toluene (12 mL) were added trimethoxymethane (3.54 g, 33.4 mmol) and 4-methylbenzenesulfonic acid (60.5 mg, 0.35 mmol). The solution was stirred at 100° C. for 2 hours under $N_2$ atmosphere. The solvent was removed to give a residue, which was purified by silica gel chromatography (petroleum ether/ethyl acetate=5/1 to 1/1) to afford 69-5.

Step 4: A mixture of 69-5 (3.2 g, 16.7 mmol) and Pd/C (10%, 300 mg) in MeOH (10 mL) and THF (30 mL) was stirred at room temperature under hydrogen atmosphere for 6 hours. Then filtered and the filtrate was concentrated to afford 69-6.

Step 5: To a solution of 69-6 (2.51 g, 15.5 mmol) in HOAc (25 mL) was added bromine (2.5 g, 15.5 mmol). After stirring at room temperature for 1 hour, the solution was diluted with $H_2O$ and basified to pH=8 with a saturated sodium bicarbonate solution. The solution was extracted with ethyl acetate. The combined organic layers were dried over $Na_2SO_4$, filtered and concentrated to give a residue which was purified by silica gel column chromatography (petroleum ether/ethyl acetate=1/1 to 1/4) to afford 69-7.

Step 6: To a mixture of 69-7 (1.6 g, 6.6 mmol), 4,4,5,5-tetramethyl-2-(prop-1-en-2-yl)-1,3,2-dioxaborolane (1.67 g, 10.0 mmol) and $Cs_2CO_3$ (5.41 g, 16.6 mmol) in dioxane (16 mL) and water (3 mL) was added $Pd(dppf)Cl_2$ (243 mg, 0.33 mmol) under $N_2$. The mixture was stirred at 80° C. for 2.5 hours under nitrogen atmosphere. The solution was diluted with ethyl acetate and $H_2O$. The organic layer was dried over $Na_2SO_4$ and concentrated to give a residue which was purified by silica gel chromatography (petroleum ether/ethyl acetate=1/1 to 1/3) to afford 69-8.

Step 7: A mixture of 69-8 (1.1 g, 5.4 mmol) and Pd/C (10%, 100 mg) in ethyl acetate (10 mL) was stirred at room temperature under hydrogen atmosphere for 2 hours. Then filtered and the filtrate was concentrated to afford 69-2.

Followed similar steps in example 1 to synthesize 69. LCMS (ESI, m/z): $[M+H]^+$=614.1; HNMR (300 MHz, DMSO-$d_6$, ppm): δ 8.49-8.42 (m, 1H), 8.08 (s, 1H), 7.54-7.41 (m, 1H), 7.33-7.13 (m, 4H), 6.94-6.80 (m, 1H), 6.22 (d, J=16.4 Hz, 1H), 5.78 (dd, J=10.4, 2.4 Hz, 1H), 4.92 (brs, 1H), 4.46-4.04 (m, 3H), 3.78 (s, 3H), 3.70-3.05 (m, 3H), 2.78 (d, J=7.1 Hz, 1H), 1.98 (s, 3H), 1.43-1.20 (m, 9H). FNMR (282 MHz, DMSO-$d_6$, ppm): δ -114.52 (1F).

Example 15 Synthesis of Compound 117

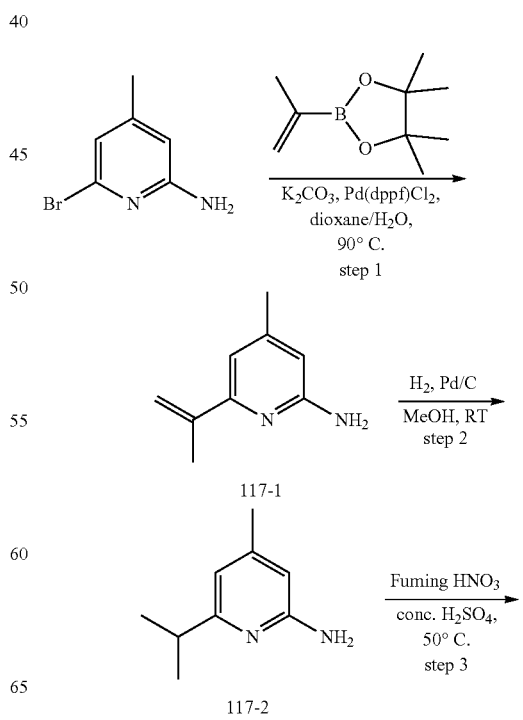

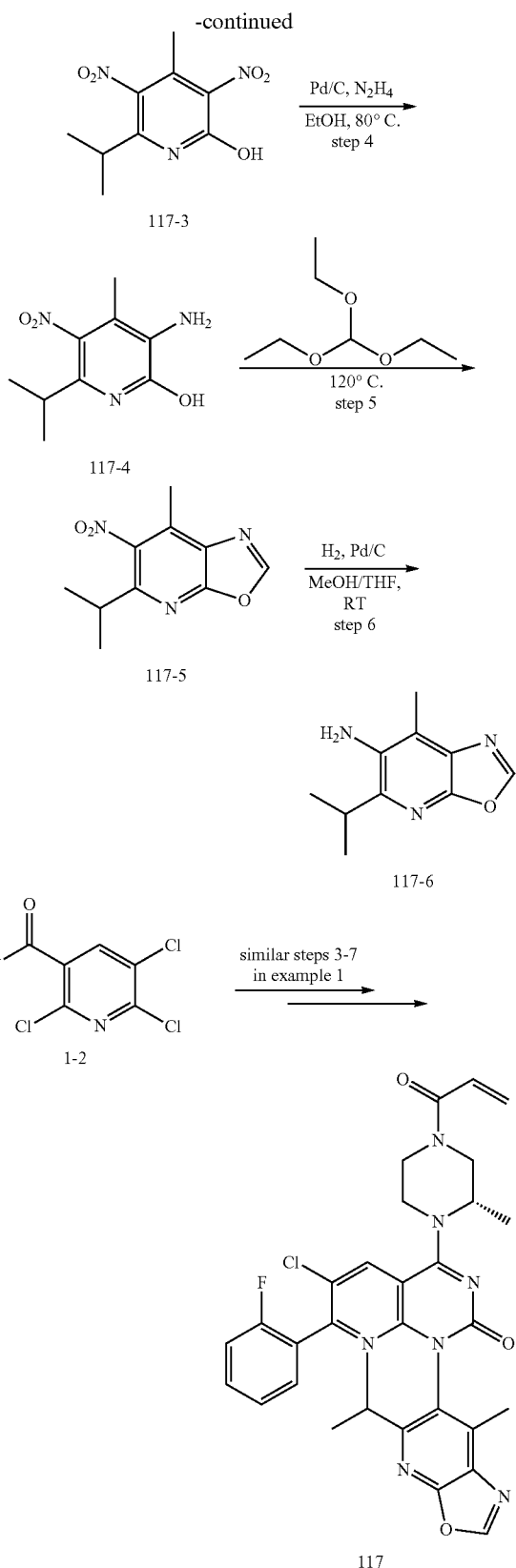

(11.7 g, 69.5 mmol) in dioxane (100 mL) and $H_2O$ (20 mL) was added Pd(dppf)$Cl_2$ (3.91 g, 5.35 mmol) at room temperature under argon atmosphere. The resulting mixture was stirred at 90° C. for 2 hours under argon atmosphere. The reaction was quenched with water and the mixture was extracted with ethyl acetate. The combined organic layers were washed with brine, dried over anhydrous $Na_2SO_4$ and concentrated. The residue was purified by silica gel column chromatography (petroleum ether/ethyl acetate=5/1) to afford 117-1.

Step 2: A mixture of 117-1 (6.0 g, 40.5 mmol) and 10% Pd/C (1.2 g) in methanol (60 mL) was stirred at room temperature overnight under hydrogen atmosphere. The resulting mixture was filtered, and the filter cake was washed with MeOH. The filtrate was concentrated to afford 117-2.

Step 3: To a solution of 117-2 (3.0 g, 20 mmol) in $H_2SO_4$ (35 mL) was added fuming $HNO_3$ (4.5 mL, 71 mmol) dropwise at 0° C. The mixture was stirred at 50° C. for 2 hours. The reaction was quenched with ice at 0° C. The resulting mixture was extracted with ethyl acetate. The combined organic layers were washed with brine, dried over anhydrous $Na_2SO_4$ and concentrated to afford 117-3.

Step 4: A mixture of 117-3 (3.8 g, 15.75 mmol), 10% Pd/C (1.0 g) and hydrazine hydrate (80%, 3.8 mL) in ethyl alcohol (80 mL) was stirred at 80° C. for 1.5 hours under argon atmosphere. The mixture was filtered, and the filter cake was washed with acetonitrile. The filtrate was concentrated to afford 117-4.

Step 5: A mixture of 117-4 (2.0 g, 9.47 mmol), HCl in MeOH (1 mL, 4.0 mmol) and triethyl orthoformate (20 mL) was stirred at 120° C. for 2 days under argon atmosphere. The mixture was concentrated to give a residue which was purified by silica gel column chromatography (petroleum ether/ethyl acetate=10/1) to afford 117-5.

Step 6: A mixture of 117-5 (1.1 g, 4.97 mmol) and 10% Pd/C (354 mg) in MeOH (10 mL) and THF (10 mL) stirred at room temperature overnight under hydrogen atmosphere. The mixture was filtered, the filter cake was washed with MeOH. The filtrate was concentrated to afford 117-6.

Followed similar steps in example 1 to synthesize 117. LCMS (ESI, m/z): [M+H]$^+$=602.4; HNMR (300 MHz, DMSO-$d_6$, ppm): δ 8.83 (s, 1H), 8.55-8.45 (m, 1H), 7.54-7.41 (m, 1H), 7.36-7.13 (m, 3H), 6.96-6.80 (m, 1H), 6.25 (d, J=16.8 Hz, 1H), 5.78 (dd, J=10.4, 2.4 Hz, 1H), 4.99 (brs, 1H), 4.43-4.33 (m, 2H), 4.25-4.00 (m, 1H), 3.83-3.79 (m, 1H), 3.69-3.44 (m, 1H), 3.27-3.12 (m, 1H), 2.84-2.78 (m, 1H), 2.20 (d, J=2.4 Hz, 3H), 1.34 (d, J=6.6 Hz, 3H), 1.10 (d, J=6.6 Hz, 3H), 1.00-0.98 (m, 3H). FNMR (282 MHz, DMSO-$d_6$, ppm): δ −114.30 (1F).

Example 16 Synthesis of Compound 44

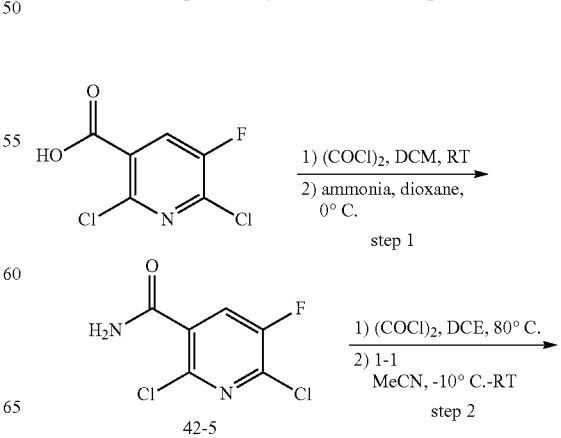

Step 1: To a mixture of 6-bromo-4-methylpyridin-2-amine (10 g, 53.5 mmol), $K_2CO_3$ (18.5 g, 133.7 mmol) and 4,4,5,5-tetramethyl-2-(prop-1-en-2-yl)-1,3,2-dioxaborolane

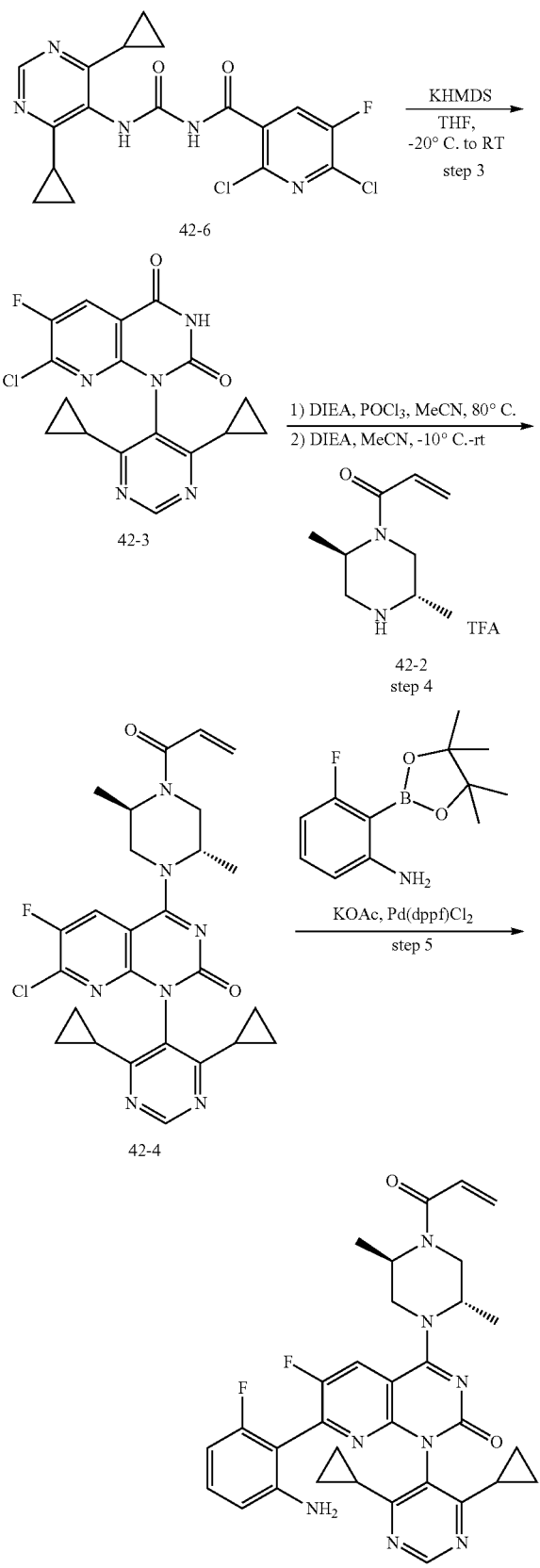

Step 1: To a mixture of 2, 6-dichloro-5-fluoronicotinic acid (23 g, 0.11 mol) in dichloromethane (300 mL) was added dimethylformamide (0.2 mL). Then oxalyl chloride (33 g, 0.26 mol) was added slowly over 30 minutes at room temperature. The mixture was stirred at room temperature for an hour and then concentrated to give an oil which was dissolved in dioxane (50 mL). The solution was added to ammonium hydroxide (150 mL) at 0° C. over 30 minutes. The resulting mixture was stirred at 0° C. for 30 minutes and then filtered. The filter cake was washed with cooled water (50 mL) and dried to afford 42-5.

Step 2: A solution of 42-5 (11 g, 52.6 mmol) in 1,2-dichloroethane (80 mL) was treated with oxalyl chloride (8.68 g, 68.4 mmol). The mixture was stirred at 80° C. for 45 minutes and the reaction was concentrated. The residue was dissolved in acetonitrile (100 mL), cooled to −10° C., and a solution of 1-1 (9.6 g, 55.2 mmol) in THF (30 mL) was then added. The resulting mixture was stirred at room temperature for 2 hours. The solution was diluted with a sat. aqueous $NaHCO_3$ solution and extracted with ethyl acetate. The organic layer was dried over anhydrous sodium sulfate and concentrated. The residue was purified by column chromatography on silica gel (petroleum ether to petroleum ether/ethyl acetate=4/1) to afford 42-6.

Step 3: To a stirred solution of 42-6 (7.9 g, 19.3 mmol) in THF (100 mL) at −20° C. was added KHMDS (38.6 mL, 1 M in THF, 38.6 mmol). The resulting mixture was stirred at room temperature for 2 hours. The reaction was quenched with sat. aqueous $NH_4Cl$ solution and extracted with ethyl acetate. The combined organic layers were dried over anhydrous sodium sulfate and concentrated. The residue was purified by flash column chromatography on silica gel (petroleum ether to petroleum ether/ethyl acetate=2/1) to afford 42-3.

Step 4: To a solution of 42-3 (746 mg, 2 mmol) and DIEA (387 mg, 3 mmol) in MeCN (20 mL) was added $POCl_3$ (367 mg, 2.4 mmol) dropwise at room temperature. The resulting mixture was stirred at 80° C. for 45 minutes, followed by addition of DIEA (3.87 g, 30 mmol) and a solution of 42-2 (1.58 g, 4 mmol) in MeCN (10 mL) dropwise at −10° C. After stirring at room temperature for 1 hour, the reaction was quenched with ice-water and the mixture was extracted with ethyl acetate. The combined organic layers were dried over anhydrous sodium sulfate and concentrated. The residue was purified by flash column chromatography on silica gel (dichloromethane to dichloromethane/methanol=10/1) to afford 42-4.

Step 5: A mixture of 42-4 (8 mg, 0.15 mmol), 3-fluoro-2-(4,4,5,5-tetramethyl-1,3,2-dioxaborolan-2-yl)aniline (42 mg, 0.18 mmol), Pd(dppf)Cl$_2$ (13 mg, 0.018 mmol) and KOAc (40 mg, 0.41 mmol) in dioxane (3 mL)/H$_2$O (1 drop) was stirred at 80° C. for 2 hours under nitrogen atmosphere. The mixture was diluted with water and extracted with ethyl acetate. The combined organic layers were dried over anhydrous $Na_2SO_4$ and concentrated. The residue was purified by a Prep-HPLC (acetonitrile with 0.05% of TFA in water (30% to 65%) to afford 44. LCMS (ESI, m/z): $[M+H]^+$=599.1; HNMR (400 MHz, methanol-d$_4$, ppm): δ 8.73 (s, 1H), 8.26-8.22 (m, 1H), 7.15-7.09 (m, 1H), 6.84-6.74 (m, 1H), 6.53 (d, J=8.4 Hz, 1H), 6.42-6.38 (m, 1H), 6.30-6.24 (m, 1H), 5.83-5.78 (m, 1H), 5.01 (brs, 1H), 4.91-4.83 (m, 1H), 4.53-4.29 (m, 2H), 3.96-3.89 (m, 1.5H), 3.54-3.50 (m, 0.5H), 1.82-1.75 (m, 1H), 1.73-1.66 (m, 1H), 1.47 (d, J=6.8 Hz, 3H), 1.37-1.27 (m, 3H), 1.16-1.05 (m, 4H), 1.03-0.97

(m, 2H), 0.88-0.83 (m, 2H). FNMR (376 MHz, methanol-$d_4$, ppm): δ −114.9 (1F), −125.6 (1F).

Example 17 Synthesis of Compound 126

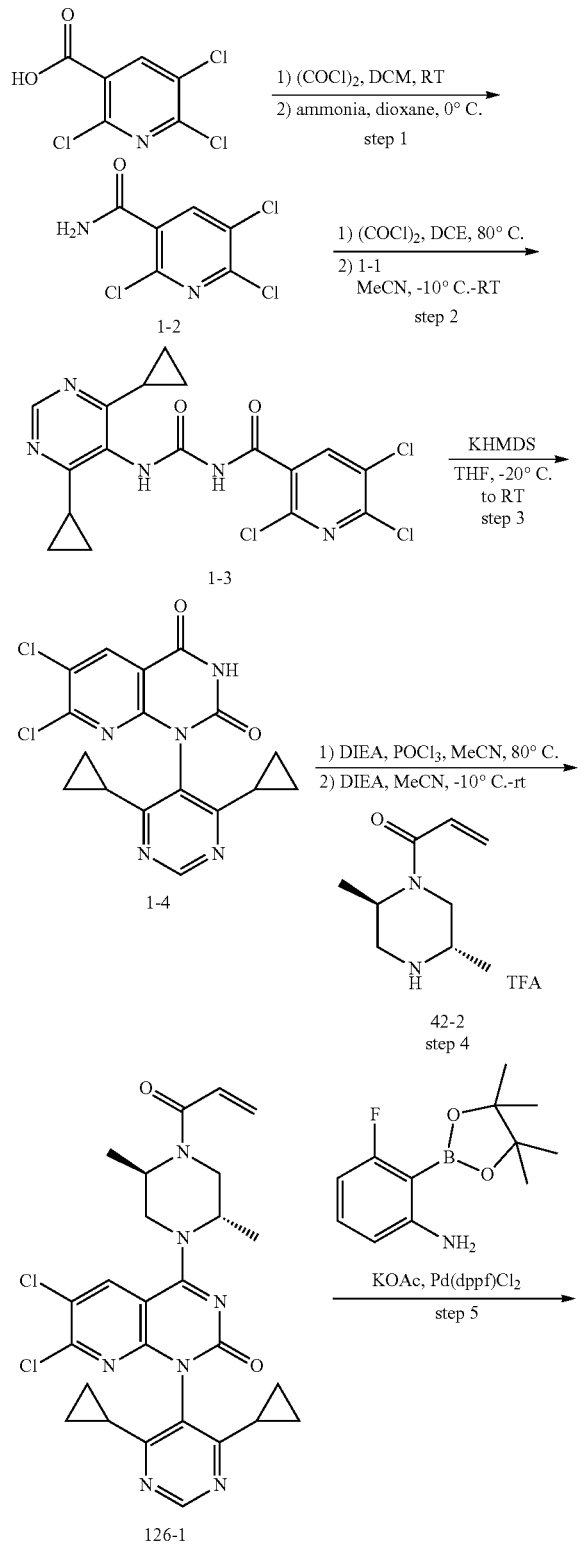

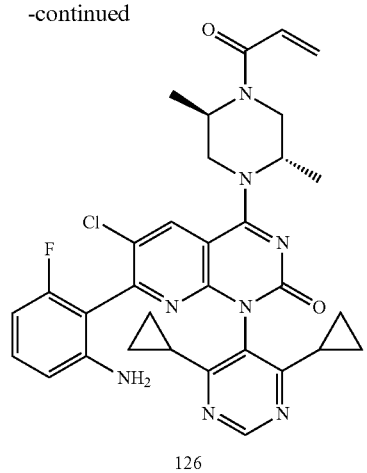

Step 1: To a suspension of 2,5,6-trichloronicotinic acid (10 g, 44 mmol) in dichloromethane (100 mL) at room temperature was added oxalyl chloride (11 g, 88 mmol) and 15 drops of dry DMF. After 30 minutes, the resulting solution was concentrated to give a residue which was dissolved in dioxane (40 mL). 100 mL of ammonia (28% $NH_3$ in water) was added dropwise at 0° C., and the reaction mixture was allowed to stir for additional 10 minutes, filtered, and washed with water. The filter cake was collected and freeze-dried to afford 1-2.

Step 2: A solution of 1-2 (550 mg, 2.44 mmol) in DCE (5 mL) was treated with oxalyl chloride (464.5 mg, 3.66 mmol). The mixture was stirred at 80° C. for 45 minutes and then concentrated. The residue was dissolved in acetonitrile (5 mL), cooled to −10° C., and a solution of 1-1 (1 g, 5.86 mmol) in acetonitrile (5 mL) was added. The resulting mixture was stirred at room temperature for overnight and then concentrated. The residue was purified by flash column chromatography on silica gel (ethyl acetate/petroleum ether=1/9 to 1/3) to afford 1-3.

Step 3: To a stirred solution of 1-3 (845 mg, 1.98 mmol) in THF (40 mL) at −20° C. was added KHMDS (5 mL, 1 M in THF, 5.0 mmol). The resulting mixture was then stirred at room temperature for 2 hours. The reaction was quenched with sat. aqueous $NH_4Cl$ solution and extracted with ethyl acetate. The combined organic layers were dried over anhydrous sodium sulfate and concentrated. The residue was purified by flash column chromatography on silica gel (ethyl acetate/petroleum ether=1/9 to 2/1) to afford 1-4.

Step 4: To a solution of 1-4 (1.0 g, 2.56 mmol) and DIEA (1.32 g, 10.25 mmol) in MeCN (20 mL) was added $POCl_3$ (790 mg, 5.12 mmol) dropwise at room temperature. The resulting solution was stirred at 80° C. for 45 minutes, followed by addition of DIEA (6.62 g, 51.25 mmol) and a solution of 42-2 (1.45 g, 5.12 mmol) in MeCN (5 mL) dropwise at −10° C. After stirring at room temperature for 1 hour, the reaction was then quenched with ice-water and the mixture was extracted with ethyl acetate. The combined organic layers were dried over anhydrous sodium sulfate and concentrated. The residue was purified by flash column chromatography on silica gel (ethyl acetate/petroleum ether=0/1 to 3/1) to afford 126-1.

Step 5: A mixture of 126-1 (120 mg, 0.22 mmol), 3-fluoro-2-(4,4,5,5-tetramethyl-1,3,2-dioxaborolan-2-yl) aniline (104 mg, 0.44 mmol), Pd(dppf)$Cl_2$ (16 mg, 0.022 mmol) and KOAc (108 mg, 1.11 mmol) in dioxane (3 mL)/$H_2O$ (1 drop) was stirred at 80° C. for 2 hours under nitrogen atmosphere. The mixture was diluted with water and extracted with ethyl acetate. The combined organic layers were dried over anhydrous $Na_2SO_4$ and concentrated. The residue was purified by a Prep-HPLC (acetonitrile with 0.05% of TFA in water (34% to 45%) to afford 126. LCMS (ESI, m/z): $[M+H]^+$=615.3; HNMR (400 MHz, DMSO-$d_6$, ppm): δ 8.74 (s, 1H), 8.52-8.35 (m, 1H), 7.16-7.07 (m, 1H), 6.94-6.76 (m, 1H), 6.51 (d, J=6.0 Hz, 1H), 6.38 (t, J=6.6 Hz, 1H), 6.20 (dd, J=12.6, 1.8 Hz, 1H), 5.76 (dd, J=12.6, 1.6 Hz, 1H), 4.91-4.80 (m, 2H), 4.51-3.50 (m, 6H), 1.91-1.65 (m, 1H), 1.45-1.15 (m, 6H), 1.10-0.70 (m, 8H). FNMR (376 MHz, DMSO-$d_6$, ppm): δ −114.30 (1F).

Example 18 Synthesis of Compound 127

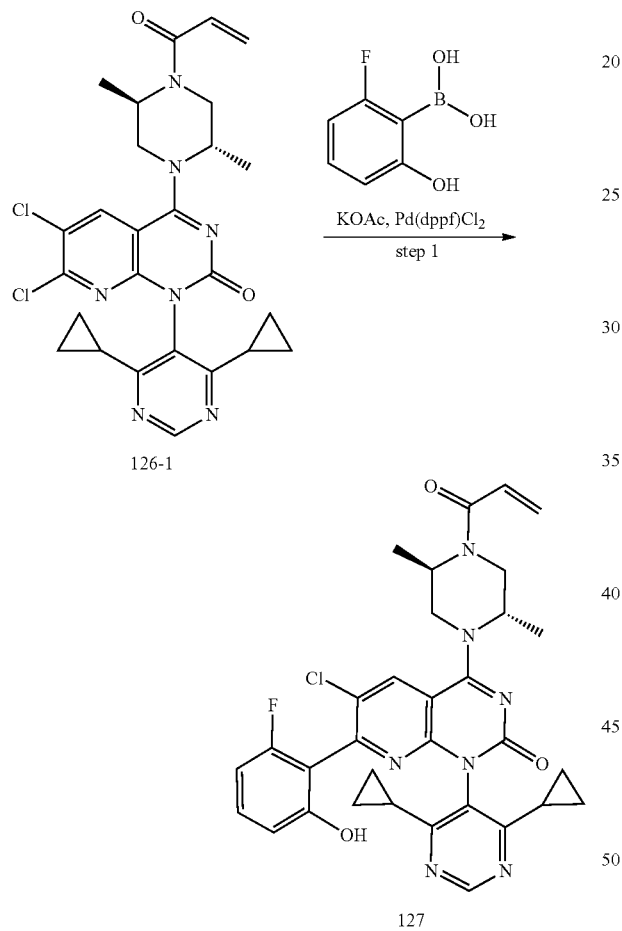

Step 1: A mixture of 126-1 (200 mg, 0.37 mmol), 2-fluoro-6-hydroxyphenylboronic acid (115 mg, 0.74 mmol), Pd(dppf)Cl₂ (27 mg, 0.037 mmol) and KOAc (181 mg, 1.85 mmol) in dioxane (3 mL)/H₂O (1 drop) was stirred at 80° C. for 2 hours under nitrogen atmosphere. The mixture was diluted with water and extracted with ethyl acetate. The combined organic layers were dried over anhydrous $Na_2SO_4$ and concentrated. The residue was purified by a Prep-HPLC (acetonitrile with 0.05% of TFA in water: 25% to 48%) to afford 127. LCMS (ESI, m/z): $[M+H]^+$=616.2; HNMR (300 MHz, DMSO-$d_6$, ppm): δ 10.16 (s, 1H), 8.71 (s, 1H), 8.50-8.40 (m, 1H), 7.31-7.23 (m, 1H), 6.86-6.67 (m, 3H), 6.20 (d, J=16.5 Hz, 1H), 5.79-5.74 (m, 1H), 4.99-4.78 (m, 1.5H), 4.55-4.45 (m, 0.5H), 4.40-4.05 (m, 1.5H), 3.95-3.68 (m, 2H), 3.55-3.45 (m, 0.5H), 1.80-1.60 (m, 2H), 1.34 (s, 3H), 1.30-1.23 (m, 3H), 0.95 (d, J=5.7 Hz, 2H), 0.90 (s, 4H), 0.82 (s, 2H). FNMR (282 MHz, DMSO-$d_6$, ppm): δ −115.33 (1F).

Example 19 Synthesis of Compound 124

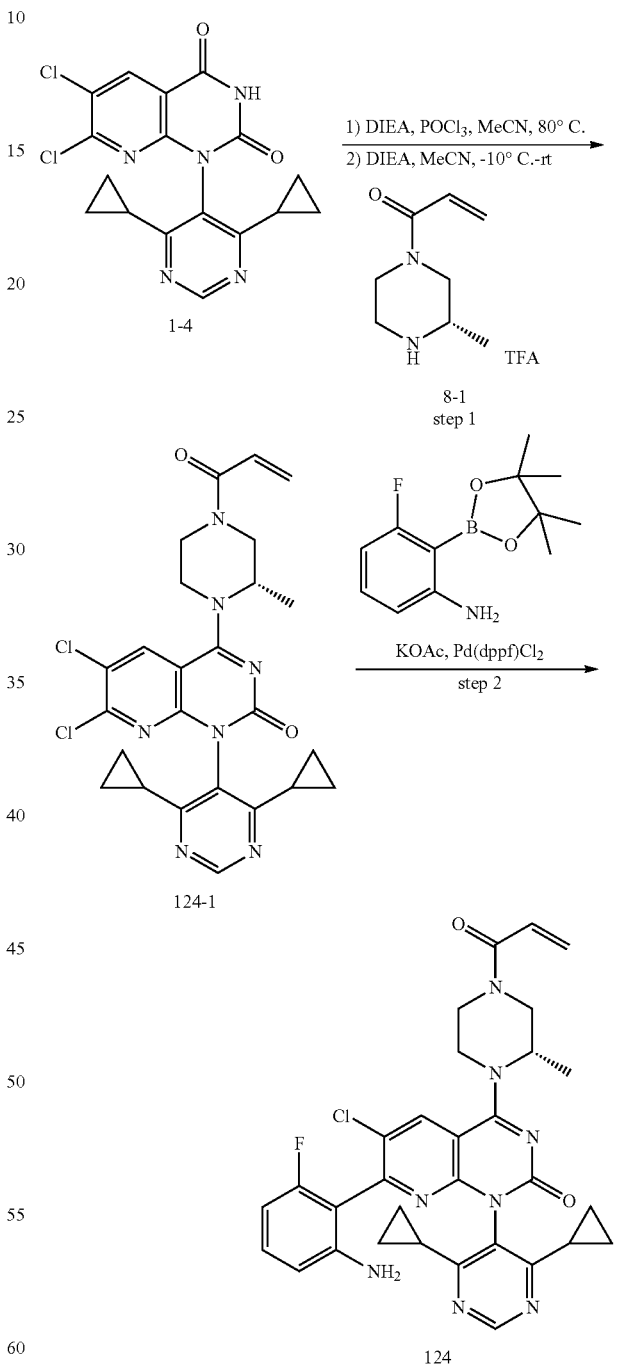

Step 1: To a solution of 8-1 (900 mg, 2.3 mmol) and DIEA (1.2 g, 9.3 mmol) in MeCN (3 mL) was added POCl₃ (707 mg, 4.6 mmol) dropwise at room temperature. The resulting solution was stirred at 80° C. for 45 minutes, followed by addition of DIEA (6.62 g, 51.25 mmol) and a solution of 8-1

(889 mg, 5.8 mmol) in MeCN (2 mL) dropwise at −10° C. After stirring at room temperature for 1 hour, the reaction was quenched with ice-water and the mixture was extracted with ethyl acetate. The combined organic layers were dried over anhydrous sodium sulfate and concentrated. The residue was purified by flash column chromatography on silica gel (ethyl acetate/petroleum ether=0/1 to 3/1) to afford 124-1.

Step 2: A mixture of 124-1 (170 mg, 0.32 mmol), 3-fluoro-2-(4,4,5,5-tetramethyl-1,3,2-dioxaborolan-2-yl) aniline (153 mg, 0.64 mmol), Pd(dppf)Cl$_2$ (36 mg, 0.048 mmol) and KOAc (158 mg, 1.61 mmol) in dioxane (3 mL)/H$_2$O (1 drop) was stirred at 80° C. for 2 hours under nitrogen atmosphere. The mixture was diluted with water and extracted with ethyl acetate. The combined organic layers were dried over anhydrous Na$_2$SO$_4$ and concentrated. The residue was purified by a Prep-HPLC (10 mM aqueous NH$_4$HCO$_3$ with acetonitrile (26% to 42%)) to afford 124. LCMS (ESI, m/z): [M+H]$^+$=601.4; HNMR (300 MHz, DMSO-d$_6$, ppm): δ 8.74 (s, 1H), 8.52-8.35 (m, 1H), 7.19-7.07 (m, 1H), 6.86-6.80 (m, 1H), 6.51 (d, J=8.1 Hz, 1H), 6.38 (t, J=9.0 Hz, 1H), 6.22 (d, J=16.8 Hz, 1H), 5.78 (dd, J=10.5, 2.4 Hz, 1H), 5.22 (brs, 2H), 5.12-4.96 (m, 1H), 4.49-4.29 (m, 1H), 4.20-4.03 (m, 1H), 3.71-3.64 (m, 1H), 3.25-3.17 (m, 1H), 1.90-1.75 (m, 2H), 1.35 (dd, J=23.7, 6.4 Hz, 3H), 1.15-0.75 (m, 8H). FNMR (282 MHz, DMSO-d$_6$, ppm): δ −114.17 (1F).

Example 20 Synthesis of Compound 151 and Compound 152

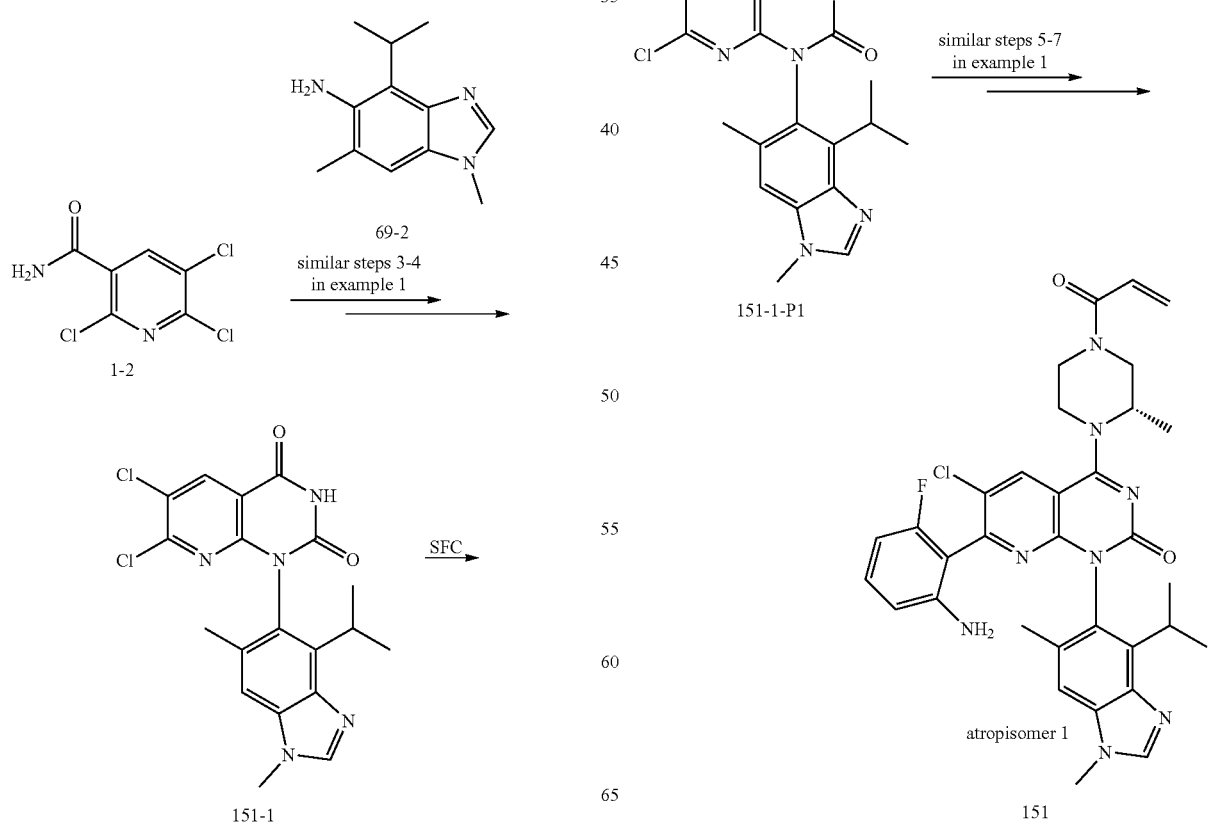

173
-continued

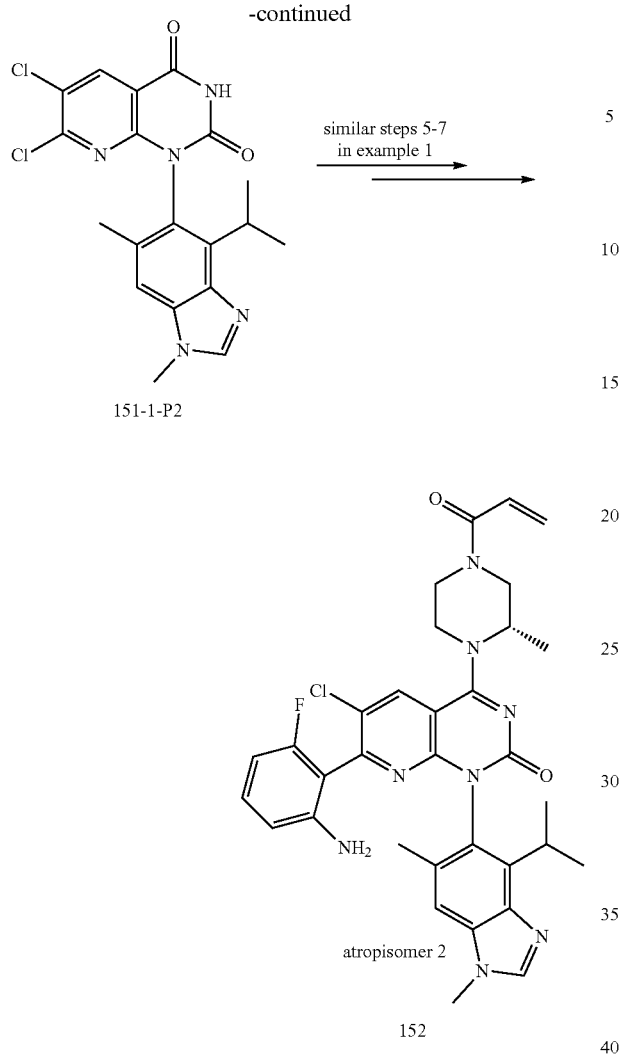

151-1-P2 similar steps 5-7 in example 1 →

152 atropisomer 2

Followed similar steps in example 1 to synthesize 151-1. 151-1 (1.7 g) was purified by SFC (Dr. Maisch MIC, 250×25 mm, 10 μm, 55% MeOH/CO$_2$, 70 mL/min, 100 bar) to obtain two peaks: 151-1-P1 (peak 1, 623 mg, 98.1% ee) and 151-1-P2 (peak 2, 756 mg, >99% ee).

Followed similar steps in example 1 to synthesize 151. LCMS (ESI, m/z): [M+H]$^+$=629.3; HNMR (400 MHz, DMSO-d$_6$, ppm): δ 8.45-8.40 (m, 1H), 8.07 (s, 1H), 7.27 (s, 1H), 7.01 (dd, J=15.2, 8.0 Hz, 1H), 6.90-6.86 (m, 1H), 6.40 (d, J=8.0 Hz, 1H), 6.34-6.18 (m, 2H), 5.77 (dd, J=10.4, 2.4 Hz, 1H), 5.07-5.02 (m, 2H), 4.92 (s, 1H), 4.44-4.41 (m, 0.5H), 4.32-4.15 (m, 2H), 4.08-4.04 (m, 0.5H), 3.84-3.61 (m, 4.5H), 3.50-3.47 (m, 0.5H), 3.18-3.01 (m, 1H), 2.92-2.86 (m, 0.5H), 2.74-2.70 (m, 0.5H), 2.01 (s, 2H), 1.88 (s, 1H), 1.35-1.18 (m, 9H).

Followed similar steps in example 1 to synthesize 152. LCMS (ESI, m/z): [M+H]$^+$=629.1; HNMR (400 MHz, DMSO-d$_6$, ppm): δ 8.40 (s, 1H), 8.06 (s, 1H), 7.27 (s, 1H), 7.01 (dd, J=15.2, 7.9 Hz, 1H), 6.95-6.80 (m, 1H), 6.40 (d, J=8.2 Hz, 1H), 6.29 (t, J=8.8 Hz, 1H), 6.21 (d, J=16.4 Hz, 1H), 5.77 (dd, J=10.4, 2.3 Hz, 1H), 5.04 (s, 2H), 4.89 (s, 1H), 4.47-3.99 (m, 3H), 3.85-3.39 (m, 5H), 3.21-3.01 (m, 1H), 2.91-2.63 (m, 1H), 2.05-1.86 (m, 3H), 1.39-1.14 (m, 9H).

174

Example 21 Synthesis of Compound 157 and Compound 158

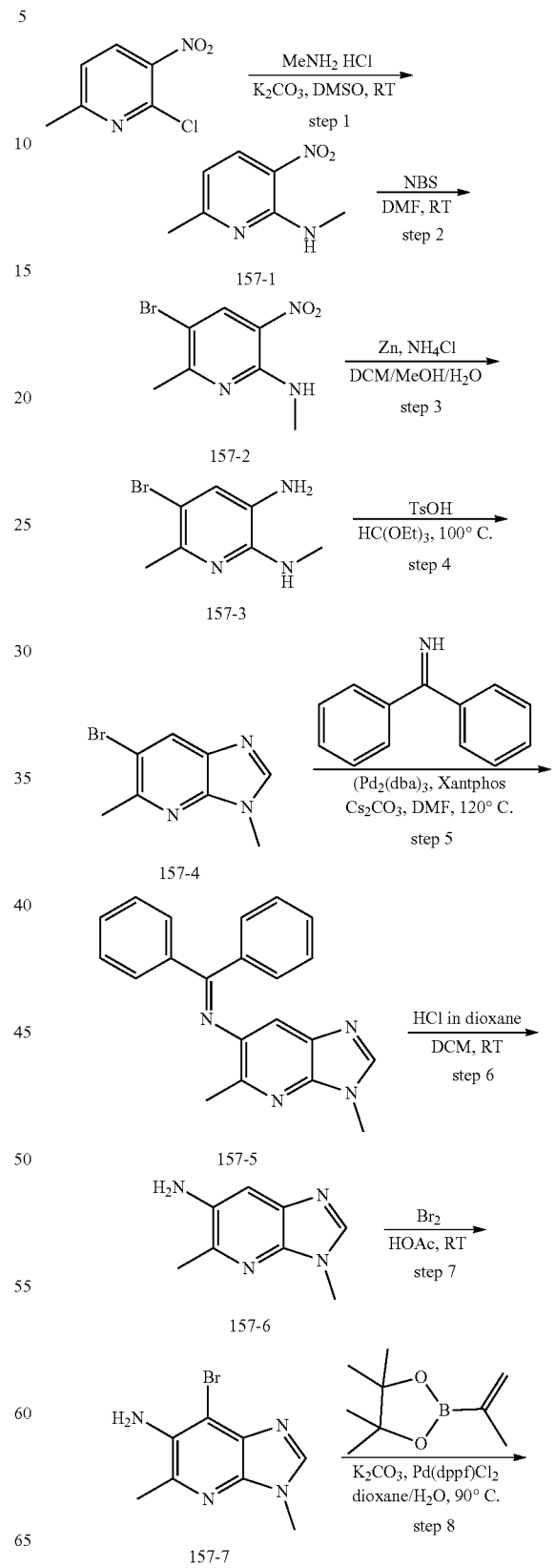

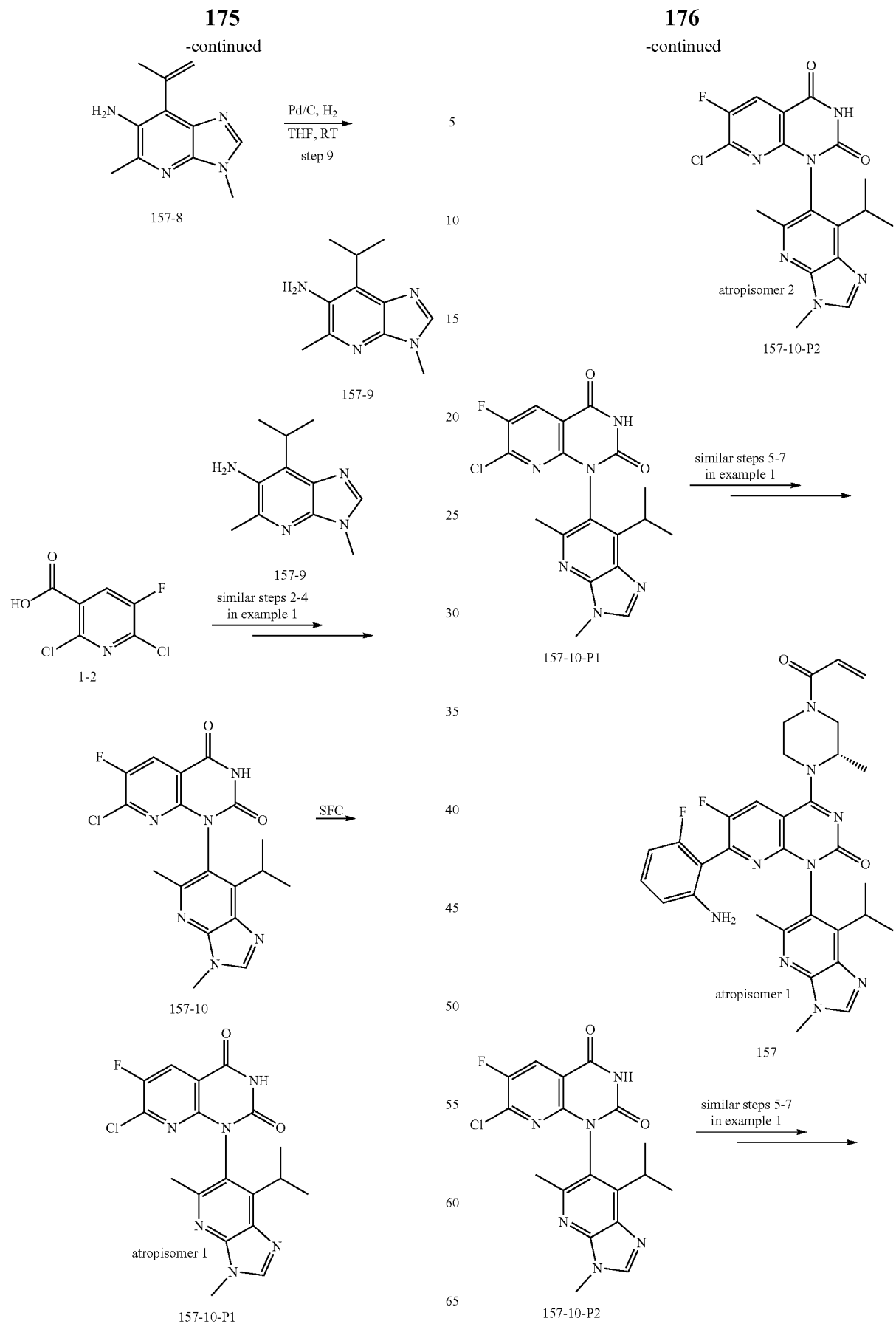

-continued

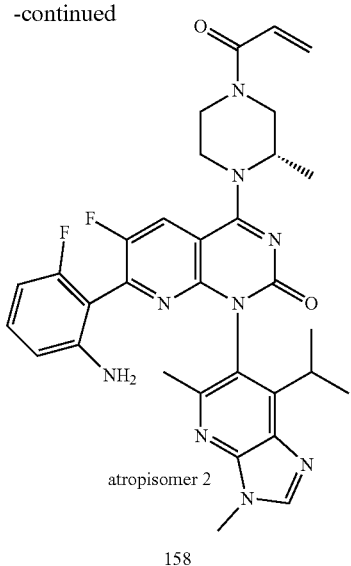

158

Step 1: To a mixture of 2-chloro-6-methyl-3-nitropyridine (25 g, 144.5 mmol) and $K_2CO_3$ (59.8 g, 433.5 mmol) in DMSO (200 mL) was added methylamine hydrochloride (11.8 g, 173.4 mmol) dropwise. After stirring at room temperature for overnight, the reaction mixture was diluted with water and extracted with ethyl acetate. The combined organic layers were dried over anhydrous $Na_2SO_4$ and concentrated to afford 157-1.

Step 2: A solution of 157-1 (23.3 g, 139.5 mmol) and N-bromosuccinimide (26 g, 146.5 mmol) in DMF (250 mL) was stirred for 2 hours at room temperature. The reaction mixture was diluted with water and extracted with ethyl acetate. The combined organic layers were washed with brine, dried over anhydrous $Na_2SO_4$ and concentrated to afford 157-2.

Step 3: A mixture of 157-2 (32 g, 131 mmol), Zn power (85 g, 1310 mmol), a solution of $NH_4Cl$ (34.7 g, 655 mmol) in water (30 mL) and dichloromethane/methanol (1/1, 150 mL) was stirred at room temperature for 2 hours under $N_2$ atmosphere. Filtered and the filter cake was washed with dichloromethane. The combined filtrates were diluted with water and extracted with dichloromethane. The combined organic layers were washed with brine, dried over anhydrous $Na_2SO_4$ and concentrated to afford 157-3.

Step 4: A solution of 157-3 (19.3 g, 89.8 mmol) and p-toluenesulfonic acid monohydrate (1.7 g, 8.97 mmol) in triethyl orthoformate (150 mL) was stirred at 100° C. for 2 hours under $N_2$ atmosphere. The resulting mixture was diluted with water and extracted with ethyl acetate. The combined organic layers were washed with brine, dried over anhydrous $Na_2SO_4$, and concentrated to give a residue which was purified by silica gel chromatography (petroleum ether/ethyl acetate=10/1 to 1/1) to afford 157-4.

Step 5: A mixture of 157-4 (11 g, 48.9 mmol), diphenylmethanimine (13.3 g, 73.3 mmol), cesium carbonate (31.9 g, 97.8 mmol), $Pd_2(dba)_3$ (2.23 g, 2.44 mmol) and Xantphos (2.83 g, 4.88 mmol) in DMF (100 mL) was stirred at 120° C. for overnight under $N_2$ atmosphere. The resulting mixture was cooled, diluted with water and extracted with ethyl acetate. The combined organic layers were washed with brine, dried over $Na_2SO_4$ and give a residue which was purified by silica gel chromatography (petroleum ether/ethyl acetate=10/1 to 1/5) to afford 157-5.

Step 6: To a solution of 157-5 (12.80 g, 39.26 mmol) in dichloromethane (60 mL) was added a solution of HCl in dioxane (4 M, 30 mL) dropwise. The mixture was stirred at room temperature for 1 hour. To the solution was added acetonitrile (30 mL), and filtered to afford 157-6.

Step 7: To a solution of 157-6 (8.8 g, 54.3 mmol) in acetic acid (150 mL) was added $Br_2$ (8.7 g, 54.3 mmol) dropwise. The mixture was stirred at room temperature for 2 hours under $N_2$ atmosphere. The resulting solution was adjusted to pH=7-8 with a saturated sodium bicarbonate solution. The mixture was extracted with ethyl acetate. The combined organic layers were washed with brine, dried over $Na_2SO_4$, and concentrated to give a residue which was purified by silica gel chromatography (petroleum ether/ethyl acetate=10/1 to 1/5) to afford 157-7.

Step 8: A mixture of 157-7 (6.3 g, 26.25 mmol), 2-isopropenyl-4,4,5,5-tetramethyl-1,3,2-dioxaborolane (7.93 g, 47.25 mmol), potassium carbonate (9.1 g, 65.6 mmol) and $Pd(dppf)Cl_2$ (1.54 g, 2.1 mmol) in 1,4-dioxane (60 mL) and $H_2O$ (12 mL) was stirred at 80° C. overnight under $N_2$ atmosphere. The mixture was cooled, diluted with water and extracted with ethyl acetate. The organic layers were combined, washed with brine, dried over $Na_2SO_4$ and concentrated to give a residue which was purified by silica gel chromatography (petroleum ether/ethyl acetate=10/1 to 1/1) to afford 157-8.

Step 9: A mixture of 157-8 (4.5 g, 22.28 mmol) and 10% Pd/C (0.45 g) in tetrahydrofuran (50 mL) was stirred at room temperature overnight under hydrogen atmosphere. The mixture was filtered and the solid was washed with tetrahydrofuran. The filtrate was concentrated to afford 157-9.

Followed similar steps in example 1 to synthesize 157-10. 157-10 (1.15 g) was purified by SFC (Dr. Maisch MIC, 250×25 mm, 10 μm, 40% EtOH/$CO_2$, 70 mL/min, 100 bar) to give two peaks: 157-10-P1 (peak 1, 523 mg, >99% ee) and 157-10-P2 (peak 2, 578 mg, >99% ee).

Followed similar steps in example 1 to synthesize 157. LCMS (ESI, m/z): [M+H]$^+$=614.6; HNMR (400 MHz, DMSO-$d_6$, ppm): δ 8.40-8.25 (m, 2H), 7.06 (dd, J=15.0, 8.1 Hz, 1H), 6.95-6.80 (m, 1H), 6.42 (d, J=8.2 Hz, 1H), 6.37-6.30 (m, 1H), 6.22 (d, J=16.8 Hz, 1H), 5.77 (dd, J=10.4, 2.2 Hz, 1H), 5.29 (s, 2H), 4.95 (s, 1H), 4.45-4.41 (m, 0.5H), 4.31-4.28 (m, 1.5H), 4.17 (d, J=11.6 Hz, 0.5H), 4.04 (d, J=13.0 Hz, 0.5H), 3.81 (s, 3H), 3.75-3.59 (m, 1H), 3.53-3.46 (m, 1H), 3.11 (t, J=11.3 Hz, 1H), 2.85-2.70 (m, 1H), 2.16 (s, 3H), 1.34 (d, J=6.8 Hz, 6H), 1.24 (d, J=6.9 Hz, 3H).

Followed similar steps in example 1 to synthesize 158. LCMS (ESI, m/z): [M+H]$^+$=614.2; HNMR (400 MHz, DMSO-$d_6$, ppm): δ 8.40-8.25 (m, 2H), 7.06 (dd, J=15.0, 8.2 Hz, 1H), 6.94-6.81 (m, 1H), 6.42 (d, J=8.2 Hz, 1H), 6.37-6.31 (m, 1H), 6.21 (dd, J=16.2, 4.6 Hz, 1H), 5.77 (dd, J=10.4, 2.2 Hz, 1H), 5.29 (s, 2H), 4.90 (s, 1H), 4.45-4.41 (m, 0.5H), 4.31-4.28 (m, 1.5H), 4.17 (d, J=11.6 Hz, 0.5H), 4.04 (d, J=13.0 Hz, 0.5H), 3.81 (s, 3H), 3.72-3.68 (m, 1.5H), 3.49-3.33 (m, 0.5H), 3.12 (t, J=12.0 Hz, 1H), 2.82-2.72 (m, 1H), 2.15 (s, 3H), 1.35 (d, J=6.8 Hz, 6H), 1.24 (d, J=6.8 Hz, 3H).

Example 22 Synthesis of Compound 145 and Compound 146

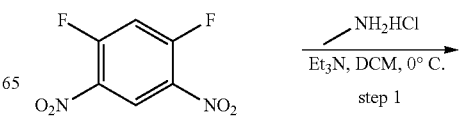

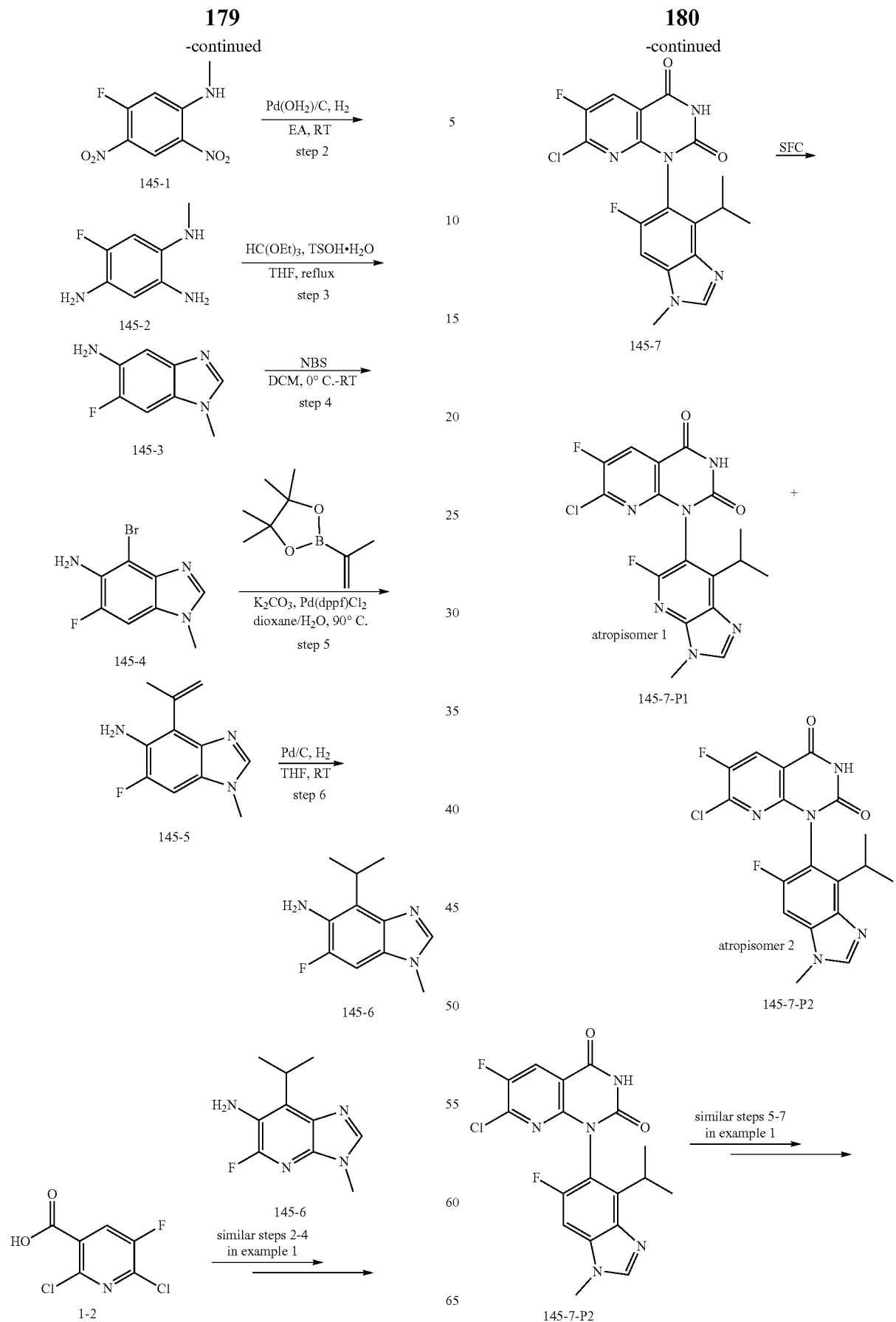

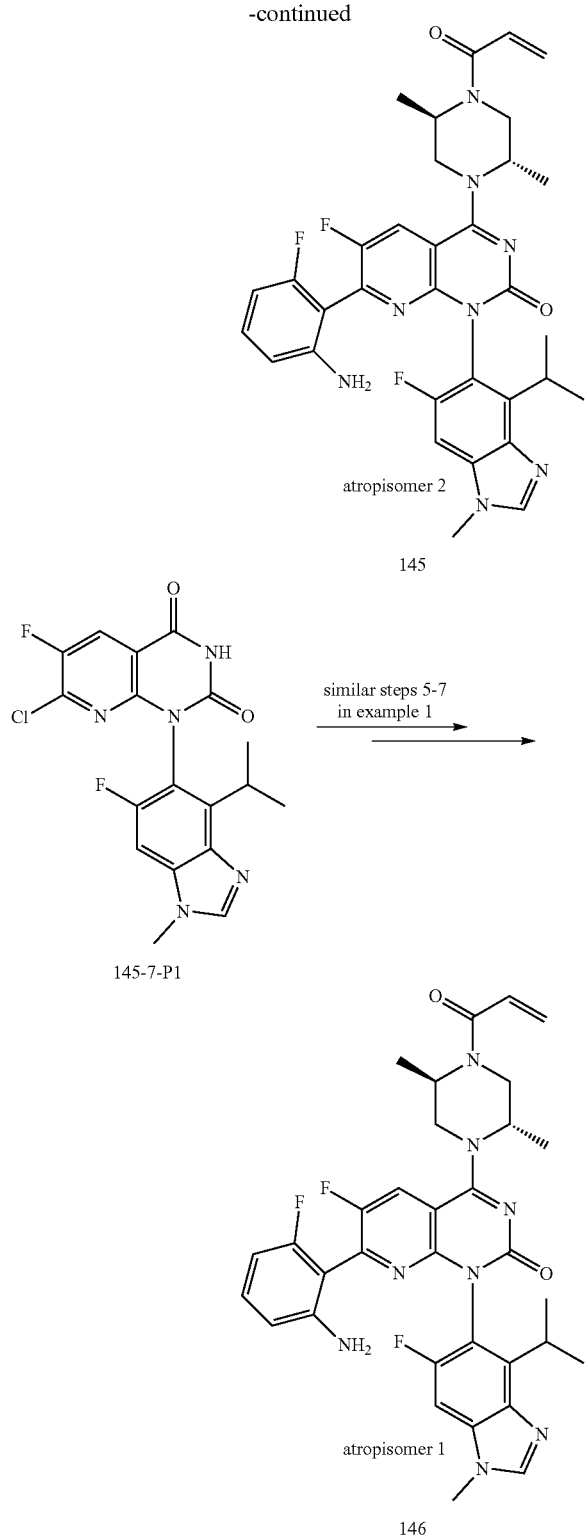

layers were combined, washed with brine, dried over $Na_2SO_4$ and concentrated to give a residue which was purified by silica gel chromatography (petroleum ether/ethyl acetate=1/1) to afford 145-1.

Step 2: To a solution of 145-1 (34.0 g, 158 mmol) in ethyl acetate (500 mL) was added 10% $Pd(OH)_2/C$ (3.4 g). The resulting mixture was stirred at room temperature overnight under hydrogen atmosphere. Filtered and the filter cake was washed with ethyl acetate. The filtrate was concentrated to afford 145-2.

Step 3: A mixture of 145-2 (19 g, 122 mmol), triethyl orthoformate (36.1 g, 244 mmol) and p-toluenesulfonic acid monohydrate (2.32 g, 12.2 mmol) in tetrahydrofuran (200 mL) was refluxed for 2 hours. The mixture was cooled, diluted with water and extracted with ethyl acetate/tetrahydrofuran (1/1). The organic layers were combined, washed with brine, dried over $Na_2SO_4$ and concentrated to give a residue which was purified by silica gel chromatography (petroleum ether/ethyl acetate=1/3) to afford 145-3.

Step 4: To a solution of 145-3 (9 g, 54.5 mmol) in dichloromethane (100 mL) was added N-bromosuccinimide (9.7 g, 54.5 mmol) in portions at 0° C. The resulting solution was allowed to warm to room temperature and stirred for 1 hour. The mixture was diluted with water and extracted with dichloromethane. The organic layers were combined, washed with brine, dried over $Na_2SO_4$ and concentrated to give a residue which was purified by silica gel chromatography (petroleum ether/ethyl acetate=1/2) to afford 145-4.

Step 5: A mixture of 145-4 (5.95 g, 23.4 mmol), 2-isopropenyl-4,4,5,5-tetramethyl-1,3,2-dioxaborolane (6.14 g, 36.6 mmol), potassium carbonate (8.07 g, 58.5 mmol) and $Pd(dppf)Cl_2$ (1.71 g, 2.34 mmol) in dioxane (60 mL) and $H_2O$ (12 mL) was stirred at 90° C. overnight under argon atmosphere. The mixture was cooled, diluted with water and extracted with ethyl acetate. The organic layers were combined, washed with brine, dried over $Na_2SO_4$ and concentrated to give a residue which was purified by silica gel chromatography (petroleum ether/ethyl acetate=1/1) to afford 145-5.

Step 6: A mixture of 145-5 (2.53 g, 12.3 mmol) and 10% Pd/C (0.25 g) in tetrahydrofuran (50 mL) was stirred at room temperature overnight under hydrogen atmosphere. The mixture was filtered and the solid was washed with tetrahydrofuran. The filtrate was concentrated to afford 145-6.

Followed similar steps in example 1 to synthesize 145-7. 145-7 (1.08 g) was purified by SFC (Dr. Maisch MIC, 250×25 mm, 10 μm, 50% $MeOH/CO_2$, 80 mL/min, 100 bar) to give two peaks: 145-7-P1 (peak 1, 600 mg, >99% ee) and 145-7-P2 (peak 2, 326 mg, >99% ee).

Followed similar steps in example 1 to synthesize 145. LCMS (ESI, m/z): $[M+H]^+$=631.4; HNMR (400 MHz, DMSO-$d_6$, ppm): δ 8.28-8.20 (m, 1H), 8.20 (s, 1H), 7.43 (d, J=9.6 Hz, 1H), 7.08 (dd, J=15.2, 8.0 Hz, 1H), 6.91-6.78 (m, 1H), 6.44 (d, J=8.4 Hz, 1H), 6.37 (t, J=8.0 Hz, 1H), 6.19 (d, J=16.8 Hz, 1H), 5.77-5.74 (m, 1H), 5.35 (s, 2H), 4.85-4.72 (m, 1.5H), 4.50-4.47 (m, 0.5H), 4.25-4.15 (m, 1.5H), 3.91-3.70 (m, 5H), 3.50-3.42 (m, 0.5H), 2.94-2.89 (m 1H), 1.47-1.08 (m 12H).

Followed similar steps in example 1 to synthesize 146. LCMS (ESI, m/z): $[M+H]^+$=631.3; HNMR (400 MHz, DMSO-$d_6$, ppm): δ 8.33 (d, J=9.6 Hz, 1H), 8.20 (s, 1H), 7.44 (d, J=9.6 Hz, 1H), 7.09 (dd, J=15.2, 8.0 Hz, 1H), 6.90-6.79 (m, 1H), 6.45 (d, J=8.0 Hz, 1H), 6.37 (t, J=8.0 Hz, 1H), 6.19 (dd, J=16.8, 2.0 Hz, 1H), 5.76-5.74 (m, 1H), 5.37 (s, 2H), 4.90-4.82 (m, 1H), 4.79-4.74 (m, 0.5H), 4.49-4.45 (m, 0.5H), 4.18-4.02 (m, 1.5H), 3.99-3.66 (m, 5H), 3.58-3.54 (m, 1H), 3.04-2.99 (m, 1H), 1.50-0.95 (m, 12H).

Step 1: To a solution of 1,5-difluoro-2,4-dinitrobenzene (50.0 g. 245 mmol) and DCM (500 mL) was added triethylamine (49.5 g, 490 mmol) at 0° C., followed by methylamine hydrochloride (16.5 g, 245 mmol) in portions. The resulting solution was stirred at 0° C. for 2 hours. Water (1 L) and ethyl acetate (1 L) were added. The aqueous layer was separated and extracted with ethyl acetate. The organic Example 23 Synthesis of Compound 179 and Compound 180
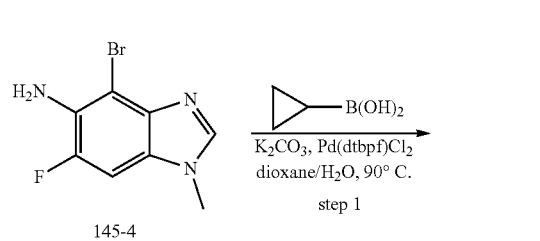
145-4
step 1
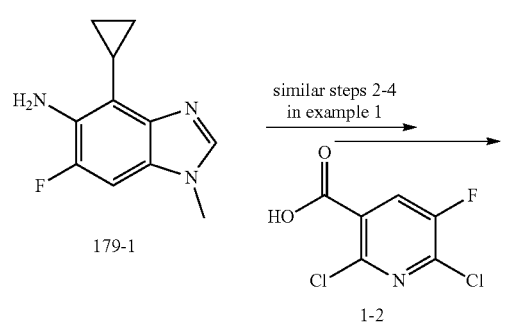
179-1
similar steps 2-4 in example 1
1-2
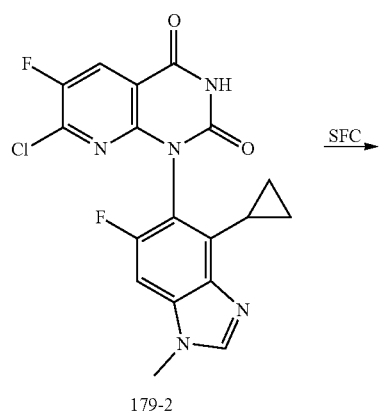
179-2
SFC
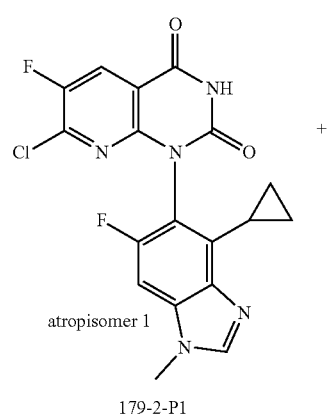
atropisomer 1
179-2-P1
+
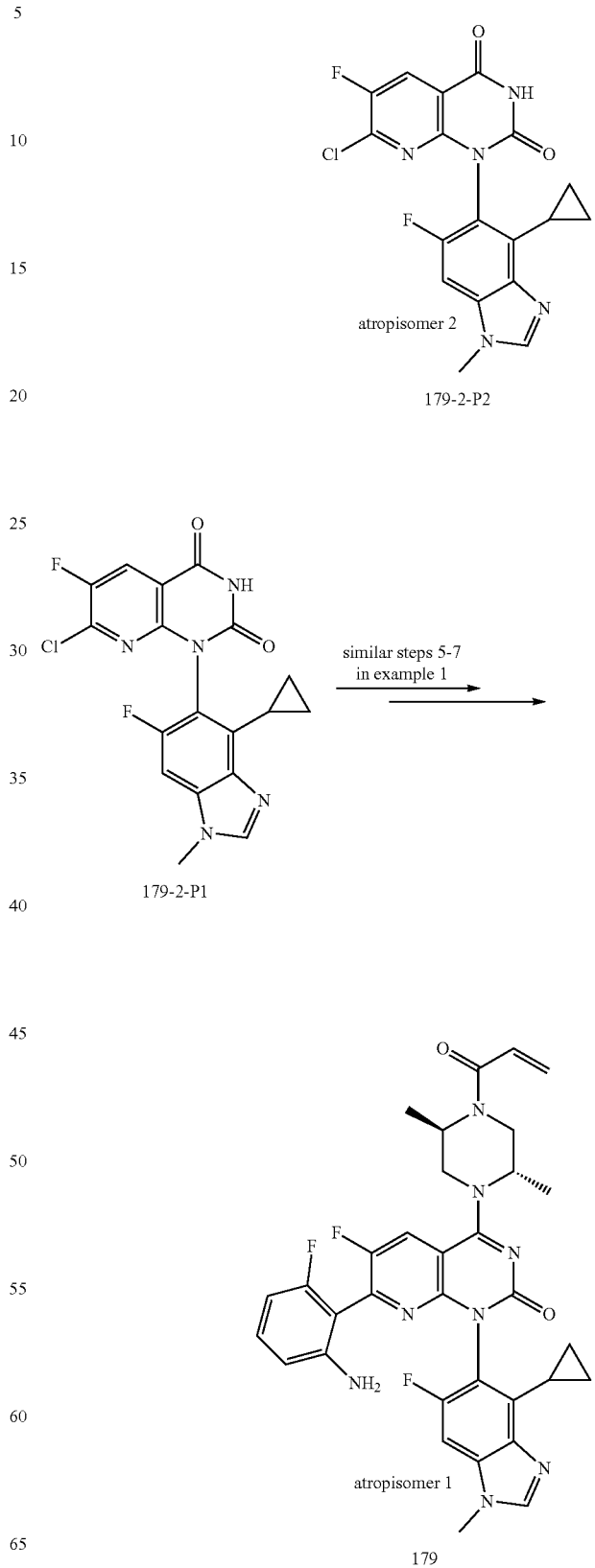
atropisomer 2
179-2-P2
179-2-P1
similar steps 5-7 in example 1
atropisomer 1
179

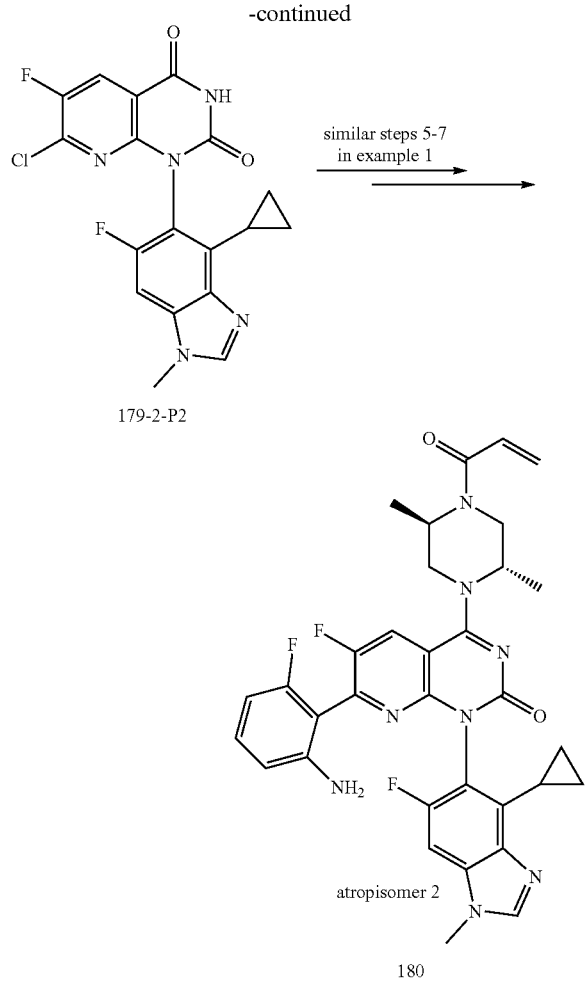

Step 1: A mixture of 145-4 (1 g, 4.1 mmol), cyclopropylboronic acid (2.8 g, 32.9 mmol), Pd(dtbpf)Cl$_2$ (270 mg, 0.4 mmol) and K$_2$CO$_3$ (1.4 g, 10.1 mmol) in dioxane (50 mL) and water (10 mL) was stirred at 90° C. overnight under nitrogen atmosphere. The mixture was cooled, and concentrated to give a residue which was purified by a reverse phase HPLC (acetonitrile with 0.05% TFA in water: 18% to 20%) to afford 179-1.

Followed similar steps in example 1 to synthesize 179-2. 179-2 (1.34 g) was purified by SFC (Dr. Maisch MIC, 250×25 mm, 10 μm, 55% MeOH/CO$_2$, 100 mL/min, 100 bar) to give two peaks: 179-2-P1 (peak 1, 560 mg, >99% ee) and 179-2-P2 (peak 2, 730 mg, >99% ee).

Followed similar steps in example 1 to synthesize 179. LCMS (ESI, m/z): [M+H]$^+$=629.3; HNMR (400 MHz, DMSO-d$_6$, ppm): δ 8.30 (d, J=9.6 Hz, 1H), 8.12 (s, 1H), 7.34 (d, J=9.6 Hz, 1H), 7.10-7.04 (m, 1H), 6.86-6.75 (m, 1H), 6.43 (d, J=8 Hz, 1H), 6.38-6.32 (m, 1H), 6.18-6.13 (m, 1H), 5.74-5.70 (m, 1H), 5.43 (s, 2H), 4.91-4.70 (m, 2H), 4.50-4.40 (m, 0.5H), 4.12-4.06 (m, 1.5H), 3.86-3.82 (m, 2H), 3.77 (s, 3H), 1.70-1.66 (m, 1H), 1.49-1.46 (m, 2H), 1.29-1.27 (m, 3H), 1.23-1.13 (m, 3H), 0.79-0.75 (m, 1H), 0.68-0.66 (m, 1H). FNMR (376 MHz, DMSO-d$_6$, ppm): δ −113.81 (1F), −126.99 (1F), −127.16 (1F).

Followed similar steps in example 1 to synthesize 180 as TFA salt. LCMS (ESI, m/z): [M+H]$^+$=629.3; HNMR (400 MHz, MeOD-d$_4$, ppm): δ 9.24 (s, 1H), 8.26-8.21 (m, 1H), 7.74 (d, J=8.8 Hz, 1H), 7.10-7.05 (m, 1H), 6.90-6.70 (m, 1H), 6.42 (d, J=8.4 Hz, 1H), 6.37-6.25 (m, 2H), 5.84-5.79 (m, 1H), 5.03-4.90 (m, 2H), 4.61-4.56 (m, 1H), 4.50-4.32 (m, 1H), 4.06 (s, 3H), 3.91-3.86 (m, 2H), 1.95-1.85 (m, 1H), 1.53-1.50 (m, 3H), 1.39-1.30 (m, 3H), 0.94-0.81 (m, 3H), 0.55-0.53 (m, 1H). FNMR (3761 Hz, DMSO-d$_6$, ppm): δ −116.28 (1F), −123.46 (1F), −126.84 (1F).

Compounds of Formulae (I) and (II) can be prepared by following the synthetic methods described herein. Table 1 lists representative analytical data for some of compounds prepared similarly to the processes described in Examples 1-23.

TABLE 1

Characterization of the compounds of Formulas (I) and (II)

| Compound No. | Structure | [M + H]$^+$ | $^1$H-NMR and $^{19}$F-NMR |
|---|---|---|---|
| 2 | 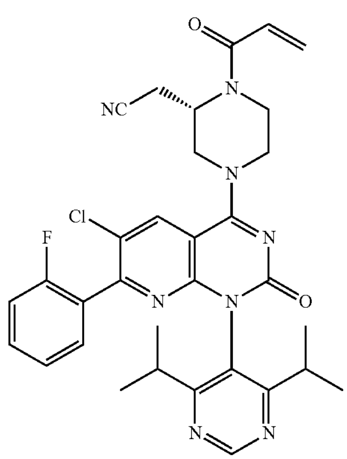 [SMILES: C=CC(=O)N1CCN(c2nc(=O)n(-c3c(C(C)C)ncnc3C(C)C)c3nc(-c4ccccc4F)c(Cl)cc23)C[C@@H]1CC#N] | 615.3 | HNMR (300 MHz, DMSO-d$_6$, ppm): δ 9.07 (s, 1H), 8.67 (s, 1H), 7.57-7.46 (m, 1H), 7.37-7.28 (m, 2H), 7.18 (t, J = 7.1 Hz, 1H), 7.03-6.78 (m, 1H), 6.24 (d, J = 15.4 Hz, 1H), 5.82 (d, J = 10.6 Hz, 1H), 4.94 (brs, 1H), 4.52-4.28 (m, 2H), 4.15-3.55 (m, 3H), 3.45-3.25 (m, 1H), 3.19-2.95 (m, 2H), 2.87-2.77 (m, 1H), 2.71-2.60 (m, 1H), 1.13-1.05 (m, 6H), 0.99-0.88 (m, 6H). FNMR (282 MHz, DMSO-d$_6$, ppm): δ −114.71 (1F). |

TABLE 1-continued

Characterization of the compounds of Formulas (I) and (II)

| Compound No. | Structure | [M + H]⁺ | ¹H-NMR and ¹⁹F-NMR |
|---|---|---|---|
| 3 | 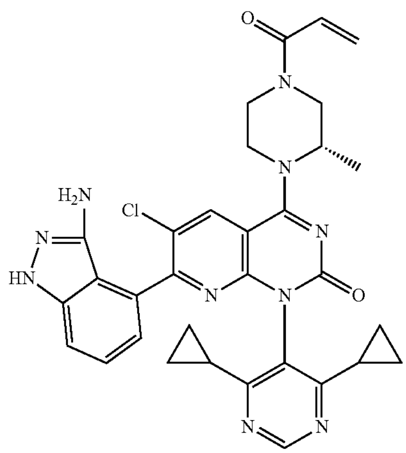 [SMILES: C=CC(=O)N1CCN(c2nc(=O)n(-c3c(C4CC4)ncnc3C3CC3)c3nc(-c4cccc5[nH]nc(N)c45)c(Cl)cc23)[C@@H](C)C1] | 623.1 | HNMR (400 MHz, DMSO-$d_6$, ppm): δ 11.81 (s, 1H), 8.67 (s, 1H), 8.45 (s, 1H), 7.37-7.35 (m, 1H), 7.32-7.28 (m, 1H), 6.93-6.87 (m, 1H), 6.84-6.79 (m, 1H), 6.22 (d, J = 17.2 Hz, 1H), 5.78 (dd, J = 10.4, 2.4 Hz, 1H), 5.00 (brs, 1H), 4.44-4.34 (m, 2H), 4.30 (s, 2H), 4.21-4.05 (m, 1H), 3.85-3.81 (m, 1H), 3.67-3.64 (m, 1H), 3.16-3.10 (m, 1H), 1.78 (brs, 2H), 1.36 (d, J = 6.8 Hz, 3H), 0.97-0.86 (m, 8H). |
| 4 | 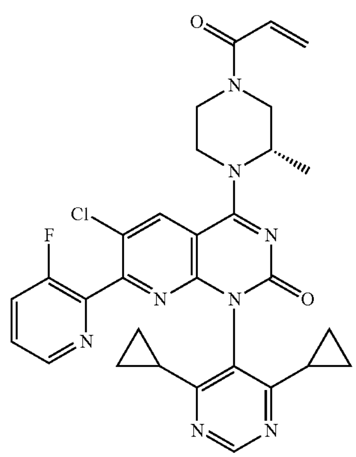 [SMILES: C=CC(=O)N1CCN(c2nc(=O)n(-c3c(C4CC4)ncnc3C3CC3)c3nc(-c4ncccc4F)c(Cl)cc23)[C@@H](C)C1] | 587.1 | HNMR (400 MHz, DMSO-$d_6$, ppm): δ 8.66 (s, 1H), 8.48-8.47 (m, 2H), 7.85 (t, J = 8.8 Hz, 1H), 7.60-7.56 (m, 1H), 6.85-6.79 (m, 1H), 6.21-6.15 (m, 1H), 5.73 (dd, J = 10.4, 2.4 Hz, 1H), 4.94 (brs, 1H), 4.38-4.11 (m, 3H), 3.62-3.42 (m, 2H), 3.22-3.07 (m, 1H), 1.73-1.68 (m, 2H), 1.31 (d, J = 8.0 Hz, 3H), 0.96-0.72 (m, 8H). FNMR (376 MHz, DMSO-$d_6$, ppm): δ −123.33 (1F). |
| 5 | 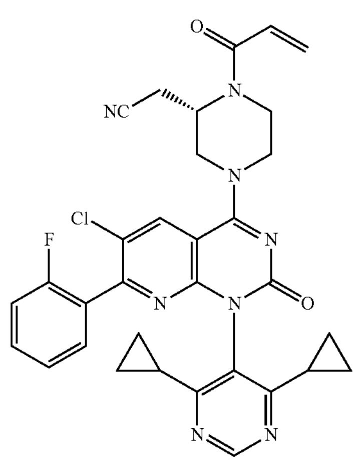 [SMILES: C=CC(=O)N1CCN(c2nc(=O)n(-c3c(C4CC4)ncnc3C3CC3)c3nc(-c4ccccc4F)c(Cl)cc23)C[C@@H]1CC#N] | 611.1 | HNMR (400 MHz, DMSO-$d_6$, ppm): δ 8.69 (s, 1H), 8.60 (s, 1H), 7.53-7.49 (m, 1H), 7.32-7.28 (m, 3H), 6.85-6.78 (m, 1H), 6.19 (dd, J = 16.8, 2.0 Hz, 1H), 5.77 (d, J = 11.6 Hz, 1H), 4.90 (brs, 1H), 4.34-4.31 (m, 3H), 3.93-3.92 (m, 1H), 3.75-3.73 (m, 1H), 3.57-3.53 (m, 1H), 3.25-2.98 (m, 2H), 1.80-1.79 (m, 1H), 1.66-1.65 (m, 1H), 0.96-0.80 (m, 8H). |

TABLE 1-continued

Characterization of the compounds of Formulas (I) and (II)

| Compound No. | Structure | [M + H]+ | 1H-NMR and 19F-NMR |
|---|---|---|---|
| 7 | 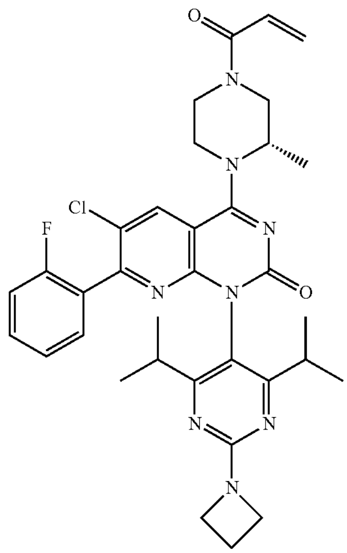 [SMILES: C=CC(=O)N1CCN(c2nc(=O)n(-c3c(C(C)C)nc(N4CCC4)nc3C(C)C)c3nc(-c4ccccc4F)c(Cl)cc23)[C@@H](C)C1] | 645.1 | HNMR (400 MHz, DMSO-$d_6$, ppm): δ 8.41-8.39 (m, 1H), 7.53-7.47 (m, 1H), 7.32-7.26 (m, 2H), 7.19-7.15 (m, 1H), 6.88-6.77 (m, 1H), 6.20-6.15 (m, 1H), 5.73 (dd, J = 10.4, 2.0 Hz, 1H), 4.97-4.86 (m, 1H), 4.37-4.25 (m, 2H), 4.13-3.97 (m, 5H), 3.38-3.04 (m, 3H), 2.35-2.22 (m, 4H), 1.29 (d, J = 6.8 Hz, 3H), 0.98 (d, J = 6.4 Hz, 6H), 0.82 (d, J = 6.8 Hz, 6H). FNMR (376 MHz, DMSO-$d_6$, ppm): δ −114.91 (1F). |
| 9 | 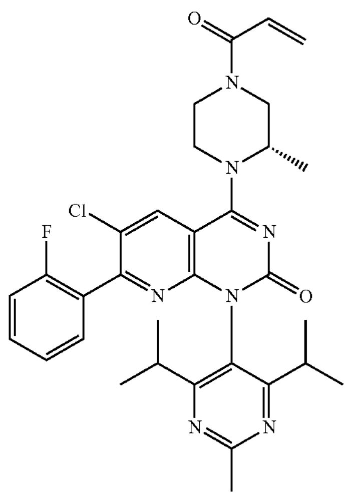 [SMILES: C=CC(=O)N1CCN(c2nc(=O)n(-c3c(C(C)C)nc(C)nc3C(C)C)c3nc(-c4ccccc4F)c(Cl)cc23)[C@@H](C)C1] | 604.1 | HNMR (400 MHz, DMSO-$d_6$, ppm): δ 8.47-8.40 (m, 1H), 7.50-7.45 (m, 1H), 7.30-7.23 (m, 2H), 7.16-7.12 (m, 1H), 6.87-6.78 (m, 1H), 6.19-6.15 (m, 1H), 5.73 (dd, J = 10.4, 2.0 Hz, 1H), 4.97-4.90 (m, 1H), 4.37-4.23 (m, 2H), 4.13-3.98 (m, 1H), 3.85-3.60 (m, 2H), 3.24-3.05 (m, 1H), 2.69-2.59 (m, 2H), 2.55 (s, 3H), 1.30 (d, J = 6.8 Hz, 3H), 1.02 (d, J = 6.8 Hz, 6H) 0.87 (d, J = 6.4 Hz, 6H). FNMR (376 MHz, DMSO-d6, ppm): δ −114.81 (1F). |
| 11 | 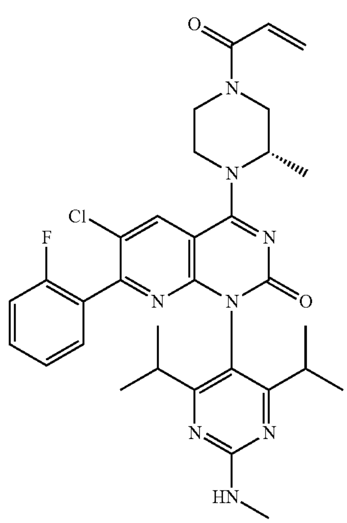 [SMILES: C=CC(=O)N1CCN(c2nc(=O)n(-c3c(C(C)C)nc(NC)nc3C(C)C)c3nc(-c4ccccc4F)c(Cl)cc23)[C@@H](C)C1] | 619.1 | HNMR (400 MHz, DMSO-$d_6$, ppm): δ 8.45-8.36 (m, 1H), 7.52-7.46 (m, 1H), 7.32-7.25 (m, 2H), 7.20-7.15 (m, 1H), 7.06-6.73 (m, 2H), 6.20-6.15 (m, 1H), 5.73 (dd, J = 10.4, 2.4 Hz, 1H), 4.99-4.83 (m, 1H), 4.38-4.24 (m, 2H), 4.13-3.97 (m, 1H), 3.80-3.40 (m, 2H), 3.23-3.03 (m, 1H), 2.76 (s, 3H), 2.46-2.38 (m, 2H), 1.29 (d, J = 6.8 Hz, 3H), 1.04-0.96 (m, 6H), 0.90-0.79 (m, 6H). FNMR (376 MHz, DMSO-$d_6$, ppm): δ −114.83 (1F). |

TABLE 1-continued
Characterization of the compounds of Formulas (I) and (II)
| Compound No. | Structure | [M + H]+ | 1H-NMR and 19F-NMR |
|---|---|---|---|
| 12 | 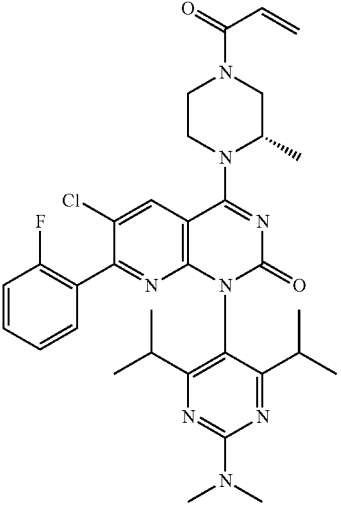 [SMILES: C=CC(=O)N1CCN(c2nc(=O)n(-c3c(C(C)C)nc(N(C)C)nc3C(C)C)c3nc(-c4ccccc4F)c(Cl)cc23)[C@@H](C)C1] | 633.1 | HNMR (400 MHz, methanol-d4, ppm): δ 8.45-8.36 (m, 1H), 7.48-7.43 (m, 1H), 7.24-7.20 (m, 2H), 7.18-7.13 (m, 1H), 6.87-6.76 (m, 1H), 6.29 (dd, J = 16.4, 4.4 Hz, 1H), 5.81 (dd, J = 10.8 Hz, 2.0 Hz, 1H), 5.15-4.97 (m, 1H), 4.54-4.38 (m, 2H), 4.19-4.04 (m, 1H), 3.87-3.56 (m, 2H), 3.40-3.32 (m, 1H), 3.17 (s, 6H), 2.56-2.42 (m, 2H), 1.46 (d, J = 4.4 Hz, 3H), 1.11 (d, J = 6.4 Hz, 6H), 0.93 (d, J = 6.8 Hz, 6H). FNMR (376 MHz, DMSO-d6, ppm): δ −115.63 (1F). |
| 14 | 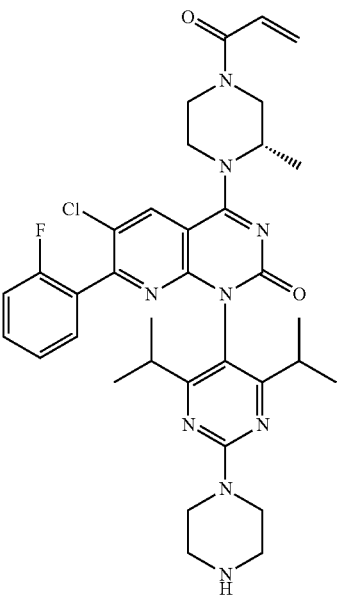 [SMILES: C=CC(=O)N1CCN(c2nc(=O)n(-c3c(C(C)C)nc(N4CCNCC4)nc3C(C)C)c3nc(-c4ccccc4F)c(Cl)cc23)[C@@H](C)C1] | 674.2 | HNMR (400 MHz, DMSO-d6, ppm): δ 8.76 (br s, 2H), 8.43-8.41 (m, 1H), 7.53-7.47 (m, 1H), 7.33-7.25 (m, 2H), 7.20-7.15 (m, 1H), 6.88-6.78 (m, 1H), 6.20-6.15 (m, 1H), 5.73 (dd, J = 10.4, 2.0 Hz, 1H), 4.97-4.86 (m, 1H), 4.37-4.25 (m, 2H), 4.13-3.93 (m, 5H), 3.81-3.52 (m, 2H), 3.31-3.01 (m, 5H), 2.54-2.47 (m, 2H), 1.30 (d, J = 6.4 Hz, 3H), 1.01 (d, J = 6.8 Hz, 6H), 0.85 (d, J = 6.4 Hz, 6H). FNMR (376 MHz, DMSO-d6, ppm): δ −115.08 (1F). |

TABLE 1-continued
Characterization of the compounds of Formulas (I) and (II)
| Compound No. | Structure | [M + H]+ | 1H-NMR and 19F-NMR |
|---|---|---|---|
| 16 | 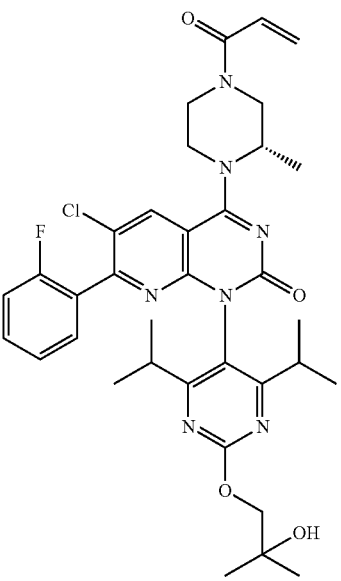 [SMILES: C=CC(=O)N1CCN(c2nc(=O)n(-c3c(C(C)C)nc(OCC(C)(C)O)nc3C(C)C)c3nc(-c4ccccc4F)c(Cl)cc23)[C@@H](C)C1] | 678.4 | HNMR (300 MHz, DMSO-d$_6$, ppm): δ 8.48-8.47 (m, 1H), 7.60-7.49 (m, 1H), 7.32 (m, 2H), 7.25-7.16 (m, 1H), 6.88 (m, 1H), 6.22 (m, 1H), 5.78 (dd, J = 10.4, 2.4 Hz, 1H), 4.98 (brs, 1H), 4.35-4.69 (m, 2H), 4.08 (m, 4H), 3.81 (m, 1H), 3.72-3.42 (m, 1H), 3.18 (m, 1H), 2.78-2.56 (m, 2H), 1.35 (d, J = 6.6 Hz, 3H), 1.20 (s, 6H), 1.07 (d, J = 6.6 Hz, 6H), 0.92 (d, J = 6.6 Hz, 6H). FNMR (282 MHz, DMSO-d$_6$, ppm): δ −114.70 (1F). |
| 21 | 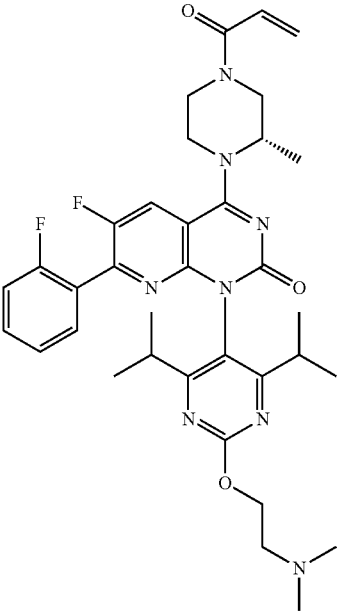 [SMILES: C=CC(=O)N1CCN(c2nc(=O)n(-c3c(C(C)C)nc(OCCN(C)C)nc3C(C)C)c3nc(-c4ccccc4F)c(F)cc23)[C@@H](C)C1] | 657.2 | HNMR (400 MHz, DMSO-d$_6$, ppm): δ 9.51 (brs, 1H), 8.35-8.25 (m, 1H), 7.58-7.54 (m, 1H), 7.41-7.30 (m, 3H), 6.85-6.81 (m, 1H), 6.17 (d, J = 16.8 Hz, 1H), 5.74 (dd, J = 10.8, 2.0 Hz, 1H), 4.90 (brs, 1H), 4.50-4.48 (m, 2H), 4.28-3.98 (m, 3H), 3.70-3.57 (m, 2H), 3.45-3.23 (m, 2H), 3.20-3.12 (m, 1H), 2.82 (d, J = 4.0 Hz, 6H), 1.69 (brs, 2H), 1.30 (d, J = 6.8 Hz, 3H), 0.99-0.78 (m, 8H). FNMR (376 MHz, DMSO-d$_6$, ppm): δ −113.74 (1F), −129.25 (1F). |

TABLE 1-continued

Characterization of the compounds of Formulas (I) and (II)

| Compound No. | Structure | [M + H]+ | ¹H-NMR and ¹⁹F-NMR |
|---|---|---|---|
| 22 | 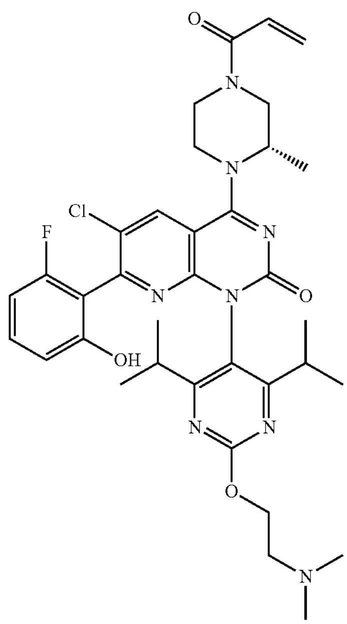 [SMILES: C=CC(=O)N1CCN(c2nc(=O)n(-c3c(C(C)C)nc(OCCN(C)C)nc3C(C)C)c3nc(-c4c(O)cccc4F)c(Cl)cc23)[C@@H](C)C1] | 693.1 | HNMR (400 MHz, methanol-$d_4$, ppm): δ 8.45-8.44 (m, 1H), 7.24-7.18 (m, 1H), 6.87-6.77 (m, 1H), 6.64-6.55 (m, 2H), 6.30 (dd, J = 16.8, 2.0 Hz, 1H), 5.81 (dd, J = 10.8, 2.0 Hz, 1H), 5.08 (brs, 1H), 4.74 (t, J = 4.8 Hz, 2H), 4.53-4.39 (m, 2H), 4.20-4.05 (m, 1H), 4.09-4.05 (m, 1H), 3.87-3.85 (m, 1H), 3.74-3.63 (m, 1H), 3.59 (t, J = 4.8 Hz, 2H), 3.37-3.29 (m, 1H), 2.97 (s, 6H), 2.75-2.70 (m, 2H), 1.48 (d, J = 6.4 Hz, 3H), 1.15 (d, J = 6.8 Hz, 6H), 1.00 (d, J = 6.8 Hz, 6H). FNMR (376 MHz, methanol-$d_4$, ppm): δ −117.41 (1F). |
| 23 | 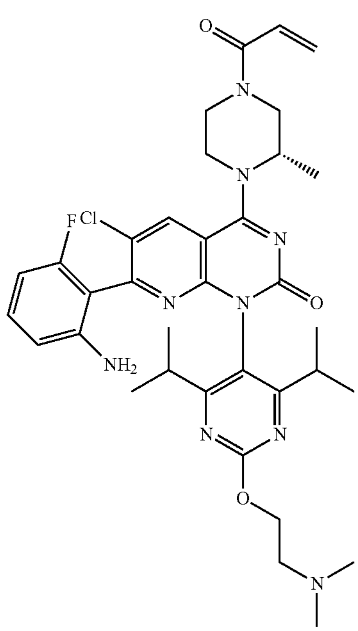 [SMILES: C=CC(=O)N1CCN(c2nc(=O)n(-c3c(C(C)C)nc(OCCN(C)C)nc3C(C)C)c3nc(-c4c(N)cccc4F)c(Cl)cc23)[C@@H](C)C1] | 692.2 | HNMR (400 MHz, methanol-$d_4$, ppm): δ 8.47-8.44 (m, 1H), 7.11-7.05 (m, 1H), 6.84-6.81 (m, 1H), 6.49 (d, J = 8.4 Hz, 1H), 6.35-6.28 (m, 2H), 5.82 (dd, J = 10.8, 2.0 Hz, 1H), 5.12-5.04 (m, 1H), 4.76-4.73 (m, 2H), 4.53-4.38 (m, 2H), 4.21-4.06 (m, 1H), 3.91-3.83 (m, 1H), 3.74-3.61 (m, 1H), 3.60-3.58 (m, 2H), 3.28-3.26 (m, 1H), 2.97 (s, 6H), 2.82-2.79 (m, 1H), 2.62- 2.59 (m, 1H), 1.48-1.46 (m, 3H), 1.18-1.13 (m, 6H), 1.07 (d, J = 6.4 Hz, 3H), 0.95 (d, J = 6.4 Hz, 3H). FNMR (376 MHz, methanol-$d_4$, ppm): δ −117.38 (1F). |

TABLE 1-continued

Characterization of the compounds of Formulas (I) and (II)

| Compound No. | Structure | [M + H]+ | 1H-NMR and 19F-NMR |
|---|---|---|---|
| 24 | 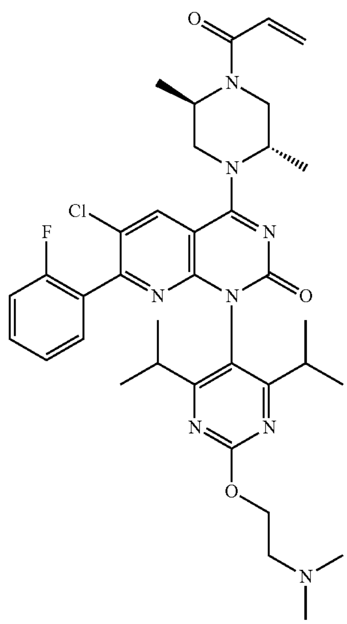 [SMILES: C=CC(=O)N1C[C@H](C)N(c2nc(=O)n(-c3c(C(C)C)nc(OCCN(C)C)nc3C(C)C)c3nc(-c4ccccc4F)c(Cl)cc23)C[C@H]1C] | 691.2 | HNMR (400 MHz, methanol-d$_4$, ppm): δ 8.47-8.45 (m, 1H), 7.51-7.45 (m, 1H), 7.22-7.14 (m, 3H), 6.88-6.74 (m, 1H), 6.31-6.25 (m, 1H), 5.83-5.78 (m, 1H), 5.02-5.01 (m, 1H), 4.75-4.73 (m, 2H), 4.53-4.29 (m, 2H), 3.98-3.90 (m, 2H), 3.59 (t, J = 4.8 Hz, 2H), 3.01-3.00 (m, 1H), 2.97 (s, 6H), 2.78- 2.64 (m, 2H), 1.50-1.27 (m, 6H), 1.17-1.14 (m, 6H), 1.02-0.98 (m, 6H). FNMR (376 MHz, methanol-d$_4$, ppm): δ −116.00 (1F). |
| 27 | 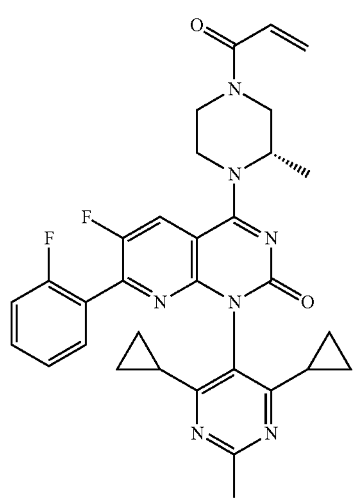 [SMILES: C=CC(=O)N1CCN(c2nc(=O)n(-c3c(C4CC4)nc(C)nc3C3CC3)c3nc(-c4ccccc4F)c(F)cc23)[C@@H](C)C1] | 584.1 | HNMR (400 MHz, DMSO-d$_6$, ppm): δ 8.32-8.26 (m, 1H), 7.57-7.51 (m, 1H), 7.38-7.30 (m, 3H), 6.87-6.77 (m, 1H), 6.20-6.15 (m, 1H), 5.72 (dd, J = 10.4, 2.0 Hz, 1H), 4.97-4.85 (m, 1H), 4.39-3.97 (m, 3H), 3.77-3.35 (m, 2H), 3.29-3.01 (m, 1H), 2.42 (s, 3H), 1.73-1.61 (m, 2H), 1.30 (d, J = 6.8 Hz, 3H), 0.98-0.89 (m, 4H), 0.87-0.72 (m, 4H). FNMR (376 MHz, DMSO-d$_6$, ppm): δ −113.71 (1F), −129.20 (1F). |

TABLE 1-continued

Characterization of the compounds of Formulas (I) and (II)

| Compound No. | Structure | [M + H]+ | $^{1}$H-NMR and $^{19}$F-NMR |
|---|---|---|---|
| 28 | 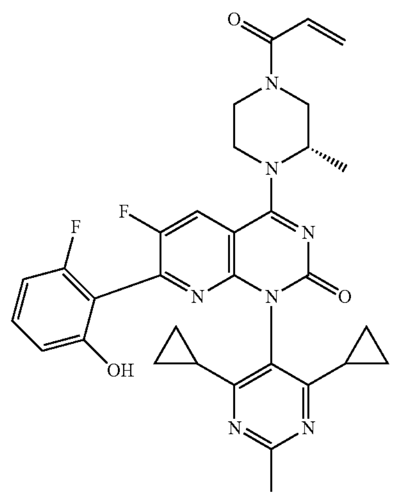 [SMILES: C=CC(=O)N1CCN(c2nc(=O)n(-c3c(C4CC4)nc(C)nc3C3CC3)c3nc(-c4c(O)cccc4F)c(F)cc23)[C@@H](C)C1] | 600.1 | HNMR (400 MHz, DMSO-d$_6$, ppm): δ 10.19 (s, 1H), 8.26-8.21 (m, 1H), 7.29-7.23 (m, 1H), 6.87-6.77 (m, 1H), 6.74-6.66 (m, 2H), 6.20-6.15 (m, 1H), 5.72 (dd, J = 10.4, 2.4 Hz, 1H), 4.97-4.85 (m, 1H), 4.39-3.97 (m, 3H), 3.71-3.40 (m, 2H), 3.23-3.03 (m, 1H), 2.40 (s, 3H), 1.66-1.56 (m, 2H), 1.30 (d, J = 6.4 Hz, 3H), 0.91-0.79 (m, 6H), 0.72-0.67 (m, 2H). FNMR (376 MHz, DMSO-d$_6$, ppm): δ -115.13 (1F), -128.41 (1F). |
| 29 | 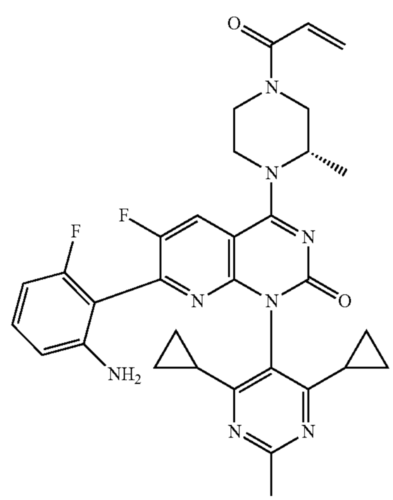 | 599.1 | HNMR (400 MHz, DMSO-d$_6$, ppm): δ 8.31-8.25 (m, 1H), 7.11 (dd, J = 14.8, 8.0 Hz, 1H), 6.87-6.77 (m, 1H), 6.50 (d, J = 8.0 Hz, 1H), 6.40-6.35 (m, 1H), 6.20-6.15 (m, 1H), 5.73 (dd, J = 10.4, 2.4 Hz, 1H), 4.97-4.85 (m, 1H), 4.39-3.97 (m, 3H), 3.73-3.42 (m, 2H), 3.22-3.02 (m, 1H), 2.43 (s, 3H), 1.73-1.65 (m, 2H), 1.29 (d, J = 6.8 Hz, 3H), 0.91-0.81 (m, 6H), 0.73-0.68 (m, 2H). FNMR (376 MHz, DMSO-d$_6$, ppm): δ -113.98 (1F), -126.93 (1F). |

TABLE 1-continued

Characterization of the compounds of Formulas (I) and (II)

| Compound No. | Structure | [M + H]+ | 1H-NMR and 19F-NMR |
|---|---|---|---|
| 31 | 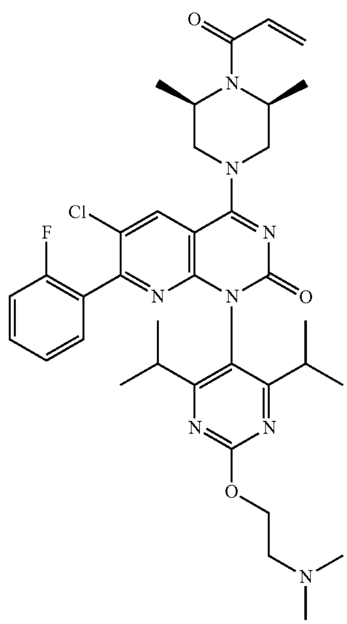 [SMILES: C=CC(=O)N1[C@H](C)CN(c2nc(=O)n(-c3c(C(C)C)nc(OCCN(C)C)nc3C(C)C)c3nc(-c4ccccc4F)c(Cl)cc23)C[C@@H]1C] | 691.2 | HNMR (400 MHz, methanol-d$_4$, ppm): δ 8.61 (s, 1H), 7.49-7.46 (m, 1H), 7.23-7.14 (m, 3H), 6.84-6.77 (m, 1H), 6.28 (dd, J = 16.8, 2.0 Hz, 1H), 5.78 (dd, J = 10.8, 2.0 Hz, 1H), 4.75-4.74 (m, 2H), 4.73-4.69 (m, 1H), 4.49-4.46 (m, 2H), 3.83-3.78 (m, 2H), 3.61-3.58 (m, 2H), 3.02-2.97 (m, 1H), 2.97 (s, 6H), 2.73-2.69 (m, 2H), 1.47 (d, J = 6.8 Hz, 3H), 1.18-1.15 (m, 6H), 1.01-0.99 (m, 6H). |
| 32 | 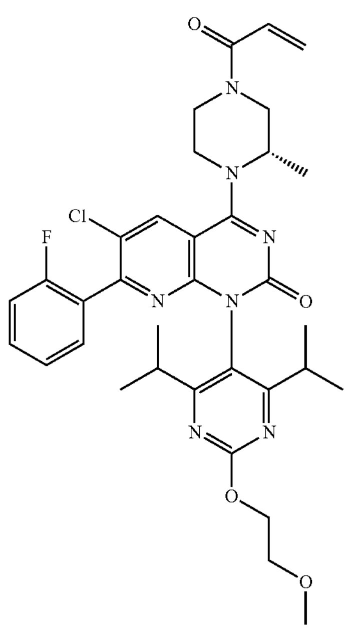 [SMILES: C=CC(=O)N1CCN(c2nc(=O)n(-c3c(C(C)C)nc(OCCOC)nc3C(C)C)c3nc(-c4ccccc4F)c(Cl)cc23)[C@@H](C)C1] | 664.1 | HNMR (400 MHz, DMSO-d$_6$, ppm): δ 8.44-8.42 (m, 1H), 7.51-7.46 (m, 1H), 7.31-7.25 (m, 2H), 7.18-7.14 (m, 1H), 6.88-6.79 (m, 1H), 6.20-6.16 (m, 1H), 5.73 (dd, J = 10.4, 2.4 Hz, 1H), 4.94 (brs, 1H), 4.39-4.37 (m, 2H), 4.34-4.24 (m, 2H), 4.14-3.99 (m, 1H), 3.80-3.75 (m, 1H), 3.65-3.59 (m, 2H), 3.47-3.41 (m, 1H), 3.26 (s, 3H), 3.21-3.05 (m, 1H), 2.60-2.59 (m, 2H), 1.31 (d, J = 6.4 Hz, 3H), 1.02 (d, J = 6.8 Hz, 6H), 0.87 (d, J = 6.4 Hz, 6H). FNMR (376 MHz, DMSO-d$_6$, ppm): δ −113.74 (1F). |

TABLE 1-continued

Characterization of the compounds of Formulas (I) and (II)

| Compound No. | Structure | [M + H]+ | 1H-NMR and 19F-NMR |
|---|---|---|---|
| 35 | 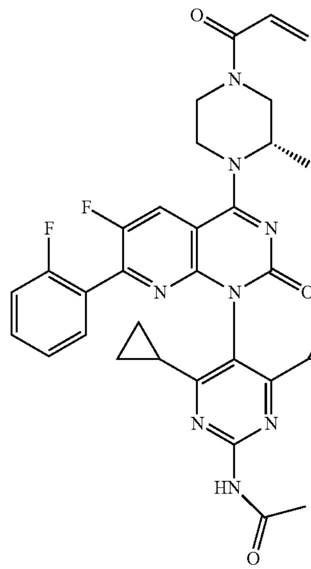 | 627.1 | HNMR (400 MHz, methanol-d$_4$, ppm): δ 8.26-8.22 (m, 1H), 7.53-7.43 (m, 2H), 7.27-7.18 (m, 2H), 6.84-6.77 (m, 1H), 6.31-6.27 (m, 1H), 5.81 (dd, J = 10.8, 2.0 Hz, 1H), 5.07 (brs, 1H), 4.54-4.40 (m, 2H), 4.20-4.05 (m, 1H), 3.84-3.81 (m, 1H), 3.73-3.56 (m, 1H), 3.29-3.19 (m, 1H), 2.34 (s, 3H), 1.75-1.65 (m, 2H), 1.50-1.45 (m, H), 1.18-1.09 (m, 4H), 0.96-0.79 (m, 4H). FNMR (376 MHz, methanol-d$_4$, ppm): δ −114.92 (1F), −128.80 (1F). |
| 36 | 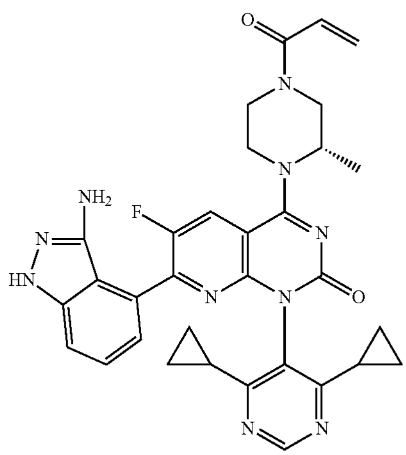 [SMILES: C=CC(=O)N1CCN(c2nc(=O)n(-c3c(C4CC4)ncnc3C3CC3)c3nc(-c4cccc5[nH]nc(N)c45)c(F)cc23)[C@@H](C)C1] | 607.1 | HNMR (400 MHz, methanol-d$_4$, ppm): δ 8.69 (s, 1H), 8.37-8.32 (m, 1H), 7.50-7.43 (m, 2H), 7.36-7.34 (m, 1H), 6.88-6.78 (m, 1H), 6.30 (dd, J = 16.4, 5.2 Hz, 1H), 5.82 (dd, J = 10.8, 2.0 Hz, 1H), 5.10 (brs, 1H), 4.51-4.41 (m, 2H), 4.22-4.06 (m, 1H), 3.91-3.81 (m, 1H), 3.75-3.59 (m, 1H), 3.38-3.34 (m, 1H), 1.77-1.75 (m, 2H), 1.50-1.47 (m, 3H), 1.13-1.09 (m, 2H), 0.96-0.94 (m, 4H), 0.77-0.76 (m, 2H). FNMR (376 MHz, methanol-d$_4$, ppm): δ −128.50 (1F). |
| 37 | 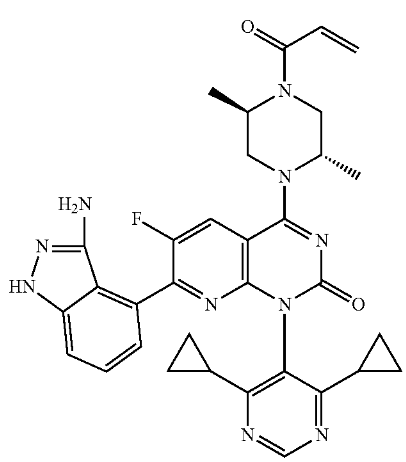 [SMILES: C=CC(=O)N1C[C@H](C)N(c2nc(=O)n(-c3c(C4CC4)ncnc3C3CC3)c3nc(-c4cccc5[nH]nc(N)c45)c(F)cc23)C[C@H]1C] | 621.2 | HNMR (400 MHz, methanol-d$_4$, ppm): δ 8.69 (s, 1H), 8.34 (t, J = 9.6 Hz, 1H), 7.50 (d, J = 3.6 Hz, 2H), 7.40-7.39 (m, 1H), 6.82-6.75 (m, 1H), 6.31-6.25 (m, 1H), 5.83-5.79 (m, 1H), 5.04 (brs, 1H), 4.95-4.91 (m, 0.5H), 4.52-4.40 (m, 1H), 4.36-4.31 (m, 1H), 4.02-3.91 (m, 2H), 3.56-3.52 (m, 0.5H), 1.80-1.68 (m, 2H), 1.50-1.47 (m, 3H), 1.39-1.29 (m, 3H), 1.13-1.08 (m, 2H), 0.98-0.94 (m, 4H), 0.80-0.72 (m, 2H). FNMR (376 MHz, methanol-d$_4$, ppm): δ −128.32 (1F). |

TABLE 1-continued

Characterization of the compounds of Formulas (I) and (II)

| Compound No. | Structure | [M + H]+ | 1H-NMR and 19F-NMR |
|---|---|---|---|
| 38 | 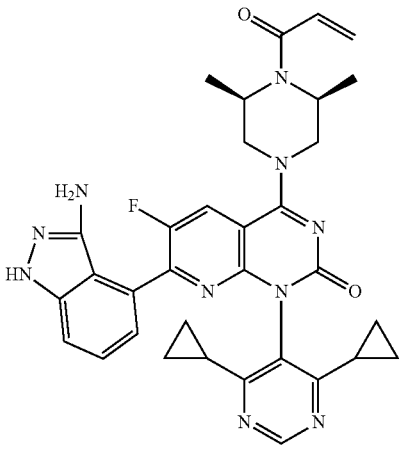 [SMILES: C=CC(=O)N1[C@H](C)CN(c2nc(=O)n(-c3c(C4CC4)ncnc3C3CC3)c3nc(-c4cccc5[nH]nc(N)c45)c(F)cc23)C[C@@H]1C] | 621.2 | HNMR (400 MHz, DMSO-d$_6$, ppm): δ 11.97 (brs, 1H), 8.67 (s, 1H), 8.34 (d, J = 9.6 Hz, 1H), 7.38-7.34 (m, 1H), 7.34-7.30 (m, 1H), 7.00-6.98 (m, 1H), 6.82-6.75 (m, 1H), 6.16 (dd, J = 16.8, 2.4 Hz, 1H), 5.72 (dd, J = 10.4, 2.4 Hz, 1H), 4.56 (s, 2H), 4.33-4.29 (m, 2H), 3.67-3.62 (m, 2H), 1.74-1.69 (m, 2H), 1.39 (d, J = 6.8 Hz, 6H), 0.93-0.84 (m, 6H), 0.77-0.72 (m, 2H). FNMR (376 MHz, DMSO-d$_6$, ppm): δ −128.89 (1F). |
| 39 | 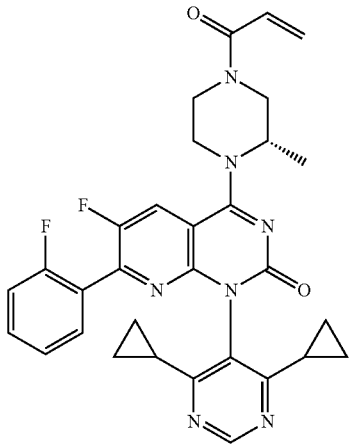 [SMILES: C=CC(=O)N1CCN(c2nc(=O)n(-c3c(C4CC4)ncnc3C3CC3)c3nc(-c4ccccc4F)c(F)cc23)[C@@H](C)C1] | 570.1 | HNMR (400 MHz, DMSO-d$_6$, ppm): δ 8.72 (s, 1H), 8.34-8.28 (m, 1H), 7.57-7.51 (m, 1H), 7.36-7.29 (m, 3H), 6.88-6.78 (m, 1H), 6.19-6.15 (m, 1H), 5.73 (dd, J = 10.4, 2.4 Hz, 1H), 4.97-4.87 (m, 1H), 4.39-4.36 (m, 1H), 4.30-4.23 (m, 1H), 4.02-3.98 (m, 1H), 3.76-3.67 (m, 1H), 3.61-3.40 (m, 1H), 3.23-3.04 (m, 1H), 1.77-1.66 (m, 2H), 1.31 (d, J = 6.8 Hz, 3H), 0.98-0.86 (m, 6H), 0.82-0.77 (m, 2H). FNMR (376 MHz, DMSO-d$_6$, ppm): δ −113.53 (1F), −128.96 (1F). |
| 40 | 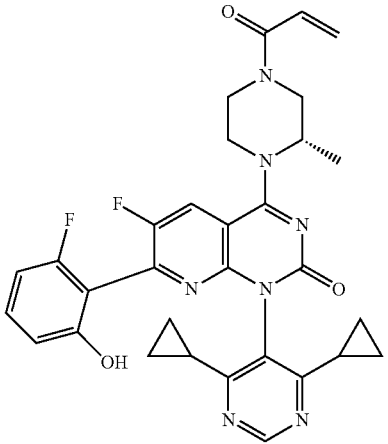 [SMILES: C=CC(=O)N1CCN(c2nc(=O)n(-c3c(C4CC4)ncnc3C3CC3)c3nc(-c4c(O)cccc4F)c(F)cc23)[C@@H](C)C1] | 586.1 | HNMR (400 MHz, DMSO-d$_6$, ppm): δ 10.20 (br s, 1H), 8.68 (s, 1H), 8.28-8.22 (m, 1H), 7.25 (dd, J = 15.2, 8.4 Hz, 1H), 6.87-6.78 (m, 1H), 6.74-6.65 (m, 2H), 6.19-6.15 (m, 1H), 5.73 (dd, J = 10.4 Hz, 2.4 Hz, 1H), 4.94-4.86 (m, 1H), 4.39-4.36 (m, 1H), 4.29-4.25 (m, 1H), 4.13-3.98 (m, 1H), 3.72-3.66 (m, 1H), 3.62-3.41 (m, 1H), 3.24-3.04 (m, 1H), 1.72-1.62 (m, 2H), 1.31 (d, J = 6.4 Hz, 3H), 0.95-0.84 (m, 6H), 0.77-0.73 (m, 2H). FNMR (376 MHz, DMSO-d$_6$, ppm): δ −115.16 (1F), −128.10 (1F). |

TABLE 1-continued

Characterization of the compounds of Formulas (I) and (II)

| Compound No. | Structure | [M + H]⁺ | ¹H-NMR and ¹⁹F-NMR |
|---|---|---|---|
| 41 | 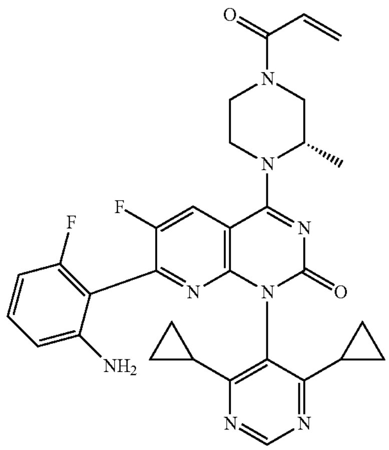 [SMILES: C=CC(=O)N1CCN(c2nc(=O)n(-c3c(C4CC4)ncnc3C3CC3)c3nc(-c4c(N)cccc4F)c(F)cc23)[C@@H](C)C1] | 585.1 | HNMR (400 MHz, DMSO-$d_6$, ppm): δ 8.73 (s, 1H), 8.32-8.27 (m, 1H), 7.10 (dd, J = 15.2, 8.0 Hz, 1H), 6.87-6.78 (m, 1H), 6.49 (d, J = 8.4 Hz, 1H), 6.40-6.35 (m, 1H), 6.19-6.15 (m, 1H), 5.73 (dd, J = 10.4, 2.0 Hz, 1H), 4.96-4.85 (m, 1H), 4.39-3.98 (m, 3H), 3.61-3.39 (m, 2H), 3.23-3.03 (m, 1H), 1.80-1.70 (m, 2H), 1.30 (d, J = 6.4 Hz, 3H), 0.95-0.88 (m, 6H), 0.78-0.73 (m, 2H). FNMR (376 MHz, DMSO-$d_6$, ppm): δ −113.86 (1F), −126.67 (1F). |
| 43 | 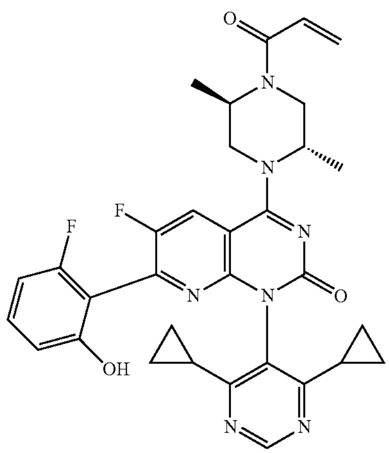 [SMILES: C=CC(=O)N1C[C@H](C)N(c2nc(=O)n(-c3c(C4CC4)ncnc3C3CC3)c3nc(-c4c(O)cccc4F)c(F)cc23)C[C@H]1C] | 600.1 | HNMR (400 MHz, DMSO-$d_6$, ppm): δ 10.19 (s, 1H), 8.68 (s, 1H), 8.28-8.24 (m, 1H), 7.29-7.23 (m, 1H), 6.87-6.65 (m, 3H), 6.17-6.13 (m, 1H), 5.74-5.69 (m, 1H), 4.91-4.72 (m, 1.5H), 4.59-4.51 (m, 0.5H), 4.20-4.05 (m, 1.5H), 3.82-3.75 (m, 2H), 3.49-3.45 (m, 0.5H), 1.68-1.62 (m, 2H), 1.30-1.15 (m, 6H), 0.97-0.72 (m, 8H). FNMR (376 MHz, DMSO-$d_6$, ppm): δ −115.09 (1F), −127.86 (1F). |
| 45 | 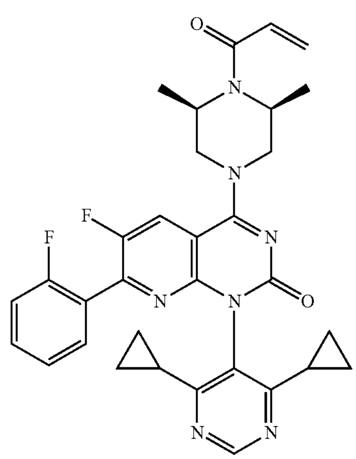 [SMILES: C=CC(=O)N1[C@H](C)CN(c2nc(=O)n(-c3c(C4CC4)ncnc3C3CC3)c3nc(-c4ccccc4F)c(F)cc23)C[C@@H]1C] | 584.1 | HNMR (400 MHz, DMSO-$d_6$, ppm): δ 8.72 (s, 1H), 8.34 (d, J = 10.0 Hz, 1H), 7.57-7.49 (m, 2H), 7.38-7.30 (m, 2H), 6.80-6.74 (m, 1H), 6.15 (dd, J = 16.8, 2.4 Hz, 1H), 5.72 (dd, J = 10.4 Hz, 2.0 Hz, 1H), 4.54 (brs, 2H), 4.32-4.28 (m, 2H), 3.66-3.61 (m, 2H), 1.75-1.68 (m, 2H), 1.37 (d, J = 6.8 Hz, 6H), 1.00-0.86 (m, 8H). FNMR (376 MHz, DMSO-$d_6$, ppm): δ −113.40 (1F), −128.61 (1F). |

TABLE 1-continued

Characterization of the compounds of Formulas (I) and (II)

| Compound No. | Structure | [M + H]+ | 1H-NMR and 19F-NMR |
|---|---|---|---|
| 46 | 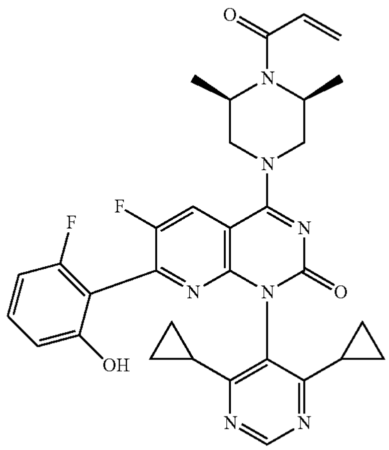 [SMILES: C=CC(=O)N1[C@H](C)CN(c2nc(=O)n(-c3c(C4CC4)ncnc3C3CC3)c3nc(-c4c(O)cccc4F)c(F)cc23)C[C@@H]1C] | 600.1 | HNMR (400 MHz, DMSO-$d_6$, ppm): δ 10.20 (brs, 1H), 8.68 (s, 1H), 8.28 (d, J = 9.2 Hz, 1H), 7.28-7.23 (m, 1H), 6.80-6.65 (m, 3H), 6.15 (dd, J = 16.8, 2.4 Hz, 1H), 5.71 (dd, J = 10.4, 2.4 Hz, 1H), 4.53 (s, 2H), 4.30-4.26 (m, 2H), 3.63-3.58 (m, 2H), 1.70-1.63 (m, 2H), 1.38 (d, J = 6.8 Hz, 6H), 0.96-0.82 (m, 6H), 0.76-0.71 (m, 2H). FNMR (376 MHz, DMSO-$d_6$, ppm): δ −115.19 (1F), −127.81 (1F). |
| 47 | 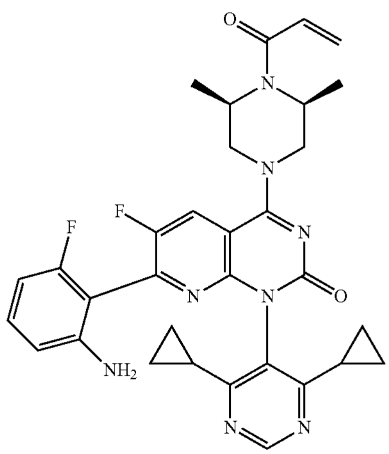 [SMILES: C=CC(=O)N1[C@H](C)CN(c2nc(=O)n(-c3c(C4CC4)ncnc3C3CC3)c3nc(-c4c(N)cccc4F)c(F)cc23)C[C@@H]1C] | 599.1 | HNMR (400 MHz, methanol-$d_4$, ppm): δ 8.74 (s, 1H), 8.38 (d, J = 9.2 Hz, 1H), 7.16-7.10 (m, 1H), 6.85-6.78 (m, 1H), 6.54 (d, J = 8.4 Hz, 1H), 6.43-6.39 (m, 1H), 6.31-6.26 (m, 1H), 5.80 (d, J = 10.4 Hz, 1H), 4.69 (s, 2H), 4.50-4.46 (m, 2H), 3.82-3.78 (m, 2H), 1.80-1.73 (m, 2H), 1.49 (d, J = 6.8 Hz, 6H), 1.13-1.11 (m, 4H), 1.02-0.98 (m, 2H), 0.87-0.84 (m, 2H). FNMR (376 MHz, methanol-$d_4$, ppm): δ −114.97 (1F), −125.58 (1F). |
| 50 | 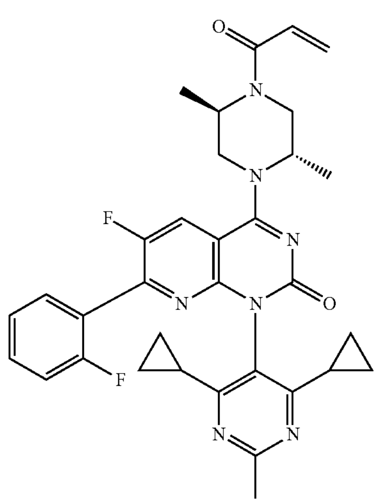 [SMILES: C=CC(=O)N1C[C@H](C)N(c2nc(=O)n(-c3c(C4CC4)nc(C)nc3C3CC3)c3nc(-c4ccccc4F)c(F)cc23)C[C@H]1C] | 598.1 | HNMR (400 MHz, DMSO-$d_6$, ppm): δ 8.33-8.28 (m, 1H), 7.58-7.52 (m, 1H), 7.40-7.31 (m, 3H), 6.87-6.74 (m, 1H), 6.17-6.13 (m, 1H), 5.74-5.69 (m, 1H), 4.84-4.44 (m, 2H), 4.18-4.10 (m, 1H), 3.82-3.77 (m, 3H), 2.42 (s, 3H), 1.66-1.58 (m, 2H), 1.30-1.26 (m, 3H), 1.23-1.14 (m, 3H), 0.95-0.73 (m, 8H). FNMR (376 MHz, DMSO-$d_6$, ppm): δ −113.54 (1F), −128.96 (1F). |

| Compound No. | Structure | [M + H]⁺ | ¹H-NMR and ¹⁹F-NMR |
|---|---|---|---|
| 51 | 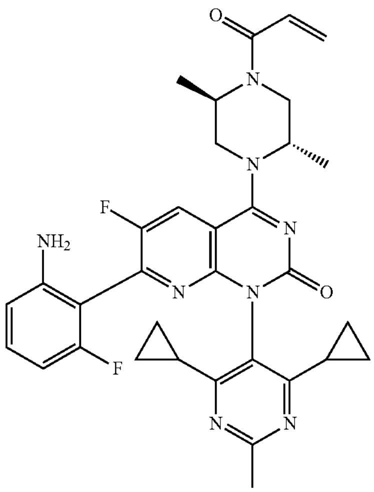 [SMILES: C=CC(=O)N1C[C@H](C)N(c2nc(=O)n(-c3c(C4CC4)nc(C)nc3C3CC3)c3nc(-c4c(N)cccc4F)c(F)cc23)C[C@H]1C] | 613.1 | HNMR (400 MHz, methanol-$d_4$, ppm): δ 8.26-8.21 (m, 1H), 7.13 (dd, J = 14.8, 8.0 Hz, 1H), 6.88-6.74 (m, 1H), 6.54 (d, J = 8.4 Hz, 1H), 6.42-6.38 (m, 1H), 6.30-6.24 (m, 1H), 5.83-5.78 (m, 1H), 5.02-4.90 (m, 2H), 4.53-4.29 (m, 2H), 3.97-3.50 (m, 2H), 2.55 (s, 3H), 1.81-1.65 (m, 2H), 1.47 (d, J = 6.8 Hz, 3H), 1.37-1.27 (m, 3H), 1.15-1.08 (m, 4H), 1.02-0.94 (m, 2H), 0.85-0.72 (m, 2H). FNMR (376 MHz, methanol-$d_4$, ppm): δ −115.04 (1F), −125.80 (1F). |
| 52 | 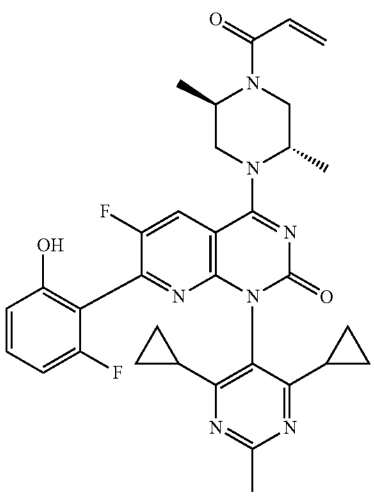 [SMILES: C=CC(=O)N1C[C@H](C)N(c2nc(=O)n(-c3c(C4CC4)nc(C)nc3C3CC3)c3nc(-c4c(O)cccc4F)c(F)cc23)C[C@H]1C] | 614.1 | HNMR (400 MHz, DMSO-$d_6$, ppm): δ 10.19 (s, 1H), 8.26-8.23 (m, 1H), 7.26 (dd, J = 15.6, 8.4 Hz, 1H), 6.87-6.67 (m, 3H), 6.17-6.13 (m, 1H), 5.70 (dd, J = 10.4, 2.4 Hz, 1H), 4.81-4.45 (m, 2H), 4.16-3.75 (m, 4H), 2.40 (s, 3H), 1.60-1.54 (m, 2H), 1.29-1.16 (m, 6H), 0.90-0.77 (m, 6H), 0.71-0.69 (m, 2H). FNMR (376 MHz, DMSO-$d_6$, ppm): δ −115.06 (1F), −128.17 (1F). |
| 53 | 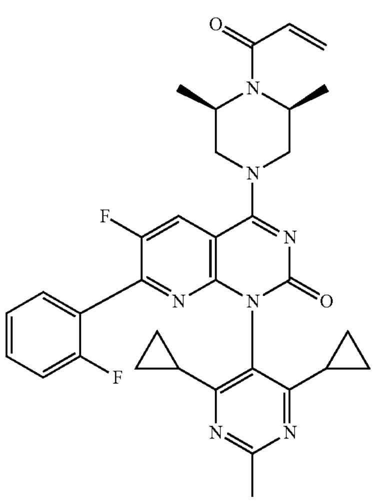 [SMILES: C=CC(=O)N1[C@H](C)CN(c2nc(=O)n(-c3c(C4CC4)nc(C)nc3C3CC3)c3nc(-c4ccccc4F)c(F)cc23)C[C@@H]1C] | 598.1 | HNMR (400 MHz, methanol-$d_4$, ppm): δ 8.37 (d, J = 9.6 Hz, 1H), 7.54-7.48 (m, 1H), 7.44-7.40 (m, 1H), 7.26-7.18 (m, 2H), 6.80 (dd, J = 16.8, 10.4 Hz, 1H), 6.27 (dd, J = 16.8, 1.6 Hz, 1H), 5.79 (dd, J = 10.4, 1.6 Hz, 1H), 4.76-4.58 (m, 2H), 4.50-4.46 (m, 2H), 3.79 (dd, J = 13.6 Hz, 5.2 Hz, 2H), 2.54 (s, 3H), 1.75-1.69 (m, 2H), 1.47 (d, J = 6.8 Hz, 6H), 1.18-1.05 (m, 4H), 0.98-0.92 (m, 2H), 0.87-0.80 (m, 2H). FNMR (376 MHz, methanol-$d_4$, ppm): δ −114.80 (1F), −128.40 (1F). |

TABLE 1-continued

Characterization of the compounds of Formulas (I) and (II)

| Compound No. | Structure | [M + H]+ | $^1$H-NMR and $^{19}$F-NMR |
|---|---|---|---|
| 54 | 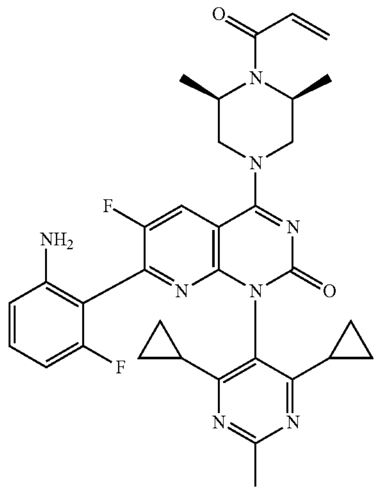 [SMILES: C=CC(=O)N1[C@H](C)CN(c2nc(=O)n(-c3c(C4CC4)nc(C)nc3C3CC3)c3nc(-c4c(N)cccc4F)c(F)cc23)C[C@@H]1C] | 613.1 | HNMR (400 MHz, methanol-$d_4$, ppm): δ 8.37 (d, J = 9.2 Hz, 1H), 7.12 (dd, J = 14.8, 8.0 Hz, 1H), 6.80 (dd, J = 16.8 Hz, 10.8 Hz, 1H), 6.54 (d, J = 8.4 Hz, 1H), 6.40 (t, J = 9.2 Hz, 1H), 6.27 (dd, J = 16.8, 1.6 Hz, 1H), 5.79 (dd, J = 10.8, 1.6 Hz, 1H), 4.76-4.59 (m, 2H), 4.48-4.45 (m, 2H), 3.78 (dd, J = 13.6, 4.8 Hz, 2H), 2.55 (s, 3H), 1.76-1.70 (m, 2H), 1.47 (d, J = 7.2 Hz, 6H), 1.18-1.06 (m, 4H), 1.00-0.94 (m, 2H), 0.85-0.79 (m, 2H). FNMR (376 MHz, methanol-$d_4$, ppm): δ −115.06 (1F), −125.72 (1F). |
| 55 | 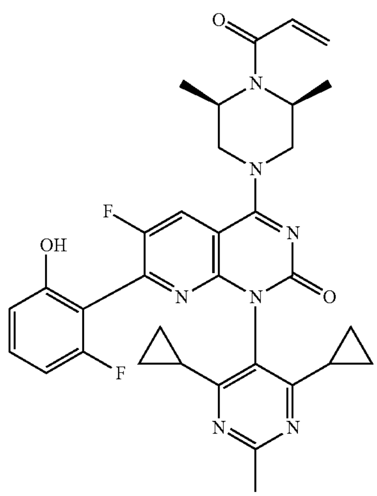 [SMILES: C=CC(=O)N1[C@H](C)CN(c2nc(=O)n(-c3c(C4CC4)nc(C)nc3C3CC3)c3nc(-c4c(O)cccc4F)c(F)cc23)C[C@@H]1C] | 614.1 | HNMR (400 MHz, methanol-$d_4$, ppm): δ 8.34 (d, J = 9.2 Hz, 1H), 7.28-7.22 (m, 1H), 6.80 (dd, J = 16.8, 10.8 Hz, 1H), 6.67 (d, J = 8.4 Hz, 1H), 6.62 (t, J = 8.8 Hz, 1H), 6.27 (dd, J = 16.8, 2.0 Hz, 1H), 5.78 (dd, J = 10.8, 2.0 Hz, 1H), 4.77-4.59 (m, 2H), 4.50-4.42 (m, 2H), 3.78 (dd, J = 13.6, 4.8 Hz, 2H), 2.54 (s, 3H), 1.74-1.70 (m, 2H), 1.47 (d, J = 7.2 Hz, 6H), 1.17-1.01 (m, 4H), 0.97-0.78 (m, 4H). FNMR (376 MHz, methanol-$d_4$, ppm): δ −116.09 (1F), −127.30 (1F). |
| 19 | 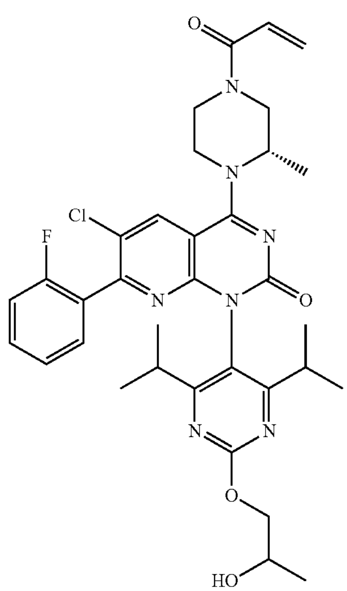 [SMILES: C=CC(=O)N1CCN(c2nc(=O)n(-c3c(C(C)C)nc(OCC(C)O)nc3C(C)C)c3nc(-c4ccccc4F)c(Cl)cc23)[C@@H](C)C1] | 664.4 | HNMR (300 MHz, DMSO-$d_6$, ppm): δ 8.48 (s, 1H), 7.61-7.46 (m, 1H), 7.39-7.25 (m, 2H), 7.20 (m, 1H), 6.88 (m, 1H), 6.22-6.15 (d, J = 16.8 Hz, 1H), 5.78 (dd, J = 10.4, 2.4 Hz, 1H), 4.92 (brs, 1H), 4.91-4.89 (d, J = 4.5 Hz, 1H), 4.45-4.25 (m, 2H), 4.20-4.10 (m, 2H), 4.05-3.95 (m, 1H), 3.85-3.72 (m, 1H), 3.70-3.40 (m, 2H), 3.19-3.05 (m, 1H), 2.70-2.56 (m, 2H), 1.35 (d, J = 6.6 Hz, 3H), 1.14 (d, J = 6.3 Hz, 3H), 1.06 (d, J = 6.6 Hz, 6H), 0.91 (d, J = 6.6 Hz, 6H). FNMR (282 MHz, DMSO-$d_6$, ppm): δ −114.72 (1F). |

TABLE 1-continued

Characterization of the compounds of Formulas (I) and (II)

| Compound No. | Structure | [M + H]+ | 1H-NMR and 19F-NMR |
|---|---|---|---|
| 30 | 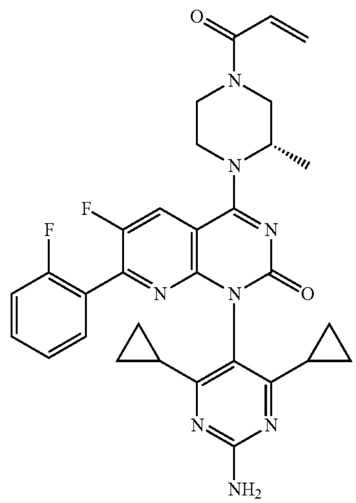 [SMILES: C=CC(=O)N1CCN(c2nc(=O)n(-c3c(C4CC4)nc(N)nc3C3CC3)c3nc(-c4ccccc4F)c(F)cc23)[C@@H](C)C1] | 585.1 | HNMR (400 MHz, methanol-d₄, ppm): δ 8.29-8.24 (m, 1H), 7.56-7.46 (m, 2H), 7.30-7.20 (m, 2H), 6.87-6.77 (m, 1H), 6.31-6.27 (m, 1H), 5.81 (dd, J = 10.8, 2.0 Hz, 1H), 5.10-5.05 (m, 1H), 4.48-4.40 (m, 2H), 4.20-4.05 (m, 1H), 3.85-3.82 (m, 1H), 3.72-3.54 (m, 1H), 3.33-3.22 (m, 1H), 1.79-1.74 (m, 2H), 1.47 (d, J = 4.4 Hz, 3H), 1.17-0.93 (m, 8H). FNMR (376 MHz, methanol-d₄, ppm): δ −115.1 (1F), −128.6 (1F). |
| 34 | 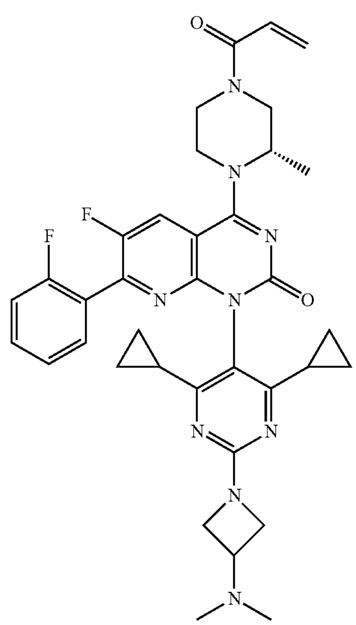 [SMILES: C=CC(=O)N1CCN(c2nc(=O)n(-c3c(C4CC4)nc(N4CC(N(C)C)C4)nc3C3CC3)c3nc(-c4ccccc4F)c(F)cc23)[C@@H](C)C1] | 668.2 | HNMR (400 MHz, methanol-d₄, ppm): δ 8.24-8.19 (m, 1H), 7.55-7.49 (m, 1H), 7.46-7.42 (m, 1H), 7.27-7.19 (m, 2H), 6.87-6.76 (m, 1H), 6.26 (dd, J = 16.8, 4.4 Hz, 1H), 5.79 (dd, J = 10.8, 1.6 Hz, 1H), 5.10-5.01 (m, 1H), 4.52-4.41 (m, 2H), 4.45-4.32 (m, 2H), 4.19-4.03 (m, 4H), 3.83-3.77 (m, 1H), 3.71-3.54 (m, 1H), 3.30-3.17 (m, 1H), 2.90 (s, 6H), 1.60-1.55 (m, 2H), 1.47-1.43 (m, 3H), 1.09-0.99 (m, 4H), 0.85-0.73 (m, 4H). FNMR (376 MHz, methanol-d₄, ppm): δ −115.0 (1F), −129.2 (1F). |

TABLE 1-continued

Characterization of the compounds of Formulas (I) and (II)

| Compound No. | Structure | [M + H]⁺ | ¹H-NMR and ¹⁹F-NMR |
|---|---|---|---|
| 48 | 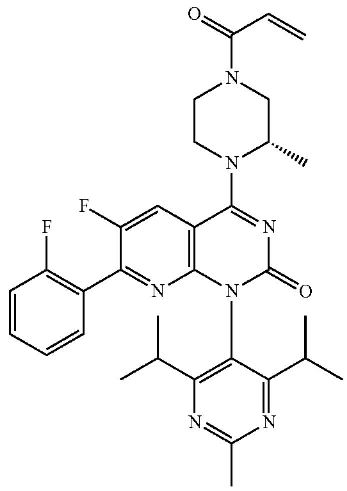 [SMILES: C=CC(=O)N1CCN(c2nc(=O)n(-c3c(C(C)C)nc(C)nc3C(C)C)c3nc(-c4ccccc4F)c(F)cc23)[C@@H](C)C1] | 588.2 | HNMR (400 MHz, DMSO-d$_6$, ppm): δ 8.35-8.30 (m, 1H), 7.55-7.49 (m, 1H), 7.34-7.26 (m, 2H), 7.23-7.19 (m, 1H), 6.88-6.79 (m, 1H), 6.20-6.15 (m, 1H), 5.73 (dd, J = 10.4, 2.0 Hz, 1H), 4.92 (brs, 1H), 4.38-4.28 (m, 3H), 3.70-3.42 (m, 2H), 3.24-3.06 (m, 1H), 2.63 (s, 2H), 2.62 (s, 3H), 1.30 (d, J = 6.4 Hz, 3H), 1.03 (d, J = 6.0 Hz, 6H), 0.88 (d, J = 6.4 Hz, 6H). FNMR (376 MHz, DMSO-d$_6$, ppm): δ −114.45 (1F), −129.22 (1F). |
| 49 | 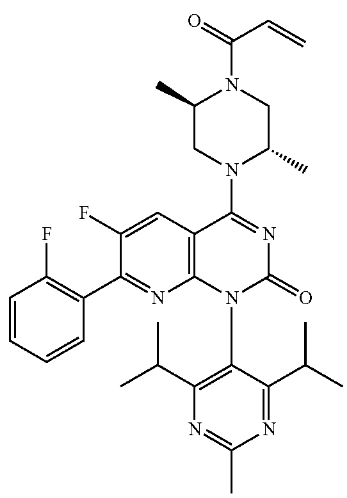 [SMILES: C=CC(=O)N1C[C@H](C)N(c2nc(=O)n(-c3c(C(C)C)nc(C)nc3C(C)C)c3nc(-c4ccccc4F)c(F)cc23)C[C@H]1C] | 602.2 | HNMR (400 MHz, methanol-d$_4$, ppm): δ 8.28-8.24 (m, 1H), 7.51-7.49 (m, 1H), 7.32-7.28 (m, 1H), 7.24-7.16 (m, 2H), 6.81-6.74 (m, 1H), 6.31-6.24 (m, 1H), 5.83-5.78 (m, 1H), 5.08-5.00 (m, 1H), 4.93-4.88 (m, 0.5H), 4.52-4.44 (m, 1H), 4.37-4.29 (m, 1H), 4.00-3.89 (m, 2H), 3.56-3.51 (m, 0.5H), 2.77-2.67 (m, 5H), 1.47 (d, J = 6.8 Hz, 3H), 1.36-1.26 (m, 3H), 1.18-1.15 (m, 6H), 1.01-0.97 (m, 6H). FNMR (376 MHz, methanol-d$_4$, ppm): δ −115.34 (1F), −128.47 (1F). |
| 77 | 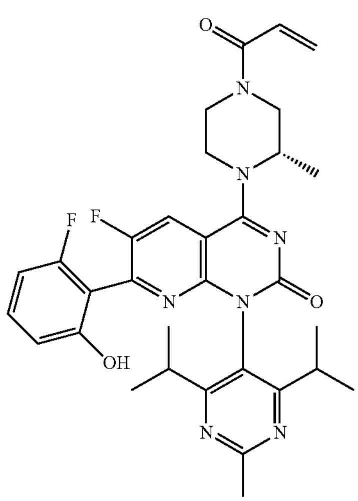 [SMILES: C=CC(=O)N1CCN(c2nc(=O)n(-c3c(C(C)C)nc(C)nc3C(C)C)c3nc(-c4c(O)cccc4F)c(F)cc23)[C@@H](C)C1] | 604.2 | HNMR (400 MHz, DMSO-d$_6$, ppm): δ 10.18 (s, 1H), 8.30-8.24 (m, 1H), 7.26-7.21 (m, 1H), 6.85-6.78 (m, 1H), 6.71-6.63 (m, 2H), 6.19-6.15 (m, 1H), 5.73 (dd, J = 10.4, 2.0 Hz, 1H), 4.92 (brs, 1H), 4.38-4.28 (m, 2H), 4.01-3.97 (m, 1H), 3.70-3.59 (m, 2H), 3.25-3.07 (m, 1H), 2.59 (s, 2H), 2.57 (s, 3H), 1.30 (d, J = 6.4 Hz, 3H), 1.02 (d, J = 6.0 Hz, 6H), 0.87 (d, J = 6.4 Hz, 6H). FNMR (376 MHz, DMSO-d$_6$, ppm): δ −115.82 (1F), −128.85 (1F). |

TABLE 1-continued

Characterization of the compounds of Formulas (I) and (II)

| Compound No. | Structure | [M + H]⁺ | ¹H-NMR and ¹⁹F-NMR |
|---|---|---|---|
| 78 | 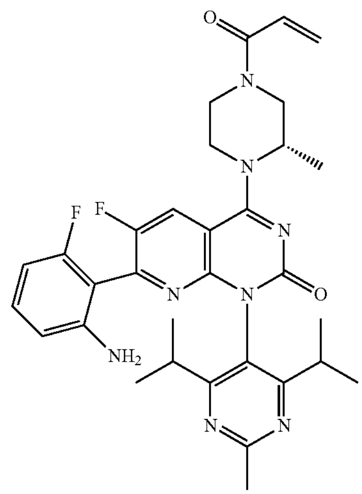 [SMILES: C=CC(=O)N1CCN(c2nc(=O)n(-c3c(C(C)C)nc(C)nc3C(C)C)c3nc(-c4c(N)cccc4F)c(F)cc23)[C@@H](C)C1] | 603.2 | HNMR (400 MHz, methanol-$d_4$, ppm): δ 8.35-8.20 (m, 1H), 7.13-7.07 (m, 1H), 6.88-6.77 (m, 1H), 6.50 (d, J = 8.4 Hz, 1H), 6.39-6.27 (m, 2H), 5.81 (dd, J = 10.4, J = 2.0 Hz, 1H), 5.06 (brs, 1H), 4.54-4.40 (m, 2 H), 4.21-4.05 (m, 1H), 3.88-3.46 (m, 3H), 2.82-2.66 (m, 5H), 1.53-1.45 (m, 3H), 1.21-1.11 (m, 6H), 1.09-0.95 (m, 6H). FNMR (376 MHz, methanol-$d_4$, ppm): δ −115.58 (1F), −126.35 (1F). |
| 18 | 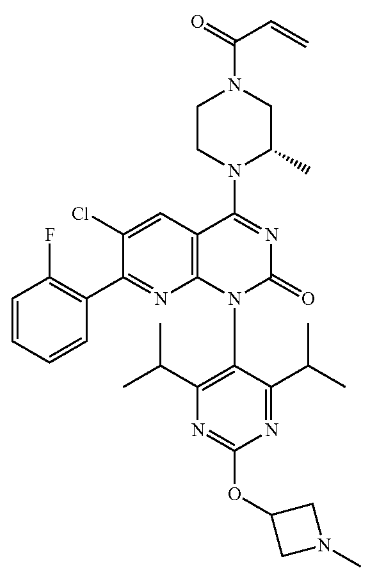 [SMILES: C=CC(=O)N1CCN(c2nc(=O)n(-c3c(C(C)C)nc(OC4CN(C)C4)nc3C(C)C)c3nc(-c4ccccc4F)c(Cl)cc23)[C@@H](C)C1] | 675.6 | HNMR (300 MHz, DMSO-$d_6$, ppm): δ 8.47 (m, 1H), 7.55-7.50 (m, 1H), 7.36-7.30 (m, 2H), 7.25-7.15 (m, 1H), 6.95-6.80 (m, 1H), 6.22 (d, J = 16.9 Hz, 1H), 5.77 (dd, J = 10.4, 2.4 Hz, 1H), 5.10-4.95 (m, 2H), 4.42-4.03 (m, 3H), 3.77-3.66 (m, 3H), 3.04-2.96 (m, 2H), 2.74-2.64 (m, 2H), 2.29 (s, 3H), 1.35 (d, J = 6.7 Hz, 3H), 1.05 (d, J = 6.7 Hz, 6H), 0.90 (d, J = 6.8 Hz, 6H). FNMR (282 MHz, DMSO-$d_6$, ppm): δ −114.72 (1F). |
| 25 | 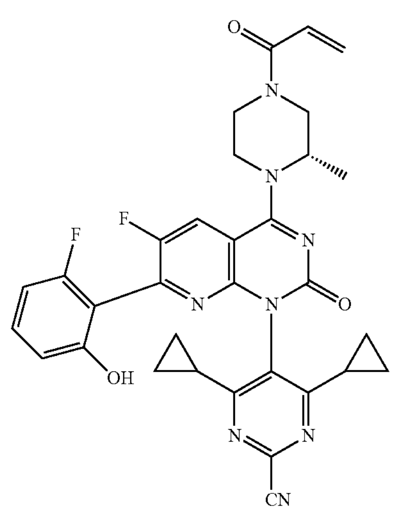 [SMILES: C=CC(=O)N1CCN(c2nc(=O)n(-c3c(C4CC4)nc(C#N)nc3C3CC3)c3nc(-c4c(O)cccc4F)c(F)cc23)[C@@H](C)C1] | 611.2 | HNMR (400 MHz, methanol-$d_4$, ppm): δ 8.35-8.25 (m, 1H), 7.34-7.25 (m, 1H), 6.97-6.78 (m, 1H), 6.75-6.63 (m, 2H), 6.33 (d, J = 18.3 Hz, 1H), 5.85 (dd, J = 10.6, 2.0 Hz, 1H), 5.18-5.06 (m, 1H), 4.57-4.48 (m, 2H), 4.25-4.05 (m, 1H), 3.93-3.85 (m, 1H), 3.80-3.60 (m, 1H), 3.30-3.25 (m, 1H), 1.88-1.80 (m, 2H), 1.60-1.55 (m, 3H), 1.25-0.89 (m, 8H). |

TABLE 1-continued

Characterization of the compounds of Formulas (I) and (II)

| Compound No. | Structure | [M + H]+ | 1H-NMR and 19F-NMR |
|---|---|---|---|
| 59 | 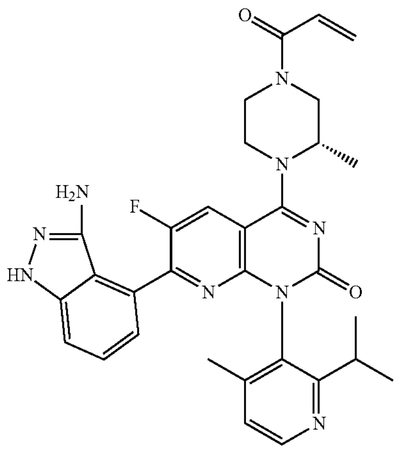 [SMILES: C=CC(=O)N1CCN(c2nc(=O)n(-c3c(C)ccnc3C(C)C)c3nc(-c4cccc5[nH]nc(N)c45)c(F)cc23)[C@@H](C)C1] | 582.3 | HNMR (400 MHz, DMSO-$d_6$, ppm): δ 11.85 (s, 1H), 8.51-8.26 (m, 2H), 7.39 (d, J = 8.4 Hz, 1H), 7.30 (t, J = 7.7 Hz, 1H), 7.23 (d, J = 4.8 Hz, 1H), 6.97 (dt, J = 6.6, 3.0 Hz, 1H), 6.94-6.84 (m, 1H), 6.22 (d, J = 16.2 Hz, 1H), 5.78 (dd, J = 10.4, 2.4 Hz, 1H), 4.95 (brs, 1H), 4.43-4.25 (m, 2H), 4.18-4.05 (m, 1H), 3.85-3.60 (m, 1H), 3.54-3.46 (m, 1H), 3.20-3.10 (m, 1H), 2.72-2.58 (m, 1H), 2.01 (d, J = 3.0 Hz, 2H), 1.47-1.28 (m, 3H), 1.02 (d, J = 6.6 Hz, 3H), 0.83 (dd, J = 6.6, 3.6 Hz, 3H). FNMR (376 MHz, DMSO-$d_6$, ppm): δ −129.05 (1F). |
| 60 | 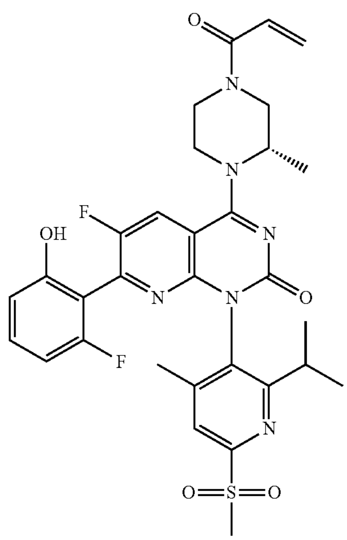 [SMILES: C=CC(=O)N1CCN(c2nc(=O)n(-c3c(C)cc(S(C)(=O)=O)nc3C(C)C)c3nc(-c4c(O)cccc4F)c(F)cc23)[C@@H](C)C1] | 639.2 | HNMR (400 MHz, DMSO-$d_6$, ppm): δ 10.30 (brs, 1H), 8.39-8.25 (m, 1H), 7.92 (s, 1H), 7.28 (td, J = 8.2, 6.8 Hz, 1H), 6.95-6.80 (m, 1H), 6.79-6.65 (m, 2H), 6.22 (d, J = 16.0 Hz, 1H), 5.78 (dd, J = 10.4, 2.4 Hz, 1H), 5.05-4.89 (m, 1H), 4.38-4.31 (m, 2H), 4.21-3.99 (m, 1H), 3.77-3.44 (m, 2H), 3.40-3.25 (m, 3H), 3.20-3.05 (m, 1H), 2.90-2.80 (m, 1H), 2.06 (s, 3H), 1.35 (dd, J = 11.2, 6.6 Hz, 3H), 1.13 (d, J = 6.6 Hz, 3H), 0.98 (d, J = 6.6 Hz, 3H). FNMR (376 MHz, DMSO-$d_6$, ppm): δ −115.72 (1F), −125.98 (1F). |
| 56 | 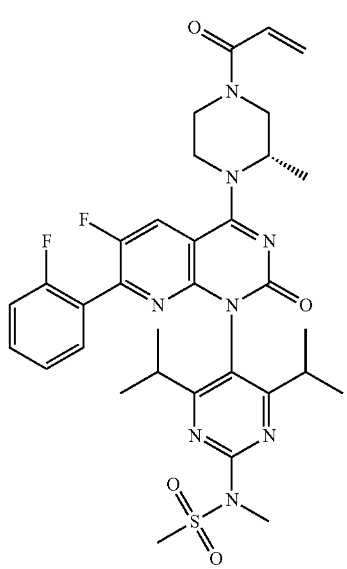 [SMILES: C=CC(=O)N1CCN(c2nc(=O)n(-c3c(C(C)C)nc(N(C)S(C)(=O)=O)nc3C(C)C)c3nc(-c4ccccc4F)c(F)cc23)[C@@H](C)C1] | 681.3 | HNMR (400 MHz, methanol-$d_4$, ppm): δ 8.27 (t, J = 9.6 Hz, 1H), 7.52-7.46 (m, 1H), 7.34-7.30 (m, 1H), 7.25-7.16 (m, 2H), 6.84-6.80 (m, 1H), 6.32-6.28 (m, 1H), 5.83-5.80 (m, 1H), 5.12-5.03 (m, 1H), 4.51-4.40 (m, 2H), 4.20-4.05 (m, 1H), 3.88-3.80 (m, 1H), 3.74-3.61 (m, 1H), 3.54 (s, 3H), 3.52 (s, 3H), 3.37-3.31-3.19 (m, 1H), 2.74-2.68 (m, 2H), 1.51-1.42 (m, 3H), 1.19-1.17 (m, 6H), 1.01-0.99 (m, 6H). FNMR (376 MHz, methanol-$d_4$, ppm): δ −115.37 (1F), −128.78 (1F). |

TABLE 1-continued

Characterization of the compounds of Formulas (I) and (II)

| Compound No. | Structure | [M + H]+ | 1H-NMR and 19F-NMR |
|---|---|---|---|
| 114 | 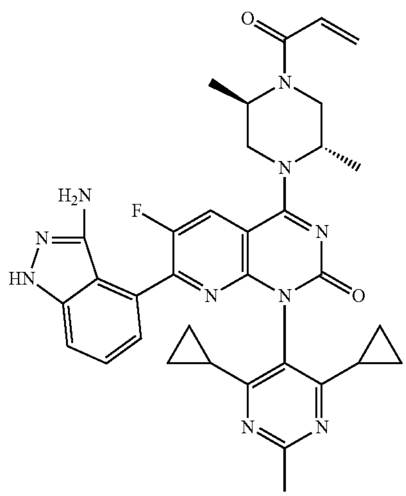 [SMILES: C=CC(=O)N1C[C@H](C)N(c2nc(=O)n(-c3c(C4CC4)nc(C)nc3C3CC3)c3nc(-c4cccc5[nH]nc(N)c45)c(F)cc23)C[C@H]1C] | 635.2 | HNMR (400 MHz, methanol-$d_4$, ppm): δ 8.35-8.30 (m, 1H), 7.52-7.47 (m, 2H), 7.41-7.37 (m, 1H), 6.89-6.75 (m, 1H), 6.28 (dd, J = 16.8 Hz, 4.4 Hz, 1H), 5.83-5.79 (m, 1H), 5.03-4.89 (m, 2H), 4.54-4.31 (m, 2H), 4.02-3.52 (m, 2H), 2.49 (s, 3H), 1.78-1.59 (m, 2H), 1.49-1.47 (m, 3H), 1.38-1.28 (m, 3H), 1.12-1.04 (m, 2H), 1.00-0.86 (m, 4H), 0.77-0.67 (m, 2H). FNMR (376 MHz, methanol-$d_4$, ppm): δ −128.38 (1F). |
| 84 | 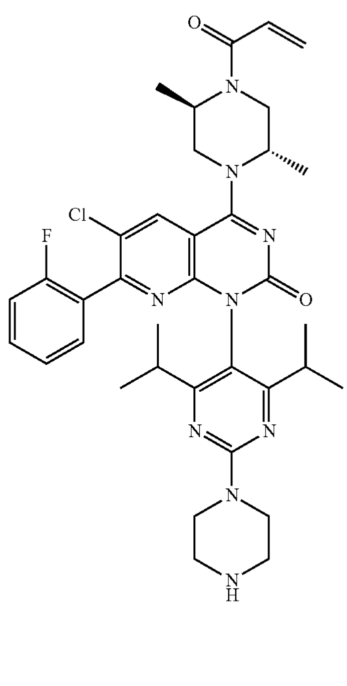 [SMILES: C=CC(=O)N1C[C@H](C)N(c2nc(=O)n(-c3c(C(C)C)nc(N4CCNCC4)nc3C(C)C)c3nc(-c4ccccc4F)c(Cl)cc23)C[C@H]1C] | 688.4 | HNMR (400 MHz, methanol-$d_4$, ppm): δ 8.45-8.42 (m, 1H), 7.51-7.44 (m, 1H), 7.24-7.21 (m, 2H), 7.20-7.14 (m, 1H), 6.87-6.73 (m, 1H), 6.31-6.24 (m, 1H), 5.83-5.77 (m, 1H), 5.02-4.86 (m, 1.5H), 4.52-4.27 (m, 2H), 4.15-4.09 (m, 4H), 4.03-3.85 (m, 2H), 3.55-3.50 (m, 0.5H), 3.29-3.25 (m, 4H), 2.63-2.51 (m, 2H), 1.47 (d, J = 6.8 Hz, 3H), 1.35-1.25 (m, 3H), 1.13-1.10 (m, 6H), 0.97-0.93 (m, 6H). FNMR (376 MHz, methanol-$d_4$, ppm): δ −115.83 (1F). |

TABLE 1-continued
Characterization of the compounds of Formulas (I) and (II)
| Compound No. | Structure | [M + H]+ | 1H-NMR and 19F-NMR |
|---|---|---|---|
| 17 | 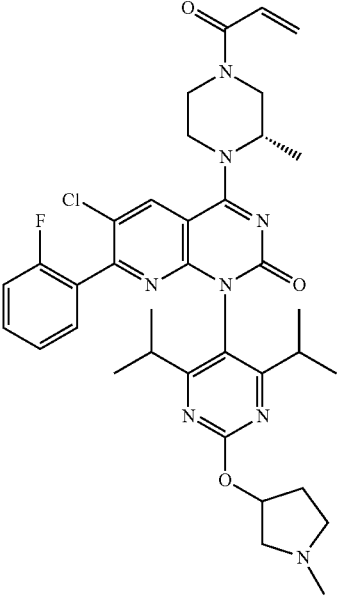 [SMILES: C=CC(=O)N1CCN(c2nc(=O)n(-c3c(C(C)C)nc(OC4CCN(C)C4)nc3C(C)C)c3nc(-c4ccccc4F)c(Cl)cc23)[C@@H](C)C1] | 689.1 | HNMR (300 MHz, DMSO-$d_6$, ppm): δ 8.50-8.46 (m, 1H), 7.59-7.48 (m, 1H), 7.40-7.15 (m, 3H), 6.93-6.81 (m, 1H), 6.21 (d, J = 16.6 Hz, 1H), 5.77 (dd, J = 10.4, 2.3 Hz, 1H), 5.31-5.27 (m, 1H), 4.98 (brs, 1H), 4.45-3.96 (m, 3H), 3.90-3.55 (m, 3H), 3.30-3.05 (m, 1H), 2.89-2.52 (m, 5H), 2.40-2.30 (m, 1H), 2.26 (s, 3H), 1.91-1.78 (m, 1H), 1.35 (d, J = 6.6 Hz, 3H), 1.07 (t, J = 7.2 Hz, 6H), 0.90 (d, J = 6.8 Hz, 6H). FNMR (282 MHz, DMSO-$d_6$, ppm): δ −114.82 (1F). |
| 66 | 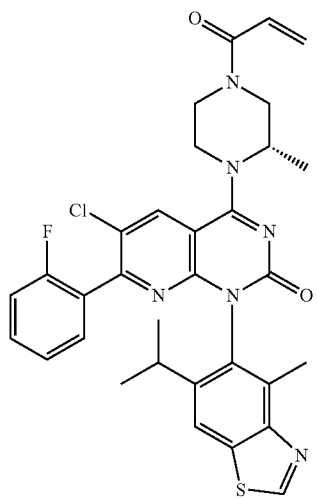 [SMILES: C=CC(=O)N1CCN(c2nc(=O)n(-c3c(C(C)C)cc4scnc4c3C)c3nc(-c4ccccc4F)c(Cl)cc23)[C@@H](C)C1] | 617.1 | HNMR (400 MHz, DMSO-$d_6$, ppm): δ 9.32 (s, 1H), 8.51-8.45 (s, 1H), 8.04 (s, 1H), 7.51-7.44 (m, 1H), 7.30-7.16 (m, 3H), 6.93-6.83 (m, 1H), 6.22 (d, J = 12 Hz, 1H), 5.81-5.72 (m, 1H), 4.96 (brs, 1H), 4.44-4.28 (m, 2H), 4.25-4.01 (m, 1H), 3.88-3.61 (m, 1H), 3.56-3.44 (m, 1H), 3.18-3.09 (m, 1H), 2.65-2.58 (m, 1H), 2.31 (s, 3H), 1.36 (t, J = 6.4 Hz, 3H), 1.19-1.11 (m, 3H), 1.08-0.98 (m, 3H). FNMR (376 MHz, DMSO-$d_6$, ppm): δ −114.25 (1F). |

TABLE 1-continued

Characterization of the compounds of Formulas (I) and (II)

| Compound No. | Structure | [M + H]+ | 1H-NMR and 19F-NMR |
|---|---|---|---|
| 82 | 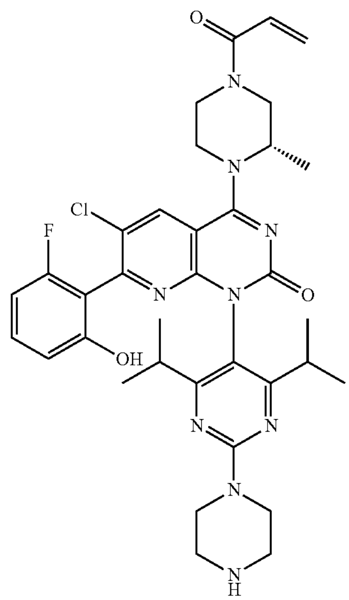 [SMILES: C=CC(=O)N1CCN(c2nc(=O)n(-c3c(C(C)C)nc(N4CCNCC4)nc3C(C)C)c3nc(-c4c(O)cccc4F)c(Cl)cc23)[C@@H](C)C1] | 690.3 | HNMR (400 MHz, methanol-$d_4$, ppm): δ 8.42-8.40 (m, 1H), 7.24-7.18 (m, 1H), 6.87-6.77 (m, 1H), 6.64 (d, J = 8.4 Hz, 1H), 6.58 (t, J = 8.4 Hz, 1H), 6.29 (dd, J = 16.8, 4.0 Hz, 1H), 5.81 (dd, J = 10.4, 1.6 Hz, 1H), 5.11-4.99 (m, 1H), 4.57-4.33 (m, 2H), 4.23-3.98 (m, 5H), 3.91-3.78 (m, 1H), 3.76-3.53 (m, 1H), 3.38-3.33 (m, 1H), 3.26-3.18 (m, 4H), 2.63-2.47 (m, 2H), 1.46 (d, J = 6.8 Hz, 3H), 1.11 (d, J = 6.4 Hz, 6H), 0.95 (d, J = 6.4 Hz, 6H). FNMR (376 MHz, methanol-$d_4$, ppm): δ −117.33 (1F). |
| 83 | 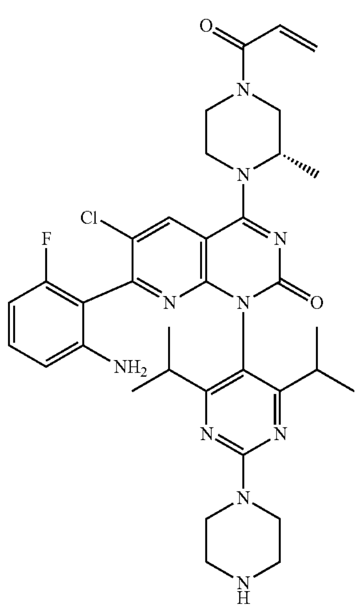 [SMILES: C=CC(=O)N1CCN(c2nc(=O)n(-c3c(C(C)C)nc(N4CCNCC4)nc3C(C)C)c3nc(-c4c(N)cccc4F)c(Cl)cc23)[C@@H](C)C1] | 689.4 | HNMR (400 MHz, methanol-$d_4$, ppm): δ 8.44-8.41 (m, 1H), 7.11-7.05 (m, 1H), 6.88-6.77 (m, 1H), 6.52 (d, J = 8.4 Hz, 1H), 6.36-6.27 (m, 2H), 5.82 (dd, J = 10.4, 2.0 Hz, 1H), 5.13-4.96 (m, 1H), 4.56-4.35 (m, 2H), 4.23-4.02 (m, 5H), 3.94-3.79 (m, 1H), 3.76-3.52 (m, 1H), 3.40-3.32 (m, 1H), 3.28-3.24 (m, 4H), 2.72-2.60 (m, 1H), 2.55-2.41 (m, 1H), 1.46 (d, J = 6.4 Hz, 3H), 1.14-1.08 (m, 6H), 1.03-0.89 (m, 6H). FNMR (376 MHz, methanol-$d_4$, ppm): δ −116.98 (1F). |

TABLE 1-continued

Characterization of the compounds of Formulas (I) and (II)

| Compound No. | Structure | [M + H]+ | 1H-NMR and 19F-NMR |
|---|---|---|---|
| 61 | 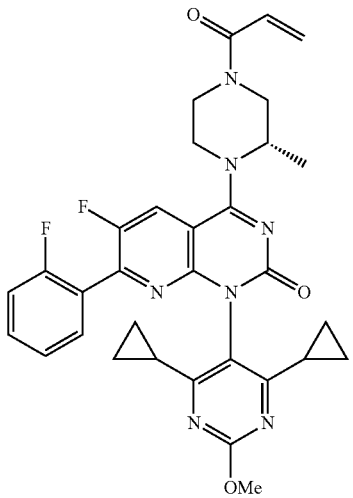 [SMILES: C=CC(=O)N1CCN(c2nc(=O)n(-c3c(C4CC4)nc(OC)nc3C3CC3)c3nc(-c4ccccc4F)c(F)cc23)[C@@H](C)C1] | 600.3 | HNMR (400 MHz, DMSO-$d_6$, ppm): δ 8.31-8.26 (m, 1H), 7.58-7.52 (m, 1H), 7.40-7.32 (m, 3H), 6.88-6.78 (m, 1H), 6.19-6.15 (m, 1H), 5.73 (dd, J = 10.4, 2.4 Hz, 1H), 4.95-4.85 (m, 1H), 4.39-4.2 (m, 2H), 4.13-3.95 (m, 2H), 3.77 (s, 3H), 3.60-3.03 (m, 2H), 1.70-1.59 (m, 2H), 1.30 (d, J = 6.8 Hz, 3H), 0.96-0.94 (m, 4H), 0.86-0.76 (m, 4H). FNMR (376 MHz, DMSO-$d_6$, ppm): δ −113.68 (1F), −129.30 (1F). |
| 62 | 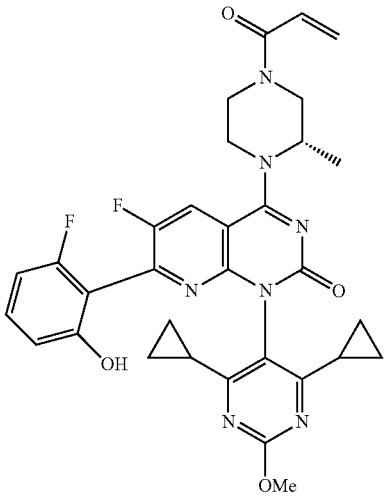 [SMILES: C=CC(=O)N1CCN(c2nc(=O)n(-c3c(C4CC4)nc(OC)nc3C3CC3)c3nc(-c4c(O)cccc4F)c(F)cc23)[C@@H](C)C1] | 616.3 | HNMR (400 MHz, DMSO-$d_6$, ppm): δ 10.22 (s, 1H), 8.25-8.20 (m, 1H), 7.29-7.24 (m, 1H), 6.87-6.80 (m, 1H), 6.77-6.67 (m, 2H), 6.19-6.14 (m, 1H), 5.73 (dd, J = 10.4, 2.4 Hz, 1H), 4.95-4.85 (m, 1H), 4.39-4.23 (m, 2H), 4.12-3.97 (m, 1H), 3.75 (s, 3H), 3.61-3.40 (m, 2H), 3.23-3.03 (m, 1H), 1.65-1.55 (m, 2H), 1.30 (d, J = 6.4 Hz, 3H), 0.93-0.90 (m, 2H), 0.86-0.83 (m, 4H), 0.73-0.70 (m, 2H). FNMR (376 MHz, DMSO-$d_6$, ppm): δ −115.13 (1F), −128.47 (1F). |
| 74 | 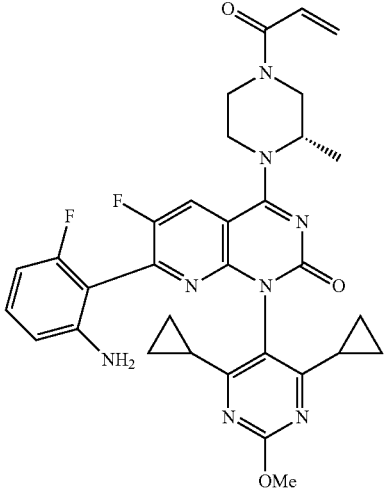 [SMILES: C=CC(=O)N1CCN(c2nc(=O)n(-c3c(C4CC4)nc(OC)nc3C3CC3)c3nc(-c4c(N)cccc4F)c(F)cc23)[C@@H](C)C1] | 615.4 | HNMR (400 MHz, DMSO-$d_6$, ppm): δ 8.30-8.25 (m, 1H), 7.15-7.09 (m, 1H), 6.87-6.78 (m, 1H), 6.51 (d, J = 8.0 Hz, 1H), 6.41-6.36 (m, 1H), 6.19-6.15 (m, 1H), 5.73 (dd, J = 10.4, 2.4 Hz, 1H), 4.95-4.85 (m, 1H), 4.39-4.23 (m, 2H), 4.13-3.98 (m, 1H), 3.78 (m, 3H), 3.70-3.39 (m, 2H), 3.22-3.02 (m, 1H), 1.71-1.61 (m, 2H), 1.29 (d, J = 6.4 Hz, 3H), 0.94-0.89 (m, 4H), 0.87-0.72 (m, 4H). FNMR (376 MHz, DMSO-$d_6$, ppm): δ −113.92 (1F), −127.97 (1F). |

TABLE 1-continued
Characterization of the compounds of Formulas (I) and (II)
| Compound No. | Structure | [M + H]+ | 1H-NMR and 19F-NMR |
|---|---|---|---|
| 79 | 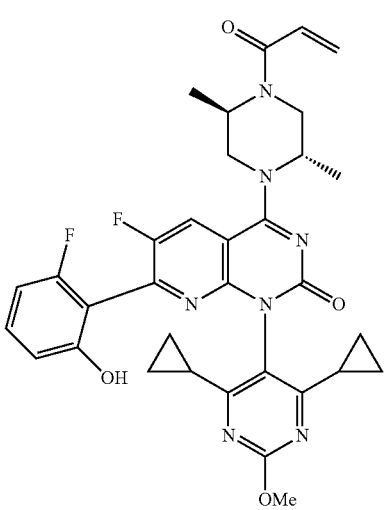 [SMILES: C=CC(=O)N1C[C@H](C)N(c2nc(=O)n(-c3c(C4CC4)nc(OC)nc3C3CC3)c3nc(-c4c(O)cccc4F)c(F)cc23)C[C@H]1C] | 630.3 | HNMR (400 MHz, DMSO-$d_6$, ppm): δ 10.21 (s, 1H), 8.26-8.23 (m, 1H), 7.30-7.24 (m, 1H), 6.86-6.67 (m, 3H), 6.15 (d, J = 16.8 Hz, 1H), 5.74-5.69 (m, 1H), 4.81-4.77 (m, 2H), 4.55-4.47 (m, 1H), 4.15-4.08 (m, 2H), 3.82-3.78 (m, 1H), 3.75 (s, 3H), 1.59-1.54 (m, 2H), 1.29-1.16 (m, 6H), 0.92-0.83 (m, 6H), 0.82-0.64 (m, 2H). FNMR (376 MHz, DMSO-$d_6$, ppm): δ −115.06 (1F), −128.21 (1F). |
| 88 | 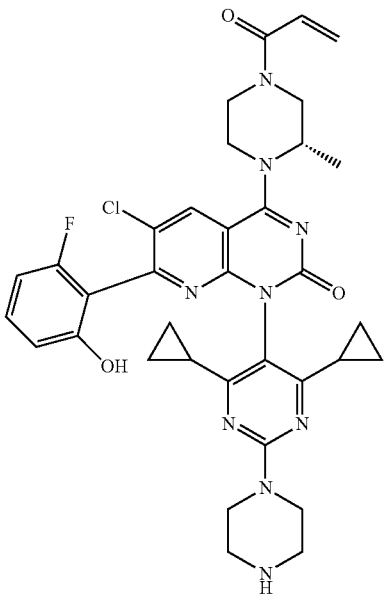 [SMILES: C=CC(=O)N1CCN(c2nc(=O)n(-c3c(C4CC4)nc(N4CCNCC4)nc3C3CC3)c3nc(-c4c(O)cccc4F)c(Cl)cc23)[C@@H](C)C1] | 686.3 | HNMR (400 MHz, methanol-$d_4$, ppm): δ 8.43-8.36 (m, 1H), 7.26-7.19 (m, 1H), 6.87-6.76 (m, 1H), 6.66 (d, J = 8.4 Hz, 1H), 6.60 (t, J = 8.8 Hz, 1H), 6.29 (dd, J = 16.8, 5.6 Hz, 1H), 5.80 (dd, J = 10.8, 2.0 Hz, 1H), 5.11-4.99 (m, 1H), 4.53-4.37 (m, 2H), 4.18-4.03 (m, 1H), 3.97-3.94 (m, 4H), 3.89-3.76 (m, 1H), 3.75-3.51 (m, 1H), 3.42-3.31 (m, 1H), 3.24-3.14 (m, 4H), 1.66-1.51 (m, 2H), 1.46 (d, J = 6.8 Hz, 3H), 1.08-0.98 (m, 2H), 0.97-0.89 (m, 2H), 0.87-0.78 (m, 2H), 0.77-0.68 (m, 2H). FNMR (376 MHz, methanol-$d_4$, ppm): δ −116.73 (1F). |

TABLE 1-continued
Characterization of the compounds of Formulas (I) and (II)
| Compound No. | Structure | [M + H]⁺ | ¹H-NMR and ¹⁹F-NMR |
|---|---|---|---|
| 89 | 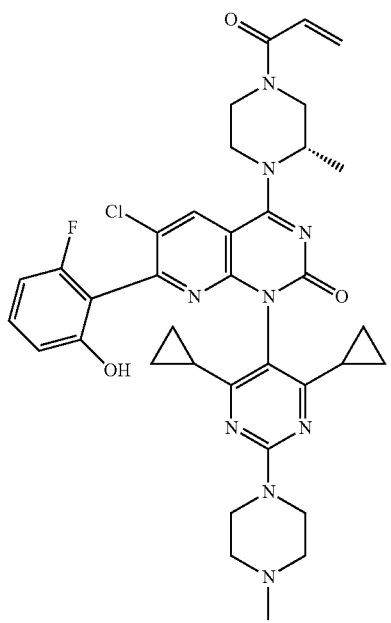 [SMILES: C=CC(=O)N1CCN(c2nc(=O)n(-c3c(C4CC4)nc(N4CCN(C)CC4)nc3C3CC3)c3nc(-c4c(O)cccc4F)c(Cl)cc23)[C@@H](C)C1] | 700.3 | HNMR (400 MHz, methanol-$d_4$, ppm): δ 8.40-8.39 (m, 1H), 7.26-7.20 (m, 1H), 6.83-6.76 (m, 1H), 6.67-6.59 (m, 2H), 6.31-6.27 (m, 1H), 5.82-5.79 (m, 1H), 5.11-4.99 (m, 1H), 4.95-4.71 (m, 1H), 4.53-4.38 (m, 2H), 4.18-4.04 (m, 1H), 3.83-3.46 (m, 5H), 3.19-3.03 (m, 5H), 2.88 (s, 3H), 1.62-1.52 (m, 2H), 1.46 (d, J = 6.4 Hz, 3H), 1.05-0.92 (m, 4H), 0.85-0.72 (m, 4H). FNMR (376 MHz, methanol-$d_4$, ppm): δ −116.78 (1F). |
| 116 | 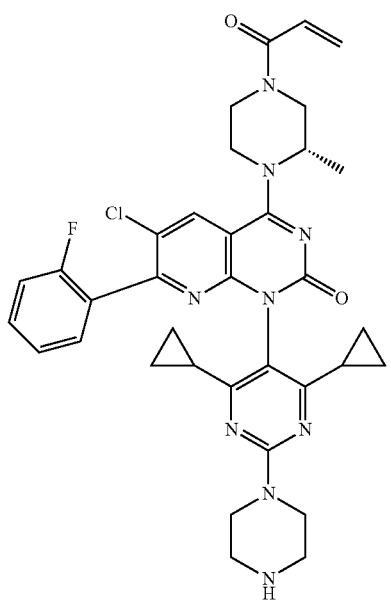 [SMILES: C=CC(=O)N1CCN(c2nc(=O)n(-c3c(C4CC4)nc(N4CCNCC4)nc3C3CC3)c3nc(-c4ccccc4F)c(Cl)cc23)[C@@H](C)C1] | 670.3 | HNMR (400 MHz, methanol-$d_4$, ppm): δ 8.43-8.36 (m, 1H), 7.52-7.46 (m, 1H), 7.35-7.31 (m, 1H), 7.25-7.15 (m, 2H), 6.87-6.76 (m, 1H), 6.29 (dd, J = 16.8, 4.8 Hz, 1H), 5.81 (dd, J = 10.4, 2.0 Hz, 1H), 5.11-4.99 (m, 1H), 4.53-4.37 (m, 2H), 4.18-4.03 (m, 1H), 3.97-3.94 (m, 4H), 3.89-3.76 (m, 1H), 3.75-3.51 (m, 1H), 3.42-3.31 (m, 1H), 3.24-3.14 (m, 4H), 1.66-1.51 (m, 2H), 1.46 (d, J = 6.4 Hz, 3H), 1.08-1.03 (m, 2H), 1.02-0.93 (m, 2H), 0.91-0.81 (m, 2H), 0.80-0.71 (m, 2H). FNMR (376 MHz, methanol-$d_4$, ppm): δ −114.81 (1F). |

| Compound No. | Structure | [M + H]+ | 1H-NMR and 19F-NMR |
|---|---|---|---|
| 93 | 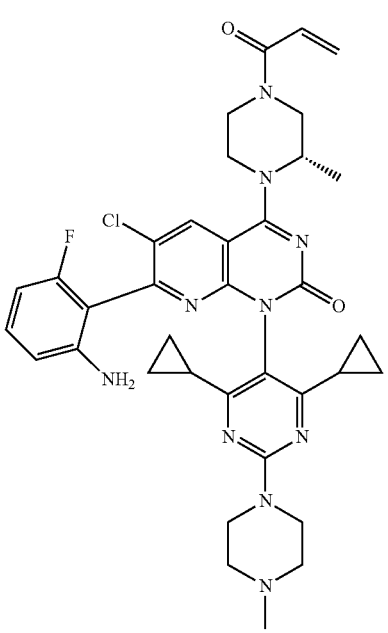 [SMILES: C=CC(=O)N1CCN(c2nc(=O)n(-c3c(C4CC4)nc(N4CCN(C)CC4)nc3C3CC3)c3nc(-c4c(N)cccc4F)c(Cl)cc23)[C@@H](C)C1] | 699.3 | HNMR (400 MHz, methanol-$d_4$, ppm): δ 8.47-8.40 (m, 1H), 7.15-7.09 (m, 1H), 6.83-6.80 (m, 1H), 6.55 (d, J = 8.0 Hz, 1H), 6.39 (t, J = 8.8 Hz, 1H), 6.32-6.26 (m, 1H), 5.83-5.79 (m, 1H), 5.06-4.96 (m, 1H), 4.53-4.50 (m, 1H), 4.41-4.35 (m, 1H), 4.16-4.06 (m, 1H), 3.94-3.46 (m, 5H), 3.20-3.05 (m, 5H), 2.89 (s, 3H), 1.65-1.41 (m, 5H), 1.13-1.01 (m, 3H), 0.94-0.71 (m, 5H). FNMR (376 MHz, methanol-$d_4$, ppm): δ −115.40 (1F). |
| 87 | 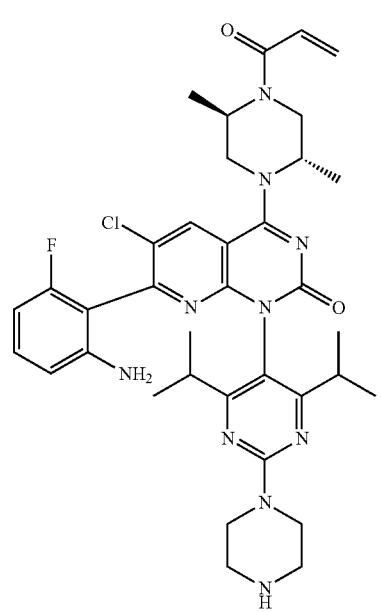 [SMILES: C=CC(=O)N1C[C@H](C)N(c2nc(=O)n(-c3c(C(C)C)nc(N4CCNCC4)nc3C(C)C)c3nc(-c4c(N)cccc4F)c(Cl)cc23)C[C@H]1C] | 703.3 | HNMR (400 MHz, methanol-$d_4$, ppm): δ 8.43-8.40 (m, 1H), 7.09 (dd, J = 14.8, 8.0 Hz, 1H), 6.87-6.74 (m, 1H), 6.52 (d, J = 8.0 Hz, 1H), 6.36-6.25 (m, 2H), 5.83-5.78 (m, 1H), 5.05-4.86 (m, 1.5H), 4.56-4.24 (m, 2H), 4.16-3.82 (m, 6H), 3.61-3.43 (m, 0.5H), 3.27-3.20 (m, 4H), 2.74-2.58 (m, 1H), 2.55-2.40 (m, 1H), 1.52-1.42 (m, 3H), 1.38-1.22 (m, 3H), 1.16-1.07 (m, 6H), 1.06-0.88 (m, 6H). FNMR (376 MHz, methanol-$d_4$, ppm): δ −117.07 (1F). |

TABLE 1-continued

Characterization of the compounds of Formulas (I) and (II)

| Compound No. | Structure | [M + H]+ | 1H-NMR and 19F-NMR |
|---|---|---|---|
| 80 | 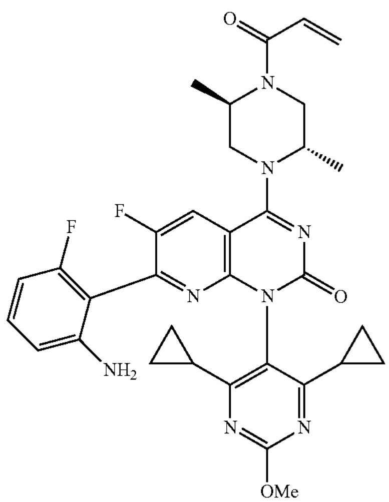 [SMILES: C=CC(=O)N1C[C@H](C)N(c2nc(=O)n(-c3c(C4CC4)nc(OC)nc3C3CC3)c3nc(-c4c(N)cccc4F)c(F)cc23)C[C@H]1C] | 629.3 | HNMR (400 MHz, DMSO-d6, ppm): δ 8.31-8.27 (m, 1H), 7.15-7.09 (m, 1H), 6.87-6.74 (m, 1H), 6.51 (d, J = 8.4 Hz, 1H), 6.41-6.36 (m, 1H), 6.17-6.13 (m, 1H), 5.74-5.70 (m, 1H), 4.80-4.77 (m, 2H), 4.14-4.07 (m, 1H), 3.82-3.78 (m, 2H), 3.76 (s, 3H), 3.50-3.47 (m, 1H), 1.70-1.60 (m, 2H), 1.28-1.13 (m, 6H), 0.95-0.86 (m, 4H), 0.86-0.73 (m, 4H). FNMR (376 MHz, DMSO-d6, ppm): δ −113.81 (1F), −126.79 (1F). |
| 85 | 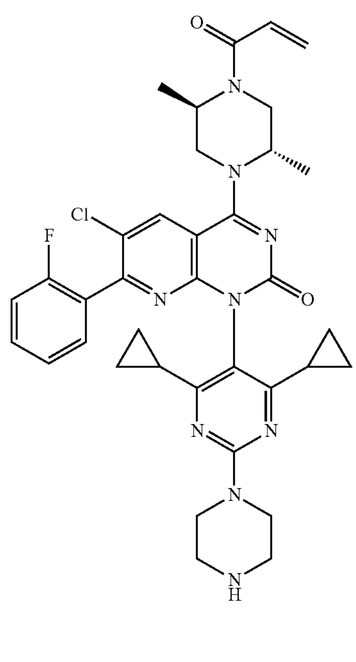 | 684.3 | HNMR (400 MHz, methanol-d4, ppm): δ 8.42-8.39 (m, 1H), 7.50-7.47 (m, 1H), 7.36-7.32 (m, 1H), 7.26-7.16 (m, 2H), 6.81-6.74 (m, 1H), 6.30-6.24 (m, 1H), 5.83-5.78 (m, 1H), 5.00-4.84 (m, 2H), 4.52-4.28 (m, 2H), 3.98-3.88 (m, 5.5H), 3.54-3.46 (m, 0.5H), 3.29-3.19 (m, 4H), 1.62-1.50 (m, 2H), 1.47 (d, J = 6.8 Hz, 3H), 1.35-1.25 (m, 3H), 1.07-0.98 (m, 4H), 0.88-0.76 (m, 4H). FNMR (376 MHz, methanol-d4, ppm): δ −114.71 (1F). |

TABLE 1-continued

Characterization of the compounds of Formulas (I) and (II)

| Compound No. | Structure | [M + H]+ | 1H-NMR and 19F-NMR |
|---|---|---|---|
| 86 | 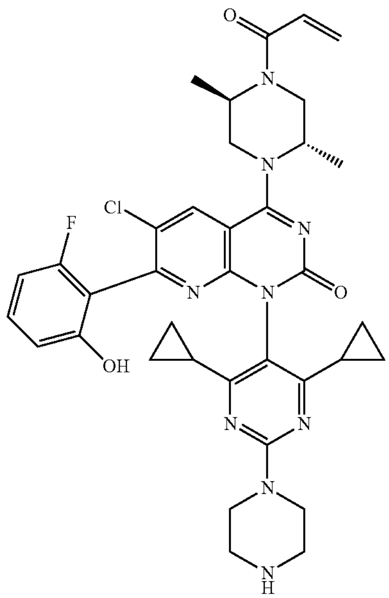 [SMILES: C=CC(=O)N1C[C@H](C)N(c2nc(=O)n(-c3c(C4CC4)nc(N4CCNCC4)nc3C3CC3)c3nc(-c4c(O)cccc4F)c(Cl)cc23)C[C@H]1C] | 700.3 | HNMR (400 MHz, methanol-d$_4$, ppm): δ 8.40 (d, J = 5.6 Hz, 1H), 7.25-7.20 (m, 1H), 6.87-6.74 (m, 1H), 6.68-6.59 (m, 2H), 6.30-6.24 (m, 1H), 5.82-5.78 (m, 1H), 4.99-4.87 (m, 2H), 4.51-4.27 (m, 2H), 3.96-3.89 (m, 5.5H), 3.54-3.51 (m, 0.5H), 3.21-3.18 (m, 4H), 1.58-1.52 (m, 2H), 1.47 (d, J = 6.8 Hz, 3H), 1.36-1.26 (m, 3H), 1.05-0.93 (m, 4H), 0.83-0.71 (m, 4H). FNMR (376 MHz, methanol-d$_4$, ppm): δ −116.71 (1F). |
| 91 | 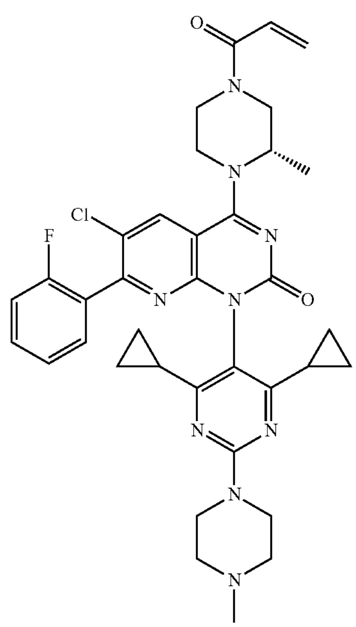 [SMILES: C=CC(=O)N1CCN(c2nc(=O)n(-c3c(C4CC4)nc(N4CCN(C)CC4)nc3C3CC3)c3nc(-c4ccccc4F)c(Cl)cc23)[C@@H](C)C1] | 684.3 | HNMR (400 MHz, methanol-d$_4$, ppm): δ 8.43-8.38 (m, 1H), 7.50-7.48 (m, 1H), 7.34-7.31 (m, 1H), 7.26-7.16 (m, 2H), 6.83-6.77 (m, 1H), 6.31-6.26 (m, 1H), 5.81 (dd, J = 10.4, 2.4 Hz, 1H), 5.12-5.02 (m, 1H), 4.84-4.81 (m, 1H), 4.53-4.39 (m, 2H), 4.19-4.04 (m, 1H), 3.88-3.84 (m, 1H), 3.71-3.46 (m, 4H), 3.20-3.01 (m, 5H), 2.89 (s, 3H), 1.67-1.53 (m, 2H), 1.46 (d, J = 6.0 Hz, 3H), 1.08-0.74 (m, 8H). FNMR (376 MHz, methanol-d$_4$, ppm): δ −114.87 (1F). |

TABLE 1-continued
Characterization of the compounds of Formulas (I) and (II)
| Compound No. | Structure | [M + H]+ | 1H-NMR and 19F-NMR |
|---|---|---|---|
| 92 | 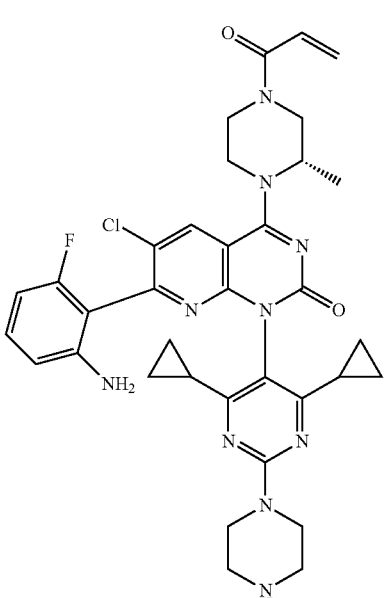 | 685.3 | HNMR (400 MHz, methanol-d4, ppm): δ 8.47-8.39 (m, 1H), 7.12 (dd, J = 14.8, 8.4 Hz, 1H), 6.87-6.75 (m, 1H), 6.55 (d, J = 8.4 Hz, 1H), 6.39 (t, J = 9.2 Hz, 1H), 6.29 (dd, J = 16.4, 5.2 Hz, 1H), 5.81 (dd, J = 10.4, 1.6 Hz, 1H), 5.23-4.93 (m, 1H), 4.60-4.30 (m, 2H), 4.25-3.86 (m, 6H), 3.81-3.37 (m, 2H), 3.26-3.02 (m, 4H), 1.71-1.37 (m, 5H), 1.13-1.00 (m, 3H), 0.99-0.81 (m, 3H), 0.79-0.65 (m, 2H). FNMR (376 MHz, methanol-d4, ppm): δ −115.33 (1F). |
| 94 | 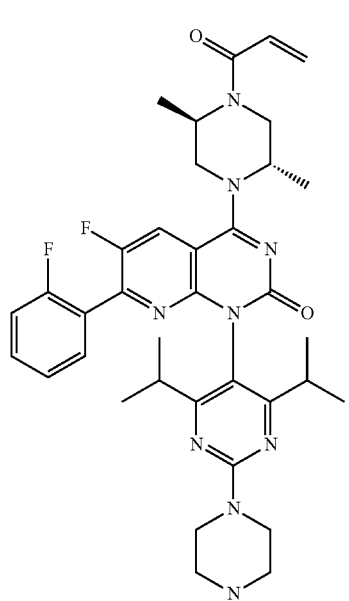 | 672.4 | HNMR (400 MHz, methanol-d4, ppm): δ 8.26-8.22 (m, 1H), 7.52-7.50 (m, 1H), 7.36-7.32 (m, 1H), 7.26-7.18 (m, 2H), 6.88-6.74 (m, 1H), 6.30-6.24 (m, 1H), 5.83-5.78 (m, 1H), 5.03-5.01 (m, 1H), 4.91-4.88 (m, 0.5H), 4.52-4.40 (m, 1H), 4.34-4.28 (m, 1H), 4.14-4.12 (m, 4H), 4.00-3.90 (m, 2H), 3.56-3.52 (m, 0.5H), 3.31-3.28 (m, 4H), 2.61-2.55 (m, 2H), 1.46 (d, J = 6.8 Hz, 3H), 1.35-1.25 (m, 3H), 1.13 (dd, J = 6.4 Hz, 2.4 Hz, 6H), 0.97-0.94 (m, 6H). FNMR (376 MHz, methanol-d4, ppm): δ -115.39 (1F), -128.98 (1F). |

TABLE 1-continued

Characterization of the compounds of Formulas (I) and (II)

| Compound No. | Structure | [M + H]⁺ | ¹H-NMR and ¹⁹F-NMR |
|---|---|---|---|
| 95 | 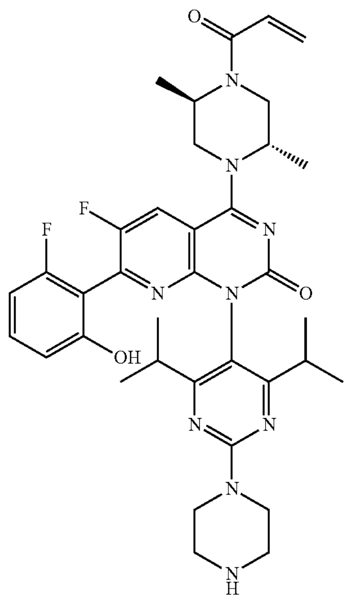 [SMILES: C=CC(=O)N1C[C@H](C)N(c2nc(=O)n(-c3c(C(C)C)nc(N4CCNCC4)nc3C(C)C)c3nc(-c4c(O)cccc4F)c(F)cc23)C[C@H]1C] | 688.4 | HNMR (400 MHz, methanol-d₄, ppm): δ 8.21-8.18 (m, 1H), 7.27-7.21 (m, 1H), 6.87-6.74 (m, 1H), 6.67-6.59 (m, 2H), 6.30-6.24 (m, 1H), 5.82-5.78 (m, 1H), 5.02-5.01 (m, 1H), 4.90-4.89 (m, 0.5H), 4.51-4.39 (m, 1H), 4.34-4.27 (m, 1H), 4.12-4.10 (m, 4H), 3.96-3.89 (m, 2H), 3.57-3.53 (m, 0.5H), 3.27-3.20 (m, 4H), 2.58-2.53 (m, 2H), 1.45 (d, J = 6.4 Hz, 3H), 1.35-1.25 (m, 3H), 1.13-1.10 (m, 6H), 0.97-0.95 (m, 6H). FNMR (376 MHz, methanol-d₄, ppm): δ −116.75 (1F), −128.43 (1F). |
| 96 | 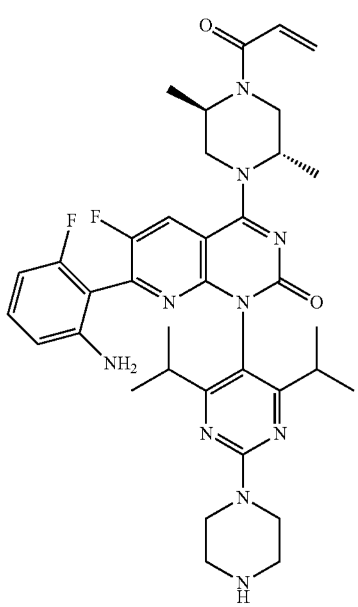 [SMILES: C=CC(=O)N1C[C@H](C)N(c2nc(=O)n(-c3c(C(C)C)nc(N4CCNCC4)nc3C(C)C)c3nc(-c4c(N)cccc4F)c(F)cc23)C[C@H]1C] | 687.4 | HNMR (400 MHz, methanol-d₄, ppm): δ 8.24-8.20 (m, 1H), 7.13-7.09 (m, 1H), 6.88-6.74 (m, 1H), 6.51 (d, J = 8.4 Hz, 1H), 6.40-6.36 (m, 1H), 6.31-6.24 (m, 1H), 5.83-5.78 (m, 1H), 5.02-5.00 (m, 1H), 4.90-4.89 (m, 0.5H), 4.52-4.40 (m, 1H), 4.34-4.28 (m, 1H), 4.14-4.12 (m, 4H), 4.00-3.89 (m, 2H), 3.56-3.51 (m, 0.5H), 3.29-3.28 (m, 4H), 2.60-2.56 (m, 2H), 1.46 (d, J = 6.8 Hz, 3H), 1.36-1.26 (m, 3H), 1.13-1.11 (m, 6H), 0.98-0.95 (m, 6H). FNMR (376 MHz, methanol-d₄, ppm): δ −115.67 (1F), −126.72 (1F). |

TABLE 1-continued

Characterization of the compounds of Formulas (I) and (II)

| Compound No. | Structure | [M + H]⁺ | ¹H-NMR and ¹⁹F-NMR |
|---|---|---|---|
| 97 | 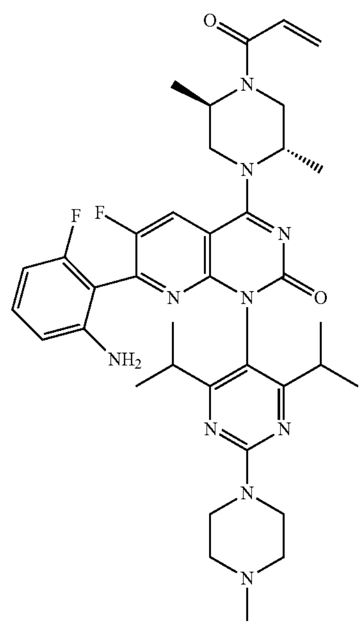 [SMILES: C=CC(=O)N1C[C@H](C)N(c2nc(=O)n(-c3c(C(C)C)nc(N4CCN(C)CC4)nc3C(C)C)c3nc(-c4c(N)cccc4F)c(F)cc23)C[C@H]1C] | 701.4 | HNMR (400 MHz, methanol-d₄, ppm): δ 8.23-8.20 (m, 1H), 7.14-7.09 (m, 1H), 6.81-6.74 (m, 1H), 6.51 (d, J = 8.4 Hz, 1H), 6.37 (t, J = 8.4 Hz, 1H), 6.31-6.24 (m, 1H), 5.81-5.78 (m, 1H), 5.05-5.01 (m, 2H), 4.51-4.28 (m, 2H), 4.00-3.85 (m, 2H), 3.58-3.55 (m, 4H), 3.16-3.10 (m, 2H), 2.93 (s, 3H), 2.62-2.53 (m, 2H), 1.46 (d, J = 6.8 Hz, 3H), 1.35 (d, J = 6.8 Hz, 1H), 1.27 (d, J = 6.8 Hz, 1H), 1.23 (d, J = 3.6 Hz, 1H), 1.13-1.11 (m, 6H), 0.98-0.95 (m, 6H). FNMR (376 MHz, methanol-d₄, ppm): δ −115.82 (1F), −126.89 (1F). |
| 98 | 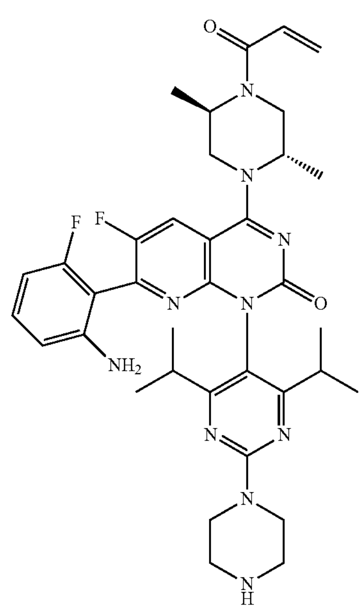 [SMILES: C=CC(=O)N1C[C@H](C)N(c2nc(=O)n(-c3c(C(C)C)nc(N4CCNCC4)nc3C(C)C)c3nc(-c4c(N)cccc4F)c(F)cc23)C[C@H]1C] | 683.4 | HNMR (400 MHz, methanol-d₄, ppm): δ 8.23-8.19 (m, 1H), 7.16-7.11 (m, 1H), 6.87-6.74 (m, 1H), 6.55 (d, J = 8.4 Hz, 1H), 6.43-6.39 (m, 1H), 6.30-6.24 (m, 1H), 5.82-5.78 (m, 1H), 5.01-5.00 (m, 1H), 4.96-4.79 (m, 1H), 4.52-4.28 (m, 2H), 4.00-3.88 (m, 5.5H), 3.54-3.50 (m, 0.5H), 3.23-3.21 (m, 4H), 1.63-1.52 (m, 2H), 1.46 (d, J = 6.8 Hz, 3H), 1.36-1.26 (m, 3H), 1.07-1.01 (m, 4H), 0.89-0.74 (m, 4H). FNMR (376 MHz, methanol-d₄, ppm): δ −115.00 (1F), −126.22 (1F). |

TABLE 1-continued
Characterization of the compounds of Formulas (I) and (II)
| Compound No. | Structure | [M + H]+ | 1H-NMR and 19F-NMR |
|---|---|---|---|
| 100 | 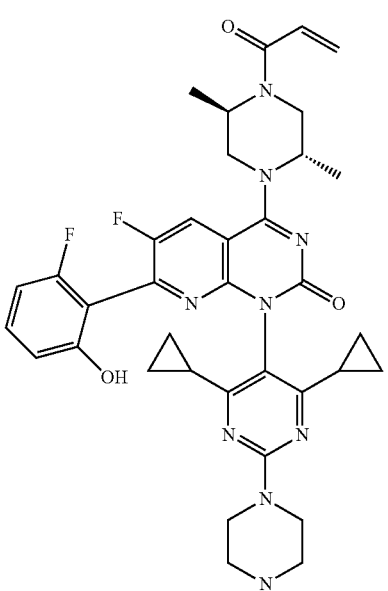 | 684.3 | HNMR (400 MHz, methanol-d$_4$, ppm): δ 8.22-8.18 (m, 1H), 7.30-7.24 (m, 1H), 6.85-6.62 (m, 3H), 6.30-6.24 (m, 1H), 5.82-5.78 (m, 1H), 5.00-4.84 (m, 2H), 4.52-4.27 (m, 2H), 3.99-3.89 (m, 5.5H), 3.55-3.51 (m, 0.5H), 3.22-3.19 (m, 4H), 1.57-1.52 (m, 2H), 1.46 (d, J = 6.8 Hz, 3H), 1.36-1.25 (m, 3H), 1.06-0.95 (m, 4H), 0.83-0.72 (m, 4H). FNMR (376 MHz, methanol-d$_4$, ppm): δ −115.46 (1F), −127.64 (1F). |
| 102 | 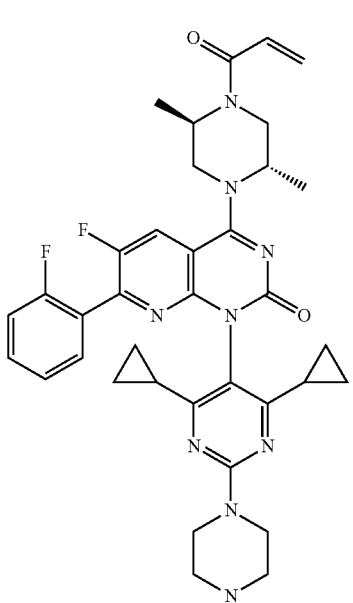 | 668.4 | HNMR (400 MHz, methanol-d$_4$, ppm): δ 8.23-8.19 (m, 1H), 7.53-7.45 (m, 2H), 7.27-7.19 (m, 2H), 6.83-6.74 (m, 1H), 6.30-6.28 (m, 1H), 5.81-5.78 (m, 1H), 5.02-4.89 (m, 2H), 4.51-4.28 (m, 2H), 4.00-3.89 (m, 5.5H), 3.55-3.50 (m, 0.5H), 3.23-3.20 (m, 4H), 1.62-1.53 (m, 2H), 1.45 (d, J = 6.8 Hz, 3H), 1.35-1.25 (m, 3H), 1.08-0.99 (m, 4H), 0.87-0.73 (m, 4H). FNMR (376 MHz, DMSO-d$_6$, ppm): δ −114.82, −128.93 (1F). |

TABLE 1-continued

Characterization of the compounds of Formulas (I) and (II)

| Compound No. | Structure | [M + H]⁺ | ¹H-NMR and ¹⁹F-NMR |
|---|---|---|---|
| 118 | 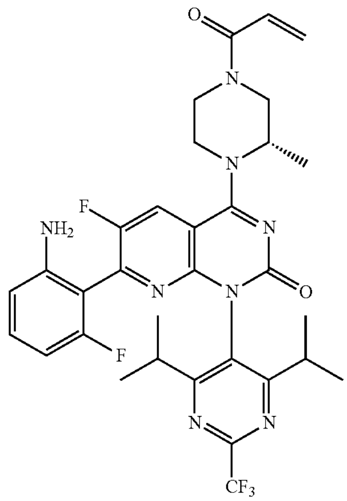 [SMILES: C=CC(=O)N1CCN(c2nc(=O)n(-c3c(C(C)C)nc(C(F)(F)F)nc3C(C)C)c3nc(-c4c(N)cccc4F)c(F)cc23)[C@@H](C)C1] | 657.3 | HNMR (400 MHz, methanol-$d_4$, ppm): δ 8.32-8.27 (m, 1H), 7.13-7.10 (m, 1H), 6.84-6.78 (m, 1H), 6.51 (d, J = 8.4 Hz, 1H), 6.39-6.37 (m, 1H), 6.35-6.27 (m, 1H), 5.82 (dd, J = 10.4 Hz, 2.0 Hz, 1H), 5.11 (s, 1H), 4.54-4.40 (m, 2H), 4.21-4.06 (m, 1H), 3.87-3.75 (m, 1H), 3.74-3.55 (m, 1H), 3.38-2.32 (m, 1H), 2.87-2.82 (m, 2H), 1.49-1.47 (m, 3H), 1.19 (dd, J = 6.4 Hz, 2.4 Hz, 6H), 1.03 (dd, J = 6.0 Hz, 2.4 Hz, 6H). |
| 105 | 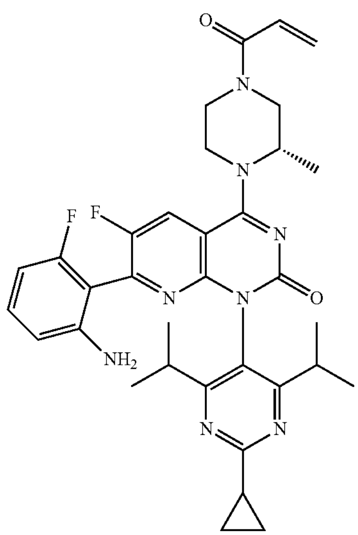 [SMILES: C=CC(=O)N1CCN(c2nc(=O)n(-c3c(C(C)C)nc(C4CC4)nc3C(C)C)c3nc(-c4c(N)cccc4F)c(F)cc23)[C@@H](C)C1] | 629.3 | HNMR (400 MHz, methanol-$d_4$, ppm): δ 8.32-8.22 (m, 1H), 7.14-7.08 (m, 1H), 6.84-6.81 (m, 1H), 6.52 (d, J = 8.0 Hz, 1H), 6.40-6.35 (m, 1H), 6.29 (dd, J = 16.0, 4.0 Hz, 1H), 5.81 (dd, J = 10.4, 1.6 Hz, 1H), 5.06 (s, 1H), 4.50-4.43 (m, 2 H), 4.20-4.05 (m, 1H), 3.84-3.75 (m, 1H), 3.74-3.55 (m, 1H), 3.36-3.30 (m, 1H), 2.72-2.66 (m, 2H), 2.30-2.25 (m, 1H), 1.45 (d, J = 5.6 Hz, 3H), 1.23-1.14 (m, 8H), 1.09-1.06 (m, 2H), 0.99-0.98 (m, 6H). |
| 109 | 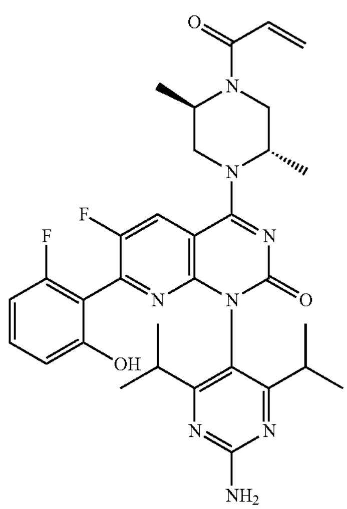 [SMILES: C=CC(=O)N1C[C@H](C)N(c2nc(=O)n(-c3c(C(C)C)nc(N)nc3C(C)C)c3nc(-c4c(O)cccc4F)c(F)cc23)C[C@H]1C] | 619.5 | HNMR (400 MHz, DMSO-$d_6$, ppm): δ 10.20 (s, 1H), 8.30-8.27 (m, 1H), 7.32-7.26 (m, 1H), 6.90-6.86 (m, 1H), 6.83-6.69 (m, 2H), 6.50 (s, 2H), 6.21 (dd, J = 14.4, 2.4 Hz, 1H), 5.78-5.73 (m, 1H), 4.90-4.75 (m, 2H), 4.55-4.45 (m, 0.5H), 4.17-4.12 (m, 1H), 3.90-3.75 (m, 2H), 3.55-3.45 (m, 0.5H), 2.44-2.40 (m, 2H), 1.35-1.15 (m, 6H), 1.00 (d, J = 6.8 Hz, 6H), 0.86 (d, J = 6.8 Hz, 6H). FNMR (376 MHz, DMSO-$d_6$, ppm): δ -115.72, -129.06 (1F). |

TABLE 1-continued
Characterization of the compounds of Formulas (I) and (II)
| Compound No. | Structure | [M + H]+ | 1H-NMR and 19F-NMR |
|---|---|---|---|
| 115 | 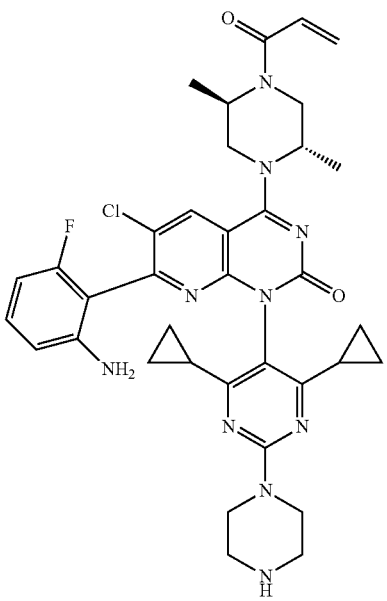 [SMILES: C=CC(=O)N1C[C@H](C)N(c2nc(=O)n(-c3c(C4CC4)nc(N4CCNCC4)nc3C3CC3)c3nc(-c4c(N)cccc4F)c(Cl)cc23)C[C@H]1C] | 699.3 | HNMR (400 MHz, methanol-d$_4$, ppm): δ 8.46-8.38 (m, 1H), 7.11-7.09 (m, 1H), 6.86-6.73 (m, 1H), 6.56 (d, J = 8.4 Hz, 1H), 6.42-6.38 (m, 1H), 6.30-6.25 (m, 1H), 5.82-5.78 (m, 1H), 5.07-4.84 (m, 2H), 4.60-4.19 (m, 2H), 4.09-4.80 (m, 6H), 3.22-3.19 (m, 4H), 1.57-1.52 (m, 2H), 1.51-1.40 (m, 3H), 1.34-1.21 (m, 3H), 1.06-0.92 (m, 4H), 0.90-0.72 (m, 4H). FNMR (376 MHz, methanol-d$_4$, ppm): δ -115.20 (1F). |
| 99 | 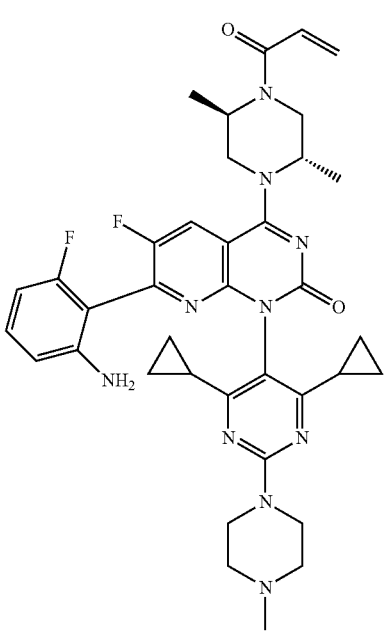 | 697.3 | HNMR (400 MHz, methanol-d$_4$, ppm): δ 8.23-8.20 (m, 1H), 7.17-7.11 (m, 1H), 6.81-6.74 (m, 1H), 6.55 (d, J = 8.4 Hz, 1H), 6.43-6.39 (m, 1H), 6.30-6.25 (m, 1H), 5.83-5.78 (m, 1H), 5.01-4.89 (m, 2H), 4.42-4.28 (m, 2H), 3.96-3.89 (m, 2H), 3.54-3.46 (m, 2H), 3.40-3.06 (m, 6H), 2.91 (s, 3H), 1.64-1.54 (m, 2H), 1.46 (d, J = 6.4 Hz, 3H), 1.36-1.26 (m, 3H), 1.05-1.04 (m, 4H), 0.89-0.78 (m, 4H). FNMR (376 MHz, methanol-d$_4$, ppm): δ -115.06 (1F), -126.25 (1F). |

TABLE 1-continued

Characterization of the compounds of Formulas (I) and (II)

| Compound No. | Structure | [M + H]+ | 1H-NMR and 19F-NMR |
|---|---|---|---|
| 101 | 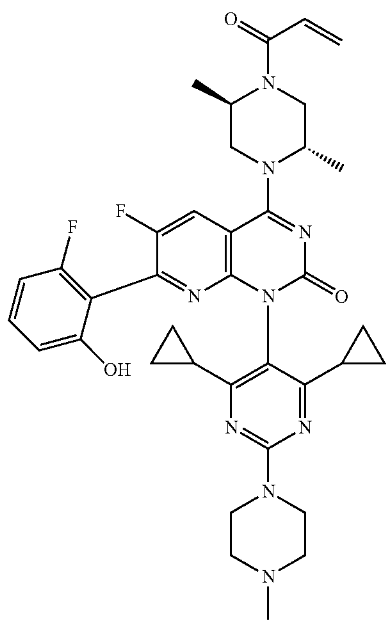 [SMILES: C=CC(=O)N1C[C@H](C)N(c2nc(=O)n(-c3c(C4CC4)nc(N4CCN(C)CC4)nc3C3CC3)c3nc(-c4c(O)cccc4F)c(F)cc23)C[C@H]1C] | 698.4 | HNMR (400 MHz, methanol-$d_4$, ppm): δ 8.22-8.18 (m, 1H), 7.30-7.24 (m, 1H), 6.80-6.70 (m, 1H), 6.68-6.62 (m, 2H), 6.30-6.24 (m, 1H), 5.82-5.78 (m, 1H), 5.00-4.89 (m, 2H), 4.52-4.27 (m, 2H), 3.98-3.89 (m, 2H), 3.55-3.48 (m, 2H), 3.40-3.07 (m, 6H), 2.89 (s, 3H), 1.61-1.52 (m, 2H), 1.46 (d, J = 6.4 Hz, 3H), 1.36-1.25 (m, 3H), 1.05-0.97 (m, 4H), 0.84-0.73 (m, 4H). FNMR (376 MHz, methanol-$d_4$, ppm): δ −115.57 (1F), −127.69 (1F). |
| 103 | 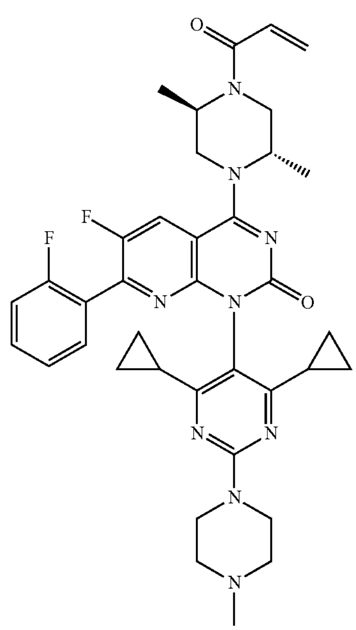 [SMILES: C=CC(=O)N1C[C@H](C)N(c2nc(=O)n(-c3c(C4CC4)nc(N4CCN(C)CC4)nc3C3CC3)c3nc(-c4ccccc4F)c(F)cc23)C[C@H]1C] | 682. | HNMR (400 MHz, methanol-$d_4$, ppm): δ 8.24-8.20 (m, 1H), 7.53-7.44 (m, 2H), 7.27-7.19 (m, 2H), 6.81-6.74 (m, 1H), 6.30-6.27 (m, 1H), 5.81-5.78 (m, 1H), 5.02-4.89 (m, 2H), 4.51-4.28 (m, 2H), 4.00-3.89 (m, 2H), 3.54-3.46 (m, 2H), 3.40-3.08 (m, 6H), 2.90 (s, 3H), 1.62-1.54 (m, 2H), 1.46 (d, J = 6.8 Hz, 3H), 1.35-1.25 (m, 3H), 1.08-0.99 (m, 4H), 0.89-0.74 (m, 4H). FNMR (376 MHz, methanol-$d_4$, ppm): δ −114.87 (1F), −128.95 (1F). |

TABLE 1-continued

Characterization of the compounds of Formulas (I) and (II)

| Compound No. | Structure | [M + H]+ | 1H-NMR and 19F-NMR |
|---|---|---|---|
| 81 | 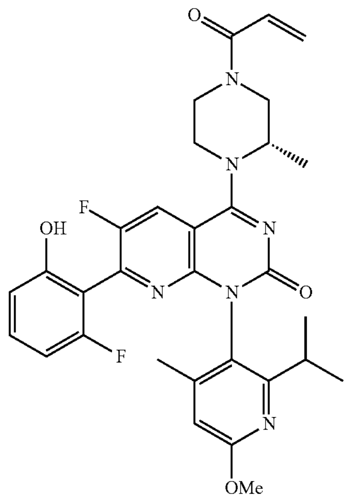 [SMILES: C=CC(=O)N1CCN(c2nc(=O)n(-c3c(C)cc(OC)nc3C(C)C)c3nc(-c4c(O)cccc4F)c(F)cc23)[C@@H](C)C1] | 591.2 | HNMR (400 MHz, CDCl$_3$, ppm): δ 9.62 (s, 1H), 7.92 (dd, J = 9.4, 4.6 Hz, 1H), 7.39-7.29 (m, 1H), 6.77 (d, J = 8.4 Hz, 1H), 6.70-6.56 (m, 3H), 6.44 (dd, J = 16.6, 1.9 Hz, 1H), 5.84 (dd, J = 10.4, 1.9 Hz, 1H), 5.31-5.01 (m, 1H), 4.95-4.65 (m, 1H), 4.61-4.25 (m, 1H), 4.35-4.03 (m, 1H), 3.96 (s, 3H), 3.81-3.48 (m, 2H), 3.38-2.95 (m, 1H), 2.81-2.59 (m, 1H), 2.02 (d, J = 7.7 Hz, 3H), 1.54 (t, J = 27.5 Hz, 3H), 1.26 (dd, J = 6.9, 4.0 Hz, 3H), 1.08 (d, J = 7.0 Hz, 3H). FNMR (376 MHz, CDCl$_3$, ppm): δ −107.71 (1F), −121.95 (1F). |
| 106 | 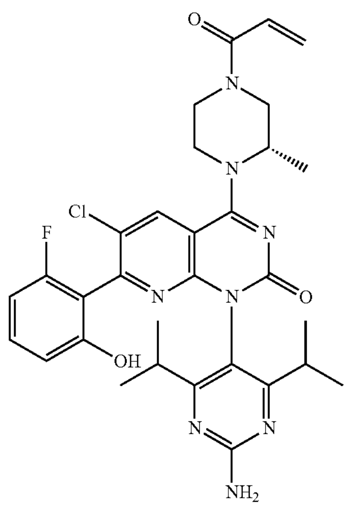 [SMILES: C=CC(=O)N1CCN(c2nc(=O)n(-c3c(C(C)C)nc(N)nc3C(C)C)c3nc(-c4c(O)cccc4F)c(Cl)cc23)[C@@H](C)C1] | 621.2 | HNMR (400 MHz, DMSO-d$_6$, ppm): δ 10.13 (s, 1H), 8.42-8.38 (m, 1H), 7.31-7.21 (m, 1H), 6.88-6.81 (m, 1H), 6.74-6.71 (m, 1H), 6.68-6.66 (m, 2H), 6.21 (dd, J = 16.8, 6.8 Hz, 1H), 5.77 (dd, J = 10.4, 2.4 Hz, 1H), 4.95 (brs, 1H), 4.41-4.27 (m, 2H), 4.16-4.13 (m, 2H), 3.68-3.63 (m, 1H), 3.50-3.46 (m, 1H), 3.27-3.24 (m, 1H), 3.12-3.11 (m, 1H), 2.60-2.40 (m, 2H), 1.33 (d, J = 6.4 Hz, 3H), 1.02 (d, J = 6.4 Hz, 6H), 0.96-0.82 (m, 6H). FNMR (376 MHz, DMSO-d$_6$, ppm): δ −115.38 (1F). |
| 107 | 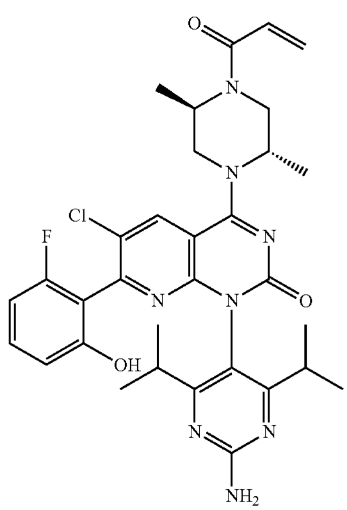 [SMILES: C=CC(=O)N1C[C@H](C)N(c2nc(=O)n(-c3c(C(C)C)nc(N)nc3C(C)C)c3nc(-c4c(O)cccc4F)c(Cl)cc23)C[C@H]1C] | 635.4 | HNMR (300 MHz, DMSO-d$_6$, ppm): δ 10.11 (s, 1H), 8.43 (s, 1H), 7.30-7.22 (m, 1H), 6.87-6.81 (m, 1H), 6.77-6.66 (m, 2H), 6.51 (s, 2H), 6.21 (dd, J = 16.5, 2.4 Hz, 1H), 5.78-5.73 (m, 1H), 4.84-4.48 (m, 2H), 4.22-4.02 (m, 1.5H), 3.95-3.78 (m, 2H), 3.55-3.45 (m, 0.5H), 2.46-2.40 (m, 2H), 1.31 (t, J = 6.3 Hz, 3H), 1.29-1.24 (m, 3H), 1.00 (d, J = 6.6, 6H), 0.86 (d, J = 6.6 Hz, 6H). FNMR (282 MHz, DMSO-d$_6$, ppm): δ −115.86 (1F). |

TABLE 1-continued

Characterization of the compounds of Formulas (I) and (II)

| Compound No. | Structure | [M + H]⁺ | ¹H-NMR and ¹⁹F-NMR |
|---|---|---|---|
| 110 | 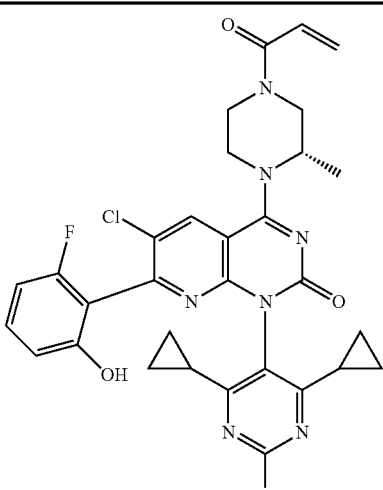 | 617.3 | HNMR (400 MHz, DMSO-d₆, ppm): δ 10.13 (s, 1H), 8.37 (s, 1H), 7.32-7.22 (m, 1H), 6.95-6.80 (m, 1H), 6.78-6.65 (m, 2H), 6.26-6.19 (m, 3H), 5.77 (dd, J = 10.4, 2.4 Hz, 1H), 4.94-4.86 (m, 1H), 4.42-3.99 (m, 3H), 3.75-3.69 (m, 1H), 3.65-3.61 (m, 1H), 3.11-3.06 (m, 1H), 1.58-1.40 (m, 2H), 1.33 (s, 3H), 0.90-0.80 (m, 2H), 0.78-0.70 (m, 4H), 0.64-0.60 (m, 2H). FNMR (376 MHz, DMSO-d₆, ppm): δ −115.34 (1F). |
| 111 | 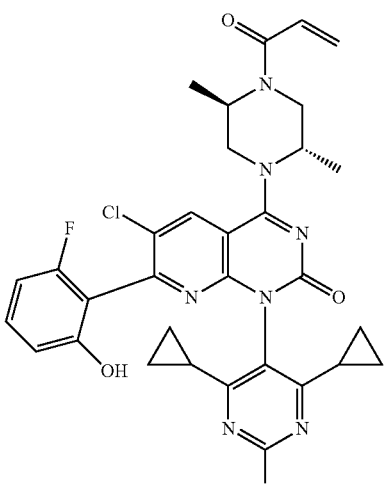 | 631.2 | HNMR (300 MHz, DMSO-d₆, ppm): δ 10.18 (s, 1H), 8.40 (s, 1H), 7.32-7.24 (m, 1H), 6.85-6.72 (m, 3H), 6.28 (s, 1H), 6.21-6.16 (m, 2H), 5.77-5.73 (m, 1H), 4.80-4.48 (m, 2H), 4.30-3.99 (m, 1.5H), 3.92-3.75 (m, 2H), 3.55-3.45 (m, 0.5H), 1.44-1.20 (m, 8H), 0.86-0.73 (m, 8H). FNMR (282 MHz, DMSO-d₆, ppm): δ −115.34 (1F). |
| 10 | 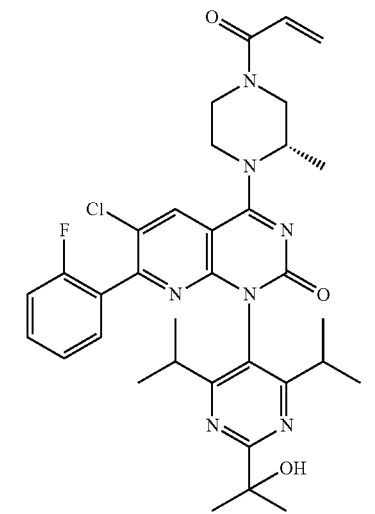 [SMILES: C=CC(=O)N1CCN(c2nc(=O)n(-c3c(C(C)C)nc(C(C)(C)O)nc3C(C)C)c3nc(-c4ccccc4F)c(Cl)cc23)[C@@H](C)C1] | 648. | HNMR (300 MHz, DMSO-d₆, ppm): δ 8.49 (s, 1H), 7.52-7.48 (m, 1H), 7.34-7.25 (m, 2H), 7.19-7.15 (m, 1H), 6.95-6.78 (m, 1H), 6.22 (d, J = 16.7 Hz, 1H), 5.78 (d, J = 10.4 Hz, 1H), 5.00 (brs, 1H), 4.93 (s, 1H), 4.50-3.94 (m, 3H), 3.91-3.56 (m, 2H), 3.14-3.10 (m, 1H), 2.82-2.64 (m, 2H), 1.50 (s, 6H), 1.35 (d, J = 6.6 Hz, 3H), 1.10 (d, J = 6.6 Hz, 6H), 0.95 (d, J = 6.6 Hz, 6H). FNMR (282 MHz, DMSO-d₆, ppm): δ −114.39 (1F). | ns259-260

TABLE 1-continued

Characterization of the compounds of Formulas (I) and (II)

| Compound No. | Structure | [M + H]+ | 1H-NMR and 19F-NMR |
|---|---|---|---|
| 135 | 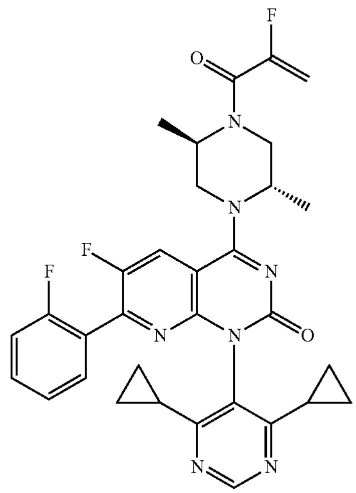 [SMILES: C=C(F)C(=O)N1C[C@H](C)N(c2nc(=O)n(-c3c(C4CC4)ncnc3C3CC3)c3nc(-c4ccccc4F)c(F)cc23)C[C@H]1C] | 602.3 | HNMR (400 MHz, methanol-$d_4$, ppm): δ 8.71 (s, 1H), 8.27-8.19 (m, 1H), 7.54-7.47 (m, 1H), 7.43-7.38 (m, 1H), 7.25-7.17 (m, 2H), 5.36-5.18 (m, 2H), 5.11-4.98 (m, 1H), 4.81-4.72 (m, 0.5H), 4.51-4.23 (m, 2H), 3.99-3.80 (m, 2H), 3.56-3.52 (m, 0.5H), 1.82-1.64 (m, 2H), 1.48 (d, J = 6.4 Hz, 3H), 1.43-1.28 (m, 3H), 1.18-1.03 (m, 4H), 1.01-0.81 (m, 4H). FNMR (376 MHz, methanol-$d_4$, ppm): δ −106.11 (0.5F), −106.96 (0.5F), −114.72 (1F), −128.35 (1F). |
| 108 | 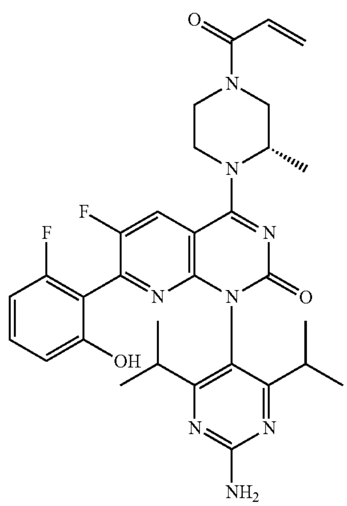 [SMILES: C=CC(=O)N1CCN(c2nc(=O)n(-c3c(C(C)C)nc(N)nc3C(C)C)c3nc(-c4c(O)cccc4F)c(F)cc23)[C@@H](C)C1] | 605.4 | HNMR (300 MHz, DMSO-$d_6$, ppm): δ 10.22 (s, 1H), 8.30-8.24 (m, 1H), 7.32-7.25 (m, 1H), 7.00-6.60 (m, 4H), 6.23 (d, J = 8.7 Hz, 1H), 5.75 (d, J = 16.5 Hz, 1H), 4.91 (brs, 1H), 4.42-4.38 (m, 1H), 4.31-4.27 (m, 2H), 3.71-3.58 (m, 2H), 3.28-3.07 (m, 1H), 2.36-2.27 (m, 2H), 1.33 (d, J = 6.3 Hz, 3H), 1.02 (d, J = 6.0 Hz, 6H), 0.86 (d, J = 6.6 Hz, 6H). FNMR (282 MHz, DMSO-$d_6$, ppm): δ −115.76 (1F), −128.27 (1F). |
| 112 | 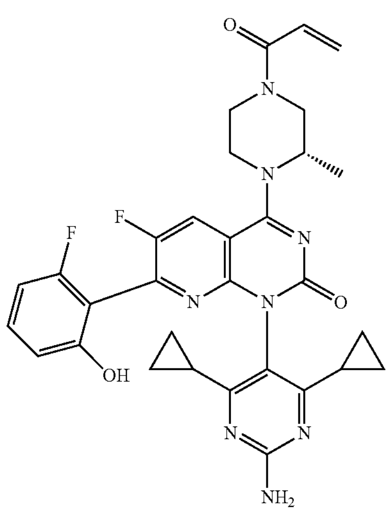 [SMILES: C=CC(=O)N1CCN(c2nc(=O)n(-c3c(C4CC4)nc(N)nc3C3CC3)c3nc(-c4c(O)cccc4F)c(F)cc23)[C@@H](C)C1] | 601.5 | HNMR (300 MHz, DMSO-$d_6$, ppm): δ 10.22 (s, 1H), 8.26-8.20 (m, 1H), 7.32-7.30 (m, 1H), 6.89-6.70 (m, 3H), 6.26-6.17 (m, 3H), 5.77 (d, J = 10.4 Hz, 1H), 4.89 (brs, 1H), 4.45-4.02 (m, 3H), 3.69-3.61 (m, 2H), 3.22-3.08 (m, 1H), 1.52-1.39 (m, 2H), 1.33 (d, J = 6.0 Hz, 3H), 0.90-0.55 (m, 8H). FNMR (282 MHz, DMSO-$d_6$, ppm): δ −114.87 (1F), −128.82 (1F). |

TABLE 1-continued

Characterization of the compounds of Formulas (I) and (II)

| Compound No. | Structure | [M + H]⁺ | ¹H-NMR and ¹⁹F-NMR |
|---|---|---|---|
| 113 | 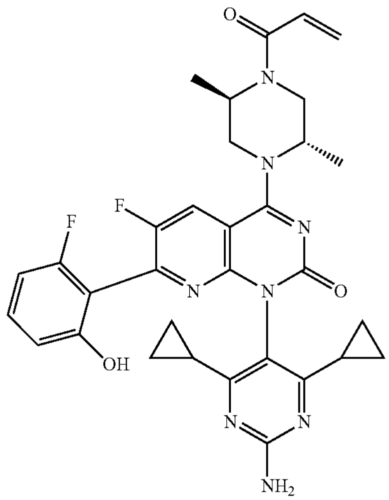 | 615.3 | HNMR (300 MHz, DMSO-$d_6$, ppm): δ 10.25 (s, 1H), 8.35-8.21 (m, 1H), 7.40-7.25 (m, 1H), 6.88-6.68 (m, 4H), 6.19 (dd, J = 16.8, 2.4 Hz, 1H), 5.76 (dt, J = 10.5, 3.0 Hz, 1H), 4.81 (brs, 2H), 4.55-3.70 (m, 3.5H), 3.55-3.45 (m, 0.5H), 1.48 (s, 2H), 1.37-1.11 (m, 6H), 0.96-0.56 (m, 8H). FNMR (282 MHz, DMSO-$d_6$, ppm): δ −115.21 (1F), −128.21 (1F). |
| 128 | 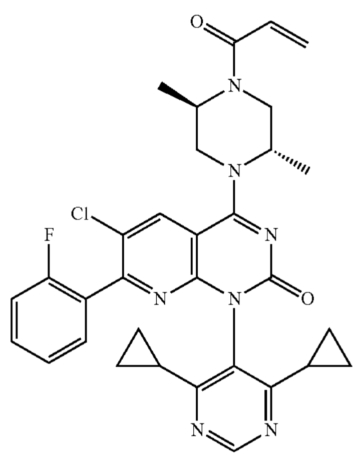 [SMILES: C=CC(=O)N1C[C@H](C)N(c2nc(=O)n(-c3c(C4CC4)ncnc3C3CC3)c3nc(-c4ccccc4F)c(Cl)cc23)C[C@H]1C] | 600.2 | HNMR (300 MHz, DMSO-$d_6$, ppm): δ 8.73 (s, 1H), 8.46 (d, J = 4.2 Hz, 1H), 7.57-7.53 (m, 1H), 7.38-7.30 (m, 3H), 6.87-6.78 (m, 1H), 6.20 (d, J = 16.8 Hz, 1H), 5.76 (d, J = 10.3 Hz, 1H), 4.95-4.77 (m, 1.5H), 4.55-4.45 (m, 0.5H), 4.27-4.16 (m, 1.5H), 3.93-3.81 (m, 2H), 3.51-3.47 (m, 0.5H), 1.85-1.65 (m, 2H), 1.35 (dd, J = 6.4, 2.8 Hz, 3H), 1.24 (dd, J = 19.5, 6.6 Hz, 3H), 1.08-0.74 (m, 8H). FNMR (282 MHz, DMSO-$d_6$, ppm): δ −112.94 (1F). |
| 133 | 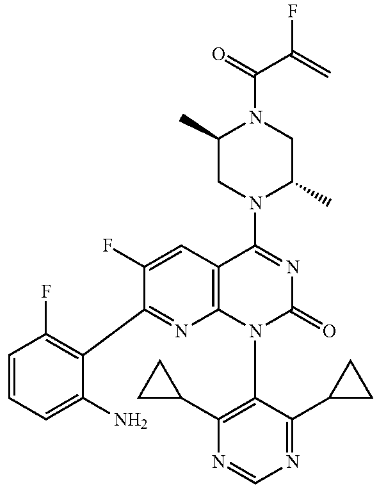 | 617.3 | HNMR (400 MHz, methanol-$d_4$, ppm): δ 8.73 (s, 1H), 8.27-8.19 (m, 1H), 7.15-7.09 (m, 1H), 6.53 (d, J = 8.0 Hz, 1H), 6.42-6.36 (m, 1H), 5.35-5.19 (m, 2H), 5.11-4.97 (m, 1H), 4.81-4.72 (m, 0.5H), 4.51-4.23 (m, 2H), 3.99-3.78 (m, 2H), 3.56-3.51 (m, 0.5H), 1.85-1.64 (m, 2H), 1.48 (d, J = 6.8 Hz, 3H), 1.43-1.28 (m, 3H), 1.15-1.05 (m, 4H), 1.02-0.95 (m, 2H), 0.87-0.79 (m, 2H). FNMR (376 MHz, methanol-$d_4$, ppm): δ −106.08 (0.5F), −107.03 (0.5F), −114.93 (1F), −125.60 (1F). |

TABLE 1-continued

Characterization of the compounds of Formulas (I) and (II)

| Compound No. | Structure | [M + H]+ | 1H-NMR and 19F-NMR |
|---|---|---|---|
| 134 | 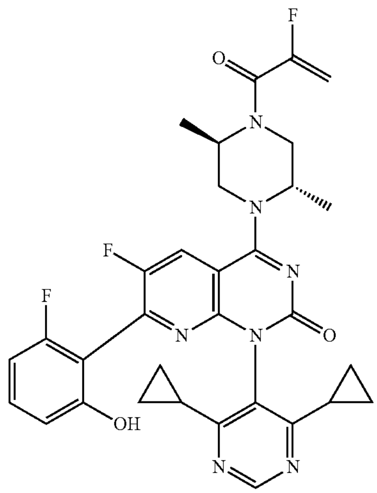 [SMILES: C=C(F)C(=O)N1C[C@H](C)N(c2nc(=O)n(-c3c(C4CC4)ncnc3C3CC3)c3nc(-c4c(O)cccc4F)c(F)cc23)C[C@H]1C] | 618.2 | HNMR (400 MHz, methanol-$d_4$, ppm): δ 8.69 (s, 1H), 8.24-8.17 (m, 1H), 7.28-7.21 (m, 1H), 6.66 (d, J = 8.4 Hz, 1H), 6.61 (t, J = 8.8 Hz, 1H), 5.35-5.19 (m, 2H), 5.11-4.97 (m, 1H), 4.81-4.72 (m, 0.5H), 4.51-4.23 (m, 2H), 3.99-3.80 (m, 2H), 3.58-3.52 (m, 0.5H), 1.82-1.64 (m, 2H), 1.48 (d, J = 6.4 Hz, 3H), 1.43-1.28 (m, 3H), 1.16-0.99 (m, 4H), 0.98-0.79 (m, 4H). FNMR (376 MHz, methanol-$d_4$, ppm): δ −106.09 (0.5F), −106.94 (0.5F), −116.11 (1F), −127.30 (1F). |
| 136 | 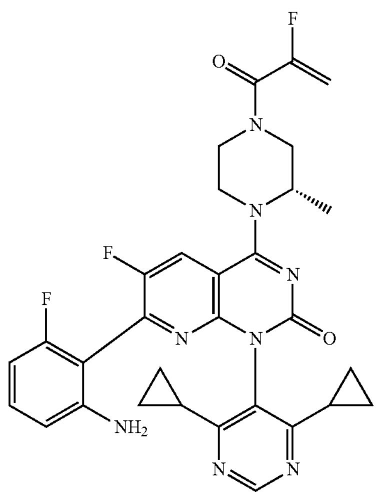 | 603.3 | HNMR (400 MHz, methanol-$d_4$, ppm): δ 8.73 (s, 1H), 8.25 (d, J = 9.2 Hz, 1H), 7.15-7.09 (m, 1H), 6.53 (d, J = 8.4 Hz, 1H), 6.42-6.37 (m, 1H), 5.33 (dd, J = 21.2, 4.0 Hz, 1H), 5.25 (dd, J = 10.8, 4.0 Hz, 1H), 5.11-5.03 (m, 1H), 4.51-3.92 (m, 3H), 3.91-3.33 (m, 3H), 1.82-1.72 (m, 2H), 1.49 (d, J = 6.8 Hz, 3H), 1.18-1.05 (m, 4H), 1.02-0.80 (m, 4H). FNMR (376 MHz, methanol-$d_4$, ppm): δ −106.88 (1F), −115.04 (1F), −125.77 (1F). |
| 137 | 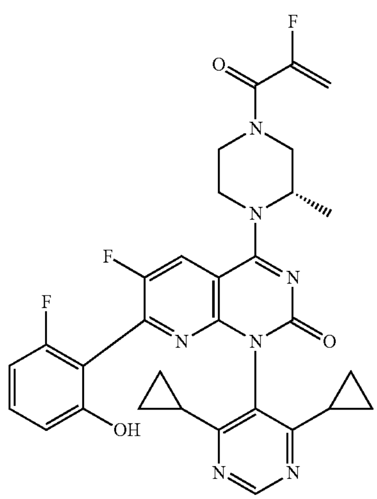 [SMILES: C=C(F)C(=O)N1CCN(c2nc(=O)n(-c3c(C4CC4)ncnc3C3CC3)c3nc(-c4c(O)cccc4F)c(F)cc23)[C@@H](C)C1] | 604.2 | HNMR (400 MHz, methanol-$d_4$, ppm): δ 8.69 (s, 1H), 8.22 (d, J = 9.2 Hz, 1H), 7.27-7.20 (m, 1H), 6.66 (d, J = 8.4 Hz, 1H), 6.63-6.58 (m, 1H), 5.33 (dd, J = 21.2, 4.0 Hz, 1H), 5.25 (dd, J = 10.8, 4.0 Hz, 1H), 5.11-5.03 (m, 1H), 4.51-3.92 (m, 3H), 3.91-3.33 (m, 3H), 1.79-1.69 (m, 2H), 1.49 (d, J = 6.8 Hz, 3H), 1.15-1.00 (m, 4H), 0.99-0.79 (m, 4H). FNMR (376 MHz, methanol-$d_4$, ppm): δ −106.84 (1F), −116.16 (1F), −127.44 (1F). |

TABLE 1-continued

Characterization of the compounds of Formulas (I) and (II)

| Compound No. | Structure | [M + H]+ | 1H-NMR and 19F-NMR |
|---|---|---|---|
| 138 | 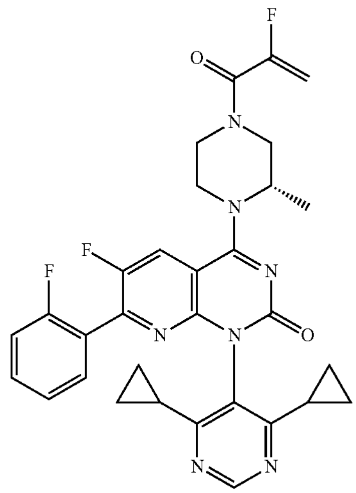 [SMILES: C=C(F)C(=O)N1CCN(c2nc(=O)n(-c3c(C4CC4)ncnc3C3CC3)c3nc(-c4ccccc4F)c(F)cc23)[C@@H](C)C1] | 588.3 | HNMR (400 MHz, methanol-d$_4$, ppm): δ 8.71 (s, 1H), 8.25 (d, J = 9.2 Hz, 1H), 7.53-7.47 (m, 1H), 7.42-7.37 (m, 1H), 7.25-7.16 (m, 2H), 5.33 (dd, J = 21.6, 4.0 Hz, 1H), 5.25 (dd, J = 10.4, 4.0 Hz, 1H), 5.11-5.03 (m, 1H), 4.51-3.92 (m, 3H), 3.91-3.33 (m, 3H), 1.79-1.71 (m, 2H), 1.49 (d, J = 6.8 Hz, 3H), 1.18-1.03 (m, 4H), 1.01-0.81 (m, 4H). FNMR (376 MHz, methanol-d$_4$, ppm): δ −106.87 (1F), −114.83 (1F), −128.55 (1F). |
| 125 | 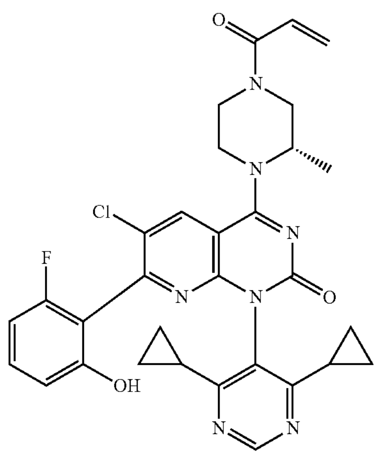 [SMILES: C=CC(=O)N1CCN(c2nc(=O)n(-c3c(C4CC4)ncnc3C3CC3)c3nc(-c4c(O)cccc4F)c(Cl)cc23)[C@@H](C)C1] | 602.4 | HNMR (400 MHz, DMSO-d$_6$, ppm): δ 10.15 (s, 1H), 8.70 (s, 1H), 8.43 (brs, 1H), 7.27-7.25 (m, 1H), 6.91-6.82 (m, 1H), 6.75-6.67 (m, 2H), 6.23-6.19 (m, 1H), 5.78 (dd, J = 10.4, 2.4 Hz, 1H), 4.99-4.93 (m, 1H), 4.42-4.28 (m, 2H), 4.18-4.03 (m, 1H), 3.81-3.62 (m, 2H), 3.18-3.02 (m, 1H), 1.77-1.72 (m, 2H), 1.41-1.30 (m, 3H), 1.03-0.73 (m, 8H). FNMR (376 MHz, DMSO-d$_6$, ppm): δ −115.40 (1F). |
| 130 | 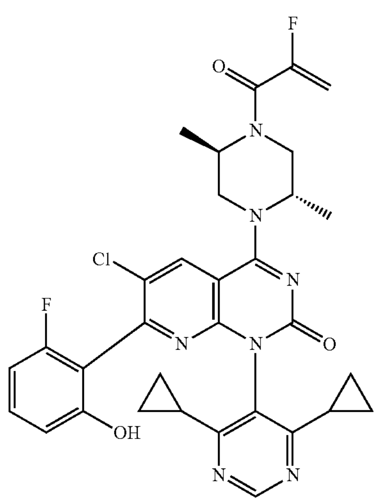 [SMILES: C=C(F)C(=O)N1C[C@H](C)N(c2nc(=O)n(-c3c(C4CC4)ncnc3C3CC3)c3nc(-c4c(O)cccc4F)c(Cl)cc23)C[C@H]1C] | 634.4 | HNMR (400 MHz, DMSO-d$_6$, ppm): δ 10.16 (s, 1H), 8.71 (s, 1H), 8.51-8.30 (m, 1H), 7.32-7.20 (m, 1H), 6.79-6.64 (m, 2H), 5.42-5.16 (m, 2H), 5.01-4.80 (m, 1H), 4.85-4.72 (m, 0.5H), 4.35-4.12 (m, 2H), 3.92-3.42 (m, 2.5H), 1.78-1.60 (m, 2H), 137-1.28 (m, 6H), 0.97-0.80 (m, 8H). FNMR (376 MHz, DMSO-d$_6$, ppm): δ −105.08 (1F), −115.35 (1F). |

TABLE 1-continued

Characterization of the compounds of Formulas (I) and (II)

| Compound No. | Structure | [M + H]+ | 1H-NMR and 19F-NMR |
|---|---|---|---|
| 67 | 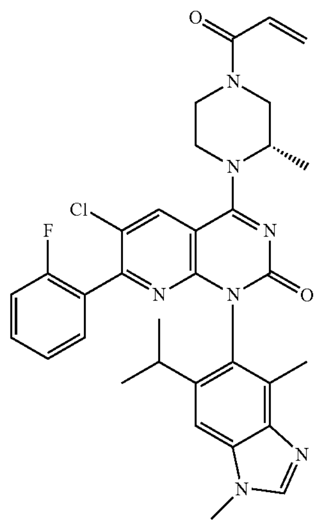 [SMILES: C=CC(=O)N1CCN(c2nc(=O)n(-c3c(C(C)C)cc4c(ncn4C)c3C)c3nc(-c4ccccc4F)c(Cl)cc23)[C@@H](C)C1] | 614.3 | HNMR (400 MHz, DMSO-$d_6$, ppm): δ 8.48-8.46 (m, 1H), 8.11 (s, 1H), 7.51-7.42 (m, 1H), 7.36 (s, 1H), 7.31-7.13 (m, 3H), 6.88 (q, J = 14.8, 14.0 Hz, 1H), 6.22 (d, J = 16.5 Hz, 1H), 5.78 (dd, J = 10.4, 2.4 Hz, 1H), 4.93 (brs, 1H), 4.44-4.30 (m, 2H), 4.11 (dd, J = 49.1, 13.3 Hz, 1H), 3.83 (s, 3H), 3.79-3.61 (m, 2H), 3.13-3.09 (m, 1H), 2.65-2.50 (m, 1H), 2.18-2.09 (m, 3H), 1.35-1.30 (m, 3H), 1.20-1.10 (m, 3H), 1.09-0.99 (m, 3H). FNMR (376 MHz, DMSO-$d_6$, ppm): δ −114.49 (1F). |
| 129 | 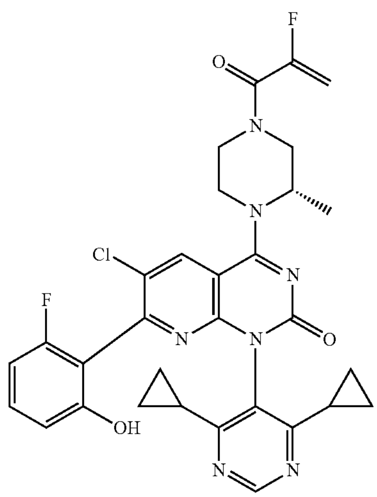 | 620.3 | HNMR (400 MHz, DMSO-$d_6$, ppm): δ 10.16 (s, 1H), 8.70 (s, 1H), 8.48-8.39 (m, 1H), 7.57-7.49 (m, 1H), 7.29-7.23 (m, 1H), 6.75-6.67 (m, 2H), 5.38 (dd, J = 18.4, 4.0 Hz, 1H), 5.01-5.00 (m, 1H), 4.34-4.02 (m, 3H), 3.86-3.30 (m, 3H), 1.77-1.66 (m, 2H), 1.42-1.32 (m, 3H), 0.98-0.80 (m, 8H). FNMR (376 MHz, DMSO-$d_6$, ppm): δ −104.95 (1F), −115.42 (1F). |
| 131 | 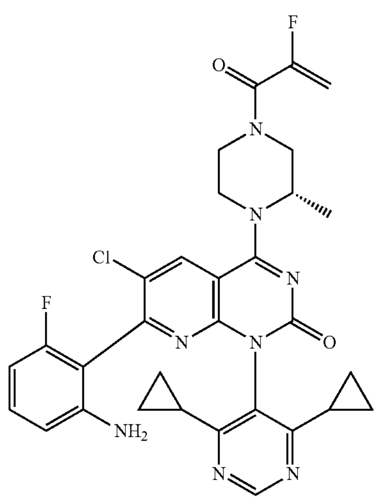 [SMILES: C=C(F)C(=O)N1CCN(c2nc(=O)n(-c3c(C4CC4)ncnc3C3CC3)c3nc(-c4c(O)cccc4F)c(Cl)cc23)[C@@H](C)C1] | 619.2 | HNMR (300 MHz, DMSO-$d_6$, ppm): δ 8.74 (s, 1H), 8.51-8.40 (m, 1H), 7.15-7.05 (m, 1H), 6.51 (d, J = 8.4 Hz, 1H), 6.39 (t, J = 9.0 Hz, 1H), 5.45-5.22 (m, 3H), 5.05-4.95 (m, 1H), 4.37-4.26 (m, 2H), 4.10-3.96 (m, 1H), 3.78-3.64 (m, 1H), 3.60-3.10 (m, 2H), 1.91-1.73 (m, 2H), 1.38 (dd, J = 25.2, 6.6 Hz, 3H), 1.13-0.69 (m, 8H). FNMR (282 MHz, DMSO-$d_6$, ppm): δ −104.95 (1F), −114.15 (1F). |

TABLE 1-continued

Characterization of the compounds of Formulas (I) and (II)

| Compound No. | Structure | [M + H]+ | 1H-NMR and 19F-NMR |
|---|---|---|---|
| 120 | 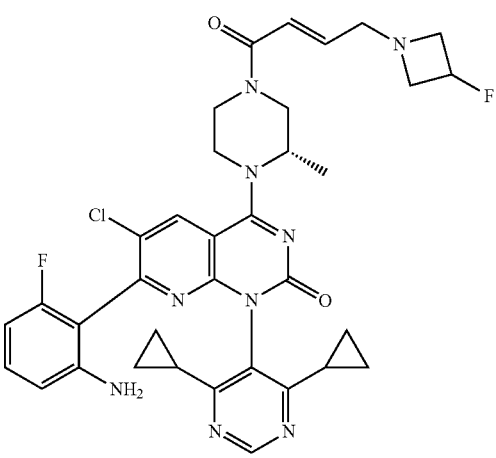 [SMILES: C[C@H]1CN(C(=O)/C=C/CN2CC(F)C2)CCN1c1nc(=O)n(-c2c(C3CC3)ncnc2C2CC2)c2nc(-c3c(N)cccc3F)c(Cl)cc12] | 688.5 | HNMR (300 MHz, DMSO-$d_6$, ppm): δ 8.74 (s, 1H), 8.50-8.40 (m, 1H), 7.23-7.01 (m, 1H), 6.61 (d, J = 3.4 Hz, 2H), 6.51 (d, J = 8.3 Hz, 1H), 6.38 (t, J = 9.4 Hz, 1H), 5.33-4.81 (m, 4H), 4.48-3.86 (m, 5H)), 3.69-3.61 (m, 3H), 3.22-3.14 (m, 2H), 1.92-1.71 (m, 2H), 1.44-1.26 (m, 3H), 1.10-0.75 (m, 8H). FNMR (282 MHz, DMSO-$d_6$, ppm): δ −114.15 (1F), −177.44 (1F). |
| 121 | 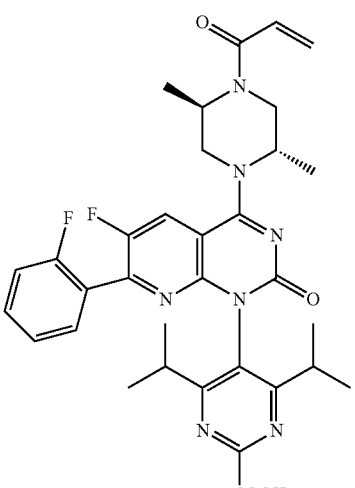 | 632.3 | HNMR (400 MHz, methanol-$d_4$, ppm): δ 8.31-8.25 (m, 1H), 7.51-7.45 (m, 1H), 7.31-7.26 (m, 1H), 7.23-7.15 (m, 2H), 6.88-6.74 (m, 1H), 6.31-6.25 (m, 1H), 5.83-5.78 (m, 1H), 5.12-5.00 (m, 1H), 4.96-4.87 (m, 0.5H), 4.60-4.46 (m, 1H), 4.40-4.30 (m, 1H), 4.05-3.85 (m, 2H), 3.58-3.50 (m, 0.5H), 2.90-2.74 (m, 2H), 1.48 (d, J = 6.4 Hz, 3H), 1.38-1.27 (m, 3H), 1.26-1.20 (m, 6H), 1.07-1.02 (m, 6H). FNMR (376 MHz, methanol-$d_4$, ppm): δ −115.25 (1F), −128.10 (1F). |
| 122 | 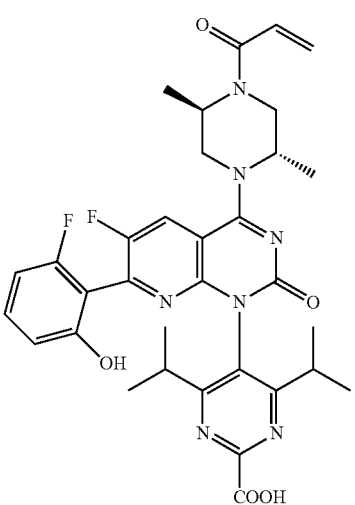 [SMILES: C=CC(=O)N1C[C@H](C)N(c2nc(=O)n(-c3c(C(C)C)nc(C(=O)O)nc3C(C)C)c3nc(-c4c(O)cccc4F)c(F)cc23)C[C@H]1C] | 648.3 | HNMR (400 MHz, methanol-$d_4$, ppm): δ 8.26-8.21 (m, 1H), 7.21 (dd, J = 14.8, 8.0 Hz, 1H), 6.88-6.74 (m, 1H), 6.63 (d, J = 8.4 Hz, 1H), 6.58 (t, J = 8.8 Hz, 1H), 6.31-6.24 (m, 1H), 5.83-5.78 (m, 1H), 5.12-5.00 (m, 1H), 4.96-4.87 (m, 0.5H), 4.60-4.45 (m, 1H), 4.43-4.27 (m, 1H), 4.05-3.85 (m, 2H), 3.61-3.52 (m, 0.5H), 2.87-2.71 (m, 2H), 1.48 (d, J = 6.4 Hz, 3H), 1.38-1.27 (m, 3H), 1.22-1.19 (m, 6H), 1.07-1.03 (m, 6H). FNMR (376 MHz, methanol-$d_4$, ppm): δ −117.11 (1F), −127.79 (1F). |

TABLE 1-continued

Characterization of the compounds of Formulas (I) and (II)

| Compound No. | Structure | [M + H]⁺ | ¹H-NMR and ¹⁹F-NMR |
|---|---|---|---|
| 123 | 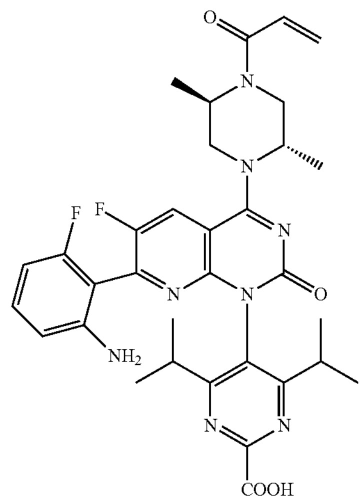 [SMILES: C=CC(=O)N1C[C@H](C)N(c2nc(=O)n(-c3c(C(C)C)nc(C(=O)O)nc3C(C)C)c3nc(-c4c(N)cccc4F)c(F)cc23)C[C@H]1C] | 647.3 | HNMR (400 MHz, methanol-$d_4$, ppm): δ 8.29-8.23 (m, 1H), 7.09 (dd, J = 14.4, 8.0 Hz, 1H), 6.88-6.74 (m, 1H), 6.47 (d, J = 8.4 Hz, 1H), 6.38-6.33 (m, 1H), 6.31-6.24 (m, 1H), 5.83-5.78 (m, 1H), 5.12-5.00 (m, 1H), 4.96-4.87 (m, 0.5H), 4.60-4.45 (m, 1H), 4.42-4.27 (m, 1H), 4.05-3.85 (m, 2H), 3.56-3.47 (m, 0.5H), 2.90-2.74 (m, 2H), 1.48 (d, J = 6.4 Hz, 3H), 1.38-1.27 (m, 3H), 1.23-1.17 (m, 6H), 1.08-1.05 (m, 6H). FNMR (376 MHz, methanol-$d_4$, ppm): δ −115.73 (1F), −125.89 (1F). |
| 119 | 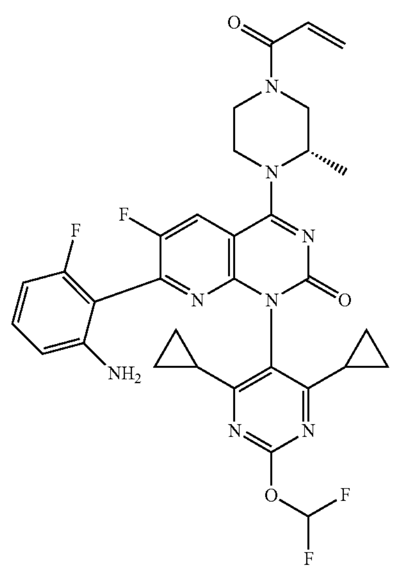 [SMILES: C=CC(=O)N1CCN(c2nc(=O)n(-c3c(C4CC4)nc(OC(F)F)nc3C3CC3)c3nc(-c4c(N)cccc4F)c(F)cc23)[C@@H](C)C1] | 651.2 | HNMR (400 MHz, methanol-$d_4$, ppm): δ 8.28-8.23 (m, 1H), 7.43 (t, J = 72.4 Hz, 1H), 7.16-7.11 (m, 1H), 6.85-6.77 (m, 1H), 6.55 (d, J = 8.4 Hz, 1H), 6.43-6.39 (m, 1H), 6.32-6.27 (m, 1H), 5.81 (dd, J = 10.4, 2.4 Hz, 1H), 5.13-5.03 (m, 1H), 4.54-4.40 (m, 2H), 4.20-4.05 (m, 1H), 3.84-3.55 (m, 2H), 3.34-3.22 (m, 1H), 1.81-1.69 (m, 2H), 1.47-1.46 (m, 3H), 1.15-1.12 (m, 4H), 1.10-0.89 (m, 4H). FNMR (376 MHz, methanol-$d_4$, ppm): δ −91.15 (2F), −115.14 (1F), −125.91 (1F). |
| 132 | 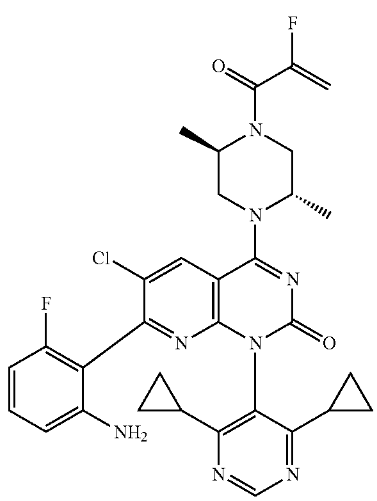 [SMILES: C=C(F)C(=O)N1C[C@H](C)N(c2nc(=O)n(-c3c(C4CC4)ncnc3C3CC3)c3nc(-c4c(N)cccc4F)c(Cl)cc23)C[C@H]1C] | 633.2 | HNMR (400 MHz, DMSO-$d_6$, ppm): δ 8.75 (s, 1H), 8.55-8.40 (m, 1H), 7.15-7.05 (m, 1H), 6.51 (d, J = 8.0 Hz, 1H), 6.38 (t, J = 9.2 Hz, 1H), 5.41-5.30 (m, 1H), 5.23-5.20 (m, 2H), 5.01-4.62 (m, 1.5H), 4.40-4.30 (m, 1H), 4.14-4.07 (m, 1H), 4.04-3.82 (m, 1H), 3.84-3.40 (m, 1.5H), 1.87-1.63 (m, 2H), 1.48-1.17 (m, 6H), 0.96-0.92 (m, 6H), 0.88-0.78 (m, 2H). FNMR (376 MHz, DMSO-$d_6$, ppm): δ −104.54 (1F), −114.23 (1F). |

TABLE 1-continued

Characterization of the compounds of Formulas (I) and (II)

| Compound No. | Structure | [M + H]+ | 1H-NMR and 19F-NMR |
|---|---|---|---|
| 140 | 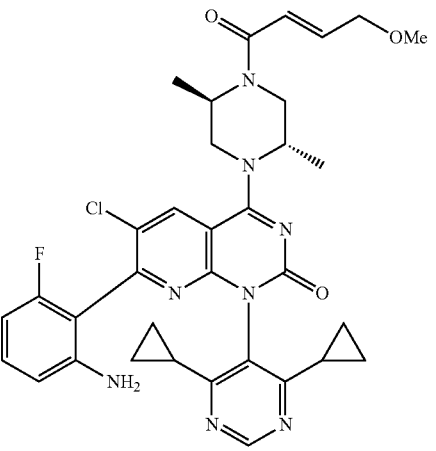 [SMILES: COC/C=C/C(=O)N1C[C@H](C)N(c2nc(=O)n(-c3c(C4CC4)ncnc3C3CC3)c3nc(-c4c(N)cccc4F)c(Cl)cc23)C[C@H]1C] | 659.4 | HNMR (300 MHz, DMSO-d$_6$, ppm): δ 8.74 (s, 1H), 8.57-8.34 (m, 1H), 7.11 (q, J = 8.1 Hz, 1H), 6.81-6.56 (m, 2H), 6.51 (d, J = 8.2 Hz, 1H), 6.38 (t, 1H), 5.25-5.15 (m, 2H), 4.92-4.47 (m, 2H), 4.40-3.69 (m, 6H), 3.63-3.30 (m, 3H), 1.86-1.67 (m, 2H), 1.42-1.11 (m, 6H), 1.10-0.77 (m, 8H). FNMR (282 MHz, DMSO-d$_6$, ppm): δ −114.15 (1F). |
| 73 | 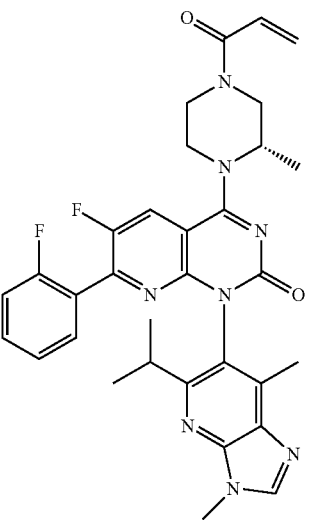 [SMILES: C=CC(=O)N1CCN(c2nc(=O)n(-c3c(C(C)C)nc4c(ncn4C)c3C)c3nc(-c4ccccc4F)c(F)cc23)[C@@H](C)C1] | 599.2 | HNMR (400 MHz, DMSO-d$_6$, ppm): δ 8.36-8.34 (m, 2H), 7.54-7.49 (m, 1H), 7.34-7.21 (m, 3H), 6.94-6.84 (m, 1H), 6.24-6.19 (m, 1H), 5.78 (dd, J = 10.4, 2 Hz, 1H), 4.94 (brs, 1H), 4.45-4.30 (m, 2H), 4.19-4.03 (m, 1H), 3.83 (s, 3H), 3.94-3.63 (m, 2H), 3.55-3.10 (m, 1H), 2.80-2.76 (m, 1H), 2.20-2.10 (m, 3H), 1.34 (d, J = 6.4 Hz, 3H), 1.20-1.10 (m, 3H), 1.08-0.99 (m, 3H). FNMR (376 MHz, DMSO-d$_6$, ppm): δ −114.34 (1F), −129.70 (1F). |
| 139 | 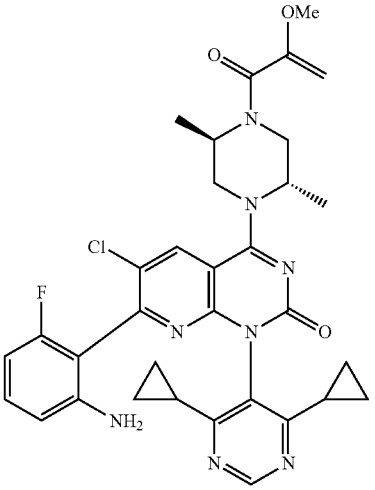 [SMILES: C=C(OC)C(=O)N1C[C@H](C)N(c2nc(=O)n(-c3c(C4CC4)ncnc3C3CC3)c3nc(-c4c(N)cccc4F)c(Cl)cc23)C[C@H]1C] | 645.5 | HNMR (400 MHz, DMSO-d$_6$, ppm): δ 8.79-8.72 (m, 1H), 8.55-8.37 (m, 1H), 7.15-7.05 (m, 1H), 6.51 (d, J = 8.4 Hz, 1H), 6.38 (t, J = 9.0 Hz, 1H), 5.30-4.65 (m, 3H), 4.51-4.03 (m, 4H), 3.90-3.35 (m, 6H), 1.82-1.72 (m, 2H), 1.39-1.14 (m, 6H), 1.09-0.75 (m, 8H). FNMR (376 MHz, DMSO-d$_6$, ppm): δ −114.00 (1F). |

TABLE 1-continued
Characterization of the compounds of Formulas (I) and (II)
| Compound No. | Structure | [M + H]+ | 1H-NMR and 19F-NMR |
|---|---|---|---|
| 141 | 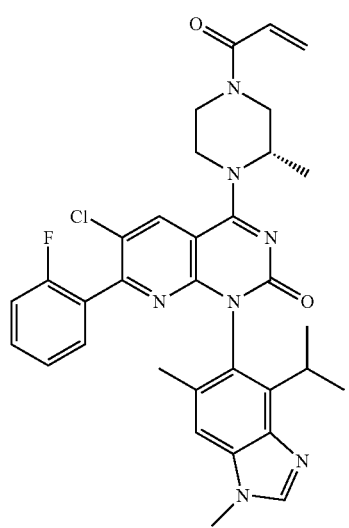 [SMILES: C=CC(=O)N1CCN(c2nc(=O)n(-c3c(C)cc4c(ncn4C)c3C(C)C)c3nc(-c4ccccc4F)c(Cl)cc23)[C@@H](C)C1]<br>atropisomer 1 | 614.1 | HNMR (300 MHz, DMSO-d$_6$, ppm): δ 8.50-8.40 (m, 1H), 8.08 (s, 1H), 7.52-7.42 (m, 1H), 7.34-7.12 (m, 4H), 6.98-6.80 (m, 1H), 6.28-6.14 (m, 1H), 5.78 (dd, J = 10.2, 2.4 Hz, 1H), 4.93 (brs, 1H), 4.48-3.99 (m, 1H), 3.78 (s, 3H), 3.72-3.43 (m, 2H), 3.10 (t, J = 11.4 Hz, 1H), 2.85-2.69 (m, 1H), 1.98 (s, 3H), 1.42-1.18 (m, 9H). FNMR (282 MHz, DMSO-d$_6$, ppm) δ -114.53 (1F). |
| 142 | 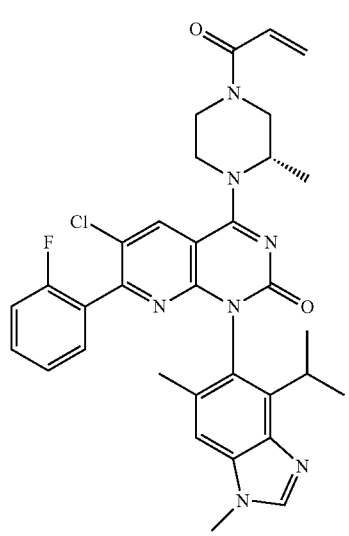 [SMILES: C=CC(=O)N1CCN(c2nc(=O)n(-c3c(C)cc4c(ncn4C)c3C(C)C)c3nc(-c4ccccc4F)c(Cl)cc23)[C@@H](C)C1]<br>atropsomer 2 | 614.1 | HNMR (300 MHz, DMSO-d$_6$, ppm): δ 8.50-8.40 (m, 1H), 8.08 (s, 1H), 7.52-7.42 (m, 1H), 7.34-7.12 (m, 4H), 6.98-6.80 (m, 1H), 6.30-6.13 (m, 1H), 5.78 (dd, J = 10.2, 2.4 Hz, 1H), 4.93 (brs, 1H), 4.48-3.99 (m, 1H), 3.78 (s, 3H), 3.72-3.43 (m, 2H), 3.10 (t, J = 11.7 Hz, 1H), 2.85-2.69 (m, 1H), 1.98 (s, 3H), 1.42-1.18 (m, 9H). FNMR (282 MHz, DMSO-d$_6$, ppm) δ -114.50 (1F). |

TABLE 1-continued

Characterization of the compounds of Formulas (I) and (II)

| Compound No. | Structure | [M + H]⁺ | ¹H-NMR and ¹⁹F-NMR |
|---|---|---|---|
| 143 | *atropisomer 2* | 617.4 | HNMR (400 MHz, DMSO-$d_6$, ppm): δ 8.36-8.30 (m, 1H), 8.20 (s, 1H), 7.43 (d, J = 9.6 Hz, 1H), 7.08 (dd, J = 14.8, 8.0 Hz, 1H), 6.92-6.82 (m, 1H), 6.44 (d, J = 8.0 Hz, 1H), 6.36 (t, J = 8.0 Hz, 1H), 6.23-6.19 (m, 1H), 5.77 (dd, J = 10.4, 2.4 Hz, 1H), 5.34 (s, 2H), 4.99 (brs, 1H), 4.45-4.37 (m, 0.5H), 4.34-4.22 (m, 1.5H), 4.18-4.10 (m, 0.5H), 4.08-4.01 (m, 0.5H), 3.82-3.76 (m, 4H), 3.68-3.62 (m, 0.5H), 3.49-3.42 (m, 0.5H), 3.26-3.23 (m, 0.5H), 3.12-3.06 (m, 0.5H), 3.00-2.90 (m, 1H), 1.39 (d, J = 6.8 Hz, 3H), 1.32-1.28 (m, 6H). |
| 144 | *atropisomer 1* | 617.3 | HNMR (400 MHz, DMSO-$d_6$, ppm): δ 8.27 (t, J = 10.8 Hz, 1H), 8.21 (s, 1H), 7.43 (d, J = 9.6 Hz, 1H), 7.11-7.05 (m, 1H), 6.91-6.82 (m, 1H), 6.44 (d, J = 8.0 Hz, 1H), 6.36 (t, J = 8.0 Hz, 1H), 6.23-6.19 (m, 1H), 5.77 (dd, J = 10.4, 2.4 Hz, 1H), 5.33 (s, 2H), 4.88 (brs, 1H), 4.45-4.27 (m, 2H), 4.18-4.13 (m, 0.5H), 4.18-4.14 (m, 0.5H), 3.82 (s, 3H), 3.65-3.62 (m, 1.5H), 3.62-3.50 (m, 0.5H), 3.23-3.18 (m, 0.5H), 3.18-3.10 (m, 0.5H), 3.00-2.90 (m, 1H), 1.40-1.35 (m, 6H), 1.29 (d, J = 6.8 Hz, 3H). |

TABLE 1-continued

Characterization of the compounds of Formulas (I) and (II)

| Compound No. | Structure | [M + H]+ | ¹H-NMR and ¹⁹F-NMR |
|---|---|---|---|
| 147 atropisomer 2 | | 613.4 | HNMR (400 MHz, DMSO-d$_6$, ppm): δ 8.28-8.23 (m, 1H), 8.10 (s, 1H), 7.32 (s, 1H), 7.06 (dd, J = 14.9, 8.2 Hz, 1H), 6.92-6.80 (m, 1H), 6.42 (d, J = 7.9 Hz, 1H), 6.38-6.28 (m, 1H), 6.21 (d, J = 17.1 Hz, 1H), 5.76 (dd, J = 10.3, 2.4 Hz, 1H), 5.28 (s, 2H), 4.85 (s, 1H), 4.45-4.38 (m, 0.5H), 4.33-4.26 (m, 1.5 H), 4.20-4.12 (m, 0.5H), 4.05-3.99 (m, 0.5H), 3.81 (s, 3H), 3.68-3.60 (m, 1.5H), 3.55-3.46 (m, 0.5H), 3.19-3.06 (m, 1H), 2.85-2.77 (m, 1H), 1.94 (s, 3H), 1.36 (t, J = 6.5 Hz, 6H), 1.24 (d, J = 6.9 Hz, 3H). |
| 148 atropisomer 1 | | 613.3 | HNMR (400 MHz, DMSO-d$_6$, ppm): δ 8.33-8.28 (m, 1H), 8.10 (s, 1H), 7.32 (s, 1H), 7.06 (dd, J = 15.2, 8.0 Hz, 1H), 6.90-6.85 (m, 1H), 6.42 (d, J = 8.0 Hz, 1H), 6.37-6.32 (m, 1H), 6.27-6.16 (m, 1H), 5.77 (dd, J = 10.4, 2.4 Hz, 1H), 5.30 (s, 2H), 4.94 (s, 1H), 4.43-4.41 (m, 0.5H), 4.32-4.14 (m, 2H), 4.06-4.03 (m, 0.5H), 3.86-3.64 (m, 4.5H), 3.49-3.44 (m, 0.5H), 3.49-3.44 (m, 0.5H), 3.30-3.26 (m, 0.5H), 3.11-3.06 (m, 0.5H), 2.87-2.76 (m, 1H), 1.95 (s, 3H), 1.36 (d, J = 6.8 Hz, 3H), 1.31 (d, J = 6.8 Hz, 3H), 1.24 (d, J = 6.8 Hz, 3H). |

TABLE 1-continued

Characterization of the compounds of Formulas (I) and (II)

| Compound No. | Structure | [M + H]⁺ | ¹H-NMR and ¹⁹F-NMR |
|---|---|---|---|
| 149 | atropisomer 1 | 644.1 | HNMR (400 MHz, DMSO-$d_6$, ppm): δ 10.03 (brs, 1H), 8.42 (s, 1H), 8.06 (s, 1H), 7.27 (s, 1H), 7.25-7.10 (m, 1H), 6.85-6.79 (m, 1H), 6.75-6.50 (m, 2H), 6.19 (dd, J = 16.6, 2.4 Hz, 1H), 5.80-5.69 (m, 1H), 4.92-4.73 (m, 1.5H), 4.53-4.42 (m, 0.5H), 4.18-4.03 (m, 1.5H), 3.97-3.84 (m, 2H), 3.77 (s, 3H), 3.53-3.49 (m, 0.5H), 2.83-2.75 (m, 1H), 1.97 (s, 3H), 1.45-1.15 (m, 12H). |
| 150 | atropisomer 2 | 644.2 | HNMR (400 MHz, DMSO-$d_6$, ppm): δ 9.88 (brs, 1H), 8.43 (s, 1H), 8.06 (s, 1H), 7.27 (s, 1H), 7.19 (dd, J = 15.4, 8.2 Hz, 1H), 6.90-6.77 (m, 1H), 6.75-6.60 (m, 2H), 6.19 (dd, J = 16.6, 2.4 Hz, 1H), 5.78-5.73 (m, 1H), 4.91-4.72 (m, 1.5H), 4.55-4.40 (m, 0.5H), 4.23-3.99 (m, 1.5H), 3.97-3.84 (m, 2H), 3.76 (s, 3H), 3.60-3.45 (m, 0.5H), 2.81-2.62 (m, 1H), 1.95 (s, 3H), 1.43-1.13 (m, 12H). |

TABLE 1-continued

Characterization of the compounds of Formulas (I) and (II)

| Compound No. | Structure | [M + H]⁺ | ¹H-NMR and ¹⁹F-NMR |
|---|---|---|---|
| 153 | atropisomer 1 | 627.2 | HNMR (400 MHz, DMSO-d$_6$, ppm): δ 8.50-8.30 (m, 2H), 7.42 (s, 1H), 7.06 (dd, J = 15.2, 8.0 Hz, 1H), 6.86-6.79 (m, 1H), 6.42 (d, J = 8.0 Hz, 1H), 6.38-6.31 (m, 1H), 6.19 (dd, J = 16.8, 2.4 Hz, 1H), 5.78-5.73 (m, 1H), 5.32 (s, 2H), 4.89-4.82 (m, 1H), 4.79-4.74 (m, 0.5H), 4.49-4.44 (m, 0.5H), 4.16-4.05 (m, 1.5H), 3.92-3.86 (m, 5H), 3.58-3.54 (m, 0.5H), 2.94-2.84 (m, 1H), 1.99 (s, 3H), 1.35-1.11 (m, 12H). |
| 154 | atropisomer 2 | 627.2 | HNMR (400 MHz, DMSO-d$_6$, ppm): δ 8.30-8.15 (m, 2H), 7.34 (s, 1H), 7.06 (dd, J = 14.9, 8.2 Hz, 1H), 6.90-6.77 (m, 1H), 6.42 (d, J = 8.2 Hz, 1H), 6.37-6.31 (m, 1H), 6.19 (dd, J = 16.7, 2.3 Hz, 1H), 5.78-5.72 (m, 1H), 5.28 (s, 2H), 4.86-4.75 (m, 1.5H), 4.53-4.44 (m, 0.5H), 4.20-4.07 (m, 1.5H), 3.90-3.75 (m, 5H), 3.56-3.47 (m, 0.5H), 2.81-2.72 (m, 1H), 1.97 (s, 3H), 1.37-1.19 (m, 12H). |

TABLE 1-continued
Characterization of the compounds of Formulas (I) and (II)
| Compound No. | Structure | [M + H]+ | 1H-NMR and 19F-NMR |
|---|---|---|---|
| 155 | 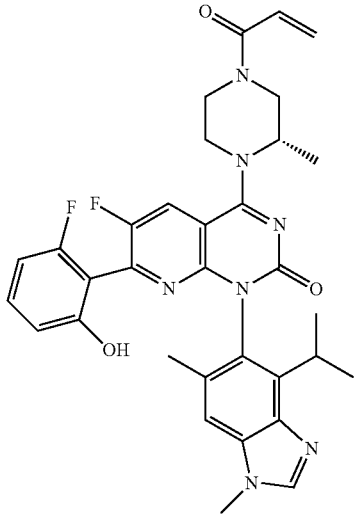 [SMILES: C=CC(=O)N1CCN(c2nc(=O)n(-c3c(C)cc4c(ncn4C)c3C(C)C)c3nc(-c4c(O)cccc4F)c(F)cc23)[C@@H](C)C1]<br>atropsomer 1 | 614.6 | HNMR (400 MHz, DMSO-d$_6$, ppm): δ 10.14 (s, 1H), 8.30-8.26 (m, 1H), 8.06 (s, 1H), 7.33-7.17 (m, 2H), 6.89-6.85 (m, 1H), 6.69-6.62 (m, 2H), 6.23-6.19 (m, 1H), 5.76 (dd, J = 10.4, 2.4 Hz, 1H), 4.92 (s, 1H), 4.44-4.41 (m, 0.5H), 4.28-4.20 (m, 1.5H), 4.16-4.13 (m, 0.5H), 4.04-4.01 (m, 0.5H), 3.88-3.65 (m, 4.5H), 3.55-3.45 (m, 0.5H), 3.28-3.26 (m, 0.5H), 3.13-3.09 (m, 0.5H), 2.85-2.70 (m, 1H), 1.94 (s, 3H), 1.35 (d, J = 6.9 Hz, 3H), 1.31 (d, J = 6.6 Hz, 3H), 1.23 (d, J = 6.9 Hz, 3H). |
| 156 | 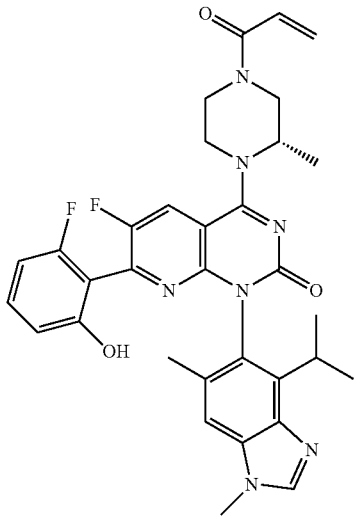 [SMILES: C=CC(=O)N1CCN(c2nc(=O)n(-c3c(C)cc4c(ncn4C)c3C(C)C)c3nc(-c4c(O)cccc4F)c(F)cc23)[C@@H](C)C1]<br>atropisomer 2 | 614.2 | HNMR (400 MHz, DMSO-d$_6$, ppm): δ 10.15 (s, 1H), 8.25 (t, J = 10.3 Hz, 1H), 8.06 (s, 1H), 7.27 (s, 1H), 7.22 (dd, J = 15.5, 8.0 Hz, 1H), 6.87 (dd, J = 25.6, 15.4 Hz, 1H), 6.70-6.54 (m, 2H), 6.25-6.16 (m, 1H), 5.76 (dd, J = 10.4, 2.2 Hz, 1H), 4.87 (s, 1H), 4.48-4.22 (m, 2H), 4.19-3.97 (m, 1H), 3.77 (s, 3H), 3.72-3.44 (m, 2H), 3.26-3.10 (m, 1H), 2.83-2.69 (m, 1H), 1.93 (s, 3H), 1.39-1.21 (m, 9H). |

TABLE 1-continued

Characterization of the compounds of Formulas (I) and (II)

| Compound No. | Structure | [M + H]⁺ | ¹H-NMR and ¹⁹F-NMR |
|---|---|---|---|
| 159 | atropisomer 1 | 628.1 | HNMR (400 MHz, DMSO-$d_6$, ppm): δ 8.46 (s, 1H), 8.06 (s, 1H), 7.50-7.44 (m, 1H), 7.32-7.16 (m, 4H), 6.89-6.79 (m, 1H), 6.19 (dd, J = 16.8, 2.4 Hz, 1H), 5.78-5.73 (m, 1H), 4.92-4.81 (m, 1H), 4.80-4.74 (m, 0.5H), 4.49-4.45 (m, 0.5H), 4.20-4.09 (m, 1.5H), 3.95-3.75 (m, 5H), 3.52-3.32 (m, 0.5H), 2.85-2.76 (m, 1H), 2.00 (s, 3H), 1.42-1.13 (m, 12H). |
| 160 | atropisomer 2 | 628.2 | HNMR (400 MHz, DMSO-$d_6$, ppm): δ 8.47 (s, 1H), 8.07 (s, 1H), 7.47 (dd, J = 12.8, 5.9 Hz, 1H), 7.31-7.16 (m, 4H), 6.94-6.73 (m, 1H), 6.19 (dd, J = 16.7, 2.1 Hz, 1H), 5.75 (dd, J = 7.4, 5.1 Hz, 1H), 4.86 (s, 1H), 4.80-4.41 (m, 1H), 4.18-4.04 (m, 1.5H), 3.97-3.84 (m, 2H), 3.77 (s, 3H), 3.57-3.47 (m, 0.5H), 2.76-2.64 (m, 1H), 1.98 (s, 3H), 1.37-1.16 (m, 12H). |

TABLE 1-continued

Characterization of the compounds of Formulas (I) and (II)

| Compound No. | Structure | [M + H]+ | 1H-NMR and 19F-NMR |
|---|---|---|---|
| 161 | atropisomer 1 | 643.1 | HNMR (400 MHz, DMSO-$d_6$, ppm): δ 8.48-8.40 (m, 1H), 8.07 (s, 1H), 7.28 (s, 1H), 7.05-6.98 (m, 1H), 6.90-6.80 (m, 1H), 6.40 (d, J = 8.4 Hz, 1H), 6.33-6.25 (m, 1H), 6.20 (d, J = 16.8 Hz, 1H), 5.80-5.72 (m, 1H), 5.17-5.02 (m, 2H), 4.90-4.72 (m, 1.5H), 4.49-4.44 (m, 0.5H), 4.16-4.04 (m, 1.5H), 3.99-3.84 (m, 2H), 3.77 (s, 3H), 3.59-3.50 (m, 0.5H), 2.93-2.73 (m, 1H), 2.04-1.92 (m, 3H), 1.40-1.00 (m, 12H). |
| 162 | atropisomer 2 | 643.2 | HNMR (400 MHz, DMSO-$d_6$, ppm): δ 8.42 (s, 1H), 8.07 (s, 1H), 7.28 (s, 1H), 7.05-6.95 (m, 1H), 6.92-6.77 (m, 1H), 6.40 (d, J = 8.2 Hz, 1H), 6.29 (t, J = 8.5 Hz, 1H), 6.23-6.13 (m, 1H), 5.83-5.68 (m, 1H), 5.15-5.01 (m, 2H), 4.90-4.70 (m, 1.5H), 4.49-4.44 (m, 0.5H), 4.22-3.98 (m, 1.5H), 3.98-3.85 (m, 2H), 3.77 (s, 3H), 3.61-3.48 (m, 0.5H), 2.91-2.57 (m, 1H), 2.09-1.86 (m, 3H), 1.36-1.13 (m, 12H). |

TABLE 1-continued

Characterization of the compounds of Formulas (I) and (II)

| Compound No. | Structure | [M + H]⁺ | ¹H-NMR and ¹⁹F-NMR |
|---|---|---|---|
| 163 | atropisomer 1 | 615.2 | HNMR (400 MHz, DMSO-d₆, ppm): δ 10.16 (brs, 1H), 8.45-8.25 (m, 2H), 7.26-7.20 (m, 1H), 6.92-6.82 (m, 1H), 6.75-6.48 (m, 2H), 6.23-6.19 (m, 1H), 5.77 (d, J = 10.7 Hz, 1H), 4.95 (s, 1H), 4.48-4.25 (m, 2H), 4.18-3.96 (m, 1H), 3.78 (s, 3H), 3.73-3.64 (m, 2H), 3.15-3.08 (m, 1H), 2.85-2.75 (m, 1H), 2.13 (s, 3H), 1.35 (d, J = 6.6 Hz, 6H), 1.24 (d, J = 6.3 Hz, 3H). |
| 164 | atropisomer 2 | 628.2 | HNMR (400 MHz, DMSO-d₆, ppm): δ 8.41-8.25 (m, 2H), 7.07 (dd, J = 15.0, 8.2 Hz, 1H), 6.85 (td, J = 16.8, 10.6 Hz, 1H), 6.43 (d, J = 8.4 Hz, 1H), 6.37-6.31 (m, 1H), 6.19 (dd, J = 16.6, 2.4 Hz, 1H), 5.80-5.70 (m, 1H), 5.32 (s, 2H), 4.97-4.75 (m, 1.5H), 4.52-4.45 (m, 0.5H), 4.21-4.04 (m, 1.5H), 3.91-3.85 (m, 2H), 3.81 (s, 3H), 3.55-3.50 (m, 0.5H), 2.85-2.75 (m, 1H), 2.18 (s, 3H), 1.33-1.16 (m, 12H). |

TABLE 1-continued

Characterization of the compounds of Formulas (I) and (II)

| Compound No. | Structure | [M + H]+ | 1H-NMR and 19F-NMR |
|---|---|---|---|
| 165 | atropisomer 1 | 628.2 | HNMR (400 MHz, DMSO-$d_6$, ppm): δ 8.41-8.23 (m, 2H), 7.10-7.04 (m, 1H), 6.90-6.79 (m, 1H), 6.43 (d, J = 8.3 Hz, 1H), 6.37-6.31 (m, 1H), 6.19 (dd, J = 16.6, 2.3 Hz, 1H), 5.79-5.74 (m, 1H), 5.32 (s, 2H), 4.97-4.75 (m, 1.5H), 4.55-4.48 (m, 0.5H), 4.17-4.09 (m, 1.5H), 3.91-3.85 (m, 2H), 3.81 (s, 3H), 3.57-3.52 (m, 0.5H), 2.81-2.76 (m, 1H), 2.18 (s, 3H), 1.37-1.10 (m, 12H). |
| 166 | 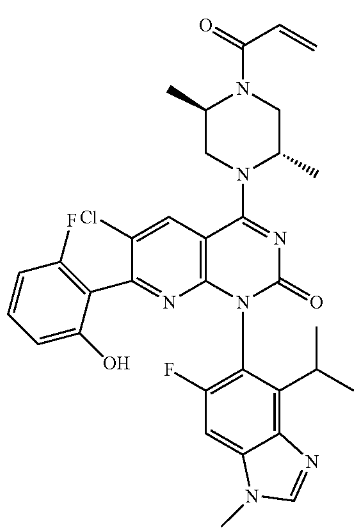 [SMILES: C=CC(=O)N1C[C@H](C)N(c2nc(=O)n(-c3c(F)cc4c(ncn4C)c3C(C)C)c3nc(-c4c(O)cccc4F)c(Cl)cc23)C[C@H]1C] | 648.2 | HNMR (400 MHz, DMSO-$d_6$, ppm): δ 10.15-10.05 (m, 1H), 8.44-8.42 (m, 1H), 8.17 (s, 1H), 7.40 (d, J = 9.0 Hz, 1H), 7.21 (q, J = 8.0 Hz, 1H), 6.92-6.77 (m, 1H), 6.64-6.69 (m, 2H), 6.20 (d, J = 16.8 Hz, 1H), 5.80-5.71 (m, 1H), 4.72-4.94 (m, 1.5 H), 4.42-4.52 (m, 0.5 H), 4.16 (d, J = 14.8 Hz, 2H), 3.99-3.85 (m, 2H), 3.79 (s, 3H), 2.99-2.75 (m, 1H), 1.45-1.10 (m, 12H). FNMR (376 MHz, DMSO-$d_6$, ppm) δ −115.47 (1F), −127.34 (1F). |

TABLE 1-continued

Characterization of the compounds of Formulas (I) and (II)

| Compound No. | Structure | [M + H]+ | 1H-NMR and 19F-NMR |
|---|---|---|---|
| 167 | atropisomer 2 | 629.2 | HNMR (400 MHz, DMSO-d6, ppm): δ 8.50 (s, 1H), 8.28 (s, 1H), 7.52-7.43 (m, 1H), 7.36-7.11 (m, 3H), 6.89-6.79 (m, 1H), 6.20 (dd, J = 16.6, 2.3 Hz, 1H), 5.78-5.72 (m, 1H), 4.96-4.72 (m, 1.5H), 4.53-4.43 (m, 0.5H), 4.20-4.13 (m, 1.5H), 3.98-3.84 (m, 2H), 3.78 (s, 3H), 3.57-3.49 (m, 0.5H), 2.81-2.65 (m, 1H), 2.17 (s, 3H), 1.50-1.10 (m, 12H). |
| 168 | atropisomer 1 | 629.6 | HNMR (400 MHz, DMSO-d6, ppm): δ 8.48 (s, 1H), 8.28 (s, 1H), 7.52-7.44 (m, 1H), 7.32-7.16 (m, 3H), 6.89-6.78 (m, 1H), 6.19 (d, J = 16.6 Hz, 1H), 5.75 (d, J = 10.2 Hz, 1H), 4.96-4.74 (m, 1.5H), 4.52-4.44 (m, 0.5H), 4.24-4.14 (m, 1.5H), 3.94-3.69 (m, 5H), 3.50-3.48 (m, 0.5H), 2.90-2.70 (m, 1H), 2.19 (s, 3H), 1.46-1.10 (m, 12H). |

TABLE 1-continued

Characterization of the compounds of Formulas (I) and (II)

| Compound No. | Structure | [M + H]+ | 1H-NMR and 19F-NMR |
|---|---|---|---|
| 169 | atropisomer 1 | 632.2 | HNMR (400 MHz, DMSO-d$_6$, ppm): δ 8.46 (s, 1H), 8.17 (s, 1H), 7.51-7.45 (m, 1H), 7.42 (d, J = 9.5 Hz, 1H), 7.34-7.18 (m, 3H), 6.89-6.77 (m, 1H), 6.19 (dd, J = 16.6, 2.2 Hz, 1H), 5.80-5.71 (m, 1H), 4.92-4.83 (m, 1H), 4.79-4.74 (m, 0.5H), 4.50-4.43 (m, 0.5H), 4.23-4.10 (m, 1.5H), 3.96-3.74 (m, 5H), 3.53-3.48 (m, 0.5H), 2.98-2.69 (m, 1H), 1.47-1.05 (m, 12H). |
| 170 | atropisomer 2 | 632.2 | HNMR (400 MHz, DMSO-d$_6$, ppm): δ 8.45 (s, 1H), 8.17 (s, 1H), 7.52-7.44 (m, 1H), 7.41 (d, J = 9.5 Hz, 1H), 7.36-7.14 (m, 3H), 6.90-6.77 (m, 1H), 6.19 (d, J = 16.7 Hz, 1H), 5.80-5.71 (m, 1H), 4.93-4.83 (m, 1H), 4.81-4.74 (m, 0.5H), 4.53-4.45 (m, 0.5H), 4.25-4.10 (m, 1.5H), 3.98-3.60 (m, 5H), 3.52-3.48 (m, 0.5H), 2.91-2.80 (m, 1H), 1.50-1.02 (m, 12H). |

TABLE 1-continued

Characterization of the compounds of Formulas (I) and (II)

| Compound No. | Structure | [M + H]+ | ¹H-NMR and ¹⁹F-NMR |
|---|---|---|---|
| 171 | atropisomer 1 | 645.6 | HNMR (400 MHz, DMSO-d$_6$, ppm): δ 10.09 (s, 1H), 8.45 (s, 1H), 8.27 (s, 1H), 7.20 (dd, J = 15.5, 8.0 Hz, 1H), 6.93-6.73 (m, 1H), 6.68-6.63 (m, 2H), 6.20 (dd, J = 16.6, 2.1 Hz, 1H), 5.83-5.66 (m, 1H), 4.87-4.78 (m, 1.5H), 4.52-4.45 (m, 0.5H), 4.18-4.14 (m, 1.5H), 3.91-3.86 (m, 2H), 3.78 (s, 3H), 3.53-3.49 (m, 0.5H), 2.85-2.70 (m, 1H), 2.18-2.13 (m, 3H), 1.36-1.17 (m, 12H). |
| 172 | atropisomer 2 | 645.2 | HNMR (400 MHz, DMSO-d$_6$, ppm): δ 10.05 (s, 1H), 8.46 (s, 1H), 8.27 (s, 1H), 7.20 (dd, J = 15.5, 8.0 Hz, 1H), 6.89-6.79 (m, 1H), 6.70-6.56 (m, 2H), 6.19 (dd, J = 16.6, 2.1 Hz, 1H), 5.80-5.72 (m, 1H), 4.92-4.73 (m, 1.5H), 4.53-4.43 (m, 0.5H), 4.24-4.07 (m, 1.5H), 3.96-3.81 (m, 2H), 3.77 (s, 3H), 3.55-3.48 (m, 0.5H), 2.79-2.65 (m, 1H), 2.14 (s, 3H), 1.46-1.10 (m, 12H). |

TABLE 1-continued

Characterization of the compounds of Formulas (I) and (II)

| Compound No. | Structure | [M + H]+ | 1H-NMR and 19F-NMR |
|---|---|---|---|
| 173 | atropisomer 1 | 647.2 | HNMR (400 MHz, DMSO-$d_6$, ppm): δ 8.52-8.45 (m, 1H), 8.17 (s, 1H), 7.44-7.36 (m, 1H), 7.08-6.98 (m, 1H), 6.90-6.79 (m, 1H), 6.46-6.38 (m, 1H), 6.35-6.27 (m, 1H), 6.20 (dd, J = 16.6, 2.1 Hz, 1H), 5.79-5.72 (m, 1H), 5.09 (d, J = 14.9 Hz, 2H), 4.90-4.74 (m, 1.5H), 4.53-4.45 (m, 0.5H), 4.18-4.07 (m, 1.5H), 3.98-3.73 (m, 5H), 3.57-3.47 (m, 0.5H), 3.06-2.99 (m, 0.5H), 2.94-2.87 (m, 0.5H), 1.45-1.08 (m, 12H). |
| 174 | atropisomer 2 | 647.2 | HNMR (400 MHz, DMSO-$d_6$, ppm): δ 8.46-8.37 (m, 1H), 8.17 (s, 1H), 7.45-7.36 (m, 1H), 7.08-6.98 (m, 1H), 6.91-6.80 (m, 1H), 6.46-6.36 (m, 1H), 6.30 (dd, J = 18.3, 9.5 Hz, 1H), 6.20 (dd, J = 16.6, 2.2 Hz, 1H), 5.80-5.72 (m, 1H), 5.20-5.10 (m, 2H), 4.89-4.75 (m, 1.5H), 4.55-4.46 (m, 0.5H), 4.20-4.08 (m, 1.5H), 4.00-3.68 (m, 5H), 3.53-3.45 (m, 0.5H), 2.99-2.94 (m, 0.5H), 2.84-2.78 (m, 0.5H), 1.50-1.05 (m, 12H). |

TABLE 1-continued

Characterization of the compounds of Formulas (I) and (II)

| Compound No. | Structure | [M + H]+ | 1H-NMR and 19F-NMR |
|---|---|---|---|
| 175 | atropisomer 1 | 644.3 | HNMR (400 MHz, DMSO-d$_6$, ppm): δ 8.50-8.40 (m, 1H), 8.27 (s, 1H), 7.06-6.97 (m, 1H), 6.90-6.78 (m, 1H), 6.41 (d, J = 8.2 Hz, 1H), 6.34-6.24 (m, 1H), 6.20 (d, J = 16.4 Hz, 1H), 5.81-5.71 (m, 1H), 5.12 (d, J = 16.0 Hz, 2H), 4.92-4.71 (m, 1.5H), 4.53-4.45 (m, 0.5H), 4.17-4.08 (m, 1.5H), 3.98-3.92 (m, 2H), 3.79 (s, 3H), 3.60-3.47 (m, 0.5H), 2.96-2.81 (m, 0.5H), 2.75-2.64 (m, 0.5H), 2.25-2.05 (m, 3H), 1.37-1.13 (m, 12H). |
| 176 | atropisomer 2 | 644.2 | HNMR (400 MHz, DMSO-d$_6$, ppm): δ 8.46 (s, 1H), 8.28 (s, 1H), 7.01 (dd, J = 15.1, 8.0 Hz, 1H), 6.92-6.77 (m, 1H), 6.40 (d, J = 8.2 Hz, 1H), 6.34-6.24 (m, 1H), 6.20 (d, J = 16.4 Hz, 1H), 5.79-5.70 (m, 1H), 5.11 (d, J = 9.0 Hz, 2H), 4.92-4.71 (m, 1.5H), 4.55-4.44 (m, 0.5H), 4.18-4.01 (m, 1.5H), 3.99-3.86 (m, 2H), 3.78 (s, 3H), 3.62-3.48 (m, 0.5H), 2.94-2.58 (m, 1H), 2.25-2.05 (m, 3H), 1.45-1.10 (m, 12H). |

TABLE 1-continued
Characterization of the compounds of Formulas (I) and (II)
| Compound No. | Structure | [M + H]+ | 1H-NMR and 19F-NMR |
|---|---|---|---|
| 177 | 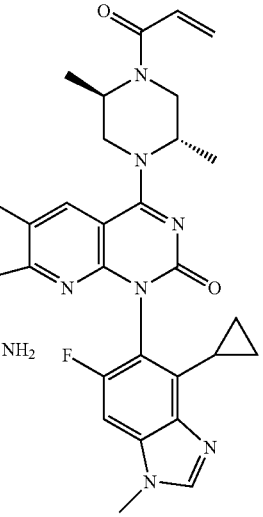<br>atropisomer 1 | 645.3 | HNMR (400 MHz, DMSO-$d_6$, ppm): δ 8.44-8.37 (m, 1H), 8.11-8.09 (m, 1H), 7.35-7.30 (m, 1H), 7.04-7.00 (m, 1H), 6.86-6.75 (m, 1H), 6.44-6.40 (m, 1H), 6.33-6.28 (m, 1H), 6.17 (dd, J = 16.8 Hz, 2.4 Hz, 1H), 5.74-5.69 (m, 1H), 5.15 (s, 2H), 4.90-4.40 (m, 2H), 4.20-3.90 (m, 2H), 3.89-3.80 (m, 2H), 3.74 (d, J = 8.0 Hz, 3H), 3.55-3.44 (m, 1H), 1.65-1.62 (m, 1H), 1.46-1.45 (m, 1H), 1.33-1.11 (m, 7H), 0.76-0.64 (m, 2H). FNMR (376 MHz, DMSO-$d_6$, ppm): δ −114.55 (1F), −126.97 (1F). |
| 178 | 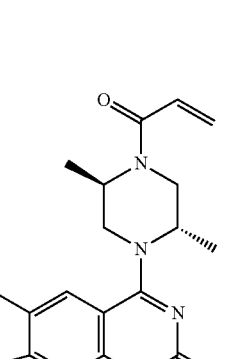<br>atropisomer 2 | 645.3 | HNMR (400 MHz, DMSO-$d_6$, ppm): δ 8.44-8.31 (m, 1H), 8.09 (s, 1H), 7.33-7.29 (m, 1H), 7.05-6.99 (m, 1H), 6.83-6.75 (m, 1H), 6.44-6.41 (m, 1H), 6.33-6.28 (m, 1H), 6.19-6.13 (m, 1H), 5.74-5.70 (m, 1H), 5.20-5.13 (m, 2H), 4.83-4.73 (m, 2H), 4.25-4.00 (m, 2H), 3.95-3.75 (m, 2H), 3.75-3.73 (m, 3H), 3.51-3.35 (m, 1H), 1.68-1.61 (m, 2H), 1.44-1.12 (m, 7H), 0.77-0.66 (m, 2H). FNMR (376 MHz, DMSO-$d_6$, ppm): δ −113.89 (1F), −127.94 (1F). |

TABLE 1-continued
Characterization of the compounds of Formulas (I) and (II)
| Compound No. | Structure | [M + H]+ | 1H-NMR and 19F-NMR |
|---|---|---|---|
| 181 | 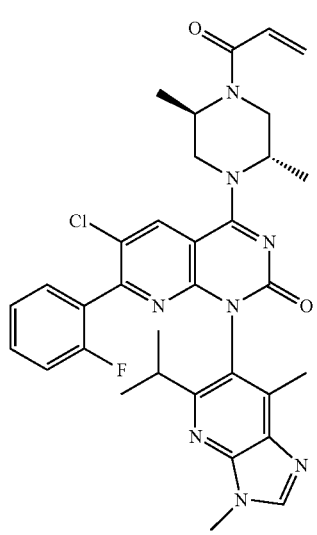 [SMILES: C=CC(=O)N1C[C@H](C)N(c2nc(=O)n(-c3c(C(C)C)nc4c(ncn4C)c3C)c3nc(-c4ccccc4F)c(Cl)cc23)C[C@H]1C] | 629.3 | HNMR (400 MHz, DMSO-d$_6$, ppm): δ 8.49 (s, 1H), 8.33 (s, 1H), 7.54-7.41 (m, 1H), 7.32-7.15 (m, 3H), 6.91-6.74 (m, 1H), 6.19 (dd, J = 16.6, 1.9 Hz, 1H), 5.81-5.71 (m, 1H), 4.96-4.82 (m, 1H), 4.82-4.73 (m, 0.5H), 4.56-4.36 (m, 0.5H), 4.24-4.06 (m, 1.5H), 4.00-3.84 (m, 2H), 3.80 (s, 3H), 3.57-3.44 (m, 0.5H), 2.83-2.68 (m, 1H), 2.19 (s, 3H), 1.40-1.30 (m, 3H), 1.28-1.14 (m, 3H), 1.12 (d, J = 6.7 Hz, 3H), 1.00 (d, J = 6.7 Hz, 3H). |
| 182 | 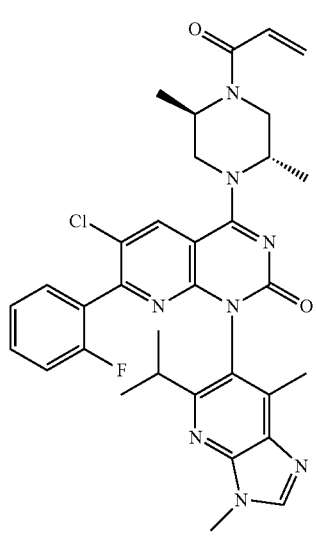 [SMILES: C=CC(=O)N1C[C@H](C)N(c2nc(=O)n(-c3c(C(C)C)nc4c(ncn4C)c3C)c3nc(-c4ccccc4F)c(Cl)cc23)C[C@H]1C]<br>atropisomer 2 | 629.4 | HNMR (400 MHz, DMSO-d$_6$, ppm): δ 8.49-8.48 (m, 1H), 8.32 (s, 1H), 7.50-7.44 (m, 1H), 7.30-7.18 (m, 3H), 6.90-6.79 (m, 1H), 6.22-6.17 (m, 1H), 5.78-5.74 (m, 1H), 4.87-4.75 (m, 1.5H), 4.56-4.44 (m, 0.5H), 4.21-4.14 (m, 1.5H), 3.97-3.78 (m, 5H), 3.53-3.49 (m, 0.5H), 2.78-2.72 (m, 1H), 2.16 (s, 3H), 1.36-1.33 (m, 3H), 1.27-1.18 (m, 3H), 1.14-1.02 (m, 6H). |

TABLE 1-continued

Characterization of the compounds of Formulas (I) and (II)

| Compound No. | Structure | [M + H]+ | 1H-NMR and 19F-NMR |
|---|---|---|---|
| 183 | atropisomer 1 | 644.3 | HNMR (400 MHz, DMSO-$d_6$, ppm): δ 8.51-8.44 (m, 1H), 8.32 (s, 1H), 7.05-6.97 (m, 1H), 6.88-6.78 (m, 1H), 6.43-6.37 (m, 1H), 6.31-6.24-6.16 (m, 2H), 5.79-5.72 (m, 1H), 5.12 (s, 2H), 4.92-4.72 (m, 1.5H), 4.52-4.44 (m, 0.5H), 4.47-4.04 (m, 1.5H), 4.03-3.76 (m, 5H), 3.60-3.53 (m, 0.5H), 2.89-2.81 (m, 0.5H), 2.75-2.62 (m, 0.5H), 2.30-2.05 (m, 2H), 2.08 (s, 1H), 1.37-1.07 (m, 9H), 1.06-0.90 (m, 3H). |
| 184 | atropisomer 2 | 644.4 | HNMR (400 MHz, DMSO-$d_6$, ppm): δ 8.45-8.43 (m, 1H), 8.32 (s, 1H), 7.04-6.99 (m, 1H), 6.91-6.80 (m, 1H), 6.42-6.38 (m, 1H), 6.32-6.18 (m, 2H), 5.78-5.74 (m, 1H), 5.13-5.04 (m, 2H), 4.95-4.75 (m, 1.5H), 4.60-4.45 (m, 0.5H), 4.18-4.08 (m, 1.5H), 3.93-3.80 (m, 5H), 3.56-3.47 (m, 0.5H), 2.95-2.85 (m, 0.5H), 2.73-2.60 (m, 0.5H), 2.19-2.02 (m, 3H), 1.35-1.20 (m, 6H), 1.14-0.95 (m, 6H). |

TABLE 1-continued

Characterization of the compounds of Formulas (I) and (II)

| Compound No. | Structure | [M + H]⁺ | ¹H-NMR and ¹⁹F-NMR |
|---|---|---|---|
| 185 | 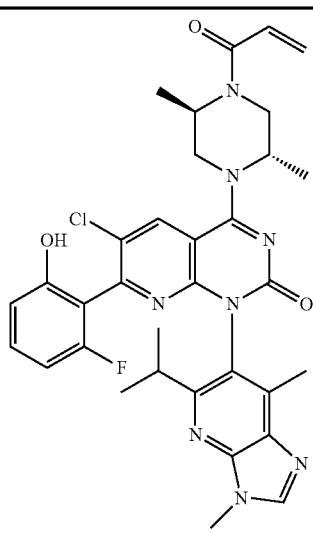<br>atropisomer 1 | 645.3 | HNMR (400 MHz, DMSO-$d_6$, ppm): δ 8.46 (s, 1H), 8.32 (s, 1H), 7.25-7.13 (m, 1H), 6.88-6.76 (m, 1H), 6.70-6.50 (m, 2H), 6.24-6.15 (m, 1H), 5.80-5.72 (m, 1H), 4.93-4.72 (m, 1.5H), 4.52-4.43 (m, 0.5H), 4.22-4.07 (m, 1.5H), 3.98-3.80 (m, 5H), 3.56-3.48 (m, 0.5H), 2.79-2.69 (m, 1H), 2.23-2.07 (m, 3H), 1.38-1.28 (m, 3H), 1.27-1.03 (m, 6H), 1.03-0.89 (m, 3H). |
| 186 | 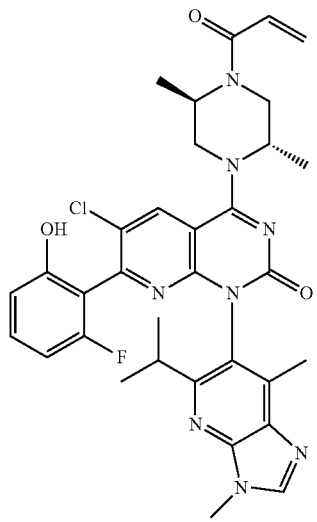 [SMILES: C=CC(=O)N1C[C@H](C)N(c2nc(=O)n(-c3c(C(C)C)nc4c(ncn4C)c3C)c3nc(-c4c(O)cccc4F)c(Cl)cc23)C[C@H]1C]<br>atropisomer 2 | 645.4 | HNMR (400 MHz, DMSO-$d_6$, ppm): δ 10.05 (s, 1H), 8.44 (s, 1H), 8.31 (s, 1H), 7.22-7.17 (m, 1H), 6.90-6.78 (m, 1H), 6.70-6.58 (m, 2H), 6.21-6.17 (m, 1H), 5.78-5.74 (m, 1H), 4.93-4.75 (m, 1.5H), 4.55-4.42 (m, 0.5H), 4.27-4.08 (m, 1.5H), 3.90-3.74 (m, 5H), 3.51-3.47 (m, 0.5H), 2.80-2.70 (m, 1H), 2.15-2.07 (m, 3H), 1.36-1.32 (m, 3H), 1.31-1.10 (m, 6H), 1.04-0.96 (m, 3H). |

Biological Example 1. Assay for Cell Proliferation

Lung cancer cell line NCI-H358 (ATCC CRL-5807) containing KRas G12C mutation was grown in RPMI 1640 medium supplemented with 10% fetal bovine serum, penicillin/streptomycin. One hundred fifty microliter (150 μL) of media containing 2000 cells per well were seeded into each well of a 96-well culture plate and left to attach overnight in a 37° C. incubator with 5% CO2. Diluted compounds of 0.75 μL for each well were added by liquid handler at a final concentration of 0.5% DMSO. Cells were treated for 5 days in the incubator. Cell-titer Glo (CTG) kit (Promega) was used to assess cell proliferation. Of note, 120 μL of CTG reagent was added to each well and incubated at RT for 10 minutes. The luminescence signal was then collected on Envision 2104 plate reader.

TABLE 2

Inhibition of NCI-H358 Cell Proliferation by Representative Compounds

| Compound | IC$_{50}$ (nM) |
|---|---|
| Control A* | 4.7 |
| 1 | 10.0 |
| 2 | 23.9 |
| 3 | 660.8 |
| 4 | 129.8 |
| 5 | 171.6 |
| 6 | 4.9 |
| 7 | 30.6 |
| 8 | 11.2 |
| 9 | 4.1 |
| 11 | 9.2 |

TABLE 2-continued

Inhibition of NCI-H358 Cell Proliferation by Representative Compounds

| Compound | IC$_{50}$ (nM) |
|---|---|
| 12 | 106.6 |
| 13 | 6.5 |
| 14 | 8.8 |
| 16 | 8.0 |
| 17 | 14.4 |
| 18 | 16.0 |
| 19 | 5.0 |
| 20 | 6.7 |
| 21 | 29.9 |
| 22 | 7.6 |
| 23 | 6.9 |
| 24 | 9.1 |
| 25 | 52.5 |
| 26 | 167.6 |
| 27 | 69.9 |
| 28 | 23.3 |
| 29 | 11.4 |
| 30 | 52.7 |
| 31 | 28.2 |
| 32 | 8.5 |
| 33 | 67.5 |
| 34 | 58.3 |
| 35 | 58.2 |
| 36 | >3000 |
| 37 | >3000 |
| 38 | >3000 |
| 39 | 38.2 |
| 40 | 7.5 |
| 41 | 6.9 |
| 42 | 38.5 |
| 43 | 15.5 |
| 44 | 2.1 |
| 45 | 298.8 |
| 46 | 81.5 |
| 47 | 23.8 |
| 48 | 25.8 |
| 49 | 25.0 |
| 50 | 106.7 |
| 51 | 12.5 |
| 52 | 22.8 |
| 53 | 617.2 |
| 54 | 34.6 |
| 55 | 74.3 |
| 56 | 27.0 |
| 59 | >3000 |
| 60 | 81.7 |
| 61 | 71.2 |
| 62 | 15.9 |
| 65 | 17.6 |
| 66 | 19.9 |
| 67 | 46.5 |
| 68 | 344.0 |
| 69 | 7.8 |
| 70 | 15.1 |
| 71 | 20.1 |
| 72 | 13.1 |
| 73 | 66.0 |
| 74 | 5.7 |
| 77 | 8.6 |
| 78 | 10.4 |
| 79 | 12.9 |
| 80 | 8.1 |
| 81 | 35.9 |
| 82 | 10.8 |
| 83 | 5.9 |
| 84 | 6.9 |
| 85 | 9.7 |
| 86 | 8.6 |
| 87 | 4.1 |
| 88 | 21.2 |
| 89 | 1.5 |
| 91 | 7.8 |
| 92 | 2.8 |
| 93 | 1.8 |
| 94 | 37.5 |
| 95 | 14.6 |
| 96 | 10.8 |
| 97 | 7.3 |
| 98 | 7.4 |
| 99 | 5.8 |
| 100 | 14.1 |
| 101 | 25.8 |
| 102 | 37.4 |
| 103 | 47.6 |
| 105 | 8.8 |
| 106 | 10.2 |
| 107 | 5.2 |
| 108 | 46.5 |
| 109 | 12.3 |
| 110 | 10.1 |
| 111 | 6.3 |
| 112 | 32.1 |
| 113 | 48.5 |
| 114 | 497.3 |
| 115 | 4.6 |
| 116 | 15.8 |
| 117 | 12.9 |
| 118 | 40.2 |
| 119 | 9.6 |
| 120 | 145.9 |
| 121 | >3000 |
| 122 | >3000 |
| 123 | >3000 |
| 124 | 2.4 |
| 125 | 6.1 |
| 126 | 0.6 |
| 127 | 3.5 |
| 128 | 8.7 |
| 131 | 210.4 |
| 132 | 157.3 |
| 140 | 58.7 |
| 141 | 38.0 |
| 142 | 2.2 |
| 143 | 1300 |
| 144 | 2.5 |
| 145 | 1.4 |
| 146 | 1100 |
| 147 | 2.7 |
| 148 | 78.6 |
| 149 | 12.8 |
| 150 | 1.1 |
| 151 | 16.2 |
| 152 | 0.4 |
| 153 | 172.2 |
| 154 | 1.4 |
| 155 | 60.0 |
| 156 | 6.9 |
| 157 | 151.9 |
| 158 | 1.8 |
| 159 | 64.2 |
| 160 | 1.3 |
| 161 | 32.4 |
| 162 | 0.5 |
| 163 | 44.2 |
| 164 | >1000 |
| 165 | 157.2 |
| 166 | 1.5 |
| 167 | 0.8 |
| 168 | 20.3 |
| 169 | 118.8 |
| 170 | 1.0 |
| 171 | 15.6 |
| 172 | 1.2 |
| 173 | 23.5 |
| 174 | 0.2 |
| 175 | 16.1 |
| 176 | 0.5 |
| 177 | 73.7 |
| 178 | 0.9 |
| 179 | 386.5 |

TABLE 2-continued

Inhibition of NCI-H358 Cell Proliferation by Representative Compounds

| Compound | IC$_{50}$ (nM) |
| --- | --- |
| 180 | 7.8 |
| 181 | 44.4 |
| 182 | 1.7 |
| 183 | 27.4 |
| 184 | 0.2 |
| 185 | 21.7 |
| 186 | 0.9 |

*Control A: (S)-4-(4-acryloyl-2-methylpiperazin-1-yl)-6-chloro-1-(4,6-diisopropylpyrimidin-5-yl)-7-(2-fluorophenyl)pyrido[2,3-d]pyrimidin-2(1H)-one The in vitro data above show that changing the R$^8$ position (see e.g., Formula I-IV) from 2-fluorophenyl group to 2-amino-6-fluoro-phenyl group can result in almost 20 fold enhancement of potency in some series of compounds but not in others. Compound Nos. 126 and 128 are identical except with respect to the R$^8$ position, but Compound No. 126 with a 2-amino-6-fluoro-phenyl group is about 15× more potent than Compound No. 128 with a 2-fluoro-phenyl group, IC$_{50}$ of 0.6 nM vs. 8.7 nM. Similarly, Compound Nos. 44 and 42 are identical except with respect to the R$^8$ position, but Compound No. 44 with a 2-amino-6-fluoro-phenyl group is about 19× more potent than Compound No. 42 with a 2-fluoro-phenyl group, IC$_{50}$ of 2.1 nM vs. 39.5 nM. However, this does not mean that any compound with a 2-amino-6-fluoro-phenyl group at the R$^8$ position has a much improved potency over those having a 2-fluoro-phenyl group at the R$^8$ position. For example, Compound Nos. 78 and 48 are also are identical except with respect to the R$^8$ position, and Compound No. 78 with a 2-amino-6-fluoro-phenyl group is only slightly more potent than Compound No. 48 with a 2-fluoro-phenyl, IC$_{50}$ of 10.4 nM vs. 25.8 nM. We have also tested the IC$_{50}$s using the same assay (NCI-H358 assay discussed above) for 4-((2S,5R)-4-acryloyl-2,5-dimethylpiperazin-1-yl)-7-(2-amino-6-fluorophenyl)-6-chloro-1-(4,6-diisopropylpyrimidin-5-yl)pyrido[2,3-d]pyrimidin-2(1H)-one and 4-((2S,5R)-4-acryloyl-2,5-dimethylpiperazin-1-yl)-7-(2-fluorophenyl)-6-chloro-1-(4,6-diisopropylpyrimidin-5-yl)pyrido[2,3-d]pyrimidin-2(1H)-one; the compound having a 2-amino-6-fluoro-phenyl group is only slightly more potent than the compound with a 2-fluoro-phenyl group, IC$_{50}$ of 1.6 nM vs. 4.0 nM. Additionally, the IC$_{50}$ of 4-((2S,5R)-4-acryloyl-2,5-dimethylpiperazin-1-yl)-7-(2-amino-6-fluorophenyl)-1-(4,6-diisopropylpyrimidin-5-yl)-6-fluoropyrido[2,3-d]pyrimidin-2(1H)-one was tested to be 5.3 nM using the same assay (NCI-H358 assay discussed above); and the corresponding compound with 2-fluorophenyl group, 4-((2S,5R)-4-acryloyl-2,5-dimethylpiperazin-1-yl)-7-(2-fluorophenyl)-1-(4,6-diisopropylpyrimidin-5-yl)-6-fluoropyrido[2,3-d]pyrimidin-2(1H)-one was tested to have an IC$_{50}$ of 19.0 nM using the same assay. These data show that compounds with 4,6-dicyclopropylpyrimidin-5-yl group and 2-amino-6-fluoro-phenyl at the R$^8$ position are better fitted for inhibiting the KRAS G12C enzyme. This is in contrast with data showing that when changing an isopropyl group into a cyclopropyl group on the pyrimidine ring, a drop in potency of about 2-6 fold is expected, compare for example, Compound Nos. 2 and 5, 49 and 50, etc. This trend is generally observed except for compounds having 2-amino-6-fluoro-phenyl at the R$^8$ position; in these series of compounds, the trend is reversed, with cyclopropyl-pyrimidyl compounds more potent than the corresponding isopropylpyrimidyl compounds.

Biological Example 2. Human Hepatocyte Clearance Study

The in vitro human hepatocyte clearance of compounds described here was studied using pooled human hepatocytes purchased from BioreclamationIVT (Westbury, N.Y., Cat #X008001, Lot #TQJ). The assay was conducted according to manufacturer's instruction. Briefly, 10 mM stock solutions of test compounds and positive control (Verapamil) were prepared in 100% DMSO. Thawing media (50 mL) used in the study consists of 31 mL Williams E medium (GIBCO Cat #12551-032), 15 mL isotonic percoll (GE Healthcare Cat #17-0891-09), 500 uL 100× GlutaMax (GIBCO Cat #35050), 750 uL HEPES (GIBCO Cat #15630-080), 2.5 mL FBS (Corning Cat #35-076-CVR), 50 uL human insulin (GIBCO Cat #12585-014) and 5 uL dexamethasone (NICPBP). Incubation media is made of Williams E medium supplemented with 1× GlutaMax. Both thawing medium and incubation medium (serum-free) were placed in a 37° C. water bath for at least 15 minutes prior to use. Compound stock solutions were diluted to 100 μM by combining 198 μL of 50% acetonitrile/50% water and 2 μL of 10 mM stock solution. Verapamil was use as positive control in the assay. Vials of cryopreserved hepatocytes were removed from storage and thawed in a 37° C. water bath with gentle shaking. Contents of the vial were poured into the 50 mL thawing medium conical tube. Vials were centrifuged at 100 g for 10 minutes at room temperature. Thawing medium was aspirated and hepatocytes were re-suspended with serum-free incubation medium to yield ~1.5×10$^6$ cells/mL. Hepatocyte viability and density were counted using a Trypan Blue exclusion, and then cells were diluted with serum-free incubation medium to a working cell density of 0.5×10$^6$ viable cells/mL. Then, a portion of the hepatocytes at 0.5×10$^6$ viable cells/mL was boiled for 5 minutes prior to adding to the plate as negative control to eliminate the enzymatic activity so that little or no substrate turnover should be observed. The boiled hepatocytes were used to prepare negative samples. Aliquots of 198 μL hepatocytes were dispensed into each well of a 96-well non-coated plate. The plate was placed in the incubator on an orbital shaker at 500 rpm for approximately 10 minutes. Aliquots of 2 μL of the 100 μM test compound or positive control were added into respective wells of the non-coated 96-well plate to start the reaction. This assay was performed in duplicate. The plate was incubated in the incubator on an orbital shaker at 500 rpm for the designated time points. Twenty-five microliter of contents were transferred and mixed with 6 volumes (150 μL) of cold acetonitrile with IS (200 nM imipramine, 200 nM labetalol and 200 nM diclofenac) to terminate the reaction at time points of 0, 15, 30, 60, 90 and 120 minutes. Samples were centrifuged at 3,220 g for 25 minutes and aliquots of 150 μL of the supernatants were used for LC-MS/MS analysis. For data analysis, all calculations were carried out using Microsoft Excel. Peak areas were determined from extracted ion chromatograms. The in vitro half-life ($t_{1/2}$) of parent compound was determined by regression analysis of the percent parent disappearance vs. time curve. The in vitro half-life (in vitro $t_{1/2}$) was determined from the slope value: in vitro $t_{1/2=0.693}$/k. Conversion of the in vitro $t_{1/2}$ (in minutes) into the scale-up unbound intrinsic clearance (Scaled-up unbound CL$_{int}$, in mL/min/kg) was done using the following equation (mean of duplicate determinations): Scaled-up unbound CL$_{int}$=kV/N×scaling factor, where V=incubation volume (0.5 mL); N=number of hepatocytes per well (0.25× 10$^6$ cells). Scaling factors for in vivo intrinsic clearance prediction using human hepatocytes are listed as: liver weight (g liver/kg body weight): 25.7; hepatocyte concentration ($10^6$ cells/g liver): 99; scaling factor: 2544.3.

TABLE 3

Human Hepatocyte Clearance of Exemplary Compounds

| Compound | Human Hepatocyte Remaining Percentage @ 120 min (%) | Human In vitro $T_{1/2}$ (min) | Human In vitro $Cl_{int}$ (pL/min/$10^6$ cells) | Human Scale-up $Cl_{int}$ (mL/min/kg) |
|---|---|---|---|---|
| Control A[a] | 22.4 | 57.6 | 24.1 | 61.2 |
| 1 | 27.9 | 66.5 | 20.8 | 53.0 |
| 6 | 33.4 | 71.7 | 19.3 | 49.2 |
| 8 | 2.1 | 21.7 | 63.8 | 162.4 |
| 9 | 18.6 | 50.2 | 27.6 | 70.2 |
| 13 | 103 | ∞ [b] | 0.00 [b] | 0.00 [b] |
| 14 | 75.7 | 306 | 4.5 | 11.5 |
| 20 | 74.3 | 274 | 5.1 | 12.9 |
| 21 | 90.6 | 784 | 1.8 | 4.5 |
| 22 | 83.3 | 472 | 2.9 | 7.5 |
| 23 | 82.4 | 554 | 2.5 | 6.4 |
| 24 | 70.1 | 234 | 5.9 | 15.1 |
| 28 | 61.1 | 164 | 8.4 | 21.5 |
| 29 | 60.8 | 163 | 8.5 | 21.7 |
| 40 [c] | 20.7 | 54.6 | 12.7 | 32.3 |
| 41 [c] | 38.9 | 84.3 | 8.2 | 20.9 |
| 44 [c] | 61.7 | 172 | 4.0 | 10.2 |
| 52 | 65.3 | 190 | 7.3 | 18.5 |
| 72 | 41.2 | 104 | 13.3 | 34.0 |
| 124 [c] | 37.5 | 81.2 | 8.5 | 21.7 |
| 125 [c] | 16.5 | 48.0 | 14.5 | 36.8 |
| 126 [c] | 47.8 | 103.9 | 6.6 | 17.0 |
| 127 [c] | 55.5 | 158.3 | 4.4 | 11.1 |
| 128 [c] | 39.9 | 67.5 | 10.3 | 26.1 |
| 145 [c] | 82.9 | 688.4 | 1.0 | 2.6 |

[a] Control A: (S)-4-(4-acryloyl-2-methylpiperazin-1-yl)-6-chloro-1-(4,6-diisopropylpyrimidin-5-yl)-7-(2-fluorophenyl)pyrido[2,3-d]pyrimidin-2(1H)-one.
[b] If calculated CLint < 0, then $T_{1/2}$ and CLint were reported as "∞" and "0.00", respectively.
[c] Working cell density is 2 × $10^6$ viable cells/mL instead of 0.5 × $10^6$ viable cells/mL.

Biological Example 3. Rat PK Studies

The pharmacokinetic (PK) profile of compounds following single i.g in SD rat obtained from SIPPER B&K Laboratory Animal Co., LTD of Shanghai was determined. Three female rats of weight around 220 g were used. Compounds were prepared at 1 mg/ml with the formulation of 10% DMSO+10% solutol HS15+80% (10% HPβCD in water). Blood samples (0.2 mL) were collected at 0 h (pre-dose) and 0.25, 0.5, 1, 2, 4, 8, 24 h time points after administration of compounds at the dose of 10 mg/kg.

The collected blood samples were centrifuged without delay and the plasma was separated and transferred into tubes before storage at −70° C. prior to analysis. Aliquots of the plasma unknowns, blank and calibration standards were placed in 1.5 mL tubes and mixed with acetonitrile/methanol (1/1, v/v) containing IS. After vortexing for 5 min, each sample was centrifuged at 14000 rpm at 4° C. for 10 min. The supernatant were injected into the LC-MS/MS system.

Samples were separated using a Simazhu LC-30D UPLC system equipped with a Shimadzu Shim-pack GIST C18, (2.1*50 mm 2 μm) at 45° C. Eluates were analyzed using an API4000 Q-Trap mass spectrometer with a TurboIonSpray interface. Chromatographic separation was done with a mobile phase composed of water with 0.1% formic acid (solution A) and acetonitrile with 0.1% formic acid (solution B). The mobile phase was delivered at a flow rate of 0.6 mL/min, using a stepwise gradient elution program. To improve the sensitivity of the test compound screening, a MRM method in positive electrospray ionization mode was employed. Mass spectrometry data was acquired and analyzed using AB Sciex Analyst version 1.6.2 software. The pharmacokinetic parameters were derived using standard noncompartmental methods with Phoenix WinNonLin Professional Version 8.1. The following pharmacokinetic parameters were calculated: terminal half-life (T1/2), area under concentration-time curve (AUC), $T_{max}$, $C_{max}$, clearance, apparent distribution volume, mean residence time and other parameters.

TABLE 4

Rat PK Data of Selected Compounds

| Compound | Rat PO (10 mpk) F % | Rat PO (10 mpk) $C_{max}$ (uM) | Rat PO (10 mpk) AUC last (uM · hr) |
|---|---|---|---|
| 44 | 71% | 1.38 | 4.3 |
| Control B[a] | 16% | 1.0 | 3.6 |
| 126 | 54% | 1.06 | 3.8 |
| Control C[b] | 12% | 1.0 | 2.3 |

[a] Control B: 4-((2S,5R)-4-acryloyl-2,5-dimethylpiperazin-1-yl)-7-(2-amino-6-fluorophenyl)-1-(4,6-diisopropylpyrimidin-5-yl)-6-fluoropyrido[2,3-d]pyrimidin-2(1H)-one
[b] Control C: 4-((2S,5R)-4-acryloyl-2,5-dimethylpiperazin-1-yl)-7-(2-amino-6-fluorophenyl)-6-chloro-1-(4,6-diisopropylpyrimidin-5-yl)pyrido[2,3-d]pyrimidin-2(1H)-one.

Biological Example 4. In Vivo Studies to Evaluate KRAS G12C Inhibitors as a Mono Drug or Combinations with Other Agents All the procedures related to animal handling, care and the treatment in this study were performed according to the guidelines approved by the Institutional Animal Care and Use Committee (IACUC) of SIPPER B&K following the guidance of the Association for Assessment and Accreditation of Laboratory Animal Care (AAALAC). At the time of routine monitoring, the animals were checked for any effects of tumor growth on normal behavior such as mobility, food and water consumption (by looking only), body weight gain/loss (body weights were measured twice weekly), eye/hair matting and any other abnormal effect. Death and observed clinical signs were recorded on the basis of the numbers of animals within each subset. Animals that were observed to be in a continuing deteriorating condition were euthanized prior to death or before reaching a comatose state The NCI-H358, SW837, NCI-H2122 tumor cells were purchased from the American Type Culture Collection (ATCC). Cells were maintained in vitro as monolayer cultured in RPMI-1640 or DMEM medium supplemented with 10% fetal bovine serum, 50 IU/ml penicillin/streptomycin (GIBCO) at 37° C. in an atmosphere of 5% $CO_2$ in air. The tumor cells were routinely sub cultured twice weekly by trypsin-EDTA treatment. The cells growing in an exponential growth phase were harvested and counted for tumor inoculation.

For tumor bearing models, female 6- to 8-week-old athymic BALB/c nude mice were used for human cancer cell lines. Each mouse was inoculated subcutaneously at the right flank with tumor cells (10×$10^6$) in 0.1 ml of PBS. The treatments were started when the average tumor size reached approximately 200-250 mm³. Carboplatin, Cisplatin was injected twice a week by i.p. Vehicles and other test articles were given orally as a suspension by gavage once daily during the study or treatment period.

Tumor volume was calculated by measuring two perpendicular diameters using the following formula: (L×W 2)/2 in which L and W refer to the length and width tumor diameter, respectively. Results are expressed as mean and standard deviation of the mean.

Figure 2:
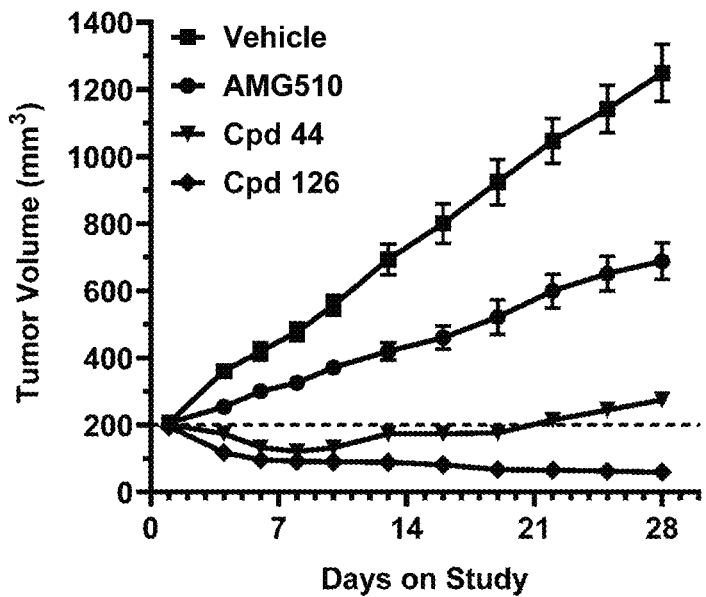
FIG. 2 is a graph showing the tumor volume growth profile vs. days on study in a NSCLC H358 xenograft model, following treatments with vehicle, AMG510 (30 mg/kg), Compound No. 44 (30 mg/kg), or Compound No. 126 (30 mg/kg).
Figure 3:
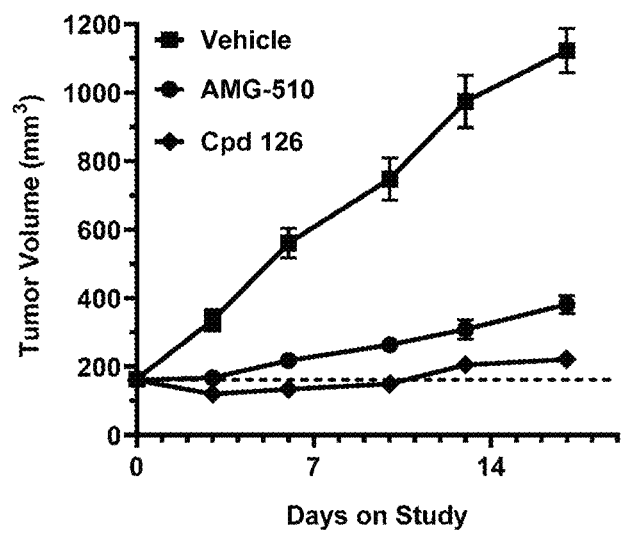
FIG. 3 is a graph showing the tumor volume growth profile vs. days on study in a NSCLC H2122 xenograft model, following treatments with vehicle, AMG510 (60 mg/kg), or Compound No. 126 (60 mg/kg).

The results of various treatments are shown in FIGS. 1-6. FIGS. 1-3 compare the efficacy of some representative compounds of the present disclosure with AMG510, which is currently in Phase I/II clinical trial for the treatment of KRAS G12C mutant non-small cell lung cancer, colorectal cancer, and appendix cancer. AMG510 is believed to be 6-fluoro-7-(2-fluoro-6-hydroxyphenyl)-1-[4-methyl-2-(propan-2-yl)pyridin-3-yl]-4-[(2S)-2-methyl-4-(prop-2-enoyl) piperazin-1-yl]-1H,2H-pyrido[2,3-d]pyrimidin-2-one. In FIG. 1, it was shown that Compound No. 44 at a dose of 60 mg/kg and Compound No. 126 at a dose of 30 mg/kg are more effective than AMG510 at 60 mg/kg in reducing tumor volume in vivo in colorectal adenocarcinoma SW837 xenograft model throughout the treatment period. FIG. 2 shows that Compound No. 44 at a dose of 30 mg/kg and Compound No. 126 at a dose of 30 mg/kg are more effective than AMG510 at 30 mg/kg in reducing tumor volume in vivo in NSCLC H358 xenograft model. FIG. 3 shows that Compound No. 126 at a dose of 60 mg/kg are more effective than AMG510 at 60 mg/kg in reducing tumor volume in vivo in NSCLC H2122 xenograft model.

Figure 4:
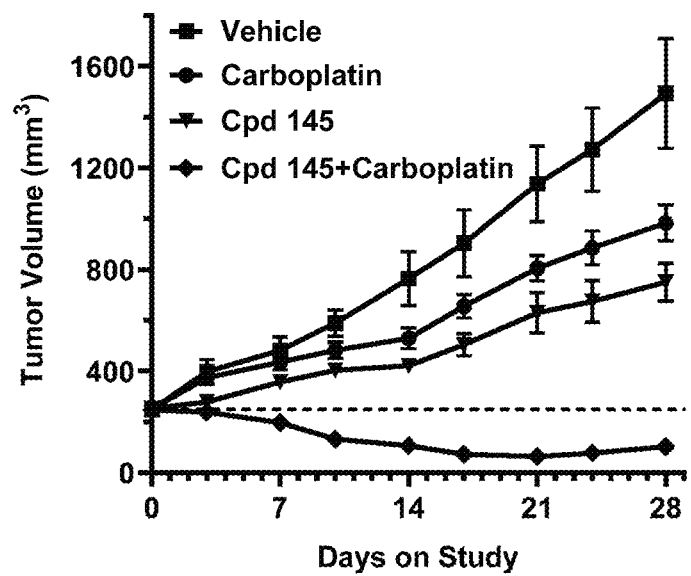
FIG. 4 is a graph showing the tumor volume growth profile vs. days on study in a NSCLC H358 xenograft model, following treatments with vehicle, carboplatin (30 mg/kg), Compound No. 145 (5 mg/kg), or carboplatin (30 mg/kg) and Compound No. 145 (5 mg/kg).
Figure 5:
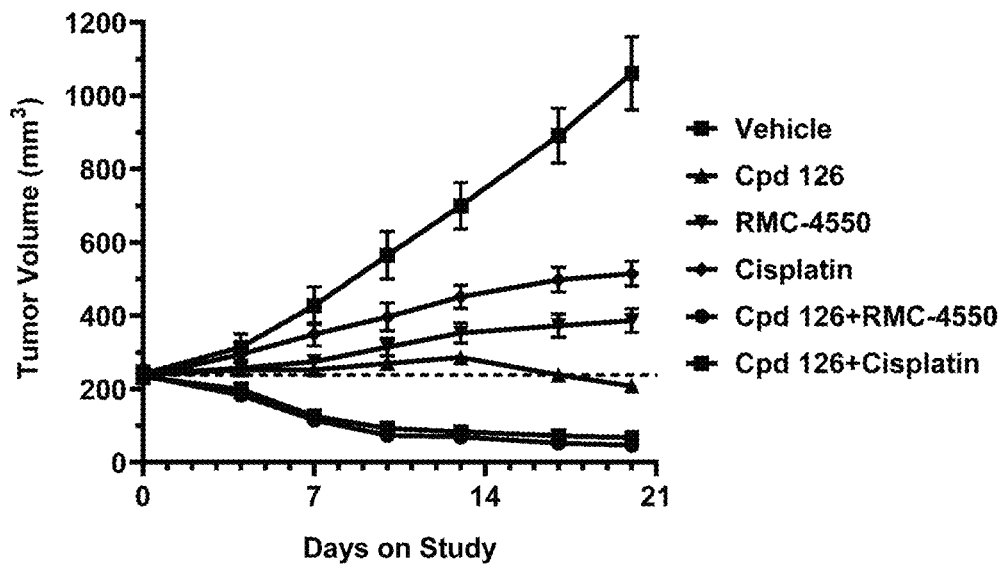
FIG. 5 is a graph showing the tumor volume growth profile vs. days on study in a NSCLC H358 xenograft model, following treatments with vehicle, cisplatin (2 mg/kg), RMC-4550 (10 mg/kg), Compound No. 126 (5 mg/kg), cisplatin (2 mg/kg) and Compound No. 126 (5 mg/kg), or RMC-4550 (10 mg/kg) and Compound No. 126 (5 mg/kg).
Figure 6:
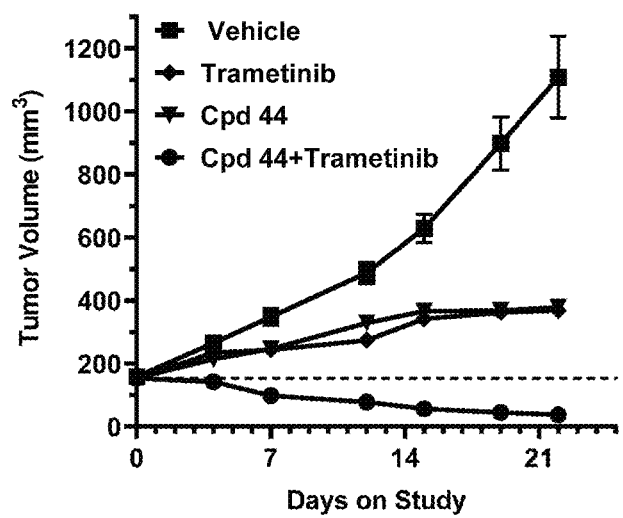
FIG. 6 is a graph showing the tumor volume growth profile vs. days on study in a colorectal adenocarcinoma SW837 xenograft model, following treatments with vehicle, trametinib (1 mg/kg), Compound No. 44 (30 mg/kg), or trametinib (1 mg/kg) and Compound No. 44 (30 mg/kg).

FIGS. 4-6 show that compounds of the present disclosure can be used in combination with other anticancer therapy to achieve synergistic effect against various cancers. FIG. 4 shows that in a NSCLC H358 xenograft model, the combined treatment with carboplatin and Compound No. 145 shows much better reduction of tumor volume throughout the course of treatment when compared to treatment with either carboplatin or Compound No. 145 alone. In this study, the treatments include: carboplatin at 30 mg/kg; Compound 145 at 5 mg/kg; or carboplatin at 30 mg/kg and Compound 145 at 5 mg/kg. FIG. 5 shows that in a NSCLC H358 xenograft model, the combined treatment with cisplatin and Compound No. 126 shows much better reduction of tumor volume throughout the course of treatment when compared to treatment with either cisplatin or Compound No. 126 alone. Similarly, the combined treatment with RMC-4550 and Compound No. 126 shows much better reduction of tumor volume throughout the course of treatment when compared to treatment with either RMC-4550 or Compound No. 126 alone. In this study, the treatments include: cisplatin at 2 mg/kg; RMC-4550 at 10 mg/kg; Compound 126 at 5 mg/kg; cisplatin at 2 mg/kg and Compound 126 at 5 mg/kg; or RMC-4550 at 10 mg/kg and Compound 126 at 5 mg/kg. FIG. 6 shows that in a colorectal adenocarcinoma SW837 xenograft model, the combined treatment with trametinib and Compound No. 44 shows much better reduction of tumor volume throughout the course of treatment when compared to treatment with either trametinib or Compound No. 44 alone. In this study, the treatments include: trametinib at 1 mg/kg; Compound 44 at 30 mg/kg; or trametinib at 1 mg/kg and Compound 44 at 30 mg/kg.

The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of" or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. A compound or a pharmaceutically acceptable salt thereof, wherein the compound is

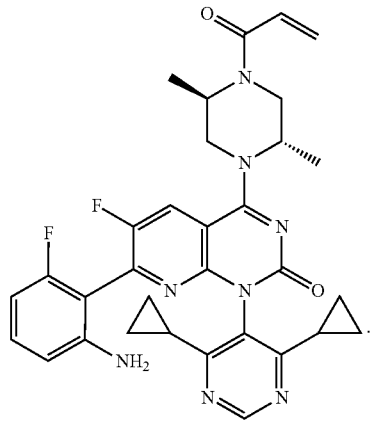 [SMILES: C=CC(=O)N1C[C@H](C)N(c2nc(=O)n(-c3c(C4CC4)ncnc3C3CC3)c3nc(-c4c(N)cccc4F)c(F)cc23)C[C@H]1C]

2. A compound, which is

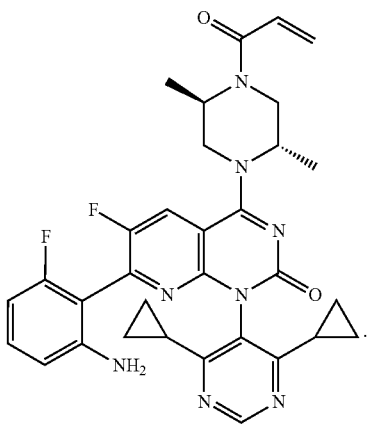 [SMILES: C=CC(=O)N1C[C@H](C)N(c2nc(=O)n(-c3c(C4CC4)ncnc3C3CC3)c3nc(-c4c(N)cccc4F)c(F)cc23)C[C@H]1C]

.

3. A pharmaceutical composition comprising the compound of claim 2 and a pharmaceutically acceptable excipient.

4. A method of treating cancer associated with KRAS G12C in a subject, the method comprising administering to the subject a therapeutically effective amount of the compound of claim 2.

5. The method of claim 4, wherein the cancer is a hematologic malignancy, lung cancer, pancreatic cancer, endometrial cancer, gall bladder cancer, thyroid cancer, bile duct cancer, and/or colorectal cancer.

6. A method of treating cancer associated with KRAS G12C in a subject, the method comprising administering to the subject a pharmaceutical composition comprising a therapeutically effective amount of the compound of claim 2.

7. The method of claim 6, wherein the cancer is a hematologic malignancy, lung cancer, pancreatic cancer, endometrial cancer, gall bladder cancer, thyroid cancer, bile duct cancer, and/or colorectal cancer.

8. A pharmaceutical composition comprising the compound of claim 1, or a pharmaceutically acceptable salt thereof, and a pharmaceutically acceptable excipient.

9. A method of treating cancer associated with KRAS G12C in a subject, the method comprising administering to the subject a therapeutically effective amount of the compound of claim 1, or a pharmaceutically acceptable salt thereof.

10. The method of claim 9, wherein the cancer is a hematologic malignancy, lung cancer, pancreatic cancer, endometrial cancer, gall bladder cancer, thyroid cancer, bile duct cancer, and/or colorectal cancer.

* * * * *